(12) United States Patent
Devarakonda et al.

(10) Patent No.: US 9,629,837 B2
(45) Date of Patent: *Apr. 25, 2017

(54) PHARMACEUTICAL COMPOSITIONS FOR EXTENDED RELEASE OF OXYCODONE AND ACETAMINOPHEN RESULTING IN A QUICK ONSET AND PROLONGED PERIOD OF ANALGESIA

(71) Applicant: MALLINCKRODT LLC, Hazelwood, MO (US)

(72) Inventors: Krishna Devarakonda, St. Louis, MO (US); Michael J. Giuliani, Creve Coeur, MO (US); Vishal K. Gupta, Hillsborough, NJ (US); Ralph A. Heasley, Webster Groves, MO (US); Susan Shelby, Town and Country, MO (US)

(73) Assignee: MALLINCKRODT LLC, Hazelwood, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/659,819

(22) Filed: Mar. 17, 2015

(65) Prior Publication Data

US 2015/0246034 A1    Sep. 3, 2015

Related U.S. Application Data

(63) Continuation of application No. 13/473,586, filed on May 16, 2012, now Pat. No. 9,050,335.

(60) Provisional application No. 61/487,047, filed on May 17, 2011, provisional application No. 61/537,527, filed on Sep. 21, 2011, provisional application No. 61/606,850, filed on Mar. 5, 2012.

(51) Int. Cl.

| | |
|---|---|
| *A61K 31/485* | (2006.01) |
| *A61K 9/24* | (2006.01) |
| *A61K 31/167* | (2006.01) |
| *A61K 9/20* | (2006.01) |
| *A61K 9/00* | (2006.01) |
| *A61K 47/10* | (2017.01) |

(52) U.S. Cl.
CPC .......... *A61K 31/485* (2013.01); *A61K 9/0053* (2013.01); *A61K 9/209* (2013.01); *A61K 9/2013* (2013.01); *A61K 9/2031* (2013.01); *A61K 9/2054* (2013.01); *A61K 9/2086* (2013.01); *A61K 31/167* (2013.01); *A61K 47/10* (2013.01)

(58) Field of Classification Search
CPC .... A61K 9/209; A61K 9/2013; A61K 9/2054; A61K 9/2086; A61K 9/0053; A61K 31/485; A61K 31/167; A61K 47/10
USPC .................. 424/468; 514/282, 731
See application file for complete search history.

(56) References Cited

U.S. PATENT DOCUMENTS

| | | |
|---|---|---|
| 4,713,243 A | 12/1987 | Schiraldi et al. |
| 4,851,226 A | 7/1989 | Julian et al. |
| 4,894,236 A | 1/1990 | Jang |
| 4,996,058 A | 2/1991 | Sinnreich |
| 5,075,114 A | 12/1991 | Roche |
| 5,266,331 A | 11/1993 | Oshlack et al. |
| 5,273,758 A | 12/1993 | Royce |
| 5,336,691 A | 8/1994 | Raffa et al. |
| 5,443,843 A | 8/1995 | Curatolo et al. |
| 5,478,577 A | 12/1995 | Sackler et al. |
| 5,508,042 A | 4/1996 | Oshlack et al. |
| 5,549,912 A | 8/1996 | Oshlack et al. |
| 5,582,837 A | 12/1996 | Shell |
| 5,626,874 A | 5/1997 | Conte et al. |
| 5,651,985 A | 7/1997 | Penners et al. |
| 5,656,295 A | 8/1997 | Oshlack et al. |
| 5,672,360 A | 9/1997 | Sackler et al. |
| 5,783,212 A | 7/1998 | Fassihi et al. |
| 5,866,161 A | 2/1999 | Childers et al. |
| 5,876,759 A | 3/1999 | Gowan, Jr. |
| 5,891,471 A | 4/1999 | Miller et al. |
| 5,945,123 A | 8/1999 | Hermelin |
| 5,945,125 A | 8/1999 | Kim |
| 5,958,459 A | 9/1999 | Chasin et al. |
| 5,965,161 A | 10/1999 | Oshlack et al. |
| 5,965,163 A | 10/1999 | Miller et al. |
| 5,965,167 A | 10/1999 | Sanghvi et al. |
| 5,968,551 A | 10/1999 | Oshlack et al. |
| 5,972,389 A | 10/1999 | Shell et al. |
| 5,980,882 A | 11/1999 | Eichman |
| 6,024,982 A | 2/2000 | Oshlack et al. |
| 6,068,855 A | 5/2000 | Leslie et al. |
| 6,071,208 A | 6/2000 | Koivunen |

(Continued)

FOREIGN PATENT DOCUMENTS

| | | |
|---|---|---|
| EP | 0159852 A2 | 10/1985 |
| EP | 1140026 B1 | 10/2001 |

(Continued)

OTHER PUBLICATIONS

Waterman K. C.; "A Critical Review of Gastric Retentive Controlled Drug Delivery;" Pharmaceutical Development and Technology; (2007); 12; pp. 1-10.

(Continued)

*Primary Examiner* — Ali Soroush
(74) *Attorney, Agent, or Firm* — Mayer Brown LLP

(57) ABSTRACT

The present disclosure provides extended release pharmaceutical compositions comprising oxycodone and acetaminophen that produce a quick initial onset of analgesia, yet, maintain analgesia for about 12 hours after administration of the composition to a subject in need thereof. The pharmaceutical compositions disclosed herein also reduce the levels of acetaminophen in a subject's blood near the end of the dosing interval because the acetaminophen released by the pharmaceutical composition is being eliminated by a subject's body faster than it is being absorbed.

20 Claims, 49 Drawing Sheets

(29 of 49 Drawing Sheet(s) Filed in Color)

(56) References Cited

U.S. PATENT DOCUMENTS

| | | |
|---|---|---|
| 6,103,219 A | 8/2000 | Sherwood et al. |
| 6,103,261 A | 8/2000 | Chasin et al. |
| 6,120,803 A | 9/2000 | Wong et al. |
| 6,126,969 A | 10/2000 | Shah et al. |
| 6,143,322 A | 11/2000 | Sackler et al. |
| 6,210,714 B1 | 4/2001 | Oshlack et al. |
| 6,245,357 B1 | 6/2001 | Edgren et al. |
| 6,251,430 B1 | 6/2001 | Zhang et al. |
| 6,254,887 B1 | 7/2001 | Miller et al. |
| 6,340,475 B2 | 1/2002 | Shell et al. |
| 6,372,254 B1 | 4/2002 | Ting et al. |
| 6,375,957 B1 | 4/2002 | Kaiko et al. |
| 6,387,404 B2 | 5/2002 | Oshlack et al. |
| 6,488,962 B1 | 12/2002 | Berner et al. |
| 6,488,963 B1 | 12/2002 | McGinity et al. |
| 6,500,459 B1 | 12/2002 | Chhabra et al. |
| 6,599,529 B1 | 7/2003 | Skinhoj et al. |
| 6,635,280 B2 | 10/2003 | Shell et al. |
| 6,667,060 B1 | 12/2003 | Vandecruys et al. |
| 6,682,759 B2 | 1/2004 | Lim et al. |
| 6,696,066 B2 | 2/2004 | Kaiko et al. |
| 6,706,281 B2 | 3/2004 | Oshlack et al. |
| 6,723,340 B2 | 4/2004 | Gusler et al. |
| 6,730,321 B2 | 5/2004 | Ting et al. |
| 6,733,783 B2 | 5/2004 | Oshlack et al. |
| 6,797,283 B1 | 9/2004 | Edgren et al. |
| 6,852,336 B2 | 2/2005 | Hunter et al. |
| 6,902,742 B2 | 6/2005 | Devane et al. |
| 7,074,430 B2 | 7/2006 | Miller et al. |
| 7,144,587 B2 | 12/2006 | Oshlack et al. |
| 7,201,920 B2 | 4/2007 | Kumar et al. |
| 7,374,781 B2 | 5/2008 | Zhang et al. |
| 7,405,238 B2 | 7/2008 | Markey et al. |
| 7,413,751 B2 | 8/2008 | Devane et al. |
| 7,438,927 B2 | 10/2008 | Berner et al. |
| 7,514,100 B2 | 4/2009 | Oshlack et al. |
| 7,674,799 B2 | 3/2010 | Chapman et al. |
| 7,674,800 B2 | 3/2010 | Chapman et al. |
| 7,683,072 B2 | 3/2010 | Chapman et al. |
| 7,691,873 B2 | 4/2010 | Duncalf et al. |
| 7,776,314 B2 | 8/2010 | Bartholomous et al. |
| 7,846,476 B2 | 12/2010 | Oshlack et al. |
| 7,897,172 B2 | 3/2011 | Qasem et al. |
| 7,939,543 B2 | 5/2011 | Kupper |
| 7,943,170 B2 | 5/2011 | Chan et al. |
| 7,976,870 B2 | 7/2011 | Berner et al. |
| 8,075,872 B2 | 12/2011 | Arkenau-Maric et al. |
| 8,309,060 B2 | 11/2012 | Bartholomaus et al. |
| 8,337,888 B2 | 12/2012 | Wright et al. |
| 8,394,408 B2 | 3/2013 | Han et al. |
| 8,409,616 B2 | 4/2013 | Kumar et al. |
| 8,465,776 B2 | 6/2013 | Hoarau |
| 8,597,681 B2 | 12/2013 | Park et al. |
| 8,658,631 B1 | 2/2014 | Devarakonda et al. |
| 8,741,885 B1 | 6/2014 | Devarakonda et al. |
| 8,790,694 B2 | 7/2014 | Devarakonda et al. |
| 8,858,963 B1 | 10/2014 | Devarakonda et al. |
| 8,980,319 B2 | 3/2015 | Park et al. |
| 8,992,975 B2 | 3/2015 | Devarakonda et al. |
| 9,050,335 B1 | 6/2015 | Devarakonda et al. |
| 2001/0008639 A1 | 7/2001 | Oshlack et al. |
| 2001/0031278 A1 | 10/2001 | Oshlack |
| 2002/0018810 A1 | 2/2002 | Oshlack et al. |
| 2002/0058050 A1 | 5/2002 | Sackler et al. |
| 2002/0192277 A1 | 12/2002 | Oshlack et al. |
| 2003/0035837 A1 | 2/2003 | Sackler et al. |
| 2003/0044466 A1 | 3/2003 | Markey et al. |
| 2003/0064099 A1 | 4/2003 | Oshlack |
| 2003/0068371 A1 | 4/2003 | Oshlack |
| 2003/0091635 A1 | 5/2003 | Baichwal et al. |
| 2003/0092724 A1* | 5/2003 | Kao et al. .................. 514/282 |
| 2003/0099704 A1 | 5/2003 | Oshlack et al. |
| 2003/0104062 A1 | 6/2003 | Berner et al. |
| 2003/0125347 A1 | 7/2003 | Anderson et al. |
| 2004/0096500 A1 | 5/2004 | Oshlack et al. |
| 2004/0105887 A1 | 6/2004 | Oshlack et al. |
| 2004/0131671 A1 | 7/2004 | Zhang et al. |
| 2004/0156899 A1 | 8/2004 | Louie-Helm et al. |
| 2005/0013863 A1 | 1/2005 | Lim et al. |
| 2005/0020613 A1 | 1/2005 | Boehm et al. |
| 2005/0031546 A1 | 2/2005 | Bartholomaus et al. |
| 2005/0089570 A1 | 4/2005 | Cruz et al. |
| 2005/0106249 A1 | 5/2005 | Hwang et al. |
| 2005/0112195 A1 | 5/2005 | Cruz et al. |
| 2005/0158382 A1 | 7/2005 | Cruz et al. |
| 2005/0165038 A1 | 7/2005 | Gordon |
| 2005/0232987 A1 | 10/2005 | Srinivasan et al. |
| 2005/0266032 A1 | 12/2005 | Srinivasan et al. |
| 2005/0267189 A1 | 12/2005 | Gao et al. |
| 2006/0002860 A1 | 1/2006 | Bartholomaus et al. |
| 2006/0057210 A1 | 3/2006 | Oshlack et al. |
| 2006/0099255 A1 | 5/2006 | Oshlack et al. |
| 2006/0165791 A1 | 7/2006 | Oshlack et al. |
| 2006/0193782 A1 | 8/2006 | Bartholomaus et al. |
| 2006/0205752 A1 | 9/2006 | Whitehead |
| 2006/0240105 A1 | 10/2006 | Devane et al. |
| 2006/0251721 A1 | 11/2006 | Cruz et al. |
| 2006/0263436 A1 | 11/2006 | Baert et al. |
| 2006/0269604 A1 | 11/2006 | Sackler et al. |
| 2006/0292214 A1 | 12/2006 | Jenkins et al. |
| 2007/0020335 A1 | 1/2007 | Chen et al. |
| 2007/0048228 A1 | 3/2007 | Arkenau-Maric et al. |
| 2007/0059359 A1 | 3/2007 | Backensfeld et al. |
| 2007/0128279 A1 | 6/2007 | Edgren et al. |
| 2007/0183980 A1 | 8/2007 | Arkenau-Maric et al. |
| 2007/0184112 A1 | 8/2007 | Wong et al. |
| 2007/0190142 A1 | 8/2007 | Breitenbach et al. |
| 2007/0207200 A1 | 9/2007 | Plachetka et al. |
| 2007/0237833 A1 | 10/2007 | Sackler et al. |
| 2007/0259033 A1 | 11/2007 | Cruz |
| 2007/0259045 A1 | 11/2007 | Mannion et al. |
| 2007/0275065 A1 | 11/2007 | Oshlack et al. |
| 2007/0281018 A1 | 12/2007 | Qiu et al. |
| 2008/0020039 A1 | 1/2008 | Parikh et al. |
| 2008/0031901 A1 | 2/2008 | Qiu et al. |
| 2008/0031963 A1 | 2/2008 | Sackler et al. |
| 2008/0044482 A1 | 2/2008 | Oshlack et al. |
| 2008/0057122 A1 | 3/2008 | Toney-Parker et al. |
| 2008/0113025 A1 | 5/2008 | Devane et al. |
| 2008/0132532 A1 | 6/2008 | Wright et al. |
| 2008/0138422 A1 | 6/2008 | Staniforth |
| 2008/0220062 A1 | 9/2008 | Ashton |
| 2009/0022798 A1 | 1/2009 | Rosenberg et al. |
| 2009/0028941 A1 | 1/2009 | Cowles et al. |
| 2009/0068269 A1 | 3/2009 | Oshlack et al. |
| 2009/0081290 A1 | 3/2009 | McKenna et al. |
| 2009/0149479 A1 | 6/2009 | Jenkins et al. |
| 2009/0155357 A1 | 6/2009 | Muhuri |
| 2009/0175937 A1 | 7/2009 | Rahmouni et al. |
| 2009/0202629 A1 | 8/2009 | Oshlack et al. |
| 2009/0304793 A1 | 12/2009 | Boehm |
| 2009/0306119 A1 | 12/2009 | Keane |
| 2009/0311320 A1 | 12/2009 | Oury et al. |
| 2009/0317355 A1 | 12/2009 | Roth et al. |
| 2009/0324714 A1 | 12/2009 | Liu et al. |
| 2010/0010030 A1 | 1/2010 | Jain et al. |
| 2010/0015222 A1 | 1/2010 | Han et al. |
| 2010/0034876 A1 | 2/2010 | Oshlack et al. |
| 2010/0040681 A1 | 2/2010 | Park et al. |
| 2010/0092570 A1 | 4/2010 | Oshlack et al. |
| 2010/0168148 A1 | 7/2010 | Wright et al. |
| 2010/0172974 A1 | 7/2010 | Oshlack et al. |
| 2010/0172989 A1 | 7/2010 | Roth et al. |
| 2010/0196425 A1 | 8/2010 | Cruz et al. |
| 2010/0196471 A1 | 8/2010 | Jain et al. |
| 2010/0196474 A1 | 8/2010 | Han et al. |
| 2010/0216829 A2 | 8/2010 | Kumar et al. |
| 2010/0221293 A1 | 9/2010 | Cruz et al. |
| 2010/0239662 A1 | 9/2010 | Rahmouni et al. |
| 2010/0260833 A1 | 10/2010 | Bartholomaus et al. |
| 2011/0020451 A1 | 1/2011 | Bartholomaus et al. |
| 2011/0038927 A1 | 2/2011 | Oshlack et al. |
| 2011/0038930 A1 | 2/2011 | Barnscheid et al. |
| 2011/0052685 A1 | 3/2011 | Hou et al. |

(56) References Cited

U.S. PATENT DOCUMENTS

| | | |
|---|---|---|
| 2011/0077238 A1 | 3/2011 | Leech et al. |
| 2011/0117196 A1 | 5/2011 | Gordon |
| 2011/0118189 A1 | 5/2011 | Farr et al. |
| 2011/0129507 A1 | 6/2011 | Cruz |
| 2011/0150969 A1 | 6/2011 | Shah et al. |
| 2011/0150970 A1 | 6/2011 | Shah et al. |
| 2011/0150971 A1 | 6/2011 | Shah et al. |
| 2011/0150989 A1 | 6/2011 | Park et al. |
| 2011/0150990 A1 | 6/2011 | Shah et al. |
| 2011/0150991 A1 | 6/2011 | Shah et al. |
| 2011/0159046 A1 | 6/2011 | Cruz |
| 2011/0166171 A1 | 7/2011 | Qiu et al. |
| 2011/0177168 A1 | 7/2011 | Chan et al. |
| 2011/0195116 A1 | 8/2011 | Hobbs et al. |
| 2011/0195989 A1 | 8/2011 | Rudnic et al. |
| 2011/0207762 A1 | 8/2011 | Chapman et al. |
| 2011/0212173 A1 | 9/2011 | Young et al. |
| 2011/0229526 A1 | 9/2011 | Rosenberg et al. |
| 2011/0229533 A1 | 9/2011 | Edgren et al. |
| 2011/0262532 A1 | 10/2011 | Oshlack et al. |
| 2011/0287095 A1 | 11/2011 | Park et al. |
| 2011/0301129 A1 | 12/2011 | Berner et al. |
| 2011/0318392 A1 | 12/2011 | Cruz et al. |
| 2012/0321713 A1 | 12/2012 | Han et al. |
| 2013/0273153 A1 | 10/2013 | Park et al. |
| 2014/0170217 A1 | 6/2014 | Devarakonda et al. |
| 2014/0275143 A1 | 9/2014 | Devarakonda et al. |
| 2014/0288113 A1 | 9/2014 | Devarakonda et al. |
| 2014/0294956 A1 | 10/2014 | Devarakonda et al. |
| 2014/0378498 A1 | 12/2014 | Devarakonda et al. |
| 2016/0184299 A1 | 6/2016 | Devarakonda et al. |

FOREIGN PATENT DOCUMENTS

| | | |
|---|---|---|
| WO | 97/18814 A1 | 5/1997 |
| WO | 9747285 A1 | 12/1997 |
| WO | 98/55107 A1 | 12/1998 |
| WO | 9856360 A2 | 12/1998 |
| WO | 9947128 A1 | 9/1999 |
| WO | 03/024426 A1 | 3/2003 |
| WO | 2005013863 A2 | 2/2005 |
| WO | 2005030182 A1 | 4/2005 |
| WO | 2006022759 A1 | 3/2006 |
| WO | 2006071208 A1 | 7/2006 |
| WO | 2008015220 A1 | 2/2008 |
| WO | 2008015221 A2 | 2/2008 |
| WO | 2009049405 A1 | 4/2009 |
| WO | 2009076764 A1 | 6/2009 |
| WO | 2009114648 A1 | 9/2009 |
| WO | 2009135846 A1 | 11/2009 |
| WO | 2010032128 A1 | 3/2010 |
| WO | 2010069050 A1 | 6/2010 |
| WO | 2010078486 A2 | 7/2010 |
| WO | 2010141505 A1 | 12/2010 |
| WO | 2011009603 A1 | 1/2011 |
| WO | 2011009604 A1 | 1/2011 |
| WO | 2011068723 A1 | 6/2011 |
| WO | 2011077451 A2 | 6/2011 |
| WO | 2011/087765 A2 | 7/2011 |
| WO | 2011106416 A2 | 9/2011 |
| WO | 2012007159 A2 | 1/2012 |
| WO | 2012/087377 A1 | 6/2012 |
| WO | 2014/149397 A1 | 9/2014 |

OTHER PUBLICATIONS

Arora et al.; "Floating Drug Delivery Systems: A Review;" AAPS PharmSciTech; (2005); 6(3); Article 47 E372-390.

Klausner et al.; "Novel Gastroretentive Dosage Forms: Evaluation of Gastroretentivity and Its Effect on Levodopa Absorption in Humans;" Pharmaceutical Research; (2003); vol. 20; No. 9; pp. 1466-1473.

Klausner et al.; "Novel Levodopa Gastroretentive Dosage Form: in-Vivo Evaluation in Dogs;" Journal of Controlled Release; (2003); 88; pp. 117-126.

Aulton M. E.; "Aulton's Pharmaceutics: The Design and Manufacture of Medicines;" Elsevier Limited; Oxford; Third Edition; (2007); pp. 270-278.

Prinderre et al.; "Advances in Gastro Retentive Drug-Delivery Systems;" Expert Opin. Drug. Deliv.; (2011); 8(9); pp. 1189-1203.

Berner et al.; "Case Studies in Swelling Polymeric Gastric Retentive Tablets;" Expert Opin. Drug. Deliv.; (2006); 3(4), pp. 541-548.

Ward et al.; "Modeling the Economic and Health Consequences of Managing Chronic Osteoarthritis Pain with Opioids in Germany: Comparison of Extended Release Oxycodone and OROS Hydromorphone;" Current Medical Research and Opinion; (2007); vol. 23; No. 10; pp. 2333-2345.

Koizumi et al.; "Efficacy and Tolerability of Cancer Pain Management with Controlled-Release Oxycodone Tablets in Opioid-Naïve Cancer Pain Patients, Starting with 5 mg Tablets;" Jpn J Clin Oncol; (2004); 34(10); pp. 608-614.

Gammaitoni et al.; "Effectiveness and Safety of New Oxycodone/Acetaminophen Formulations With Reduced Acetaminophen for the Treatment of Low Back Pain;" Pain Medicine; (2003); vol. 4; No. 1; pp. 21-30.

U.S. Appl. No. 14/627,879, filed Feb. 20, 2015; not yet published.

XARTEMIS™ XR Prescribing Information, revised Mar. 2014 (28 pages).

Requirement for Restriction/Election received in U.S. Appl. No. 13/166,770 and dated Jun. 22, 2012 (6 pages).

Non-Final Office Action received in U.S. Appl. No. 13/166,770 and dated Nov. 26, 2012 (14 pages).

Non-Final Office Action received in U.S. Appl. No. 14/092,375 and dated Feb. 24, 2014 (11 pages).

Requirement for Restriction/Election received in U.S. Appl. No. 13/473,563 and dated Sep. 11, 2012 (5 pages).

Non-Final Office Action received in U.S. Appl. No. 13/473,563 and dated May 6, 2013 (20 pages).

Non-Final Office Action received in U.S. Appl. No. 14/109,052 and dated Apr. 25, 2014 (6 pages).

Final Office Action received in U.S. Appl. No. 14/109,052 and dated Aug. 11, 2014 (7 pages).

Requirement for Restriction/Election received in U.S. Appl. No. 13/473,586 and dated Mar. 28, 2013 (6 pages).

Non-Final Office Action received in U.S. Appl. No. 13/473,586 and dated Aug. 2, 2013 (9 pages).

Non-Final Office Action received in U.S. Appl. No. 13/473,586 and dated Jun. 19, 2014 (7 pages).

Non-Final Office Action received in U.S. Appl. No. 13/473,571 and dated Aug. 31, 2012 (11 pages).

Final Office Action received in U.S. Appl. No. 13/473,571 and dated May 15, 2013 (16 pages).

Requirement for Restriction/Election received in U.S. Appl. No. 13/473,584 and dated Jun. 18, 2013 (15 pages).

Non-Final Office Action received in U.S. Appl. No. 13/473,584 and dated Oct. 24, 2013 (14 pages).

Final Office Action received in U.S. Appl. No. 13/473,584 and dated Aug. 20, 2014 (14 pages).

Non-Final Office Action received in U.S. Appl. No. 13/473,578 and dated Mar. 26, 2013 (11 pages).

Final Office Action received in U.S. Appl. No. 13/473,578 and dated Dec. 17, 2013 (7 pages).

Non-Final Office Action received in U.S. Appl. No. 14/479,129 and dated Apr. 14, 2015 (10 pages).

Requirement for Restriction/Election received in U.S. Appl. No. 14/187,939 and dated Jan. 23, 2015 (7 pages).

Requirement for Restriction/Election received in U.S. Appl. No. 14/188,582 and dated Jan. 29, 2015 (7 pages).

Non-Final Office Action received in U.S. Appl. No. 12/973,962 and dated Feb. 24, 2012 (13 pages).

Final Office Action received in U.S. Appl. No. 12/973,962 and dated Sep. 21, 2012 (15 pages).

Advisory Action received in U.S. Appl. No. 12/973,962 and dated Dec. 5, 2012 (3 pages).

Non-Final Office Action received in U.S. Appl. No. 12/973,962 and dated Jun. 19, 2014 (17 pages).

(56) References Cited

OTHER PUBLICATIONS

Requirement for Restriction/Election received in U.S. Appl. No. 13/995,810 and dated Dec. 22, 2014 (10 pages).
Final Office Action received in U.S. Appl. No. 12/973,962 and dated Apr. 20, 2015 (20 pages).
Banfai et al.; "Content Uniformity and Assay Requirements in Current Regulations;" J. Chromatogr. A.; (2007); 1156; pp. 206-212.
Zhu et al.; "Solid-State Plasticization of an Acrylic Polymer with Chlorpheniramine Maleate and Triethyl Citrate;" International Journal of Pharmaceutics; (2002); 241; pp. 301-310.
Nimmo, et al.; "Inhibition of Gastric Emptying and Drug Absorption by Narcotic Analgesics;" Br. J. Clin. Pharmac.; (1975); 2; pp. 509-513.
Altaf et al.; "Bead Compacts II. Evaluation of Rapidly Disintegrating Nonsegregating Compressed Bead Formulations;" Drug Development and Industrial Pharmacy; (1999); 25(5); pp. 635-642.
International Search Report from Application No. PCT/US2010/061400 with a mailing date of Nov. 25, 2011 (4 pages).
U.S. Department of Health & Human Services; "FDA Drugs Safety Communication: Prescription Acetaminophen Products to be Limited to 325mg per Dosage Unit; Boxed Warning Will Highlight Potential for Severe Liver Failure;" (5 pages); Downloaded on Feb. 9, 2012 from: http://www.fda.gov/Drugs/DrugSafetv/ucm239821.htm.
"Tylenol Professional Product Information;" (2010); McNeil Consumer Healthcare (62 pages).
Oxycontin; Description and Patient Information; (2010); Purdue Pharma L.P. (32 pages).
Khosla et al.; "The Effect of Tablet Size on the Gastric Emptying of Non-Disintegrating Tablets;" International Journal of Pharmaceutics; (1990); 62; R9-R11.
Khosla et al.; "Gastrointestinal Transit of Non-Disintegrating Tablets in Fed Subjects;" International Journal of Pharmaceutics; (1989); 53; pp. 107-117.
Davis et al.; "The Gastrointestinal Transit of a Controlled Release Formulation of Indomethacin;" International Journal of Pharmaceutics; (1990); 60; pp. 191-196.
Brzeznicka et al.; "Dynamics of Glutathione Levels in Liver and Indicatory Enzymes in Serum in Acetaminophen Intoxication in Mice;" Polish Journal of Occupational Medicine; (1989); vol. 2; No. 1; pp. 15-22.
Gammaitoni et al.; "Randomized, Double-Blind, Placebo-Controlled Comparison of the Analgesic Efficacy of Oxycodone 10 mg/Acetaminophen 325 mg versus Controlled-Release Oxycodone 20 mg in Postsurgical Pain;" J. Clin. Pharmacol; (2003); 43; pp. 296-304.
Moller et al.; "Time to Onset of Analgesia and Analgesic Efficacy of Effervescent Acetaminophen 1000 mg Compared to Tablet Acetaminophen 1000 mg in Postperative Dental Pain: A Single-Dose, Double-Blind, Randomized, Placebo-Controlled Study;" J. Clin. Pharmacol.; (2000); 40; pp. 370-378.
Nielsen et al; "Analgesic Efficacy of Immediate and Sustained Release Paracetamol and Plasma Concentration of Paracetamol. Double Blind Placebo-Controlled Evaluation Using Painful Laser Stimulation;" Eur. J. Clin Pharmacol; (1992); 42; pp. 261-264.
James et al; "Acetaminophen-Induced Hepatotoxicity;" Drug Metabolism and Disposition; (2003); vol. 31; No. 12; pp. 1499-1506.
Mirochnitchenko et al.; "Acetaminophen Toxicity: Opposite Effects of Two Forms of Glutathione Peroxidase;" The Journal of Biological Chemistry; (1999); vol. 274; No. 15; pp. 10349-10355.
Dart et al.; "Acetaminophen Poisoning: An Evidence-Based Consensus Guideline for Out-of-Hospital Management;" Clinical Toxicology; (2006); 44; pp. 1-18.
Bolesta et al.; "Hepatotoxicity Associated with Chronic Acetaminophen Administration in Patients without Risk Factors"; The Annals of Pharmacotherapy; (2002); vol. 36; pp. 331-333.

Rinaldi et al.; "Minireview: Reactive Intermediates and the Dynamics of Glutathione Transferases;" Drug Metabolism and Deposition; (2002); vol. 30; No. 10; pp. 1053-1058.
Barry H. Rumack; "Acetaminophen Hepatotoxicity: The First 35 Years;" Clinical Toxicology; (2002); 40(1); pp. 3-20.
Bartels et al.; "Are Recommended Doses of Acetaminophen Hepatotoxic for Recently Abstinent Alcoholics? A Randomized Trial"; (2008); Clinical Toxicology; 46; pp. 243-249.
Corcoran et al.; "Role of Glutathione in Prevention of Acetaminophen-Induced Hepatotoxicity by N-Acetyl-L-Cysteine in Vivo: Studies with N-Acetyl-D-Cysteine in Mice;" The Journal of Pharmacology and Experimental Therapeutics; (1986); vol. 238; No. 1; pp. 54-61.
Mitchell et al.; "Acetaminophen-Induced Hepatic Necrosis. IV. Protective Role of Glutathione;" The Journal of Pharmacology and Experimental Therapeutics; (1973); vol. 187; No. 1; pp. 211-217.
Kaplowitz et al.; "Drug-Induced Liver Disease;" (2003); Marcel Dekker, Inc.; Chapters 13 and 15; pp. 287-325 and pp. 345-375.
Skoglund et al.; "Efficacy of Paracetamol-Esterified Methionine Versus Cysteine or Methionine on Paracetamol-Induced Hepatic GSH Depletion and Plasma ALAT Level in Mice;" Biochemical Pharmacology; (1986); vol. 35; No. 18; pp. 3071-3075.
Talukder et al; "Gastroretentive Delivery Systems: A Mini Review;" Drug Development and Industrial Pharmacy; (2004); vol. 30; No. 10; pp. 1019-1028.
Hou et al; "Gastric Retentive Dosage Forms: A Review"; Critical Reviews in Therapeutic Drug Carrier Systems; (2003); 20(6); pp. 461-497.
Streubel et al.; "Drug Delivery to the Upper Small Intestine Window Using Gastroretentive Technologies;" Current Opinion in Pharmacology; (2006); vol. 6; pp. 501-508.
Streubel et al. "Gastroretentive Drug Delivery Systems"; Expert Opin. Drug Deilv.; (2006); 3(2); pp. 217-233.
Moes, A. J.; "Gastroretentive Dosage Forms;" Critical Reviews in Therapeutic Drug Carrier Systems; (1993); 10(2); pp. 143-195.
Davis S. S.; "Formulation Strategies for Absorption Windows;" DDT; (2005); vol. 10, No. 4; pp. 249-257.
Bardonnet et al.; "Gastroretentive Dosage Forms: Overview and Special Case of Helicobacter Pylori;" Journal of Controlled Release; (2006); vol. 111; pp. 1-18.
U.S. Appl. No. 13/473,584, filed May 16, 2012; not yet published.
U.S. Appl. No. 13/473,586, filed May 16, 2012; not yet published.
"Foremost NF Fast Flo Lactose: Modified, Spray Dried, Product Code 316; A Spray-Dried Mixture of Crystalline and Amorphose Lactose;" Foremost Farms; USA; (1 page). Online Article downloaded from the site: http://www.foremostfarms.com/Commercial/pdfs/Specifications/TDS_NF_Lactose_316.pdf Document created on Jan. 28, 2010.
Freed et al.; "pH Control on Nucleophilic/Electrophilic Oxidation;" Int. J. Pharm.; (2008); vol. 357; pp. 180-188.
International Search Report for PCT Patent application No. PCT/US2009/036864 mailed on Aug. 31, 2009.
Lab Basics Technical Library; Particle Size Conversion Table; Sigma-Aldrich; 3 pages; online article downloaded from the site: http://www.sigmaaldrich.com/chemistry/stockroom-reagents/learning-center/technical-library/particle-size-conversion. printerview.html on Apr. 17, 2012.
Polyox Water-Soluble Resins, Technical Data, "Degradation of Water-Soluble Resins"; Form 326-00027-1002AMS (2002).
Polyox Water-Soluble Resins, Technical Data, "Water-Soluble Resin Storage Stability;" Form 326-00044-0704MAB (2004).
Waterman et al.; "Stabilization of Pharmaceuticals to Oxidative Degradation;" Pharmaceutical Development and Technology; (2002); vol. 7; No. 1; pp. 1-32.
Zhang et al.; "Effect of Processing Methods and Heat Treatment on the Formation of Wax Matrix Tablets for Sustained Drug Release;" Pharmaceutical Development and Technology; (2001); vol. 6; No. 2; pp. 131-144.
Meert et al.; A Preclinical Comparison Between Different Opioids: Antinociceptive Versus Adverse Effects; Pharmacology, Biochemistry and Behavior; (2005); 80; pp. 309-326.

(56) References Cited

OTHER PUBLICATIONS

Doteuchi et al.; "Pharmacological Studies of Oxycodone Hydrochloride: 1. Antinociceptive Effect and General Pharmacology"; Oyo Yakuri/Pharmacometrics; (1995); 49(3); pp. 257-273.

Miller et al.; "Physical and Chemical Characteristics of Some High Purity Magnesium Stearate and Palmitate Powders;" International Journal of Pharmaceutics; (1985); 23; pp. 55-67.

Kim, C.-J.; "Effects of Drug Solubility, Drug Loading, and Polymer Molecular Weight on Drug Release from Polyox Tablets;" Drug Development and Industrial Pharmacy; (1998); 24(7); pp. 645-651.

Barbara Davit, Acting Director of FDA's Office of Generic Drugs Presentation titled, "Use of Partial AUC: Case Studies and BE Approaches" (Apr. 13, 2010).

Ansel et al., Pharmaceutical Dosage Forms and Drug Delivery Systems, Williams & Wilkins, 1995, pp. 77.

Gammaitoni et al., Effectiveness and Safety of New Oxycodone/Acetaminophen Formulations With Reduced Acetaminophen for the Treatment of Low Back Pain, Pain Medicine, vol. 4, No. 1, pp. 21-30 at 28 (2003).

*Mallinckrodt LLC, et al.* v. *Watson Laboratories, Inc.*, Case No. 2:15v3800 (New Jersey)—Complaint dated Jun. 5, 2015 [D.I 1] (Separated into two parts).

*Mallinckrodt LLC, et al.* v. *Watson Laboratories, Inc.*, Case No. 2:15v3800 (New Jersey)—Answer to Complaint dated Sep. 11, 2015 [D.I. 14].

*Mallinckrodt LLC, et al.* v. *Watson Laboratories, Inc.*, Case No. 2:15v3800 (New Jersey)—Actavis and Watson's Motion to Dismiss dated Sep. 11, 2015 [D.I 16].

*Mallinckrodt LLC, et al.* v. *Watson Laboratories, Inc.*, Case No. 2:15v3800 (New Jersey)—US District Court Civil Docket dated Jun. 16, 2016 (12 pages).

*Mallinckrodt LLC, et al.* v. *Watson Laboratories, Inc.*, Case No. 2:15v3800 (New Jersey)—Redaction to Actavis and Watson's Memorandum in Support of Motion to Dismiss dated Sep. 11, 2015 [D.I. 18].

*Mallinckrodt LLC, et al.* v. *Watson Laboratories, Inc.*, Case No. 2:15v3800 (New Jersey)—Order Adjourning Actavis and Watson' Motion to Dismiss dated Sep. 29, 2015 [D.I. 27].

*Mallinckrodt LLC, et al.* v. *Watson Laboratories, Inc.*, Case No. 2:15v3800 (New Jersey)—Order re Schedule as to Motion to Dismiss dated Oct. 7, 2015 [D.I. 29].

*Mallinckrodt LLC, et al.* v. *Watson Laboratories, Inc.*, Case No. 2:15v3800 (New Jersey)—Stipulation and Order Directing Plaintiffs to File Their Amended Complaint by Nov. 2, 2015 dated Oct. 30, 2015 [D.I. 36].

*Mallinckrodt LLC, et al.* v. *Watson Laboratories, Inc.*, Case No. 2:15v3800 (New Jersey)—Mallinckrodt's Amended Complaint dated Nov. 2, 2015 [D.I. 37].

*Mallinckrodt LLC, et al.* v. *Watson Laboratories, Inc.*, Case No. 2:15v3800 (New Jersey)—Actavis' Amended Answer to Amended Complaint dated Nov. 17, 2015 [D.I. 39].

*Mallinckrodt LLC, et al.* v. *Watson Laboratories, Inc.*, Case No. 2:15v3800 (New Jersey)—Mallinckrodt's Answer to Counterclaim dated Dec. 2, 2015 [D.I. 43].

*Mallinckrodt LLC, et al.* v. *Watson Laboratories, Inc.*, Case No. 2:15v3800 (New Jersey)—Discovery Confidentiality order dated Jan. 4, 2016 [D.I. 46].

*Mallinckrodt LLC, et al.* v. *Par Pharmaceuticals Inc.*, Case No. 2:15v7694 (New Jersey)—Complaint dated Oct. 23, 2015 [D.I. 1] (Separated into three parts).

*Mallinckrodt LLC, et al.* v. *Par Pharmaceuticals Inc.*, Case No. 2:15v7694 (New Jersey)—US District Court Civil Docket dated Jun. 16, 2016 (3 pages).

Moroni, et al., Application of Poly(oxyethylene) Homopolymers in Sustained Release Solid Formulations, Drug Development and Industrial Pharmacy, 21(12):1411-1428 (1995).

Maggi, "Dissolution Behavior of Hydrophilic Matrix Tablets Containing Two Different Polyethylene Oxides (PEOs) for the Controlled Release of a Water-Soluble Drug Dimensionality Study," Biomaterials, 23:1113-1119 (2002).

Apicella, et al., "Poly(ethylene oxide) (PEO) and different molecular weight PEO blends monolithic devices for drug release, Biomaterials," 14:83-90 (1993).

Gatti, A., et al., "Oxycodone/Paracetamol: A Low Dose Synergic Combination Useful in Different Types of Pain," Clin. Drug Investig. 2010, 30 Suppl. 2:3-14.

Siewert, M., "FIP Guidelines for Dissolution Testing of Solid Oral Products," Pharm. Ind. 57:362-369 (1995).

Turnbull, K., et al., "Stability of Oxycodone Hydrochloride for Injection in Dextrose and Saline Solutions," Can. J. Hosp. Pharm. (55), 2002: 272-77.

*Mallinckrodt LLC, et al.* v. *Watson Laboratories, Inc.*, Case No. 2:15v3800 (New Jersey)—Joint Claim Construction and Prehearing Statement dated May 16, 2016 [D.I. 64].

*Mallinckrodt LLC, et al.* v. *Watson Laboratories, Inc.*, Case No. 2:15v3800 (New Jersey)—Stipulation of Voluntary Dismissal of Claims and Counterclaims Pertaining to U.S. Pat. No. 8597681; 8980319; 7976870; 8668929; 3372432; 8377453; and 8394408 dated May 25, 2016 [D.I. 66].

*Mallinckrodt LLC, et al.* v. *Par Pharmaceuticals Inc.*, Case No. 2:15v7694 (New Jersey)—Notice of Dismissal of Action lated Apr. 15, 2016 [D.I. 19].

Final Office Action dated Jan. 14, 2016 and received in U.S. Appl. No. 14/187,939 (20 pages).

Final Office Action dated Jan. 14, 2016 and received in U.S. Appl. No. 14/188,582 (22 pages).

Final Office Action dated Mar. 4, 2016 and received in U.S. Appl. No. 14/479,129 (8 pages).

Non-Final Office Action dated Jun. 12, 2015 and received in U.S. Appl. No. 14/187,939 (35 pages).

Non-Final Office Action dated Jun. 12, 2015 and received in U.S. Appl. No. 14/188,582 (63 pages).

Non-Final Office Action dated May 21, 2015 and received in U.S Appl. No. 14/301,658 (10 pages).

Non-Final Office Action dated Jul. 20, 2015 and received in U.S. Appl. No. 14/627,879 (6 pages).

U.S. Unpublished U.S. Appl. No. 15/147,621, filed May 5, 2016.

\* cited by examiner

PHARMACEUTICAL COMPOSITIONS FOR EXTENDED RELEASE OF OXYCODONE AND ACETAMINOPHEN RESULTING IN A QUICK ONSET AND PROLONGED PERIOD OF ANALGESIA

RELATED CASES

This application a continuation of U.S. application Ser. No. 13/473,586 filed on May 16, 2012 which claims priority to U.S. Provisional Application No. 61/487,047 filed on May 17, 2011, U.S. Provisional Application No. 61/537,527 filed on Sep. 21, 2011, and U.S. Provisional Application No. 61/606,850 filed on Mar. 5, 2012 which are incorporated herein by reference in their entirety to the full extent permitted by law.

FIELD OF THE INVENTION

The present disclosure relates to an extended release pharmaceutical composition comprising oxycodone and acetaminophen that provides a rapid onset of analgesia, followed by an extended duration of analgesia of about 12 hours.

BACKGROUND OF THE INVENTION

Oral drug administration remains the route of choice for the majority of clinical applications. Modified release (MR) dosage forms that are administered once or twice daily offer advantages over their immediate release (IR) counterparts because they reduce the magnitude of peaks and troughs of drug plasma concentration, provide longer dosing intervals, sustained analgesic effect, and increased patient compliance. These modified release formulations may be referred to as controlled release (CR), sustained release (SR) and/or extended release (ER) etc. For certain types of patients, such as those suffering from pain, these MR products may permit the patient to sleep through the night without having to wake up during the night to take the next dose. Thus, it can significantly increase the quality of life for such patients. Both IR and MR products for pain are widely available in the market. Examples of IR products include those containing NSAIDs, opioids, profens, COX II inhibitors and aspirin (TYLENOL (acetaminophen), Advil, Celebrex, Vioxx, Aleve, Voltaren). Examples of MR products include those containing NSAIDs and opioids (TYLENOL (acetaminophen) SR, Oxycontin).

Researchers have also combined various classes of pain drugs to provide better analgesia to patients. For example, a combination of acetaminophen-oxycodone hydrochloride is commercially available as PERCOCET (oxycodone and acetaminophen) and acetaminophen-hydrocodone bitartrate as Vicodin. In randomized controlled trials, it was shown that the combination product PERCOCET (oxycodone and acetaminophen) was statistically superior to MR oxycodone in various outcome measures of pain relief. Other combination products such as Acetaminophen-Hydrocodone and Acetaminophen-Tramadol are either available or described in the literature. It is postulated that the combination of two analgesic drugs with complementary mechanisms of action results in enhanced analgesia due to an additive effect, an "opioid-sparing" effect, and an improved side effect and safety profile. The improved safety profile results from the use of reduced doses of two analgesics with different side-effects rather than an equieffective dose of a single agent.

Acetaminophen is absorbed from the small intestine and primarily metabolized by conjugation, like glucuronidation and sulfation, in the liver to nontoxic, water-soluble compounds that are eliminated in the urine. When the maximum daily dose is exceeded over a prolonged period, metabolism by conjugation becomes saturated, and excess acetaminophen is oxidatively metabolized by cytochrome P450 (CYP) enzymes (e.g., CYP2E1, 1A2, 2A6, 3A4) to a reactive metabolite, N-acetyl-p-benzoquinone-imine (NAPQI). NAPQI is a reactive free radical with an extremely short half-life that is rapidly inactivated by conjugation with glutathione, which is acting as a sulfhydryl donor. Once the pool of available glutathione is exhausted, the cysteines of cellular proteins become sulfhydryl donors to NAPQI, binding covalently and initiating a cascade of oxidative and cellular damage, resulting in necrosis and, ultimately, liver failure. Thus, avoiding excessive NAPQI formation is an important strategy when using acetaminophen, although to date acetaminophen-sparing has not been an approach any manufacturers have chosen to take. However, due to the prevalence of acetaminophen in many over-the-counter products, it is prudent to consider acetaminophen-sparing precautions when considering combination therapy lasting more than a few days to avoid an inadvertent reduction in glutathione stores.

Thus, various options for pain management are available that are both IR and MR, and contain either a single drug or a combination of analgesics. While these combination products provide the benefits associated with combining two analgesics as described above, both IR and MR, in itself, have a significant disadvantage. IR combination products lack the advantages of MR products described previously. MR combination products lack a significant benefit associated with IR products—rapid onset of analgesia—that is extremely desirable for pain management. Because MR products retard the rate of drug release to sustain the drug effect over prolonged period, release of drug is slow resulting in significant time before effective analgesic drug concentration is attained in the bloodstream. There exists a clinical need for pain management that combines the desirable features of IR and MR in combination pain products.

SUMMARY OF THE INVENTION

Among the various aspects of the present disclosure is a pharmaceutical composition for extended release of oxycodone and acetaminophen comprising at least one extended release portion comprising oxycodone, acetaminophen or a combination thereof, and at least one extended release component. The composition, when orally administered to a subject, maintains a therapeutic plasma concentration of oxycodone of at least about 5 ng/mL from about 0.75 hour to about 10 hours after administration of the composition. Additionally, at least about 90% of the acetaminophen is released from the composition by about 8 hours after administration of the composition such that, by about 10 hours after administration of the composition, acetaminophen has a blood plasma concentration that is less than about 30% of acetaminophen's maximum plasma concentration.

A further aspect of the disclosure encompasses a pharmaceutical composition for extended release of oxycodone and acetaminophen comprising (a) at least one immediate release portion comprising oxycodone, acetaminophen or a combination thereof, and (b) at least one extended release portion comprising oxycodone, acetaminophen or a combination thereof, and an extended release component, wherein about 30% of the oxycodone in the pharmaceutical composition is released in about 15 minutes and at least about 90% of the acetaminophen in the pharmaceutical composition is released in about 8 hours when measured in 900 ml of 0.1N HCl using a USP type II apparatus at a paddle speed of about 100 rpm and a constant temperature of 37° C.

Still another aspect of the disclosure provides for an extended release pharmaceutical composition, comprising at least one extended release portion comprising oxycodone or a pharmaceutically acceptable salt of oxycodone, acetaminophen, and an extended release component, wherein when the composition is orally administered to a subject in need thereof, the subject attains therapeutic blood levels of both the oxycodone and the acetaminophen within about one hour after administration of the composition and maintains analgesia for about 12 hours after administration of the composition. Further, upon placement of the composition in an in vitro dissolution test comprising USP Paddle Method at a paddle speed of about 150 rpm in 900 ml of 0.1N HCl using a USP type II apparatus at a constant temperature of 37° C., no more than about 65%, by weight, of the total amount of the oxycodone or salt is released and no more than about 75%, by weight, of the total amount of the acetaminophen is released after 2 hours; from about 65% to about 85%, by weight, of the total amount of the oxycodone or salt is released and from about 70% to about 90%, by weight, of the total amount of the acetaminophen is released after 4 hours; from about 85% to about 100%, by weight, of the total amount of the oxycodone or salt is released and from about 85% to about 100%, by weight, of the total amount of the acetaminophen is released after 8 hours; and from about 95% to about 100%, by weight, of the total amount of the oxycodone or salt is released and from about 90% to about 100%, by weight, of the total amount of the acetaminophen is released after 12 hours.

Yet another aspect of the disclosure provides for a pharmaceutical composition for extended release of oxycodone and acetaminophen, comprising at least one extended release portion comprising oxycodone or a pharmaceutically acceptable salt of oxycodone, acetaminophen, and an extended release component, wherein the total amount of acetaminophen in the composition is about 325 mg to about 650 mg, and the total amount of oxycodone or salt in the composition is about 7.5 mg to about 15 mg. Moreover, upon oral administration of the composition to a subject in a fed state, the composition provides an $AUC_{0-3.2}h$ for acetaminophen of about 7 ng·h/mL/mg to about 21 ng·h/mL/mg; an $AUC_{3.2-48h}$ for acetaminophen of about 15 ng·h/mL/mg to about 75 ng·h/mL/mg; an $AUC_{0-4.3}h$ for oxycodone or salt of about 1.5 ng·h/mL/mg to about 5.5 ng·h/mL/mg; and $AUC_{4.3-48h}$ for oxycodone or salt of about 5.0 ng·h/mL/mg to about 15 ng·h/mL/mg. In addition, upon oral administration of the composition to a subject in a fasted state, the composition provides an $AUC_{0-1.7}h$ for acetaminophen of about 5 ng·h/mL/mg to about 13 ng·h/mL/mg; an $AUC_{1.7-48h}$ for acetaminophen of about 25 ng·h/mL/mg to about 75 ng·h/mL/mg; an $AUC_{0-2.8}h$ for oxycodone or salt of about 1 ng·h/mL/mg to about 3 ng·h/mL/mg; and $AUC_{2.8-48h}$ for oxycodone or salt of about 7.5 ng·h/mL/mg to about 15 ng·h/mL/mg.

Still another aspect of the disclosure provides a dosage form comprising (a) an immediate release portion comprising acetaminophen and oxycodone, wherein the immediate release portion comprises, by weight of the immediate release portion, from about 70% to about 80% of acetaminophen and from about 0.5% to about 1% of oxycodone; and (b) an extended release portion comprising acetaminophen, oxycodone, and an extended release polymer, wherein the extended release portion comprises, by weight of the extended release portion, from about 20% to about 40% of acetaminophen, from about 0.5% to about 2% of oxycodone, and from about 30% to about 50% of the extended release polymer.

Another aspect provides a dosage form comprising from about 7.5 mg to about 30 mg of oxycodone and from about 325 mg to about 650 mg of acetaminophen. The dosage form comprises (a) at least one immediate release portion comprising about 25% of the total amount of oxycodone in the composition and about 50% of the total amount of acetaminophen in the composition; and (b) at least one extended release portion comprising about 75% of the total amount of oxycodone in the composition, about 50% of the total amount of acetaminophen in the composition, and about 35% to about 45%, by weight of the at least one extended release portion, of an extended release polymer comprising a polyethylene oxide.

A further aspect of the disclosure provides a method for reducing the risk of acetaminophen-induced hepatic damage in a subject being treated for pain with a dosage regimen that comprises administering to the subject at least two consecutive doses of a pharmaceutical composition comprising oxycodone and acetaminophen. The method comprises (a) administering a first dose of the pharmaceutical composition comprising at least one extended release portion comprising acetaminophen, oxycodone or a combination thereof, and an extended release component to the subject, wherein the composition maintains a therapeutic blood plasma concentration of oxycodone of at least 5 ng/mL from about 0.75 hours to about 10 hours after administration of the composition, and wherein at least about 90% of the acetaminophen is released from the composition by about 8 hours after administration of the composition such that, by about 10 hours after administration of the composition, acetaminophen has a blood plasma concentration that is less than about 30% of acetaminophen's maximum plasma concentration; and (b) administering a second dose of the pharmaceutical composition to the subject at about 12 hours after administration of the first dose.

Still another aspect of the disclosure provides for an extended release pharmaceutical composition, comprising at least one extended release portion comprising oxycodone or a pharmaceutically acceptable salt of oxycodone, acetaminophen, and an extended release component, wherein when the composition is orally administered to a subject in need thereof, the subject attains therapeutic blood levels of both the oxycodone and the acetaminophen within about one hour after administration of the composition and maintains analgesia for about 12 hours after administration of the composition. Further, upon placement of the composition in an in vitro dissolution test comprising USP Paddle Method at a paddle speed of about 150 rpm in 900 ml of 0.1N HCl using a USP type II apparatus at a constant temperature of 37° C., no more than about 65%, by weight, of the total amount of the oxycodone or salt is released and no more than about 75%, by weight, of the total amount of the acetaminophen is released after 2 hours; from about 65% to about 85%, by weight, of the total amount of the oxycodone or salt is released and from about 70% to about 90%, by weight, of the total amount of the acetaminophen is released after 4 hours; from about 85% to about 100%, by weight, of the total amount of the oxycodone or salt is released and from about 85% to about 100%, by weight, of the total amount of the acetaminophen is released after 8 hours; and from about 95% to about 100%, by weight, of the total amount of the oxycodone or salt is released and from about 90% to about 100%, by weight, of the total amount of the acetaminophen is released after 12 hours.

Yet another aspect of the disclosure encompasses a method for treating pain in a subject in need thereof with a pharmaceutical composition that comprises oxycodone and acetaminophen. The method comprises orally administering to the subject an effective amount of the pharmaceutical composition comprising at least one extended release portion comprising oxycodone, acetaminophen or a combination thereof, and an extended release component, wherein the composition maintains a therapeutic plasma concentration of oxycodone of at least about 5 ng/mL from about 0.75 hour to about 10 hours after administration of the composition, and wherein at least about 90% of the acetaminophen is released from the composition by about 8 hours after administration of the composition such that, by about 10 hours after administration of the composition, acetaminophen has a blood plasma concentration that is less than about 30% of acetaminophen's maximum plasma concentration.

Other features and aspects of the disclosure are described in detail below.

REFERENCE TO COLOR FIGURES

This application file contains at least one drawing executed in color. Copies of this patent application publication with color drawings will be provided by the Office upon request and payment of the necessary fee.

DETAILED DESCRIPTION OF THE INVENTION

Figure 1:
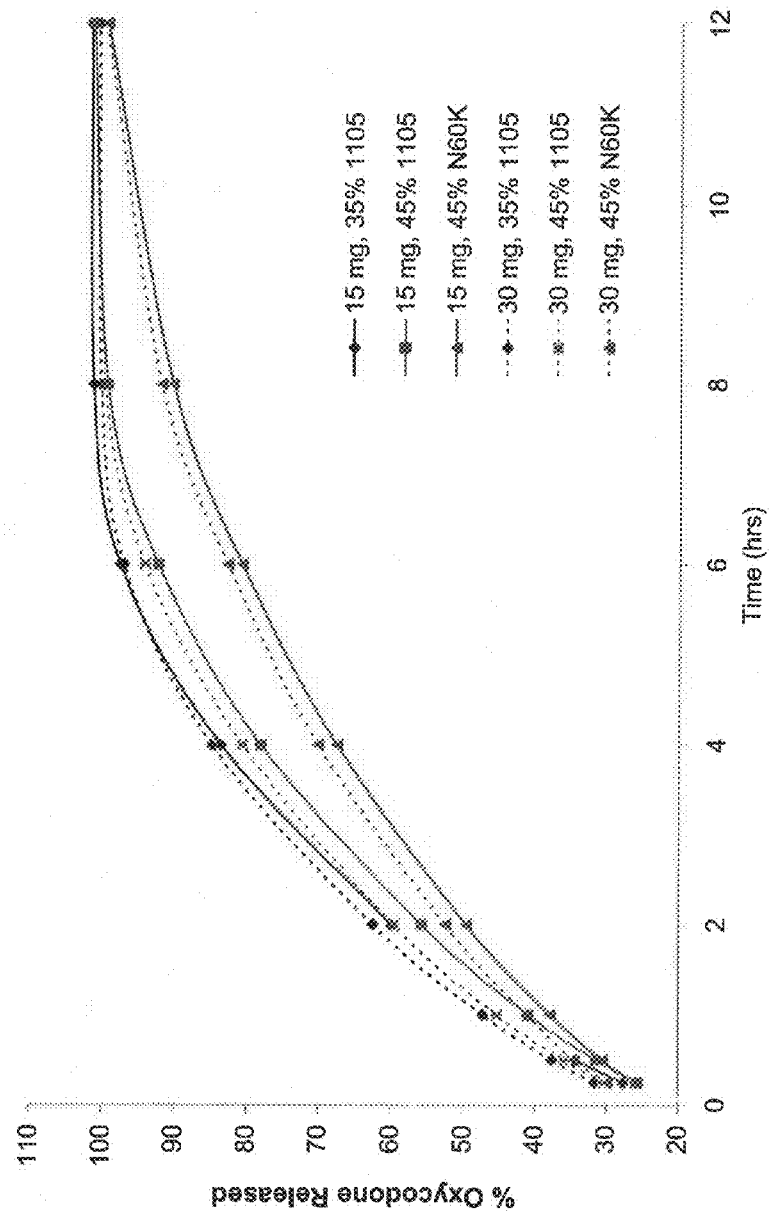
FIG. 1 presents the in vitro release profile of oxycodone from oxycodone-acetaminophen bilayer tablets comprising either 15 or 30 mg of oxycodone, 500 mg of acetaminophen (APAP), and either 35 wt % POLYOX® 1105, 45 wt % POLYOX® 1105, or 45 wt % POLYOX® N60K, as indicated.

Disclosed herein is a combination product of oxycodone and acetaminophen that has the desirable attributes of both IR and MR products. The extended release pharmaceutical composition disclosed herein comprises at least one extended release portion and, optionally, at least one immediate release portion. The extended release and immediate release portions may comprise oxycodone, acetaminophen, or combinations thereof. The at least one immediate release portion releases acetaminophen (APAP) and/or oxycodone instantly in an immediate release fashion that provides rapid onset for the attainment of therapeutically effective plasma concentrations within about the first 5 minutes, 10 minutes, 15 minutes, 20 minutes, 25 minutes, 30 minutes, 35 minutes, 40 minutes, 45 minutes, 50 minutes, 55 minutes, or 60 minutes after administration of the composition. The at least one extended release portion releases acetaminophen and/or oxycodone in an extended release fashion to maintain plasma concentrations above the minimum effective concentration for about 8-12 hours. In addition, two other important features of this composition are: 1) to allow the plasma concentrations of oxycodone to fall as rapidly as an immediate release formulation to provide the same rate of termination of drug effects as the immediate release product, and 2) to allow the concentrations of APAP to fall even quicker towards the later part of the dosing interval and bring down the levels of APAP lower than those of the immediate release product. The concentrations of APAP in the last quarter of the dosing interval are comparable to the pre-dose concentrations in a multiple dose setting, allowing for the glutathione synthase enzyme cycle to replenish the body's levels of glutathione to avoid the formation of toxic intermediates with subsequent doses of APAP. Moreover, the concentrations of APAP in the later part of the dosing interval are lower than those present when administered a conventional extended release formulation. This feature has been deliberately introduced to reduce the hepatic injury due to APAP and is termed "APAP time-off".

Abuse potential is a concern with any opioid product. The addition of APAP to the opioid, however, is likely to reduce the amount of abuse by illicit routes of administration, particularly intravenous or intranasal administration. This deterrence is likely due to the bulk (grams) that the APAP provides as well as the relative aqueous insolubility compared to freely soluble opioid salts. Further, APAP is known to be irritating to nasal passages and to make drug abusers sneeze violently when they are trying to snort it. In addition, embodiments disclosed herein may be tamper resistant in that the compositions are difficult to crush for administration intravenously or intranasally; difficult to extract with water or alcohol because the mixture becomes too viscous for injecting or snorting; and resistant to dose dumping in alcohol.

In one embodiment, the pharmaceutical composition disclosed herein, therefore, provides: 1) rapid onset of analgesia within about 15, 30, 45, or 60 minutes after administration of the composition mediated by both oxycodone and APAP, with APAP providing maximal contribution during the early phase; 2) prolonged analgesia for the entire 12 hours period, mainly contributed by oxycodone, with minimal fluctuations during this period; 3) relatively low levels of APAP toward end of dosing interval to allow for recovery of the depleted hepatic glutathione system; 4) low abuse quotient; and 5) abuse deterrence.

Headings included herein are simply for ease of reference, and are not intended to limit the disclosure in any way.

I. DEFINITIONS

Compounds useful in the compositions and methods include those described herein in any of their pharmaceutically acceptable forms, including isomers such as diastereomers and enantiomers, salts, solvates, and polymorphs, as well as racemic mixtures and pure isomers of the compounds described herein, where applicable.

When introducing elements of the various embodiment(s) of the present disclosure, the articles "a", "an", "the" and "said" are intended to mean that there are one or more of the elements. The terms "comprising", "including" and "having" are intended to be inclusive and mean that there may be additional elements other than the listed elements.

The use of individual numerical values are stated as approximations as though the values were preceded by the word "about" or "approximately." Similarly, the numerical values in the various ranges specified in this application, unless expressly indicated otherwise, are stated as approximations as though the minimum and maximum values within the stated ranges were both preceded by the word "about" or "approximately." In this manner, variations above and below the stated ranges can be used to achieve substantially the same results as values within the ranges. As used herein, the terms "about" and "approximately" when referring to a numerical value shall have their plain and ordinary meanings to a person of ordinary skill in the art to which the disclosed subject matter is most closely related or the art relevant to the range or element at issue. The amount of broadening from the strict numerical boundary depends upon many factors. For example, some of the factors which may be considered include the criticality of the element and/or the effect a given amount of variation will have on the performance of the claimed subject matter, as well as other considerations known to those of skill in the art. As used herein, the use of differing amounts of significant digits for different numerical values is not meant to limit how the use of the words "about" or "approximately" will serve to broaden a particular numerical value or range. Thus, as a general matter, "about" or "approximately" broaden the numerical value. Also, the disclosure of ranges is intended as a continuous range including every value between the minimum and maximum values plus the broadening of the range afforded by the use of the term "about" or "approximately." Consequently, recitation of ranges of values herein are merely intended to serve as a shorthand method of referring individually to each separate value falling within the range, unless otherwise indicated herein, and each separate value is incorporated into the specification as if it were individually recited herein.

The term "abuse quotient" for a pharmaceutical composition as used herein is the numerical value obtained via dividing the $C_{max}$ for a drug by the $T_{max}$ for the same drug. Generally speaking, the abuse quotient provides a means for predicting the degree of addictiveness of a given pharmaceutical composition. Pharmaceutical compositions with lower abuse quotients typically are less addictive compared to pharmaceutical compositions with higher abuse quotients.

The term "active agent" or "drug," as used herein, refers to any chemical that elicits a biochemical response when administered to a human or an animal. The drug may act as a substrate or product of a biochemical reaction, or the drug may interact with a cell receptor and elicit a physiological response, or the drug may bind with and block a receptor from eliciting a physiological response.

The term "bioequivalent," as used herein, refers to two compositions, products or methods where the 90% Confidence Intervals (CI) for AUC, partial AUC and/or $C_{max}$ are between 0.80 to 1.25.

The term "bulk density," as used herein, refers to a property of powders and is defined as the mass of many particles of the material divided by the total volume they occupy. The total volume includes particle volume, interparticle void volume and internal pore volume.

The term "content uniformity," as used herein refers to the testing of compressed tablets to provide an assessment of how uniformly the micronized or submicron active ingredient is dispersed in the powder mixture. Content uniformity is measured by use of USP Method (General Chapters, Uniformity of Dosage Forms), unless otherwise indicated. A plurality refers to five, ten or more tablet compositions.

The term "friability," as used herein, refers to the ease with which a tablet will break or fracture. The test for friability is a standard test known to one skilled in the art. Friability is measured under standardized conditions by weighing out a certain number of tablets (generally 20 tablets or less), placing them in a rotating Plexiglas drum in which they are lifted during replicate revolutions by a radial lever, and then dropped approximately 8 inches. After replicate revolutions (typically 100 revolutions at 25 rpm), the tablets are reweighed and the percentage of composition abraded or chipped is calculated.

The term "ER" as used herein refers to extended release. The phrases "extended release layer," "ER layer," "ER portion," and "extended release portion" are used interchangeable in this document. Further, as used herein the "extended release layer," "ER layer," "ER portion," and "extended release portion" can be either (i) a discrete part(s) of the pharmaceutical composition, (ii) integrated within the pharmaceutical composition, or (iii) a combination thereof.

The term "IR" as used herein refers to immediate release. The phrases "immediate release layer," "IR layer," "IR portion" and "immediate release portion" are used interchangeable in this document. In addition, as used herein the "immediate release layer," "IR layer," "IR portion" and "immediate release portion" can be either (i) a discrete part(s) of the pharmaceutical composition, (ii) integrated within the pharmaceutical composition, or (iii) a combination thereof.

The term "half life" as used herein refers to the time required for a drug's blood or plasma concentration to decrease by one half. This decrease in drug concentration is a reflection of its excretion or elimination after absorption is complete and distribution has reached an equilibrium or quasi equilibrium state. The half life of a drug in the blood may be determined graphically off of a pharmacokinetic plot of a drug's blood-concentration time plot, typically after intravenous administration to a sample population. The half life can also be determined using mathematical calculations that are well known in the art. Further, as used herein the term "half life" also includes the "apparent half-life" of a drug. The apparent half life may be a composite number that accounts for contributions from other processes besides elimination, such as absorption, reuptake, or enterohepatic recycling.

"Optional" or "optionally" means that the subsequently described element, component or circumstance may or may not occur, so that the description includes instances where the element, component, or circumstance occurs and instances where it does not.

"Partial AUC" means an area under the drug concentration-time curve (AUC) calculated using linear trapezoidal summation for a specified interval of time, for example, $AUC_{(0-1hr)}$, $AUC_{(0-2hr)}$, $AUC_{(0-4hr)}$, $AUC_{(0-6hr)}$, $AUC_{(0-8hr)}$, $AUC_{(0-(Tmax\ of\ IR\ product+2SD))}$, $AUC_{(0-(x)hr)}$, $AUC_{(x-yhr)}$, $AUC_{(Tmax-t)}$, $AUC(0-(t)hr)$, $AUC_{(Tmax\ of\ IR\ product+2SD)-t)}$, or $AUC_{(0-\infty)}$.

A drug "release rate," as used herein, refers to the quantity of drug released from a dosage form or pharmaceutical composition per unit time, e.g., milligrams of drug released per hour (mg/hr). Drug release rates for drug dosage forms are typically measured as an in vitro rate of dissolution, i.e., a quantity of drug released from the dosage form or pharmaceutical composition per unit time measured under appropriate conditions and in a suitable fluid. The specific results of dissolution tests claimed herein are performed on dosage forms or pharmaceutical compositions immersed in 900 mL of 0.1 N HCl using a USP Type II apparatus at a paddle speed of either about 100 rpm or about 150 rpm and a constant temperature of about 37° C. Suitable aliquots of the release rate solutions are tested to determine the amount of drug released from the dosage form or pharmaceutical composition. For example, the drug can be assayed or injected into a chromatographic system to quantify the amounts of drug released during the testing intervals.

The terms "subject" or "patient" are used interchangeably herein and refer to a vertebrate, preferably a mammal. Mammals include, but are not limited to, humans.

The term "tap density" or "tapped density," as used herein, refers to a measure of the density of a powder. The tapped density of a pharmaceutical powder is determined using a tapped density tester, which is set to tap the powder at a fixed impact force and frequency. Tapped density by the USP method is determined by a linear progression of the number of taps.

II. PHARMACEUTICAL COMPOSITIONS COMPRISING EXTENDED AND IMMEDIATE RELEASE PORTIONS COMPRISING OXYCODONE AND ACETAMINOPHEN

The present disclosure provides pharmaceutical compositions comprising oxycodone and its pharmaceutical salts and acetaminophen. The pharmaceutical composition comprises at least one extended release portion comprising oxycodone, acetaminophen or a combination thereof, and an extended release component. The pharmaceutical composition may also comprise at least one immediate release portion comprising oxycodone, acetaminophen, or a combination thereof. The compositions disclosed herein are formulated to deliver therapeutic concentrations of oxycodone and acetaminophen within about the first hour after oral administration and to maintain therapeutic concentrations of oxycodone and acetaminophen for an extended period of time (e.g., 10-12 hours).

The total amount of oxycodone present in the pharmaceutical composition can and will vary. In some embodiments, the total amount of oxycodone present in the pharmaceutical composition may range from about 2 mg to about 160 mg, about 5 mg to about 75 mg, about 5 mg to about 40 mg, or about 10 mg to about 30 mg. In another embodiment, the total amount of oxycodone in the pharmaceutical composition may range from about 5 mg to about 30 mg. In various embodiments, the total amount of oxycodone present in the pharmaceutical composition may be about 5 mg, 5.5 mg, 6.0 mg, 6.5 mg, 7.0 mg, 7.5 mg, 8.0 mg, 8.5 mg, 9.0 mg, 9.5 mg, 10 mg, 10.5 mg, 11 mg, 11.5 mg, 12 mg, 12.5 mg, 13 mg, 13.5 mg, 14 mg, 14.5 mg, 15 mg, 15.5 mg, 16 mg, 16.5 mg, 17 mg, 17.5 mg, 18 mg, 18.5 mg, 19 mg, 19.5 mg, 20 mg, 22.5 mg, 25 mg, 27.5 mg, 30 mg, 32.5 mg, 35 mg, 37.5 mg, 40 mg, 45 mg, 50 mg, 60 mg, 70 mg, 80 mg, 100 mg, 110 mg, 120 mg, 130 mg, 140 mg, 150 mg, or 160 mg. In one embodiment, the total amount of oxycodone in the pharmaceutical composition may be about 30 mg. In another embodiment, the total amount of oxycodone in the pharmaceutical composition may be about 15 mg. In still another embodiment, the total amount of oxycodone in the pharmaceutical composition may be about 7.5 mg.

The total amount of acetaminophen present in the pharmaceutical composition also may vary. In one embodiment, the total amount of acetaminophen present in the pharmaceutical composition may range from about 80 mg to about 1600 mg. In another embodiment, the total amount of acetaminophen present in the pharmaceutical composition may be about 250 mg to about 1300 mg. In a further embodiment, the total amount of acetaminophen present in the pharmaceutical composition may be about 300 mg to about 600 mg. In yet another embodiment, the total amount of acetaminophen present in the pharmaceutical composition may be about 325 mg to about 650 mg. In another embodiment, the total amount of acetaminophen present in the pharmaceutical composition may be about 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 600 mg, 650 mg, 700 mg, 750 mg, 1000 mg, or 1300 mg. In one embodiment, the total amount of acetaminophen in the pharmaceutical composition may be about 650 mg. In another embodiment, the total amount of acetaminophen in the pharmaceutical composition may be about 500 mg. In yet another embodiment, the total amount of acetaminophen in the pharmaceutical composition may be about 325 mg.

(a) Immediate Release Portion

The pharmaceutical composition disclosed herein may comprise at least one immediate release portion. In one embodiment, the at least one immediate release portion may comprise oxycodone. In another embodiment, the at least one immediate release portion may comprise acetaminophen. In a further embodiment, the at least one immediate release portion may comprise oxycodone and acetaminophen.

The at least one immediate release portion of the pharmaceutical composition is designed to release more than 80%, more than 90%, or essentially all of the oxycodone and/or acetaminophen in the at least one immediate release portion(s) within about one hour. In one embodiment, more than 80%, more than 90%, or essentially all of the oxycodone and/or acetaminophen in the at least one immediate release portion(s) may be released in less than about 45 min. In another embodiment, more than 80%, more than 90%, or essentially all of the oxycodone and/or acetaminophen in the at least one immediate release portion(s) may be released in less that about 30 min. In a further embodiment, more than 80%, more than 90%, or essentially all of the oxycodone and/or acetaminophen in the at least one immediate release portion(s) may be released in less than about 20 min. In yet another embodiment, more than 80%, more than 90%, or essentially all of the oxycodone and/or acetaminophen in the at least one immediate release portion(s) may be released in less that about 15 min. In an alternate embodiment, more than 80%, more than 90%, or essentially all of the oxycodone and/or acetaminophen in the at least one immediate release portion(s) may be released in less that about 10 min. In yet another embodiment, more than 80%, more than 90%, or essentially all of the oxycodone and/or acetaminophen in the at least one immediate release portion may be released in less that about 5 min.

(i) Oxycodone

The at least one immediate release portion of the pharmaceutical composition may comprise oxycodone. The amount of oxycodone in the at least one immediate release portion of the pharmaceutical composition can and will vary. In one embodiment, the amount of oxycodone in the at least one immediate release portion may range from about 1 mg to about 40 mg. In a further embodiment, the amount of oxycodone in the at least one immediate release portion of the pharmaceutical composition may range from about 1 mg to about 7.5 mg. In another embodiment, the amount of oxycodone in the at least one immediate release portion may range from about 7.5 mg to about 15 mg. In yet another embodiment, the amount of oxycodone in the at least one immediate release portion may range from about 15 mg to about 40 mg. In various embodiments, the amount of oxycodone in the at least one immediate release portion may be about 1.25 mg, 1.3 mg, 1.325 mg, 1.35 mg, 1.375 mg, 1.4 mg, 1.425 mg, 1.45 mg, 1.475 mg, 1.5 mg, 1.525 mg, 1.55 mg, 1.575 mg, 1.6 mg, 1.625 mg, 1.65 mg, 1.675 mg, 1.7 mg, 1.725 mg, 1.75 mg, 1.775 mg, 1.8 mg, 1.825 mg, 1.85 mg, 1.875 mg, 1.9 mg, 1.925 mg, 1.95 mg, 1.975 mg, 2.0 mg, 2.25 mg, 2.5 mg, 2.75 mg, 3.0 mg, 3.25 mg, 3.5 mg, 3.75 mg, 4.0 mg, 4.25 mg, 4.5 mg, 4.75 mg, 5.0 mg, 5.25 mg, 5.5 mg, 5.75 mg, 6.0 mg, 6.25 mg, 6.5 mg, 6.75 mg, 7.0 mg, 7.25 mg, 7.5 mg, 7.75 mg, 8.0 mg, 8.25 mg, 8.5 mg, 8.75 mg, 9.0 mg, 9.25 mg, 9.5 mg, 9.75 mg, 10.0 mg, 11.0 mg, 12.0 mg, 13.0 mg, 14.0 mg, 15.0 mg, 20.0 mg, or 40.0 mg. In one embodiment, the amount of oxycodone in the at least one immediate release portion may range from about 7.0 mg and about 8.0 mg, for example, about 7.5 mg. In another embodiment, the amount of oxycodone in the at least one immediate release portion may be between about 3.0 mg and about 4.0 mg, for example, about 3.75 mg. In still another embodiment, the amount of opioid in the at least one immediate release portion may be between about 1.0 mg and about 2.0 mg, for example, about 1.875 mg.

The amount of oxycodone present in the at least one immediate release portion(s) may be expressed as a percentage (w/w) of the total amount of oxycodone in the pharmaceutical composition. In one embodiment, the at least one immediate release portion may comprise from about 20% to about 30% (w/w) of the total amount of oxycodone present in the pharmaceutical composition. In certain embodiments, the percentage of oxycodone present in the at least one immediate release portion of the pharmaceutical composition may be about 20%, 21%, 22%, 23%, 24%, 25%, 26%, 27%, 28%, 29%, or 30% (w/w) of the total amount of oxycodone. In another embodiment, the percentage of oxycodone present in the at least one immediate release portion of the pharmaceutical composition may be about 25% (w/w) of the total amount of oxycodone present in the pharmaceutical composition.

The amount of oxycodone in the at least one immediate release portion also may be expressed as a percentage (w/w) of the total weight of the immediate release portion(s) of the pharmaceutical composition. In one embodiment, the amount of oxycodone in an immediate release portion may range from about 0.2 (w/w) to about 15.0% (w/w) of the total weight of such immediate release portion of the pharmaceutical composition. In another embodiment, the amount of oxycodone in an immediate release portion may range from about 0.5% (w/w) to about 2% (w/w) of the total weight of such immediate release portion. In various embodiments, an immediate release portion may comprise an amount of oxycodone that is approximately 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.25%, 3.5%, 3.75%, 4.0%, 4.25%, 4.5%, 4.75%, 5.0%, 5.25%, 5.5%, 5.75%, 6.0%, 6.25%, 6.5%, 6.75%, 7.0%, 7.25%, 7.5%, 7.75%, 8.0%, 8.25%, 8.5%, 8.75%, 9.0%, 9.25%, 9.5%, 9.75%, 10%, 11%, 12%, 13%, 14%, 15%, 16%, 17%, 18%, 19%, or 20% (w/w) of the total weight of such immediate release portion of the pharmaceutical composition. In yet another embodiment, the amount of oxycodone in an immediate release portion may be about 0.5% (w/w) to about 1.0% (w/w) of the total weight of such immediate release portion of the pharmaceutical composition.

In some embodiments, the oxycodone of the at least one immediate release portion(s) of the pharmaceutical composition may be in the form of particles comprising oxycodone and at least one excipient. The at least one immediate release portion, therefore, may comprise particles of oxycodone that are admixed with the acetaminophen and optional excipient(s). Suitable oxycodone particles are described in co-pending application U.S. application Ser. No. 13/166,770, filed Jun. 22, 2011, which is incorporated herein by reference in its entirety. The oxycodone particles may be coated or uncoated. The average size or average diameter of the particles may vary. In general, the average diameter of the particles may range from about 50 microns to about 2000 microns, from about 100 microns to about 1000 microns, or from about 150 microns to about 200 microns. In one embodiment, the maximum diameter of about 50% of the particles (d50) may be about 40 microns, 50 microns, 100 microns, 150 microns, 200 microns, 250 microns, 300 microns, 400 microns, or 500 microns. In another embodiment, the maximum diameter of about 90% of the particles (d90) may be about 100 microns, 150 microns, 200 microns, 250 microns, 300 microns, 400 microns, or 500 microns.

(ii) Acetaminophen

The at least one immediate release portion of the pharmaceutical composition may comprise acetaminophen. The amount of acetaminophen in the at least one immediate release portion(s) can and will vary. In one embodiment, the amount of acetaminophen in the at least one immediate release portion of the pharmaceutical composition may range from about 40 mg to about 800 mg. In still another embodiment, the at least one immediate release portion of the pharmaceutical composition may comprise from about 100 mg to about 600 mg of acetaminophen. In another embodiment, the at least one immediate release portion may comprise from about 125 mg to about 400 mg of acetaminophen. In a further embodiment, the amount of acetaminophen in the at least one immediate release portion may range from about 160 mg to about 325 mg. In yet another embodiment, the amount of acetaminophen in the at least one immediate release portion may be about 120 mg, 125 mg, 130 mg, 135 mg, 140 mg, 145 mg, 150 mg, 155 mg, 160 mg, 162.5 mg, 165 mg, 170 mg, 175 mg, 180 mg, 185 mg, 190 mg, 195 mg, 200 mg, 210 mg, 220 mg, 230 mg, 240 mg, 250 mg, 260 mg, 270 mg, 280 mg, 290 mg, 300 mg, 310 mg, 320 mg, 325 mg, 330 mg, 340 mg, 350 mg, 360 mg, 370 mg, 380 mg, 390 mg, 400 mg, 500 mg, 520 mg, 650 mg, or 780 mg. In one embodiment, the at least one immediate release portion may comprise about 325 mg of acetaminophen. In another embodiment, the amount of acetaminophen in the at least one immediate release portion may be about 250 mg. In yet another embodiment, the amount of acetaminophen in the at least one immediate release portion may be about 162.5 mg. In still another embodiment, the amount of acetaminophen in the at least one immediate release portion may be about 125 mg.

The at least one immediate release portion(s) of the pharmaceutical composition may comprise from about 40% to about 60% (w/w) of the total amount of acetaminophen present in the pharmaceutical composition. The amount of acetaminophen in the at least one immediate release portion may be about 40%, 41%, 42%, 43%, 44%, 45%, 46%, 47%, 48%, 49%, 50%, 51%, 52%, 53%, 54%, 55%, 56%, 57%, 58%, 59%, or 60% (w/w) of the total amount of acetaminophen present in the pharmaceutical composition. In one embodiment, the percentage of acetaminophen present in the at least one immediate release portion may be about 50% (w/w) of the total amount of acetaminophen present in the pharmaceutical composition.

The amount of acetaminophen in an immediate release portion(s) of the pharmaceutical composition may range from about 20% (w/w) to about 95% (w/w) of the total weight of such immediate release portion of the composition. In various embodiments, an immediate release portion may comprise an amount of acetaminophen that is approximately about 20%, 25%, 30%, 35%, 40%, 45%, 50%, 55%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, or 95% (w/w) of the total weight of such immediate release portion. In one embodiment, the amount of acetaminophen in an immediate release portion may range from about 70% to about 80% (w/w) of the total weight of such immediate release portion of the pharmaceutical composition.

(iii) Excipients

The at least one immediate release portion(s) of the pharmaceutical composition may further comprise at least one excipient. Suitable excipients include binders, fillers, disintegrants, lubricants, antioxidants, chelating agents, and color agents.

In one embodiment, the at least one immediate release portion(s) of the pharmaceutical composition may comprise at least one binder. Suitable binders include, without limit, starches (including corn starch and pregelatinized starch), gelatin, sugars (including sucrose, glucose, dextrose and lactose), polyethylene glycol, polyols, polyvinylalcohols, C12-C18 fatty acid alcohols, waxes, gums (e.g., guar gum, arabic gum, acacia gum, xantham gum, etc.), gelatin, pectin, sodium alginate, polyvinylpyrrolidone, cellulosic polymers (including hydroxypropyl cellulose, hydroxypropyl methylcellulose, hydroxylcellulose, methylcellulose, microcrystalline cellulose, ethylcellulose, hydroxyethyl cellulose, and the like), polyacrylamides, and polyvinyloxoazolidone. In one embodiment, the amount of binder or binders in an immediate release portion of the pharmaceutical composition may range from about 5% to about 10% (w/w) of the total weight of such immediate release portion. In various embodiments, an immediate release portion of the pharmaceutical composition may comprise at least one binder that is present in an amount that is about 5.0%, 5.25%, 5.5%, 5.75%, 6.0%, 6.25%, 6.5%, 6.75%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, or 9.0% (w/w) of such immediate release portion of the composition.

In another embodiment, the at least one immediate release portion(s) of the pharmaceutical composition may comprise at least one filler. Suitable fillers include but are not limited to microcrystalline cellulose (MCC), dibasic calcium phosphate, tribasic calcium phosphate, magnesium carbonate, magnesium oxide, calcium silicate, magnesium aluminum silicate, silicon dioxide, titanium dioxide, alumina, talc, kaolin, polyvinylpyrrolidone, dibasic calcium sulfate, tribasic calcium sulfate, starch, calcium carbonate, magnesium carbonate, carbohydrates, modified starches, lactose, sucrose, dextrose, mannitol, sorbitol, and inorganic compounds. In one embodiment, the amount of filler or fillers in an immediate release portion may range from about 1.0% to about 10.0% (w/w) of the total weight of such immediate release portion. In various embodiments, an immediate release portion of the pharmaceutical composition may comprise at least one filler that is present in an amount that is about 1.0%, 1.5%, 2.0%, 2.5%, 3.0%, 3.5%, 4.0%, 4.5%, 5.0%, 5.5%, 6.0%, 6.2%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, or 10.0%, of such immediate release portion of the pharmaceutical composition.

In still another embodiment, the at least one immediate release portion(s) of the pharmaceutical composition may further comprise a disintegrant. The disintegrant may be selected from the group consisting of croscarmellose sodium, crospovidone, alginic acid, carboxymethylcellulose calcium, carboxymethylcellulose sodium, low substituted hydroxypropylcellulose, microcrystalline cellulose, and sodium starch glycolate. In one embodiment, the amount of disintegrant in an immediate release portion may range from about 2.0% to about 15.0% (w/w) of the total weight of such immediate release portion. In some embodiments, the amount of disintegrant in an immediate release portion may be about 4.0%, 4.2%, 4.4%, 4.6%, 4.8%, 5.0%, 5.2%, 5.4%, 5.6%, 5.8%, 6.0%, 6.2%, 6.4%, 6.6%, 6.8%, or 7.0% (w/w) of such immediate release portion of the pharmaceutical composition.

In a further embodiment, the at least one immediate release portion(s) of the pharmaceutical composition may further comprise a lubricant. Useful lubricants include magnesium stearate, calcium stearate, stearic acid, and hydrogenated vegetable oil (preferably comprised of hydrogenated and refined triglycerides of stearic and palmitic acids). The lubricant may be present in an amount ranging from about 0.1% to about 3.0% (w/w) of the total weight of an immediate release portion. In certain embodiments, the amount of lubricant in at least one immediate release portion may be about 0.25%, 0.5%, 0.75%, 1.0%, 1.5%, 1.55%, 1.6%, 1.65%, 1.7%, 1.75%, 1.80%, 1.85%, 1.90%, or 2.0% (w/w) of the total weight of such immediate release portion.

In yet another embodiment, the at least one immediate release portion(s) of the pharmaceutical composition may comprise at least one antioxidant. Suitable antioxidants include, without limitation, ascorbic acid, citric acid, ascorbyl palmitate, butylated hydroxyanisole, a mixture of 2 and 3 tertiary-butyl-4-hydroxyanisole, butylated hydroxytoluene, sodium isoascorbate, dihydroguaretic acid, potassium sorbate, sodium bisulfate, sodium metabisulfate, sorbic acid, potassium ascorbate, vitamin E, 4-chloro-2,6-ditertiarybutylphenol, alphatocopherol, and propylgallate. The amount of antioxidant present in an immediate release portion of the pharmaceutical composition may range from about 0.01% to about 4.0% (w/w), or from about 0.02% to about 0.10% (w/w) of the total weight of such immediate release portion.

In various embodiments, the amount of antioxidant present in an immediate release portion of the pharmaceutical composition may be about 0.01%, 0.02%, 0.03%, 0.04%, 0.05%, 0.06%, 0.07%, 0.08%, 0.09%, 0.10%, 0.12%, 0.14%, 0.16%, 0.18%, 0.20%, 0.25%, 0.50%, 0.75%, 1.00%, 1.50%, or 2.00% (w/w) of the total weight of such immediate release portion.

In still another embodiment, the at least one immediate release portion(s) of the pharmaceutical composition may comprise at least one chelating agent. Suitable chelating agents include ethylenediamine tetracetic acid (EDTA) and its salts, N-(hydroxy-ethyl)ethylenediaminetriacetic acid, nitrilotriacetic acid (NIA), ethylene-bis(oxyethylene-nitrilo) tetraacetic acid, 1,4,7,10-tetraazacyclodo-decane-N,N',N'', N'''-tetraacetic acid, 1,4,7,10-tetraaza-cyclododecane-N,N', N''-triacetic acid, 1,4,7-tris(carboxymethyl)-10-(2'-hydroxypropyl)-1,4,7,10-tetraazocyclodecane, 1,4,7-triazacyclonane-N,N',N''-triacetic acid, 1,4,8,11-tetraazacyclotetra-decane-N,N',N'',N'''-tetraacetic acid; diethylenetriamine-pentaacetic acid (DTPA), ethylenedicysteine, bis(aminoethanethiol)carboxylic acid, triethylenetetraamine-hexaacetic acid, and 1,2-diaminocyclohexane-N,N, N',N'-tetraacetic acid. In one embodiment, the chelating agent may be the sodium salt of EDTA. The amount of chelating agent present in an immediate release portion of the pharmaceutical composition may range from about 0.001% to about 0.20% (w/w) of such immediate release portion. In some embodiments, the amount of chelating agent present in an immediate release portion of the pharmaceutical composition may be about 0.001%, 0.002%, 0.003%, 0.004%, 0.005%, 0.01%, 0.02%, 0.03%, 0.04%, 0.05%, 0.06%, 0.07%, 0.08%, 0.09%, 0.10%, 0.11%, 0.12%, 0.13%, 0.14%, or 0.15% (w/w) of the total weight of such immediate release portion.

In an alternate embodiment, the at least one immediate release portion of the pharmaceutical composition may comprise a color agent. Suitable color additives include, but are not limited to, food, drug and cosmetic colors (FD&C), drug and cosmetic colors (D&C), and external drug and cosmetic colors (Ext. D&C). In various embodiments, the amount of color agent present in an immediate release portion may range from about 2.0% to about 5.0% (w/w) of the total weight of such immediate release portion of the composition. In other embodiments, the amount of color agent present in an immediate release portion may be about 1.0%, 1.5%, 2.0%, 2.5%, 3.0%, 3.5%, 4.0%, 4.5%, or 5.0% (w/w) of the total weight of such immediate release portion.

(b) Extended Release Portion

The pharmaceutical composition disclosed herein comprises at least one extended release portion. The at least one extended release portion may comprise oxycodone, acetaminophen, or a combination thereof. The extended release portion(s) further comprise(s) an extended release component. The extended release component may comprise at least one extended release polymer.

The at least one extended release portion of the pharmaceutical composition is designed to release the active agents over an extended period of time. In general, the extended release portion(s) provides release of oxycodone and/or acetaminophen for a period of time ranging from at least about 3 hours (hrs) to at least about 12 hrs. In one embodiment, the extended release portion(s) may release oxycodone and/or acetaminophen over a period of at least about 5 hrs, or over a period at least about 6 hrs. In another embodiment, oxycodone and/or acetaminophen may be released from the extended release portion(s) over a period of at least about 7 hrs, or over a period of at least about 8 hrs. In still another embodiment, the extended release portion(s) may release oxycodone and/or acetaminophen over a period of at least about 9 hrs, or over a period of at least about 10 hrs. In a further embodiment, oxycodone and/or acetaminophen may be released from the extended release portion(s) over a period of at least about 11 hrs, or over a period of at least about 12 hrs.

(i) Oxycodone

The amount of oxycodone present in the at least one extended release portion(s) can and will vary. In one embodiment, the amount of oxycodone in the at least one extended release portion may range from about 1 mg to about 120 mg. In a further embodiment, the at least one extended release portion of the pharmaceutical composition may comprise about 1 mg to about 22.5 mg of oxycodone. In another embodiment, the amount of oxycodone in the at least one extended release portion may be about 10 mg to about 30 mg. In yet another embodiment, the amount of oxycodone in the at least one extended release portion may be about 30 mg to about 60 mg. In another embodiment, the at least one extended release portion comprises about 5 mg to about 7 mg of oxycodone. In a further embodiment, the amount of oxycodone may be about 5.625 mg to about 11.25 mg. In an additional embodiment, the amount of oxycodone may be about 10 mg to about 12.5 mg. In a further embodiment, the amount of oxycodone may be about 12 mg to about 18 mg. In another embodiment, the amount of oxycodone in the at least one extended release portion may be about 20 mg to about 25 mg. In yet another embodiment, the amount of oxycodone may be about 1.0 mg, 1.5 mg, 2.0 mg, 2.5 mg, 3.0 mg, 3.5 mg, 4.0 mg, 4.5 mg, 5.0 mg, 5.5 mg, 5.625 mg, 6.0 mg, 6.5 mg, 7.0 mg, 7.5 mg, 8.0 mg, 8.5 mg, 9.0 mg, 9.5 mg, 10.0 mg, 10.5 mg, 11.0 mg, 11.25 mg, 11.5 mg, 12.0 mg, 12.5 mg, 13.0 mg, 13.5 mg, 14.0 mg, 14.5 mg, 15.0 mg, 15.5 mg, 16.0 mg, 16.5 mg, 17.0 mg, 17.5 mg, 18.0 mg, 18.5 mg, 19.0 mg, 19.5 mg, 20.0 mg, 22.5 mg, or 25 mg. In one embodiment, the amount of oxycodone in the at least one extended release portion may be from about 22 mg to about 23 mg, for example, about 22.5 mg. In another embodiment, the amount of oxycodone in the at least one extended release portion may be about 10 mg to about 12 mg, for example, about 11.25 mg. In still another embodiment, the amount of opioid in the at least one extended release portion may be from about 5 mg to about 6 mg, for example, about 5.625 mg.

The amount of oxycodone present in the at least one extended release portion(s) may be expressed as a percentage of the total amount of oxycodone in the pharmaceutical composition. In one embodiment, the at least one extended release portion of the pharmaceutical composition comprises from about 70% to about 80% (w/w) of the total amount of oxycodone present in the pharmaceutical composition. In certain embodiments, the percentage of oxycodone present in the at least one extended release portion of the pharmaceutical composition may be about 70%, 71%, 72%, 73%, 74%, 75%, 76%, 77%, 78%, 79%, or 80% of the total amount of oxycodone. In one embodiment, the percentage of oxycodone present in the at least one extended release portion of the pharmaceutical composition may be about 75% of the total amount of oxycodone present in the pharmaceutical composition.

The amount of oxycodone in the extended release portion(s) also may be expressed as a percentage of the total weight of the extended release portion(s) of the pharmaceutical composition. In one embodiment, the amount of oxycodone in an extended release portion may range from about 0.5% to about 5.0% (w/w) of the total weight of the such extended release portion of the pharmaceutical composition. In various embodiments, an extended release portion may comprise an amount of oxycodone that is approximately 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, or 4.0% (w/w) of the total weight of such extended release portion of the pharmaceutical composition. In one embodiment, the amount of oxycodone in an extended release portion comprises about 0.5% to about 2% (w/w) of the total weight of such extended release portion of the pharmaceutical composition.

In some embodiments, the oxycodone of the extended release portion(s) may be in the form of particles comprising oxycodone and at least one excipient. Thus, the at least one extended release portion may comprise particles of oxycodone which are admixed with the acetaminophen and the extended release component, both of which are detailed below, as well as optional excipients. Suitable oxycodone particles are described in co-pending application U.S. application Ser. No. 13/166,770, filed Jun. 22, 2011, which is incorporated herein by reference in its entirety. The oxycodone particles may be coated or uncoated. The average size or average diameter of the particles may vary. In general, the average diameter of the particles may range from about 50 microns to about 2000 microns, from about 100 microns to about 1000 microns, or from about 150 microns to about 200 microns. In one embodiment, the maximum diameter of about 50% of the particles (d50) may be about 40 microns, 50 microns, 100 microns, 150 microns, 200 microns, 250 microns, 300 microns, 400 microns, or 500 microns. In another embodiment, the maximum diameter of about 90% of the particles (d90) may be about 100 microns, 150 microns, 200 microns, 250 microns, 300 microns, 400 microns, or 500 microns.

(ii) Acetaminophen

The extended release portion(s) of the pharmaceutical composition may comprise acetaminophen. The amount of acetaminophen in the extended release portion(s) of the pharmaceutical composition can and will vary. In one embodiment, the at least one extended release portion of the pharmaceutical composition may comprise an amount of acetaminophen ranging from about 40 mg to about 800 mg. In still another embodiment, the at least one extended release portion of the pharmaceutical composition may comprise from about 100 mg to about 600 mg of acetaminophen. In another embodiment, the at least one extended release portion may comprise from about 125 mg to about 400 mg of acetaminophen. In a further embodiment, the amount of acetaminophen in the at least one extended release portion may range from about 160 mg to about 325 mg. In yet another embodiment, the amount of acetaminophen in the at least one extended release portion may be about 100 mg, 110 mg, 120 mg, 125 mg, 130 mg, 135 mg, 140 mg, 145 mg, 150 mg, 155 mg, 160 mg, 162.5 mg, 165 mg, 170 mg, 175 mg, 180 mg, 185 mg, 190 mg, 195 mg, 200 mg, 210 mg, 220 mg, 230 mg, 240 mg, 250 mg, 260 mg, 270 mg, 280 mg, 290 mg, 300 mg, 310 mg, 320 mg, 325 mg, 330 mg, 340 mg, 350 mg, 360 mg, 370 mg, 380 mg, 390 mg, 400 mg, 500 mg, 520 mg, 650 mg, or 780 mg. In one embodiment, the at least one extended release portion comprises about 325 mg of acetaminophen. In another embodiment, the amount of acetaminophen in the at least one extended release portion may be about 250 mg. In yet another embodiment, the amount of acetaminophen in the at least one extended release portion may be about 162.5 mg. In still another embodiment, the amount of acetaminophen in the at least one extended release portion may be about 125 mg.

The extended release portion(s) of the pharmaceutical composition may comprise from about 40% to about 60% of the total amount of acetaminophen present in the pharmaceutical composition. The amount of acetaminophen in the at least one extended release portion may be about 40%, 41%, 42%, 43%, 44%, 45%, 46%, 47%, 48%, 49%, 50%, 51%, 52%, 53%, 54%, 55%, 56%, 57%, 58%, 59%, or 60% (w/w) of the total amount of acetaminophen present in the pharmaceutical composition. In one embodiment, the percentage of acetaminophen present in the extended release portion(s) of the pharmaceutical composition may be about 50% (w/w) of the total amount of acetaminophen.

The amount of acetaminophen in an extended release portion of the pharmaceutical composition may range from about 15% to about 60% (w/w) of the total weight of such extended release portion of the pharmaceutical composition. In various embodiments, an extended release portion may comprise an amount of acetaminophen that is approximately about 15%, 16%, 17%, 18%, 19%, 20%, 21%, 22%, 23%, 24%, 25%, 26%, 27%, 28%, 30%, 32%, 35%, 37%, 40%, 42%, 45%, 47%, 50%, 52%, or 55% (w/w) of the total weight of such extended release portion. In one embodiment, the amount of acetaminophen in an extended release portion may range from about 20% to about 40% (w/w) of the total weight of such extended release portion of the pharmaceutical composition.

(iii) Extended Release Component

The extended release portion(s) of the pharmaceutical composition also comprise(s) an extended release component. Suitable extended release components include polymers, resins, hydrocolloids, hydrogels, and the like.

In one embodiment, the extended release component may comprise at least one extended release polymer. Suitable polymers for inclusion in the at least one extended release portion of the pharmaceutical composition may be linear, branched, dendrimeric, or star polymers, and include synthetic hydrophilic polymers as well as semi-synthetic and naturally occurring hydrophilic polymers. The polymers may be homopolymers or copolymers, such as random copolymers, block copolymers, and graft copolymers. Suitable hydrophilic polymers include, but are not limited to: polyalkylene oxides, particularly poly(ethylene oxide), polyethylene glycol and poly(ethylene oxide)-poly(propylene oxide) copolymers; cellulosic polymers, such as methylcellulose, hydroxymethylcellulose, hydroxyethylcellulose, hydroxypropylcellulose, hydroxypropylmethylcellulose, and carboxymethylcellulose, microcrystalline cellulose, and polysaccharides and their derivatives; acrylic acid and methacrylic acid polymers, copolymers and esters thereof, preferably formed from acrylic acid, methacrylic acid, methyl acrylate, ethyl acrylate, methyl methacrylate, ethyl methacrylate, and copolymers thereof, with each other or with additional acrylate species such as aminoethyl acrylate; maleic anhydride copolymers; polymaleic acid; poly(acrylamides) such as polyacrylamide per se, poly(methacrylamide), poly(dimethylacrylamide), and poly(N-isopropyl-acrylamide); polyalkylene oxides; poly(olefinic alcohol)s such as poly (vinyl alcohol); poly(N-vinyl lactams) such as poly(vinyl pyrrolidone), poly(N-vinyl caprolactam), and copolymers thereof; polyols such as glycerol, polyglycerol (particularly highly branched polyglycerol), propylene glycol and trimethylene glycol substituted with one or more polyalkylene oxides, e.g., mono-, di- and tri-polyoxyethylated glycerol, mono- and di-polyoxyethylated propylene glycol, and mono- and di-polyoxyethylated trimethylene glycol; polyoxyethylated sorbitol and polyoxyethylated glucose; polyoxazolines, including poly(methyloxazoline) and poly(ethyloxazoline); polyvinylamines; polyvinylacetates, including polyvinylacetate per se as well as ethylene-vinyl acetate copolymers, polyvinyl acetate phthalate, and the like, polyimines, such as polyethyleneimine; starch and starch-based polymers; polyurethane hydrogels; chitosan; polysaccharide gums; xanthan gum; zein; and shellac, ammoniated shellac, shellac-acetyl alcohol, and shellac n-butyl stearate. The polymers may be used individually or in combination. Certain combinations will often provide a more controlled release of oxycodone and acetaminophen than their components when used individually. Suitable combinations include cellulose-based polymers combined with gums, such as hydroxyethyl cellulose or hydroxypropyl cellulose combined with xanthan gum, and poly(ethylene oxide) combined with xanthan gum.

In one embodiment, the extended release polymer(s) may be a cellulosic polymer, such as an alkyl substituted cellulose derivative as detailed above. In terms of their viscosities, one class of exemplary alkyl substituted celluloses includes those whose viscosity is within the range of about 100 to about 110,000 centipoise as a 2% aqueous solution at 20° C. Another class includes those whose viscosity is within the range of about 1,000 to about 4,000 centipoise as a 1% aqueous solution at 20° C.

In one embodiment, the extended release polymer(s) may be a polyalkylene oxide. In another aspect, the polyalkylene oxide may be poly(ethylene) oxide. In a further embodiment, the poly(ethylene) oxide may have an approximate molecular weight between 500,000 Daltons (Da) to about 10,000,000 Da or about 900,000 Da to about 7,000,000 Da. In yet a further embodiment, the poly(ethylene) oxide may have a molecular weight of approximately 600,000 Da, 700,000 Da, 800,000 Da, 900,000 Da, 1,000,000 Da, 2,000,000 Da, 3,000,000 Da, 4,000,000 Da, 5,000,000 Da, 6,000,000 Da, 7,000,000 Da, 8,000,000 Da 9,000,000 Da, or 10,000,000 Da.

In another embodiment, the polyethylene oxide may be any desirable grade of POLYOX™ or any combination thereof. By way of example and without limitation, the POLYOX™ grade may be WSR N-10, WSR N-80, WSR N-750, WSR 205, WSR 1105, WSR N-12K, WSR N-60K, WSR-301, WSR Coagulant, WSR-303, WSR-308, WSR N-3000, UCARFLOC Polymer 300, UCARFLOC Polymer 302, UCARFLOC Polymer 304, and UCARFLOC Polymer 309. In one embodiment, the polyethylene oxide may have an average molecular weight of from about 100,000 Da to about 8,000,000 Da. In another embodiment, the polyethylene oxide may have an average molecular weight of about 100,000 Da, about 200,000 Da, about 300,000 Da, about 400,000 Da, about 600,000 Da, about 900,000 Da, about 1,000,000 Da, about 2,000,000 Da, about 4,000,000 Da, about 5,000,000 Da, about 7,000,000 Da, or about 8,000,000 Da. In still another embodiment, the polyethylene oxide may have an average number of repeating ethylene oxide units ($-CH_2CH_2O-$) of about 2,000 to about 160,000. In yet another embodiment, the polyethylene oxide may have an average number of repeating ethylene oxide units of about 2,275, about 4,500, about 6,800, about 9,100, about 14,000, about 20,000, about 23,000, about 45,000, about 90,000, about 114,000, or about 159,000.

The release profile of the extended release pharmaceutical composition disclosed herein will depend partially upon the molecular weight of the extended release polymer(s). In certain embodiments, the polymers are of a moderate to high molecular weight (900,000 Da to 4,000,000 Da) to control release of oxycodone and/or acetaminophen from the composition via diffusion of the active agent(s) out of the polymer and/or erosion of the polymer. An example of suitable polyethylene oxide polymers are those having molecular weights (viscosity average) on the order of about 900,000 Da to about 2,000,000 Da. Using a lower molecular weight ("MW") polyethylene oxide, such as POLYOX® 1105 (900,000 MW), the release rates for both drugs are higher. Using a higher molecular weight polyethylene oxide (such as POLYOX® N-60K (2,000,000 MW) or POLYOX® WSR-301 (4,000,000 MW) reduces the rate of release for both drugs. In another embodiment of the invention, a hydroxypropylmethylcellulose polymer of such molecular weight is utilized so that the viscosity of a 2% aqueous solution is about 4000 cps to greater than about 100,000 cps.

The release profile of the extended release pharmaceutical composition disclosed herein may also depend upon the amount of the extended release polymer(s) in the pharmaceutical composition. In general, the release rates for oxycodone and/or acetaminophen may be decreased by increasing the amount of the extended release polymer(s) in the pharmaceutical composition. By way of example and without limitation, the release profile of acetaminophen and oxycodone may be decreased by increasing the amount of POLYOX® 1105 from about 25% by weight of the ER portion to about 35% by weight of the ER portion.

The amount of extended release polymer or polymers present in the extended release portion(s) of the pharmaceutical composition can and will vary. In one embodiment, the polymer present in an extended release portion of the pharmaceutical composition may range from about 15% to about 70% (w/w), or about 20% to about 60% (w/w), or about 25% to about 55% (w/w) of the total weight of such extended release portion of the dosage form. In another embodiment, the amount of polymer present in an extended release portion of the pharmaceutical composition may range from about 30% to about 50% (w/w) of the total weight of such extended release portion. In still another embodiment, the amount of polymer present in an extended release portion of the pharmaceutical composition may range from about 35% to about 45% (w/w) of the total weight of such extended release portion. In yet another embodiment, the amount of polymer present in an extended release portion of the pharmaceutical composition may be about 30%, 35%, 40%, 45%, 50%, 55%, or 60% (w/w) of the total weight of such extended release portion. In one embodiment, the amount of polymer present in an extended release portion of the pharmaceutical composition may be about 35% (w/w) of the total weight of such extended release portion. In another embodiment, the amount of polymer present in an extended release portion of the pharmaceutical composition may be about 45% (w/w) of the total weight of such extended release portion. In one embodiment, the ER layer swells upon imbibition of fluid to a size which is about 15%, 20%, 25%, 30%, 35% 40%, 45%, 50%, 55%, 60%, 65%, 70%, 75%, 80%, 85%, 90%, 95% or 100% larger than the size of the ER layer prior to imbibition of fluid. In another embodiment, the ER layer swells upon imbibition of fluid to a size at least about 25% larger than the size of the ER layer prior to imbibition of fluid within about 15 minutes of the start of fluid imbibition. In still another embodiment, the ER layer swells upon imbibition of fluid to a size at least about 100% larger than the size of the ER layer prior to imbibition of fluid within about 45 min, 50 min, 60 min, 75 min, or 90 min of the start of fluid imbibitions.

(iv) Excipients

The extended release portion(s) of the pharmaceutical composition may further comprise at least one excipient. Suitable excipients include binders, fillers, lubricants, antioxidants, chelating agents, and color agents.

In one embodiment, the extended release portion(s) of the pharmaceutical composition may comprise at least one binder. Suitable binders include, without limit, starches (including corn starch and pregelatinized starch), gelatin, sugars (including sucrose, glucose, dextrose and lactose), polyethylene glycol, polyols, polyvinylalcohols, C12-C18 fatty acid alcohols, waxes, gums (e.g., guar gum, arabic gum, acacia gum, xanthan gum, etc.), gelatin, pectin, sodium alginate, polyvinylpyrrolidone, cellulosic polymers (including hydroxypropyl cellulose, hydroxypropyl methylcellulose, hydroxylcellulose, methylcellulose, microcrystalline cellulose, ethylcellulose, hydroxyethyl cellulose, and the like), polyacrylamides, and polyvinyloxoazolidone. In one embodiment, the amount of binder or binders in an extended release portion of the pharmaceutical composition may range from about 0.5% to about 8.0% (w/w) of such extended release portion. In various embodiments, an extended release portion of the pharmaceutical composition may comprise at least one binder that is present in an amount that is about 0.5%, 1.0%, 1.1%, 1.2%, 1.3%, 1.4%, 1.5%, 2.0%, 2.5%, 3.0%, 3.5%, 4.0%, 4.5%, 5.0%, 5.5%, 6.0%, 6.5%, 7.0%, 7.5%, or 8.0% (w/w) of such extended release portion of the dosage form.

In another embodiment, the extended release portion(s) of the pharmaceutical composition may comprise at least one filler. Suitable fillers include but are not limited to microcrystalline cellulose (MCC), dibasic calcium phosphate, tribasic calcium phosphate, magnesium carbonate, magnesium oxide, calcium silicate, magnesium aluminum silicate, silicon dioxide, titanium dioxide, alumina, talc, kaolin, polyvinylpyrrolidone, dibasic calcium sulfate, tribasic calcium sulfate, starch, calcium carbonate, magnesium carbonate, carbohydrates, modified starches, lactose, sucrose, dextrose, mannitol, sorbitol, and inorganic compounds. In one embodiment, the amount of filler or fillers in an extended release portion may range from about 2% to about 50% (w/w) of the total weight of such extended release portion. In various embodiments, an extended release portion of the pharmaceutical composition may comprise at least one filler that is present in an amount that is about 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, or 45% (w/w) of such extended release portion of the dosage form.

In a further embodiment, the extended release portion(s) of the pharmaceutical composition may further comprise a lubricant. Useful lubricants include magnesium stearate, calcium stearate, stearic acid, and hydrogenated vegetable oil (preferably comprised of hydrogenated and refined triglycerides of stearic and palmitic acids). The lubricant may be present in an amount ranging from about 0.1% to about 3.0% (w/w) of the total weight of such extended release portion. In certain embodiments, the amount of lubricant in an extended release portion may be about 0.25%, 0.5%, 0.75%, 1.0%, 1.5%, 1.75%, 1.80%, 1.85%, 1.90%, or 2.0% (w/w) of the total weight of such extended release portion.

In yet another embodiment, the extended release portion(s) of the pharmaceutical composition may comprise at least one antioxidant. Suitable antioxidants include, without limit, ascorbic acid, citric acid, ascorbyl palmitate, butylated hydroxyanisole, a mixture of 2 and 3 tertiarybutyl-4-hydroxyanisole, butylated hydroxytoluene, sodium isoascorbate, dihydroguaretic acid, potassium sorbate, sodium bisulfate, sodium metabisulfate, sorbic acid, potassium ascorbate, vitamin E, 4-chloro-2,6-ditertiarybutylphenol, alphatocopherol, and propylgallate. The amount of antioxidant present in an extended release portion of the pharmaceutical composition may range from about 0.01% to about 4.0%, or from about 0.02% to about 0.10% (w/w). In various embodiments, the amount of antioxidant present in an extended release portion of the pharmaceutical composition may be about 0.01%, 0.02%, 0.03%, 0.04%, 0.05%, 0.06%, 0.07%, 0.08%, 0.09%, 0.10%, 0.12%, 0.14%, 0.16%, 0.18%, 0.20%, 0.25%, 0.50%, 0.75%, 1.00%, 1.50%, or 2.00% (w/w) of the total weight of such extended release portion.

In still another embodiment, the extended release portion(s) of the pharmaceutical composition may comprise at least one chelating agent. Suitable chelating agents include ethylenediamine tetracetic acid (EDTA) and its salts, N-(hydroxy-ethyl)ethylenediaminetriacetic acid, nitrilotriacetic acid (NIA), ethylene-bis(oxyethylene-nitrilo)tetraacetic acid, 1,4,7,10-tetraazacyclodo-decane-N,N',N'',N'''-tetraacetic acid, 1,4,7,10-tetraaza-cyclododecane-N,N',N''-triacetic acid, 1,4,7-tris(carboxymethyl)-10-(2'-hydroxypropyl)-1,4,7,10-tetraazocyclodecane, 1,4,7-triazacyclonane-N,N',N''-triacetic acid, 1,4,8,11-tetraazacyclotetra-decane-N,N',N'',N'''-tetraacetic acid; diethylenetriamine-pentaacetic acid (DTPA), ethylenedicysteine, bis(aminoethanethiol)carboxylic acid, triethylenetetraamine-hexaacetic acid, and 1,2-diaminocyclohexane-N,N,N',N'-tetraacetic acid. In one embodiment, the chelating agent is the sodium salt of EDTA. The amount of chelating agent present in an extended release portion of the pharmaceutical composition may range from about 0.001% to about 0.20% (w/w) of such extended release portion. In some embodiments, the amount of chelating agent present in an extended release portion of the pharmaceutical composition may be about 0.001%, 0.002%, 0.003%, 0.004%, 0.005%, 0.01%, 0.02%, 0.03%, 0.04%, 0.05%, 0.06%, 0.07%, 0.08%, 0.09%, 0.10%, 0.11%, 0.12%, 0.13%, 0.14%, or 0.15% (w/w) of the total weight of such extended release portion.

In an alternate embodiment, the extended release portion(s) of the pharmaceutical composition may comprise a color agent. Suitable color additives include, but are not limited to, food, drug and cosmetic colors (FD&C), drug and cosmetic colors (D&C), and external drug and cosmetic colors (Ext. D&C). In various embodiments, the amount of color agent present in an extended release portion may range from about 2.0% to about 5.0% (w/w) of such extended release portion of the dosage form. In other embodiments, the amount of color agent present in an extended release portion may be about 1.0%, 1.5%, 2.0%, 2.5%, 3.0%, 3.5%, 4.0%, 4.5%, or 5.0% (w/w) of such extended release portion.

(c) Dosage Forms of the Pharmaceutical Composition

The physical form of the pharmaceutical composition disclosed herein can and will vary. In general, the pharmaceutical composition is a solid dosage form comprising at least one extended release portion and, optionally, at least one immediate release portion. Suitable solid dosage forms include tablets, caplets, capsules, encapsulated beads, and gelcaps. Non-limiting types of tablets include coated tablets, uncoated tablets, bilayer tablets, multiparticle tablets, monolithic tablets, matrix tablets, compressed tablets, and molded tablets. Non-limiting types of capsules include hard capsules and multi-layer capsules.

In one embodiment, the dosage form may be a capsule. Non-limiting examples of suitable hard capsules include hard starch capsules, hard gelatin capsules, hard cellulose capsules, and hydrogel capsules. In one example, the core of the capsule may comprise the at least one extended release portion and the shell of the capsule may comprise the at least one immediate release portion of the composition. In another example, the core of the capsule may comprises one extended release portion, comprising oxycodone, acetaminophen and an extended release component, and the shell of the capsule may comprise one immediate release portion of the composition comprising oxycodone and acetaminophen. In yet another example, the core of the capsule may comprise two extended release portions, each comprising an extended release component and one of oxycodone or acetaminophen, and the shell of the capsule may comprise two immediate release portions of the composition, each comprising one of the oxycodone and the acetaminophen. In still another embodiment, the dosage form may be a sustained release capsule comprising the oxycodone or the acetaminophen and exhibiting immediate release and/or extended release properties.

In another embodiment, the dosage form may be a tablet comprising at least one extended release portion and at least one immediate release portion. The at least one immediate release portion may be adjacent to, abutting, or surrounding the at least one extended release portion. In one embodiment, the dosage form may be a bilayer tablet comprising one extended release layer comprising the oxycodone and the acetaminophen and one immediate release layer comprising the oxycodone and the acetaminophen. The bilayer tablet may comprise a coating. In another embodiment, the dosage form may be a multilayer tablet comprising two extended release portions, each comprising one of the oxycodone and the acetaminophen, and one immediate release portion comprising both the oxycodone and the acetaminophen. In yet another embodiment, the dosage form may be a multilayer tablet comprising two extended release portions, each comprising one of the oxycodone and the acetaminophen, and two immediate release portions, each comprising one of the oxycodone and the acetaminophen. In still another embodiment, the dosage form may be a sustained release tablet comprising the oxycodone and/or acetaminophen and exhibiting immediate release and/or extended release properties.

In certain embodiments, the tablet may have a friability of no greater than about 0.1%, 0.2%, 0.3%, 0.4%, 0.5%, 0.7% or 1.0%. In another embodiment, the tablet may have a friability of greater than 0 but less that about 1.0%, greater than 0 but less than about 0.5%, greater than 0 but less than about 0.3%, or greater than 0 but less than about 0.2%. In still another embodiment, the tablet may have a friability of zero.

In another embodiment, the tablet may have a hardness of at least about 10 Kilopond (also known as kilopons) (kp). In some embodiments, the tablet may have a hardness of about 9 kp to about 25 kp, or about 12 kp to about 20 kp. In further embodiments, the tablet may have a hardness of about 11 kp, 12 kp, 13 kp, 14 kp, 15 kp, 16 kp, 17 kp, 18 kp, 19 kp, or 20 kp.

In additional embodiments, the tablet may have a content uniformity of from about 85 to about 115 percent by weight or from about 90 to about 110 percent by weight, or from about 95 to about 105 percent by weight. In other embodiments, the content uniformity may have a relative standard deviation (RSD) equal to or less than about 3.5%, 3.0%, 2.5%, 2.0%, 1.5%, 1.0%, or 0.5%.

In still other embodiments, prior to administration to a patient or immersion in fluid, the pharmaceutical composition may have (i) a length of approximately 18 mm, 18.01 mm, 18.02 mm, 18.03 mm, 18.04 mm, 18.05 mm, 18.06 mm, 18.07 mm, 18.08 mm, 18.09 mm, 18.1 mm, 18.11 mm, 18.12 mm, 18.13 mm, 18.14 mm, 18.15 mm, 18.16 mm, 18.17 mm, 18.18 mm, 18.19 mm, 18.2 mm, 18.21 mm, 18.22 mm, 18.23 mm, 18.24 mm, 18.25 mm, 18.26 mm, 18.27 mm, 18.28 mm, 18.29 mm, 18.3 mm, 18.31 mm, 18.32 mm, 18.33 mm, 18.34 mm, 18.35 mm, 18.36 mm, 18.37 mm, 18.38 mm, 18.39 mm, 18.4 mm, 18.41 mm, 18.42 mm, 18.43 mm, 18.44 mm, 18.45 mm, 18.46 mm, 18.47 mm, 18.48 mm, 18.49 mm, 18.5 mm, 18.51 mm, 18.52 mm, 18.53 mm, 18.54 mm, 18.55 mm, 18.56 mm, 18.57 mm, 18.58 mm, 18.59 mm, 18.6 mm, 18.61 mm, 18.62 mm, 18.63 mm, 18.64 mm, 18.65 mm, 18.66 mm, 18.67 mm, 18.68 mm, 18.69 mm, 18.7 mm, 18.71 mm, 18.72 mm, 18.73 mm, 18.74 mm, 18.75 mm, 18.76 mm, 18.77 mm, 18.78 mm, 18.79 mm, 18.8 mm, 18.81 mm, 18.82 mm, 18.83 mm, 18.84 mm, 18.85 mm, 18.86 mm, 18.87 mm, 18.88 mm, 18.89 mm, 18.9 mm, 18.91 mm, 18.92 mm, 18.93 mm, 18.94 mm, 18.95 mm, 18.96 mm, 18.97 mm, 18.98 mm, 18.99 mm, 19 mm, 19.01 mm, 19.02 mm, 19.03 mm, 19.04 mm, 19.05 mm, 19.06 mm, 19.07 mm, 19.08 mm, 19.09 mm, 19.1 mm, 19.11 mm, 19.12 mm, 19.13 mm, 19.14 mm, 19.15 mm, 19.16 mm, 19.17 mm, 19.18 mm, 19.19 mm, 19.2 mm, 19.21 mm, 19.22 mm, 19.23 mm, 19.24 mm, 19.25 mm, 19.26 mm, 19.27 mm, 19.28 mm, 19.29 mm, 19.3 mm, 19.31 mm, 19.32 mm, 19.33 mm, 19.34 mm, 19.35 mm, 19.36 mm, 19.37 mm, 19.38 mm, 19.39 mm, 19.4 mm, 19.41 mm, 19.42 mm, 19.43 mm, 19.44 mm, 19.45 mm, 19.46 mm, 19.47 mm, 19.48 mm, 19.49 mm, 19.5 mm, 19.51 mm, 19.52 mm, 19.53 mm, 19.54 mm, 19.55 mm, 19.56 mm, 19.57 mm, 19.58 mm, 19.59 mm 19.6 mm, 19.61 mm, 19.62 mm, 19.63 mm, 19.64 mm, 19.65 mm, 19.66 mm, 19.67 mm, 19.68 mm, 19.69 mm, 19.7 mm, 19.71 mm, 19.72 mm, 19.73 mm, 19.74 mm, 19.75 mm, 19.76 mm, 19.77 mm, 19.78 mm, 19.79 mm, 19.8 mm, 19.81 mm, 19.82 mm, 19.83 mm, 19.84 mm, 19.85 mm, 19.86 mm, 19.87 mm, 19.88 mm, 19.89 mm, 19.9 mm, 19.91 mm, 19.92 mm, 19.93 mm, 19.94 mm, 19.95 mm, 19.96 mm, 19.97 mm, 19.98 mm, 19.99 mm, or 20 mm as measured on the major axis, (ii) a width of approximately 11 mm, 11.01 mm, 11.02 mm, 11.03 mm, 11.04 mm, 11.05 mm, 11.06 mm, 11.07 mm, 11.08 mm, 11.09 mm, 11.1 mm, 11.11 mm, 11.12 mm, 11.13 mm, 11.14 mm, 11.15 mm, 11.16 mm, 11.17 mm, 11.18 mm, 11.19 mm, 11.2 mm, 11.21 mm, 11.22 mm, 11.23 mm, 11.24 mm, 11.25 mm, 11.26 mm, 11.27 mm, 11.28 mm, 11.29 mm, 11.3 mm, 11.31 mm, 11.32 mm, 11.33 mm, 11.34 mm, 11.35 mm, 11.36 mm, 11.37 mm, 11.38 mm, 11.39 mm, 11.4 mm, 11.41 mm, 11.42 mm, 11.43 mm, 11.44 mm, 11.45 mm, 11.46 mm, 11.47 mm, 11.48 mm, 11.49 mm, 11.5 mm, 11.51 mm, 11.52 mm, 11.53 mm, 11.54 mm, 11.55 mm, 11.56 mm, 11.57 mm, 11.58 mm, 11.59 mm, 11.6 mm, 11.61 mm, 11.62 mm, 11.63 mm, 11.64 mm, 11.65 mm, 11.66 mm, 11.67 mm, 11.68 mm, 11.69 mm, 11.7 mm, 11.71 mm, 11.72 mm, 11.73 mm, 11.74 mm, 11.75 mm, 11.76 mm, 11.77 mm, 11.78 mm, 11.79 mm, 11.8 mm, 11.81 mm, 11.82 mm, 11.83 mm, 11.84 mm, 11.85 mm, 11.86 mm, 11.87 mm, 11.88 mm, 11.89 mm, 11.9 mm, 11.91 mm, 11.92 mm, 11.93 mm, 11.94 mm, 11.95 mm, 11.96 mm, 11.97 mm, 11.98 mm, 11.99 mm, 12 mm, 12.01 mm, 12.02 mm, 12.03 mm, 12.04 mm, 12.05 mm, 12.06 mm, 12.07 mm, 12.08 mm, 12.09 mm, 12.1 mm, 12.11 mm, 12.12 mm, 12.13 mm, 12.14 mm, 12.15 mm, 12.16 mm, 12.17 mm, 12.18 mm, 12.19 mm, 12.2 mm, 12.21 mm, 12.22 mm, 12.23 mm, 12.24 mm, 12.25 mm, 12.26 mm, 12.27 mm, 12.28 mm, 12.29 mm, 12.3 mm, 12.31 mm, 12.32 mm, 12.33 mm, 12.34 mm, 12.35 mm, 12.36 mm, 12.37 mm, 12.38 mm, 12.39 mm, 12.4 mm, 12.41 mm, 12.42 mm, 12.43 mm, 12.44 mm, 12.45 mm, 12.46 mm, 12.47 mm, 12.48 mm, 12.49 mm, 12.5 mm, 12.51 mm, 12.52 mm, 12.53 mm, 12.54 mm, 12.55 mm, 12.56 mm, 12.57 mm, 12.58 mm, 12.59 mm, 12.6 mm, 12.61 mm, 12.62 mm, 12.63 mm, 12.64 mm, 12.65 mm, 12.66 mm, 12.67 mm, 12.68 mm, 12.69 mm, 12.7 mm, 12.71 mm, 12.72 mm, 12.73 mm, 12.74 mm, 12.75 mm, 12.76 mm, 12.77 mm, 12.78 mm, 12.79 mm, 12.8 mm, 12.81 mm, 12.82 mm, 12.83 mm, 12.84 mm, 12.85 mm, 12.86 mm, 12.87 mm, 12.88 mm, 12.89 mm, 12.9 mm, 12.91 mm, 12.92 mm, 12.93 mm, 12.94 mm, 12.95 mm, 12.96 mm, 12.97 mm, 12.98 mm, 12.99 mm, or 13 mm, and (iii) a height or thickness of approximately 5 mm, 5.01 mm, 5.02 mm, 5.03 mm, 5.04 mm, 5.05 mm, 5.06 mm, 5.07 mm, 5.08 mm, 5.09 mm, 5.1 mm, 5.11 mm, 5.12 mm, 5.13 mm, 5.14 mm, 5.15 mm, 5.16 mm, 5.17 mm, 5.18 mm, 5.19 mm, 5.2 mm, 5.21 mm, 5.22 mm, 5.23 mm, 5.24 mm, 5.25 mm, 5.26 mm, 5.27 mm, 5.28 mm, 5.29 mm, 5.3 mm, 5.31 mm, 5.32 mm, 5.33 mm, 5.34 mm, 5.35 mm, 5.36 mm, 5.37 mm, 5.38 mm, 5.39 mm, 5.4 mm, 5.41 mm, 5.42 mm, 5.43 mm, 5.44 mm, 5.45 mm, 5.46 mm, 5.47 mm, 5.48 mm, 5.49 mm, 5.5 mm, 5.51 mm, 5.52 mm, 5.53 mm, 5.54 mm, 5.55 mm, 5.56 mm, 5.57 mm, 5.58 mm, 5.59 mm, 5.6 mm, 5.61 mm, 5.62 mm, 5.63 mm, 5.64 mm, 5.65 mm, 5.66 mm, 5.67 mm, 5.68 mm, 5.69 mm, 5.7 mm, 5.71 mm, 5.72 mm, 5.73 mm, 5.74 mm, 5.75 mm, 5.76 mm, 5.77 mm, 5.78 mm, 5.79 mm, 5.8 mm, 5.81 mm, 5.82 mm, 5.83 mm, 5.84 mm, 5.85 mm, 5.86 mm, 5.87 mm, 5.88 mm, 5.89 mm, 5.9 mm, 5.91 mm, 5.92 mm, 5.93 mm, 5.94 mm, 5.95 mm, 5.96 mm, 5.97 mm, 5.98 mm, 5.99 mm, or 6 mm. In yet another embodiment, the pharmaceutical composition may have (i) a length of approximately 19.1 mm, 19.11 mm, 19.12 mm, 19.13 mm, 19.14 mm, 19.15 mm, 19.16 mm, 19.17 mm, 19.18 mm, 19.19 mm, 19.2 mm, 19.21 mm, 19.22 mm, 19.23 mm, 19.24 mm, 19.25 mm, 19.26 mm, 19.27 mm, 19.28 mm, 19.29 mm, or 19.3 mm as measured on the major axis, (ii) a width of approximately 12.4 mm, 12.41 mm, 12.42 mm, 12.43 mm, 12.44 mm, 12.45 mm, 12.46 mm, 12.47 mm, 12.48 mm, 12.49 mm, or 12.5 mm, and (iii) a height or thickness of approximately 5.6 mm, 5.61 mm, 5.62 mm, 5.63 mm, 5.64 mm, 5.65 mm, 5.66 mm, 5.67 mm, 5.68 mm, 5.69 mm, 5.7 mm, 5.71 mm, 5.72 mm, 5.73 mm, 5.74 mm, 5.75 mm, 5.76 mm, 5.77 mm, 5.78 mm, 5.79 mm, or 5.8 mm.

In additional embodiments, the pharmaceutical composition may expand upon immersion in fluid to have (i) a length of about 18.5 mm, 18.6 mm, 18.7 mm, 18.8 mm, 18.9 mm, 19 mm, 19.1 mm, 19.2 mm, 19.3 mm, 19.4 mm, 19.5 mm, 19.6 mm, 19.7 mm, 19.8 mm, 19.9 mm, 20 mm, 20.1 mm, 20.2 mm, 20.3 mm, 20.4 mm, 20.5 mm, 20.6 mm, 20.7 mm, 20.8 mm, 20.9 mm, or 21 mm; and (ii) a width of about 11 mm, 11.1 mm, 11.2 mm, 11.3 mm, 11.4 mm, 11.5 mm, 11.6 mm, 11.7 mm, 11.8 mm, 11.9 mm, 12 mm, 12.1 mm, 12.2 mm, 12.3 mm, 12.4 mm, 12.5 mm, 12.6 mm, 12.7 mm, 12.8 mm, 12.9 mm, 13 mm, 13.1 mm, 13.2 mm, 13.3 mm, 13.4 mm, 13.5 mm, 13.6 mm, 13.7 mm, 13.8 mm, 13.9 mm, or 14 mm within about 5 minutes of immersion in fluid. In other embodiments, the pharmaceutical composition may expand upon immersion in fluid to (i) a length of about 18.5 mm, 18.6 mm, 18.7 mm, 18.8 mm, 18.9 mm, 19 mm, 19.1 mm, 19.2 mm, 19.3 mm, 19.4 mm, 19.5 mm, 19.6 mm, 19.7 mm, 19.8 mm, 19.9 mm, 20 mm, 20.1 mm, 20.2 mm, 20.3 mm, 20.4 mm, 20.5 mm, 20.6 mm, 20.7 mm, 20.8 mm, 20.9 mm, 21 mm, 21.1 mm, 21.2 mm, 21.3 mm, 21.4 mm, 21.5 mm, 21.6 mm, 21.7 mm, 21.8 mm, 21.9 mm, or 22 mm; and (ii) a width of about 11 mm, 11.1 mm, 11.2 mm, 11.3 mm, 11.4 mm, 11.5 mm, 11.6 mm, 11.7 mm, 11.8 mm, 11.9 mm, 12 mm, 12.1 mm, 12.2 mm, 12.3 mm, 12.4 mm, 12.5 mm, 12.6 mm, 12.7 mm, 12.8 mm, 12.9 mm, 13 mm, 13.1 mm, 13.2 mm, 13.3 mm, 13.4 mm, 13.5 mm, 13.6 mm, 13.7 mm, 13.8 mm, 13.9 mm, 14 mm, 14.1 mm, 14.2 mm, 14.3 mm, 14.4 mm, 14.5 mm, 14.6 mm, 14.7 mm, 14.8 mm, 14.9 mm, or 15 mm within about 10 minutes to about 15 minutes of immersion in fluid. In still other embodiments, the pharmaceutical composition may expand upon immersion in fluid to (i) a length of about 19 mm, 19.1 mm, 19.2 mm, 19.3 mm, 19.4 mm, 19.5 mm, 19.6 mm, 19.7 mm, 19.8 mm, 19.9 mm, 20 mm, 20.1 mm, 20.2 mm, 20.3 mm, 20.4 mm, 20.5 mm, 20.6 mm, 20.7 mm, 20.8 mm, 20.9 mm, 21 mm, 21.1 mm, 21.2 mm, 21.3 mm, 21.4 mm, 21.5 mm, 21.6 mm, 21.7 mm, 21.8 mm, 21.9 mm, 22 mm, 22.1 mm, 22.2 mm, 22.3 mm, 22.4 mm, or 22.5 mm; and (ii) a width of about 12 mm, 12.1 mm, 12.2 mm, 12.3 mm, 12.4 mm, 12.5 mm, 12.6 mm, 12.7 mm, 12.8 mm, 12.9 mm, 13 mm, 13.1 mm, 13.2 mm, 13.3 mm, 13.4 mm, 13.5 mm, 13.6 mm, 13.7 mm, 13.8 mm, 13.9 mm, 14 mm, 14.1 mm, 14.2 mm, 14.3 mm, 14.4 mm, 14.5 mm, 14.6 mm, 14.7 mm, 14.8 mm, 14.9 mm, or 15 mm within about 20 minutes to about 25 minutes of immersion in fluid. In additional embodiments, the pharmaceutical composition may expand upon immersion in fluid to (i) a length of about 19 mm, 19.1 mm, 19.2 mm, 19.3 mm, 19.4 mm, 19.5 mm, 19.6 mm, 19.7 mm, 19.8 mm, 19.9 mm, 20 mm, 20.1 mm, 20.2 mm, 20.3 mm, 20.4 mm, 20.5 mm, 20.6 mm, 20.7 mm, 20.8 mm, 20.9 mm, 21 mm, 21.1 mm, 21.2 mm, 21.3 mm, 21.4 mm, 21.5 mm, 21.6 mm, 21.7 mm, 21.8 mm, 21.9 mm, 22 mm, 22.1 mm, 22.2 mm, 22.3 mm, 22.4 mm, 22.5 mm, 22.6 mm, 22.7 mm, 22.8 mm, 22.9 mm, or 23 mm; and (ii) a width of about 12.5 mm, 12.6 mm, 12.7 mm, 12.8 mm, 12.9 mm, 13 mm, 13.1 mm, 13.2 mm, 13.3 mm, 13.4 mm, 13.5 mm, 13.6 mm, 13.7 mm, 13.8 mm, 13.9 mm, 14 mm, \14.1 mm, 14.2 mm, 14.3 mm, 14.4 mm, 14.5 mm, 14.6 mm, 14.7 mm, 14.8 mm, 14.9 mm, or 15 mm within about 30 minutes to about 35 minutes of immersion in fluid. In still other embodiments, the pharmaceutical composition may expand upon immersion in fluid to (i) a length of about 18 mm, 18.1 mm, 18.2 mm, 18.3 mm, 18.4 mm, 18.5 mm, 18.6 mm, 18.7 mm, 18.8 mm, 18.9 mm, 19 mm, 19.1 mm, 19.2 mm, 19.3 mm, 19.4 mm, 19.5 mm, 19.6 mm, 19.7 mm, 19.8 mm, 19.9 mm, 20 mm, 20.1 mm, 20.2 mm, 20.3 mm, 20.4 mm, 20.5 mm, 20.6 mm, 20.7 mm, 20.8 mm, 20.9 mm, 21 mm, 21.1 mm, 21.2 mm, 21.3 mm, 21.4 mm, 21.5 mm, 21.6 mm, 21.7 mm, 21.8 mm, 21.9 mm, 22 mm, 22.1 mm, 22.2 mm, 22.3 mm, 22.4 mm, 22.5 mm, 22.6 mm, 22.7 mm, 22.8 mm, 22.9 mm, 23 mm, 23.1 mm, 23.2 mm, 23.3 mm, 23.4 mm, or 23.5; (ii) a width of about 11.5 mm, 11.6 mm, 11.7 mm, 11.8 mm, 11.9 mm, 12 mm, 12.1 mm, 12.2 mm, 12.3 mm, 12.4 mm, 12.5 mm, 12.6 mm, 12.7 mm, 12.8 mm, 12.9 mm, 13 mm, 13.1 mm, 13.2 mm, 13.3 mm, 13.4 mm, 13.5 mm, 13.6 mm, 13.7 mm, 13.8 mm, 13.9 mm, 14 mm, 14.1 mm, 14.2 mm, 14.3 mm, 14.4 mm, 14.5 mm, 14.6 mm, 14.7 mm, 14.8 mm, 14.9 mm, 15 mm, 15.1 mm, 15.2 mm, 15.3 mm, 15.4 mm, 15.5 mm, 15.6 mm, 15.7 mm, 15.8 mm, 15.9 mm, or 16 mm; and (iii) a height or thickness of about 5.5 mm, 5.6 mm, 5.7 mm, 5.8 mm, 5.9 mm, 6 mm, 6.1 mm, 6.2 mm, 6.3 mm, 6.4 mm, 6.5 mm, 6.6 mm, 6.7 mm, 6.8 mm, 6.9 mm, or 7 mm within about 50 minutes to about 55 minutes of immersion in fluid. In yet another embodiment, the pharmaceutical composition may expand upon immersion in fluid to (i) a length of about 19.5 mm, 19.6 mm, 19.7 mm, 19.8 mm, 19.9 mm, 20 mm, 20.1 mm, 20.2 mm, 20.3 mm, 20.4 mm, 20.5 mm, 20.6 mm, 20.7 mm, 20.8 mm, 20.9 mm, 21 mm, 21.1 mm, 21.2 mm, 21.3 mm, 21.4 mm, 21.5 mm, 21.6 mm, 21.7 mm, 21.8 mm, 21.9 mm, 22 mm, 22.1 mm, 22.2 mm, 22.3 mm, 22.4 mm, 22.5 mm, 22.6 mm, 22.7 mm, 22.8 mm, 22.9 mm, 23 mm, 23.1 mm, 23.2 mm, 23.3 mm, 23.4 mm, or 23.5; (ii) a width of about 13 mm, 13.1 mm, 13.2 mm, 13.3 mm, 13.4 mm, 13.5 mm, 13.6 mm, 13.7 mm, 13.8 mm, 13.9 mm, 14 mm, 14.1 mm, 14.2 mm, 14.3 mm, 14.4 mm, 14.5 mm, 14.6 mm, 14.7 mm, 14.8 mm, 14.9 mm, 15 mm, 15.1 mm, 15.2 mm, 15.3 mm, 15.4 mm, 15.5 mm, 15.6 mm, 15.7 mm, 15.8 mm, 15.9 mm, or 16 mm; and (iii) a height or thickness of about 5.5 mm, 5.6 mm, 5.7 mm, 5.8 mm, 5.9 mm, 6 mm, 6.1 mm, 6.2 mm, 6.3 mm, 6.4 mm, 6.5 mm, 6.6 mm, 6.7 mm, 6.8 mm, 6.9 mm, or 7 mm within about 60 minutes of immersion in fluid.

In yet another embodiment, the length of the pharmaceutical composition increases by about 4%, 4.25%, 4.5% 4.75%, 5%, 5.25%, 5.5%, 5.75%, 6%, 6.25%, 6.5%, 6.75%, 7%, 7.25%, 7.5%, 7.75% 8%, 8.25%, 8.5%, 8.75%, 9%, 9.25%, 9.5%, 9.75%, 10%, 10.25%, 10.5%, 10.75%, 11%, 11.25%, 11.5%, 11.75%, 12%, 12.25%, 12.5%, 12.75%, or 13% within about 10 minutes of immersion in fluid. In still another embodiment, the length of the pharmaceutical composition increases by about 5%, 5.25%, 5.5%, 5.75%, 6%, 6.25%, 6.5%, 6.75%, 7%, 7.25%, 7.5%, 7.75%, 8%, 8.25%, 8.5%, 8.75%, 9%, 9.25%, 9.5%, 9.75%, 10%, 10.25%, 10.5%, 10.75%, 11%, 11.25%, 11.5%, 11.75%, 12%, 12.25%, 12.5%, 12.75%, 13%, 13.25%, 13.5%, 13.75%, 14%, 14.25%, 14.5%, 14.75%, or 15% within about 15 minutes of immersion in fluid. In yet another embodiment, the length of the pharmaceutical composition increases by about 5%, 5.25%, 5.5%, 5.75%, 6%, 6.25%, 6.5%, 6.75%, 7%, 7.25%, 7.5%, 7.75%, 8%, 8.25%, 8.5%, 8.75%, 9%, 9.25%, 9.5%, 9.75%, 10%, 10.25%, 10.5%, 10.75%, 11%, 11.25%, 11.5%, 11.75%, 12%, 12.25%, 12.5%, 12.75%, 13%, 13.25%, 13.5%, 13.75%, 14%, 14.25%, 14.5%, 14.75%, or 15% within about 20 minutes of immersion in fluid. In a further embodiment, the length of the pharmaceutical composition increases by about 7%, 7.25%, 7.5%, 7.75% 8%, 8.25%, 8.5%, 8.75%, 9%, 9.25% 9.5%, 9.75%, 10%, 10.25%, 10.5%, 10.75%, 11%, 11.25%, 11.5%, 11.75%, 12%, 12.25%, 12.5%, 12.75%, 13%, 13.25%, 13.5%, 13.75%, 14%, 14.25%, 14.5%, 14.75%, 15%, 15.25%, 15.5%, 15.75%, 16%, 16.25%, 16.5%, 16.75%, 17%, 17.25%, 17.5%, 17.75%, or 18% within about 30 minutes of immersion in fluid. In another embodiment, the length of the pharmaceutical composition increases by about 8%, 8.25%, 8.5%, 8.75%, 9%, 9.25%, 9.5%, 9.75%, 10%, 10.25%, 10.5%, 10.75%, 11%, 11.25%, 11.5%, 11.75%, 12%, 12.25%, 12.5%, 12.75%, 13%, 13.25%, 13.5%, 13.75%, 14%, 14.25%, 14.5%, 14.75%, 15%, 15.25%, 15.5%, 15.75%, 16%, 16.25%, 16.5%, 16.75%, 17%, 17.25%, 17.5%, 17.75%, 18%, 18.25%, 18.5%, 18.75%, or 19% within about 45 minutes of immersion in fluid. In yet another embodiment, the length of the pharmaceutical composition increases by about 8%, 8.25%, 8.5%, 8.75%, 9%, 9.25% 9.5%, 9.75%, 10%, 10.25%, 10.5%, 10.75%, 11%, 11.25%, 11.5%, 11.75%, 12%, 12.25%, 12.5%, 12.75%, 13%, 13.25%, 13.5%, 13.75%, 14%, 14.25%, 14.5%, 14.75%, 15%, 15.25%, 15.5%, 15.75%, 16%, 16.25%, 16.5%, 16.75%, 17%, 17.25%, 17.5%, 17.75%, 18%, 18.25%, 18.5%, 18.75%, or 19% within about 55 minutes of immersion in fluid. In still another embodiment, the length of the pharmaceutical composition increases by about 8%, 8.25%, 8.5%, 8.75%, 9%, 9.25%, 9.5%, 9.75%, 10%, 10.25%, 10.5%, 10.75%, 11%, 11.25%, 11.5%, 11.75%, 12%, 12.25%, 12.5%, 12.75%, 13%, 13.25%, 13.5%, 13.75%, 14%, 14.25%, 14.5%, 14.75%, 15%, 15.25%, 15.5%, 15.75%, 16%, 16.25%, 16.5%, 16.75%, 17%, 17.25%, 17.5%, 17.75%, 18%, 18.25%, 18.5%, 18.75%, 19%, 19.25%, 19.5%, 19.75%, or 20% within about 60 minutes of immersion in fluid.

In a further embodiment, the width of the pharmaceutical composition increases by about 6%, 6.25%, 6.5%, 6.75%, 7%, 7.25%, 7.5%, 7.75%, 8%, 8.25%, 8.5%, 8.75%, 9%, 9.25%, 9.5%, 9.75%, 10%, 10.25%, 10.5%, 10.75%, 11%, 11.25%, 11.5%, 11.75%, 12%, 12.25%, 12.5%, 12.75%, 13%, 13.25%, 13.5%, 13.75%, 14%, 14.25%, 14.5%, 14.75%, or 15% within about 10 minutes of immersion in fluid. In still another embodiment, the width of the pharmaceutical composition increases by about 6%, 6.25%, 6.5%, 6.75%, 7%, 7.25%, 7.5%, 7.75%, 8%, 8.25%, 8.5%, 8.75%, 9%, 9.25%, 9.5%, 9.75%, 10%, 10.25%, 10.5%, 10.75%, 11%, 11.25%, 11.5%, 11.75%, 12%, 12.25%, 12.5%, 12.75%, 13%, 13.25%, 13.5%, 13.75%, 14%, 14.25%, 14.5%, 14.75%, 15%, 15.25%, 15.5%, 15.75%, 16%, 16.25%, 16.5%, 16.75%, 17%, 17.25%, 17.5%, 17.75%, or 18%, within about 15 minutes of immersion in fluid. In yet another embodiment, the width of the pharmaceutical composition increases by about 6%, 6.25%, 6.5%, 6.75%, 7%, 7.25%, 7.5%, 7.75%, 8%, 8.25%, 8.5%, 8.75%, 9%, 9.25%, 9.5%, 9.75%, 10%, 10.25%, 10.5%, 10.75%, 11%, 11.25%, 11.5%, 11.75%, 12%, 12.25%, 12.5%, 12.75%, 13%, 13.25%, 13.5%, 13.75%, 14%, 14.25%, 14.5%, 14.75%, 15%, 15.25%, 15.5%, 15.75%, 16%, 16.25%, 16.5%, 16.75%, 17%, 17.25%, 17.5%, 17.75%, or 18%, within about 20 minutes of immersion in fluid. In a further embodiment, the width of the pharmaceutical composition increases by about 10%, 10.25%, 10.5%, 10.75%, 11%, 11.25%, 11.5%, 11.75%, 12%, 12.25%, 12.5%, 12.75%, 13%, 13.25%, 13.5%, 13.75%, 14%, 14.25%, 14.5%, 14.75%, 15%, 15.25%, 15.5%, 15.75%, 16%, 16.25%, 16.5%, 16.75%, 17%, 17.25%, 17.5%, 17.75%, 18%, 18.25%, 18.5%, 18.75%, 19%, 19.25%, 19.5%, 19.75%, 20%, 20.25%, 20.5%, 20.75%, 21%, 21.25%, 21.5%, 21.75%, 22%, 22.25%, 22.5%, 22.75%, 23%, 23.25%, 23.5%, 23.75%, or 24% within about 30 minutes of immersion in fluid. In another embodiment, the width of the pharmaceutical composition increases by about 12%, 12.25%, 12.5%, 12.75%, 13%, 13.25%, 13.5%, 13.75%, 14%, 14.25%, 14.5%, 14.75%, 15%, 15.25%, 15.5%, 15.75%, 16%, 16.25%, 16.5%, 16.75%, 17%, 17.25%, 17.5%, 17.75%, 18%, 18.25%, 18.5%, 18.75%, 19%, 19.25%, 19.5%, 19.75%, 20%, 20.25%, 20.5%, 20.75%, 21%, 21.25%, 21.5%, 21.75%, 22%, 22.25%, 22.5%, 22.75%, 23%, 23.25%, 23.5%, 23.75%, 24%, 24.25%, 24.5%, 24.75%, or 25% within about 45 minutes of immersion in fluid. In yet another embodiment, the width of the pharmaceutical composition increases by about 12%, 12.25%, 12.5%, 12.75%, 13%, 13.25%, 13.5%, 13.75%, 14%, 14.25%, 14.5%, 14.75%, 15%, 15.25%, 15.5%, 15.75%, 16%, 16.25%, 16.5%, 16.75%, 17%, 17.25%, 17.5%, 17.75%, 18%, 18.25%, 18.5%, 18.75%, 19%, 19.25%, 19.5%, 19.75%, 20.25%, 20.5%, 20.75%, 21%, 21.25%, 21.5%, 21.75%, 22%, 22.25%, 22.5%, 22.75%, 23%, 23.25%, 23.5%, 23.75%, 24%, 24.25%, 24.5%, 24.75%, or 25% within about 55 minutes of immersion in fluid. In still another embodiment, the width of the pharmaceutical composition increases by about 14%, 14.25%, 14.5%, 14.75%, 15%, 15.25%, 15.5%, 15.75%, 16%, 16.25%, 16.5%, 16.75%, 17%, 17.25%, 17.5%, 17.75%, 18%, 18.25%, 18.5%, 18.75%, 19%, 19.25%, 19.5%, 19.75%, 20%, 20.25%, 20.5%, 20.75%, 21%, 21.25%, 21.5%, 21.75%, 22%, 22.25%, 22.5%, 22.75%, 23%, 23.25%, 23.5%, 23.75%, 24%, 24.25%, 24.5%, 24.75%, 25%, 25.25%, 25.5%, 25.75%, or 26% within about 60 minutes of immersion in fluid.

The pharmaceutical composition disclosed herein includes one or more dosage forms that are designed to achieve the therapeutic concentrations of the active ingredients. In some embodiments, therefore, a therapeutically effective dose of the pharmaceutical composition may comprise one dosage form. In other embodiments, a therapeutically effective dose of the pharmaceutical composition may comprise two dosage forms. In additional embodiments, a therapeutically effective dose of the pharmaceutical composition may comprise three or more dosage forms.

(d) Abuse and Tamper Resistant Properties of the Composition

Extended release pain medications have provided many benefits to patients in the management of their chronic pain by providing a sustained release over time of a larger quantity of drug than is typically contained in an immediate release formulation. Consequently, these dosage forms (especially if they contain opioids) are attractive targets for drug abusers looking to defeat the extended release formulation to allow immediate bolus administration or "dose-dumping" of the entire drug contents of the dosage form.

Dosage forms of the pharmaceutical composition disclosed herein may be more resistant to crushing, grinding, pulverizing, or other common means used to produce a powder than an immediate release product. Accordingly, some embodiment forms are tamper resistant and less prone to abuse or misuse. For example, certain embodiments may not be crushed into a powder and snorted. Additionally, some embodiments comprising an extended release polymer may not be crushed, mixed with an aqueous solution, and injected (i.e., the resultant mixture becomes extremely viscous and cannot be drawn into a syringe.

For example, dosage forms of the pharmaceutical composition disclosed herein form a pasty semi-solid mixture when dissolved. Thus, the pharmaceutical composition is difficult to draw into a syringe and inject intravenously. The yield of active pharmaceutical ingredient(s) obtained from the pharmaceutical composition is also low (less than 20%).

Further, dosage forms of the pharmaceutical composition disclosed herein cannot easily be snorted. In order for a drug abuser to successfully snort a drug obtained from a dosage form, he must prepare a crushed, finely divided powder form of the dosage form for insufflating the powder into the nasal cavity. However, the pharmaceutical compositions disclosed herein form a clumpy, solid mass and do not allow acceptable absorption through the nasal tissue.

Dosage forms of the pharmaceutical composition disclosed herein also do not allow "dose dumping" caused by the deliberate introduction of alcohol into a drug abuser's stomach which accelerates the release of active ingredient(s) from the time-release formulation. The pharmaceutical compositions disclosed herein are resistant to the accelerated release of active ingredient(s).

In addition, dosage forms of the pharmaceutical composition disclosed herein do not allow for "free basing." Successful free basing by a drug abuser requires the generation of a salt free form of the active pharmaceutical ingredient(s). This requires physical and chemical manipulation to release the active pharmaceutical ingredient(s) from its salt(s) and selective extraction from other matrix excipients. The pharmaceutical composition disclosed herein cannot be easily manipulated to generate a free base preparation.

Moreover, the tamper resistance properties of the pharmaceutical compositions disclosed herein may be increased by increasing the average molecular weight of the extended release polymer used in the pharmaceutical composition. In another embodiment, the tamper resistance properties of the pharmaceutical compositions disclosed herein may be increased by increasing the amount of the extended release polymer used in the pharmaceutical composition.

In further embodiments, the solid oral dosage forms of the pharmaceutical compositions disclosed herein exhibit substantial differences in the release profiles of oxycodone and acetaminophen when the dosage forms are crushed or ground. Indeed, the intact solid oral dosage forms surprisingly exhibit a higher release rate of both active ingredients than one that is crushed or ground. This suggests that upon grinding or crushing the solid oral dosage forms disclosed herein, the immediate release portion and extended release portion of the dosage form combine, and the hydration and swelling of the polymer(s) in the extended release portion of the dosage form retards the release of the oxycodone and acetaminophen in the immediate release portion. Hence the incorporation of the ground or crushed components from the immediate release portion into a mixture with the ground or crushed components of the extended release portion causes the pharmaceutical composition to lose its immediate release characteristics. This feature may effectively negate a drug abuser's purpose for crushing the solid oral dosage form in the first place—to obtain an early onset of analgesia. Thus, this is an unexpected tamper resistant property of the pharmaceutical compositions disclosed herein.

In another embodiment, as the amount of oxycodone in the pharmaceutical composition increases, so does the duration of gastric retention after administration to a subject. Consequently, if a subject either intentionally or accidentally ingests a larger dose of the pharmaceutical composition than prescribed, the pharmaceutical composition will be retained in the stomach for a longer time period than an IR or traditional ER pharmaceutical composition, thereby giving a medical provider additional time to perform gastric lavage, induce vomiting, or administer activated charcoal to prevent the body from absorbing the oxycodone. In a further embodiment, the pharmaceutical composition provides a medical provider with about an additional 15 minutes, 30 minutes, 45 minutes, 60 minutes, 75 minutes, 90 minutes, 105 minutes, 2.0 hours, 2.25 hours, 2.5 hours, 2.75 hours, 3.0 hours, 3.25 hours, 3.5 hours, 3.75 hours, or 4 hours in which to prevent the absorption of oxycodone in the subject. In another embodiment, the pharmaceutical composition provides a medical provider with sufficient time to treat a subject who has overdosed on oxycodone so that death, difficulty breathing, cardiac arrest, and limp muscles do not occur in the subject.

In yet another embodiment, if vomiting is induced or naturally occurs as a result of an increased dose of oxycodone, the entire pharmaceutical composition is expelled from the subject. Thus, toxic concentrations of the oxycodone due to absorption into the subject's blood are prevented by removing the further release of oxycodone. In still another embodiment, if vomiting is induced or naturally occurs as a result of the increased dose of oxycodone about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of the pharmaceutical composition is expelled from the subject. In yet another embodiment, if vomiting is induced or naturally occurs within about 30 minutes to about 60 minutes after ingestion of the increased dose of oxycodone about 50% to about 65% of the oxycodone dose is expelled from the subject.

(e) In Vitro Release Properties of the Composition

The in vitro release rates of oxycodone and acetaminophen from the pharmaceutical compositions disclosed herein may be measured in 900 mL of 0.1 N HCl using a USP type II paddle apparatus and at a paddle speed of either about 100 rpm or 150 rpm and a constant temperature of 37° C.

In one embodiment, the at least one immediate release portion of the composition may have in vitro release rates of oxycodone and acetaminophen as follows: more than about 90% of the oxycodone and/or the acetaminophen present in the at least one immediate release portion may be released within about 15 minutes, or essentially 100% of the oxycodone and/or the acetaminophen present in the at least one immediate release portion may be released within about 15 minutes. In another embodiment, more than about 90% of the oxycodone and/or the acetaminophen present in the at least one immediate release portion may be released within about 5 minutes. In yet another embodiment, essentially 100% of the oxycodone and/or acetaminophen present in the at least one immediate release portion may be released within about 5 minutes.

In one embodiment, the at least one extended release portion of the composition may have in vitro release rates of oxycodone as follows: from about 1% to about 20% of the oxycodone present in the at least one extended release portion may be released within about 15 minutes, from about 35% to about 55% of the oxycodone present in the at least one extended release portion may be released within about 2 hours, from about 65% to about 85% of the oxycodone present in the at least one extended release portion may be released within about 4 hours, and at least about 90% of the oxycodone present in the at least one extended release portion may be released within about 8 hours.

In yet another embodiment, the at least one extended release portion may have in vitro release rates of oxycodone as follows: from about 1% to about 10% of the oxycodone present in the at least one extended release portion may be released within about 15 minutes, from about 40% to about 50% of the oxycodone present in the at least one extended release portion may be released within about 2 hours, from about 70% to about 80% of the oxycodone present in the at least one extended release portion may be released within about 4 hours, and from about 90% to about 100% of the oxycodone present in the at least one extended release portion may be released within about 8 hours.

In one embodiment, the at least one extended release portion may have in vitro release rates of acetaminophen as follows: from about 1% to about 15% of the acetaminophen present in the at least one extended release portion may be released within about 15 minutes, from about 25% to about 40% of the acetaminophen present in the at least one extended release portion may be released within about 2 hours, from about 50% to about 65% of the acetaminophen present in the at least one extended release portion may be released within about 4 hours, and from about 80% to about 95% of the acetaminophen present in the at least one extended release portion may be released within about 8 hours.

In another embodiment, the at least one extended release portion of the composition may have in vitro release rates of acetaminophen as follows: from about 1% to about 5% of the acetaminophen present in the at least one extended release portion may be released within about 15 minutes, from about 25% to about 35% of the acetaminophen present in the at least one extended release portion may be released within about 2 hours, from about 55% to about 65% of the acetaminophen present in the at least one extended release portion may be released within about 4 hours, and from about 80% to about 90% of the acetaminophen present in the at least one extended release portion may be released within about 8 hours.

In one embodiment, the in vitro release rates of oxycodone from the composition may be as follows: about 25% to about 35% of oxycodone may be released from the composition within about 15 minutes, from about 50% to about 65% of oxycodone may be released from the composition in about 2 hours, from about 70% to about 85% of oxycodone may be released from the composition within about 4 hours, and from about 90% to about 100% of oxycodone may be released from the composition within about 8 hours.

In another embodiment, the pharmaceutical composition disclosed herein may have in vitro release rates of oxycodone as follows: about 25% to about 30% of oxycodone may be released from the pharmaceutical composition within about 15 minutes, from about 50% to about 60% of oxycodone may be released from the pharmaceutical composition within about 2 hours, from about 70% to about 80% of oxycodone may be released from the pharmaceutical composition within about 4 hours, and from about 90% to about 95% of oxycodone may be released from the pharmaceutical composition within about 8 hours.

In one embodiment, the in vitro release rates of acetaminophen from the composition may be as follows: from about 50% to about 55% of acetaminophen may be released from the composition in about 15 minutes, from about 60% to about 75% of acetaminophen may be released from the composition in about 2 hours, from about 75% to about 85% of acetaminophen may be released from the composition in about 4 hours, and from about 90% to about 100% of acetaminophen may be released from the composition in about 8 hours.

In another embodiment, the in vitro release rates of acetaminophen from the pharmaceutical composition disclosed herein may be as follows: from about 50% to about 55% of acetaminophen may be released from the pharmaceutical composition within about 15 minutes, from about 60% to about 70% of acetaminophen may be released from the pharmaceutical composition within about 2 hours, from about 75% to about 85% of acetaminophen may be released from the pharmaceutical composition within about 4 hours, and from about 90% to about 100% of acetaminophen may be released from the pharmaceutical composition within about 8 hours.

Additionally, the in vitro release rates of oxycodone and acetaminophen from the pharmaceutical composition generally are not affected by low concentrations of ethanol (i.e., from about 5% v/v to about 20% v/v) when measured in 900 mL of 0.1 N HCl containing the desired percentage of ethanol using a USP type II paddle apparatus and at a paddle speed of about 150 rpm and a constant temperature of 37° C. For example, from about 25% to about 35% of oxycodone and about 50% to about 55% of acetaminophen may be released from the pharmaceutical composition within about 15 minutes when measured in the presence of 5% to 20% ethanol, and from about 50% to about 65% of oxycodone and from about 60% to about 70% of acetaminophen may be released from the pharmaceutical composition within about 2 hour when measured in the presence of 5% to 20% ethanol.

The in vitro release rates of oxycodone and acetaminophen from the pharmaceutical compositions disclosed herein generally are reduced, however, in the presence of 40% ethanol. For example, from about 5% to about 15% of the oxycodone and from about 15% to about 25% of the acetaminophen may be released from the pharmaceutical composition within about 15 minutes when measured in the presence of 40% ethanol, and from about 35% to about 45% of oxycodone and from about 45% to about 55% of acetaminophen may be released from the pharmaceutical composition within about 2 hours when measured in the presence of 40% ethanol.

Stated another way, less oxycodone is extracted from the pharmaceutical composition by a solution of 0.1 N HCl and 40% ethanol than is extracted by a solution of 0.1 N HCl. In some embodiments, less than about 75% of the oxycodone that is released in the presence of 0.1N HCl may be released in the presence of 0.1N HCl containing 40% ethanol. In additional embodiments, less than about 70%, 65%, 60%, 55%, 50%, 45%, or 40% of the oxycodone that may be released in the presence of 0.1N HCl may be released in the presence of 0.1N HCl and 40% ethanol. For example, less than about 40% of the oxycodone that may be released in the presence of 0.1N HCl in about 15 minutes may be released in the presence of 0.1N HCl and 40% ethanol within about 15 minutes. In other embodiments, less than about 60% of the oxycodone that may be released in the presence of 0.1N HCl in about 30 minutes may be released in the presence of 0.1N HCl and 40% ethanol within about 30 minutes. In additional embodiments, less than about 75% of the oxycodone that may be released in the presence of 0.1N HCl in about 2 hours may be released in the presence of 0.1N HCl and 40% ethanol within about 2 hours.

(f) Stability Data for the Pharmaceutical Composition

In one embodiment, p-aminophenol may be present in the pharmaceutical composition as a degradation product of acetaminophen in any amount up to and including, but no more than, about 100 ppm. In other embodiments, p-aminophenol may be present in the pharmaceutical composition as a degradation product of acetaminophen in an amount of about 0.2 ppm to about 6.0 ppm after storage for about 1, 2, or 3 months at a temperature of about 25° C. to about 40° C. and at about 60% to about 75% relative humidity. In yet another embodiment, p-aminophenol may be present in the pharmaceutical composition as a degradation product of acetaminophen in an amount of about 0.6 ppm to about 6.0 ppm after storage for about 1, 2, or 3 months at a temperature of about 25° C. to about 40° C. and at about 60% to about 75% relative humidity. In still another embodiment, p-aminophenol may be present in the pharmaceutical composition as a degradation product of acetaminophen in an amount of about 0.2 ppm, 0.3 ppm, 0.4 ppm, 0.5 ppm, 0.6 ppm, 0.7 ppm, 0.8 ppm, 0.9 ppm, 1.0 ppm, 1.1 ppm, 1.2 ppm, 1.3 ppm, 1.4 ppm, 1.5 ppm, 1.6 ppm, 1.7 ppm, 1.8 ppm, 1.9 ppm, 2.0 ppm, 2.1 ppm, 2.2 ppm, 2.3 ppm, 2.4 ppm, 2.5 ppm, 2.6 ppm, 2.7 ppm, 2.8 ppm, 2.9 ppm, 3.0 ppm, 3.1 ppm, 3.2 ppm, 3.3 ppm, 3.4 ppm, 3.5 ppm, 3.6 ppm, 3.7 ppm, 3.8 ppm, 3.9 ppm, 4.0 ppm, 4.1 ppm, 4.2 ppm, 4.3 ppm, 4.4 ppm, 4.5 ppm, 4.6 ppm, 4.7 ppm, 4.8 ppm, 4.9 ppm, 5.0 ppm, 5.1 ppm, 5.2 ppm, 5.3 ppm, 5.4 ppm, 5.5 ppm, 5.6 ppm, 5.7 ppm, 5.8 ppm, 5.9 ppm, and 6.0 ppm after storage for about 1, 2, or 3 months at a temperature of 25° C. to about 40° C. and at about 60% to about 75% relative humidity In one embodiment, oxycodone N-oxide may be present in the pharmaceutical composition as a degradation product of oxycodone in any amount up to and including about 0.5% by weight of the oxycodone. In other embodiments, oxycodone N-oxide may be present in the pharmaceutical composition as a degradation product of oxycodone in an amount of about 0.01% to about 0.5% by weight of the oxycodone after storage for about 1, 2, or 3 months at a constant temperature of about 25° C. to 40° C. and at about 60% to 75% relative humidity. In yet another embodiment, oxycodone N-oxide may be present in the pharmaceutical composition as a degradation product of oxycodone in an amount of about 0.05% to about 0.5% by weight of the oxycodone after storage for about 1, 2, or 3 months at a constant temperature of about 25° C. to 40° C. and at about 60% to 75% relative humidity. In additional embodiments, oxycodone N-oxide may be present in the pharmaceutical composition as a degradation product of oxycodone in an amount of about 0.01%, 0.02%, 0.03%, 0.04%, 0.05%, 0.06%, 0.07%, 0.08%, 0.09%, 0.1%, 0.11%, 0.12%, 0.13%, 0.14%, 0.15%, 0.16%, 0.17%, 0.18%, 0.19%, 0.2%, 0.21%, 0.22%, 0.23%, 0.24%, 0.25%, 0.26%, 0.27%, 0.28%, 0.29%, 0.3%, 0.31%, 0.32%, 0.33%, 0.34%, 0.35%, 0.36%, 0.37%, 0.38%, 0.39%, 0.4%, 0.41%, 0.42%, 0.43%, 0.44%, 0.45%, 0.46%, 0.47%, 0.48%, 0.49%, and 0.5% by weight of the oxycodone after storage for about 1, 2, or 3 months at a constant temperature of about 25° C. to about 40° C. and at about 60% to about 75% relative humidity.

In one embodiment, Related Substance A (i.e., C-Normorphinan-6-carboxylic acid, 4,5-epoxy-6,14-dihydroxy-3-methoxy-17-methyl-, (5α,6α)-) may be present in the pharmaceutical composition as a degradation product of oxycodone in a maximum amount of about 0.5% by weight of the oxycodone. In other embodiments, Related Substance A may be present in the pharmaceutical composition as a degradation product of oxycodone in an amount of about 0.01% to about 0.5% by weight of the oxycodone after storage for about 1, 2, or 3 months at a temperature of about 25° C. to about 40° C. and at about 60% to about 75% relative humidity. In yet another embodiment, Related Substance A may be present in the pharmaceutical composition as a degradation product of oxycodone in an amount of about 0.05% to about 0.5% by weight of the oxycodone after storage for about 1, 2, or 3 months at a temperature of about 25° C. to about 40° C. and at about 60% to about 75% relative humidity. In other embodiments, Related Substance A may be present in the pharmaceutical composition as a degradation product of oxycodone in an amount of about 0.01%, 0.02%, 0.03%, 0.04%, 0.05%, 0.06%, 0.07%, 0.08%, 0.09%, 0.1%, 0.11%, 0.12%, 0.13%, 0.14%, 0.15%, 0.16%, 0.17%, 0.18%, 0.19%, 0.2%, 0.21%, 0.22%, 0.23%, 0.24%, 0.25%, 0.26%, 0.27%, 0.28%, 0.29%, 0.3%, 0.31%, 0.32%, 0.33%, 0.34%, 0.35%, 0.36%, 0.37%, 0.38%, 0.39%, 0.4%, 0.41%, 0.42%, 0.43%, 0.44%, 0.45%, 0.46%, 0.47%, 0.48%, 0.49%, and 0.5% by weight of the oxycodone after storage for about 1, 2, or 3 months at a temperature of about 25° C. to about 40° C. and at about 60% to about 75% relative humidity.

In one embodiment, each unspecified acetaminophen degradation product may be present in the pharmaceutical composition in any amount up to about 0.15% by weight of the acetaminophen. In another embodiment, each unspecified acetaminophen degradation product may be present in the pharmaceutical composition as a degradation product of acetaminophen in an amount of about 0.01% and about 0.15% by weight of the acetaminophen after storage for about 1, 2, or 3 months at a temperature of about 25° C. to about 40° C. and at about 60% to about 75% relative humidity. In still another embodiment, each unspecified acetaminophen degradation product may be present in the pharmaceutical composition as a degradation product of acetaminophen in an amount of about 0.05% and about 0.15% by weight of the acetaminophen after storage for about 1, 2, or 3 months at a temperature of about 25° C. to about 40° C. and at about 60% to about 75% relative humidity. In other embodiments, each unspecified acetaminophen degradation product may be present in the pharmaceutical composition as a degradation product of acetaminophen in an amount of about 0.01%, 0.02%, 0.03%, 0.04%, 0.05%, 0.06%, 0.07%, 0.08%, 0.09%, 0.1%, 0.11%, 0.12%, 0.13%, 0.14%, and 0.15% by weight of the acetaminophen after storage for about 1, 2, or 3 months at a temperature of about 25° C. to about 40° C. and at about 60% to about 75% relative humidity.

In one embodiment, each unspecified oxycodone HCl degradation product may be present in the pharmaceutical composition in a maximum amount of about 0.2% by weight of the oxycodone. In other embodiments, each unspecified oxycodone HCl degradation product may be present in the pharmaceutical composition in an amount of about 0.01% to about 0.2% by weight of the oxycodone after storage for about 1, 2, or 3 months at a temperature of about 25° C. to about 40° C. and at about 60% to about 75% relative humidity. In yet another embodiment, each unspecified oxycodone HCl degradation product may be present in the pharmaceutical composition in an amount of about 0.05% to about 0.2% by weight of the oxycodone after storage for about 1, 2, or 3 months at a temperature of about 25° C. to about 40° C. and at about 60% to about 75% relative humidity. In further embodiments, each unspecified oxycodone HCl degradation product may be present in the pharmaceutical composition in an amount of about 0.01%, 0.02%, 0.03%, 0.04%, 0.05%, 0.06%, 0.07%, 0.08%, 0.09%, 0.10%, 0.11%, 0.12%, 0.13%, 0.14%, 0.15%, 0.16%, 0.17%, 0.18%, 0.19%, and 0.2% by weight of the oxycodone after storage for about 1, 2, or 3 months at a temperature of about 25° C. to about 40° C. and at about 60% to about 75% relative humidity.

In one embodiment, the total acetaminophen degradation products may be present in the pharmaceutical composition in a maximum amount of about 1.0% by weight of the acetaminophen. In other embodiments, the total acetaminophen degradation products may be present in the pharmaceutical composition in an amount of about 0.05% to about 1.0% by weight of the acetaminophen after storage for about 1, 2, or 3 months at a temperature of about 25° C. to about 40° C. and at about 60% to about 75% relative humidity. In further embodiments, the total acetaminophen degradation products may be present in the pharmaceutical composition in an amount of about 0.05%, 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, and 1.0% by weight of the acetaminophen after storage for about 1, 2, or 3 months at a temperature of about 25° C. to about 40° C. and at about 60% to about 75% relative humidity.

In one embodiment, the total oxycodone degradation products may be present in the pharmaceutical composition in a maximum amount of about 1.0% by weight of the oxycodone. In further embodiments, the total oxycodone degradation products may be present in the pharmaceutical composition in an amount of about 0.05% to about 1.0% by weight of the oxycodone after storage for about 1, 2, or 3 months at a temperature of about 25° C. to about 40° C. and at about 60% to about 75% relative humidity. In yet other embodiments, the total oxycodone degradation products may be present in the pharmaceutical composition in an amount of about 0.05%, 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, and 1.0% by weight of the oxycodone after storage for about 1, 2, or 3 months at a temperature of about 25° C. to about 40° C. and at about 60% to about 75% relative humidity.

(g) In Vivo and Pharmacokinetic Properties of the Pharmaceutical Composition

The pharmaceutical composition disclosed herein comprises at least one immediate release portion for immediate release of oxycodone and acetaminophen such that therapeutic plasma concentrations are quickly attained (e.g., within one hour) and the initial onset of action is achieved within about 5 minutes, 10 minutes, 15 minutes, 20 minutes, 25 minutes, 30 minutes, 35 minutes, 40 minutes, 45 minutes, 50 minutes, 55 minutes, or 60 minutes after administration of the composition upon oral administration to a subject. The pharmaceutical composition disclosed herein also comprises at least one extended release portion for sustained release of oxycodone and acetaminophen over an extended period of time, e.g., about 3 to about 12 hours, or about 4 to about 9 hours, or at least about 6 hours, or at least about 8 hours, to the upper gastrointestinal tract where acetaminophen, and potentially oxycodone, is best absorbed.

The pharmaceutical composition may be orally administered to a subject once in a 24 hour period (q.d. or once-daily), two times in a 24 hour period (b.i.d. or twice-daily), or three times in a 24 hour period (t.i.d. or three times daily). In one embodiment, the pharmaceutical composition may be orally administered to the subject twice a day (i.e., every 12 hours). The subject may be a mammal, and in certain embodiments, the subject may be a human.

In another embodiment, the subject may be administered a first or loading dose of the pharmaceutical composition. This first or loading dose may assist the subject in more quickly attaining steady state blood levels of the active drugs. In a further embodiment, the subject may be administered a first or loading dose of the pharmaceutical composition comprising about 22.5 mg of oxycodone and about 975 mg of acetaminophen. In yet another embodiment, the subject may be administered a first or loading dose of the pharmaceutical composition comprising 2 tablets, each tablet comprising about 11.25 mg of oxycodone and about 462.5 mg of acetaminophen. In yet another embodiment, the subject may be administered a first or loading dose of the pharmaceutical composition comprising 3 tablets, each tablet comprising about 7.5 mg of oxycodone and about 325 mg of acetaminophen. In still another embodiment, the subject may be administered a first or loading dose of the pharmaceutical composition comprising 4 tablets, each tablet comprising about 5.625 mg of oxycodone and about 231.25 mg of acetaminophen. In yet another embodiment, the subject may be administered a first or loading dose of the pharmaceutical composition comprising 2 capsules, each capsule comprising about 11.25 mg of oxycodone and about 462.5 mg of acetaminophen. In yet another embodiment, the subject may be administered a first or loading dose of the pharmaceutical composition comprising 3 capsules, each capsules comprising about 7.5 mg of oxycodone and about 325 mg of acetaminophen. In still another embodiment, the subject may be administered a first or loading dose of the pharmaceutical composition comprising 4 capsules, each capsules comprising about 5.625 mg of oxycodone and about 231.25 mg of acetaminophen.

Upon oral administration to a subject, the pharmaceutical composition disclosed herein may maintain a therapeutic blood plasma concentration of oxycodone of at least about 5 ng/mL from about 0.75 hours to about 12 hours after administration of the composition. In another embodiment, the plasma concentration of oxycodone may be maintained at a concentration of at least about 7.5 ng/mL from about 1 hour to about 12 hours after administration of the composition. In a further embodiment, the plasma concentration of oxycodone may be maintained at a concentration of at least about 7.5 ng/mL from about 0.75 hour to about 10 hours after administration of the composition. In a further embodiment, the plasma concentration of oxycodone may be maintained at a concentration of at least about 10 ng/mL from about 2 hour to about 10 hours after administration of the composition. In yet another embodiment, the plasma concentration of oxycodone may be maintained at a concentration of at least about 10 ng/mL from about 1 hour to about 10 hours after administration of the composition. In still another embodiment, the plasma concentration of oxycodone may be maintained at a concentration of at least about 10 ng/mL from about 0.75 hour to about 10 hours after administration of the composition.

In another embodiment, the pharmaceutical composition, when orally administered to a subject, may produce a plasma profile characterized by a mean $C_{max}$ (peak plasma concentration) for oxycodone from about 0.9 ng/mL/mg to about 1.6 ng/mL/mg. In another embodiment, the mean $C_{max}$ for oxycodone may range from about 1.0 ng/mL/mg to about 1.5 ng/mL/mg. In an additional embodiment, the mean $C_{max}$ for oxycodone may be 0.9, 1.0, 1.1, 1.2, 1.3, 1.4, 1.5, or 1.6 ng/mL/mg. Moreover, the mean $C_{max}$ for oxycodone at steady state may range from about 1.5 ng/mL/mg to about 2.0 ng/mL/mg, from about 1.6 ng/mL/mg to about 1.95 ng/mL/mg, or from about 1.7 ng/mL/mg to about 1.85 ng/mL/mg.

Figure 23:
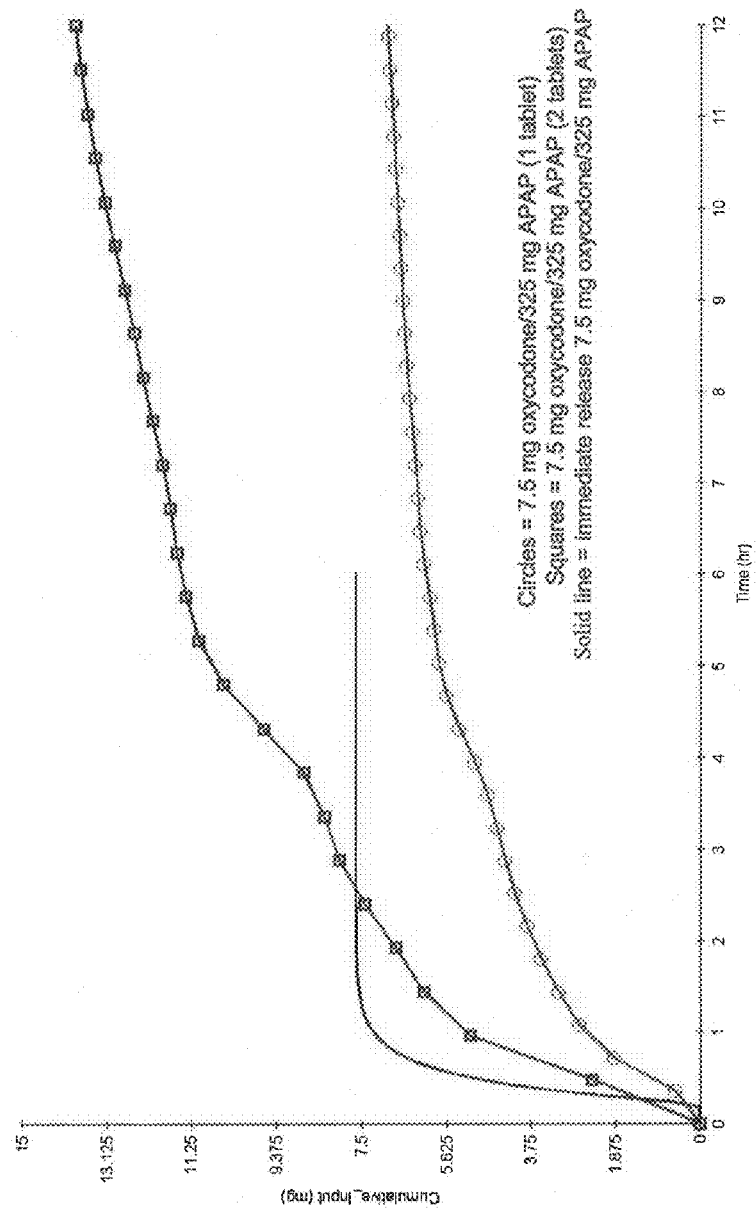
FIG. 23 shows a deconvolution plot of the biphasic absorption of oxycodone from tablets of the 7.5 mg oxycodone/325 mg acetaminophen formulation. The cumulative amount of oxycodone is plotted versus time. Circles represent one tablet of 7.5 mg oxycodone/325 mg acetaminophen; squares represent two tablets of 7.5 mg oxycodone/325 mg acetaminophen; and the immediate release 7.5 oxycodone/325 acetaminophen tablet is shown in a solid line with no symbols.

In a further embodiment, the pharmaceutical composition, when orally administered to a subject, surprisingly may produce a blood plasma concentration profile characterized by a biphasic increase in blood plasma concentrations of oxycodone. Deconvolution of the pharmaceutical composition and the target plasma profiles can be done in WinNonLin (version 5.2, Pharsight Corp., Mountain View, Calif.). The results of such a deconvolution analysis for oxycodone is depicted in FIG. 23. The biphasic absorption of oxycodone may be characterized by an initial rapid absorption resulting in a first peak in plasma concentration between about 1 hour and 2 hours, which contributes to the early onset of action, and a second peak in plasma concentrations between about 3 hours and 7 hours as a result of slower absorption taking place from the at least one extended release portion after administration of the composition, which contributes to the duration or maintenance of analgesia. In some instances, the second peak may correspond to the overall $C_{max}$ of the composition. The biphasic increase in blood plasma concentrations of oxycodone may be characterized by a plasma concentration-time profile for oxycodone in which the slope of a line drawn between 0 hour and about 2 hours is greater than the slope of a line drawn between about 2 hours and about 5 hours. See FIG. 23.

This biphasic increase in oxycodone levels resulting from the composition has several benefits. For example, providing rapid but not too high concentrations of oxycodone for quick onset of analgesia followed by maintenance of oxycodone levels over an extended time period could prevent a human subject from developing liking or dependence (abuse) for oxycodone. Further fluctuations in the oxycodone plasma levels could also prevent development of tolerance at the active site. Thus, the biphasic increase in oxycodone levels helps to prevent this acute tolerance.

In an additional embodiment, the pharmaceutical composition, when orally administered to a subject, may produce a plasma profile characterized by a mean AUC for oxycodone from about 9.0 ng·hr/mL/mg to about 18.5 ng·hr/mL/mg. In a further embodiment, the mean AUC for oxycodone may be from about 12.0 ng·hr/mL/mg to about 16.0 ng·hr/mL/mg. In another embodiment, the mean AUC for oxycodone may be about 9.0, 9.5, 10.0, 10.5, 11.0, 11.5, 12.0, 12.5, 13.0, 13.5, 14.0, 14.5, 15.0, 15.5, or 16.0 ng·hr/mL/mg. Additionally, the mean AUC for oxycodone at steady state may range from about 11.0 ng·hr/mL/mg to about 17.0 ng·hr/mL/mg, from about 12.0 ng·hr/mL/mg to about 16.0 ng·hr/mL/mg, or from about 13.0 ng·hr/mL/mg to about 15.0 ng·hr/mL/mg.

In a further embodiment, the pharmaceutical composition, when orally administered to a subject, may produce a plasma profile characterized by a median $T_{max}$ (time to peak plasma concentration) for oxycodone from about 2.0 hours to about 7.0 hours. In an alternate embodiment, the median $T_{max}$ for oxycodone may be from about 3.0 hours to about 6.0 hours. In another embodiment, the median $T_{max}$ for oxycodone may be about 2.0, 2.5, 3.0, 3.5, 4.0, 4.5, 5.0, 5.5 or 6.0 hours. Moreover, the median $T_{max}$ for oxycodone at steady state may range from about 1.5 hours to about 3.5 hours, or from about 2 hours to about 3 hours.

In still another embodiment, the pharmaceutical composition, when orally administered to a subject, may produce a plasma profile characterized by a median $t_{lag}$ for oxycodone from about 0 hours to about 0.5 hours. In an alternate embodiment, the median tlag for oxycodone may be from about 0 hours to about 0.25 hours.

Rates of absorption are often assessed by comparing standard pharmacokinetic parameters such as Tmax and Cmax. The extent of absorption is assessed by the AUC. A short Tmax has been used to indicate rapid absorption. The U.S. FDA, *Guidance for Industry: Bioavailability and Bioequivalence Studies for Orally Administered Drug Products—General Considerations* (March 2003) and related publications (Chen et al, Clin. Pharmacokinet. 40(8):565-72, 2001) also recommends the use of partial AUC for some modified-release drugs ("MR drugs"), such as the pharmaceutical compositions disclosed herein. A partial AUC calculation may be used to measure early exposure to a drug, which may signify an initial onset of pain relief and/or to measure prolonged exposure of a drug in achieving sustained relief. Partial AUC calculations can also demonstrate whether two MR drugs are truly bioequivalent by comparing, for example, an early partial AUC, which will be associated with a drug's response onset, and a late partial AUC, which will be associated with a drug's sustained response. The parameters for compositions vary greatly between subjects. The parameters also vary depending on aspects of the study protocol such as the sampling scheduling, subject posture and general subject health. Values quoted in this specification are given as mean±standard deviation unless otherwise noted.

For partial AUC calculations, the standard linear trapezoidal summation over each time interval is used. The partial AUCs are calculated from the mean pharmacokinetic profile. For time 0 to 1 hour the partial AUC is $AUC_{(0-1hr)}$; for time 0 to 2 hours the partial AUC is $AUC_{(0-2hr)}$; for time 0-4 hours the partial AUC is $AUC_{(0-4hr)}$; for time 0 to 6 hour the partial AUC is $AUC_{(0-6hr)}$; for time 0 to 8 hours the partial AUC is $AUC_{(0-8hr)}$; and for time 0 to the last measurable time point ("x") the partial AUC is $AUC_{(0-(x)hr)}$ where each partial AUC is calculated according to standard pharmaceutical industry pharmacokinetic calculation methodologies as given by:

$AUC_{(0-1hr)}$—Area under the drug concentration-time curve calculated using linear trapezoidal summation from time zero to time 1 hour.

$AUC_{(0-2hr)}$—Area under the drug concentration-time curve calculated using linear trapezoidal summation from time zero to time 2 hours.

$AUC_{(0-4hr)}$—Area under the drug concentration-time curve calculated using linear trapezoidal summation from time zero to time 4 hours.

$AUC_{(0-6hr)}$—Area under the drug concentration-time curve calculated using linear trapezoidal summation from time zero to time 6 hours.

$AUC_{(0-8hr)}$—Area under the drug concentration-time curve calculated using linear trapezoidal summation from time zero to time 8 hours.

$AUC_{(0-(t)hr)}$—Area under the drug concentration-time curve calculated using linear trapezoidal summation from time zero to the last measurable time point.

$AUC_{(0-(Tmax\ of\ IR\ product+2SD))}$—Area under the drug concentration-time curve calculated using linear trapezoidal summation from time zero to the time of the mean peak (Tmax) for the immediate release version of the drug plus two standard deviations ("2SD") for the immediate release drug. The FDA has identified this calculation in association with an early onset of response for certain modified-release dosage forms, which show complex pharmacokinetic characteristics. (See supra March 2003 Guidance; Draft Guidance on Dexmethylphenidate Hydrochloride (March 2012); Draft Guidance on Methylphenidate Hydrocholoride (November 2011)).

$AUC_{((Tmax\ of\ IR\ product+2SD)-t)}$—Area under the drug concentration-time curve calculated using linear trapezoidal summation from the time of the mean peak (Tmax) for the immediate release version of the drug plus two standard deviations ("2SD") for the immediate release drug to the last measurable time point. The FDA has identified this parameter in association with sustaining the response for modified-release dosage forms, which shows complex pharmacokinetic characteristics. (See March 2003 Guidance supra; Draft Guidance on Dexmethylphenidate Hydrochloride (March 2012); Draft Guidance on Methylphenidate Hydrocholoride (November 2011)).

$AUC_{(x-(y)hr)}$—Area under the drug concentration-time curve calculated using linear trapezoidal summation from time "x" (e.g., any measurable time point, such as 8 hours) to time "y" (e.g., any other measurable time point later than "x", such as 12 hours).

$AUC_{(0-\infty)}$—Area under the drug concentration-time curve calculated using linear trapezoidal summation from time 0 to infinity.

Further, partial AUC may be calculated using trapezoidal summation from time Tmax to time t (the last measured time point of plasma concentration profile).

In one embodiment, the pharmaceutical composition, when orally administered to a subject, may produce a plasma profile characterized by an $AUC_{0-1hr}$ for oxycodone from about 0.10 ng·hr/mL/mg to about 0.45 ng·hr/mL/mg, from about 0.15 ng·hr/mL/mg to about 0.25 ng·hr/mL/mg, or from about 0.25 ng·hr/mL/mg to about 0.35 ng·hr/mL/mg. In another embodiment, the $AUC_{0-1hr}$ for oxycodone may be about 0.10, 0.15, 0.20, 0.25, 0.30, 0.35, 0.40, or 0.45 ng·hr/mL/mg.

In an additional embodiment, the pharmaceutical composition, when orally administered to a subject, may produce a plasma profile characterized by an $AUC_{0-2hr}$ for oxycodone from about 0.65 ng·hr/mL/mg to about 1.35 ng·hr/mL/mg, from about 0.80 ng·hr/mL/mg to about 1.0 ng·hr/mL/mg, or from about 1.0 ng·hr/mL/mg to about 1.2 ng·hr/mL/mg. In another embodiment, the $AUC_{0-2hr}$ for oxycodone may be about 0.65, 0.70, 0.75, 0.80, 0.85, 0.90, 0.95, 1.0, 1.05, 1.10, 1.15, 1.20, 1.25, 1.30 or 1.35 ng·hr/mL/mg.

In a further embodiment, the pharmaceutical composition, when orally administered to a subject, may produce a plasma profile characterized by an $AUC_{0-4hr}$ for oxycodone from about 2.0 ng·hr/mL/mg to about 4.0 ng·hr/mL/mg, from about 2.5 ng·hr/mL/mg to about 3.0 ng·hr/mL/mg, or from about 3.0 ng·hr/mL/mg to about 3.5 ng·hr/mL/mg. In another embodiment, the $AUC_{0-4hr}$ for oxycodone may be about 2.0, 2.5, 3.0, 3.5, or 4.0 ng·hr/mL/mg.

In yet another embodiment, the pharmaceutical composition, when orally administered to a subject, may produce a plasma profile characterized by an $AUC_{Tmax-t}$ for oxycodone from about 5.0 ng·hr/mL/mg to about 16.0 ng·hr/mL/mg, from about 8.0 ng·hr/mL/mg to about 10.5 ng·hr/mL/mg, or from about 10.5 ng·hr/mL/mg to about 14.0 ng·hr/mL/mg. In another embodiment, the $AUC_{Tmax-t}$ for oxycodone may be about 5.0, 6.0, 7.0, 8.0, 9.0, 10.0, 11.0, 12.0, 12.5, 13.0, 13.5, 14.0, 14.5, 15.0 or 16.0 ng·hr/mL/mg.

In still another embodiment, the pharmaceutical composition, when orally administered to a subject, may produce a plasma profile characterized by an $AUC_{(0-(Tmax\ of\ IR\ product+2SD))}$ for oxycodone after a single dose from about 1.0 ng·hr/mL/mg to about 3.0 ng·hr/mL/mg, from about 1.50 ng·hr/mL/mg to about 2.5 ng·hr/mL/mg, or from about 1.75 ng·hr/mL/mg to about 2.25 ng·hr/mL/mg. In another embodiment, the $AUC_{(0-(Tmax\ of\ IR\ product+2SD))}$ for oxycodone may be about 1.25, 1.3, 1.35, 1.4, 1.45, 1.5, 1.55, 1.6, 1.65, 1.7, 1.75, 1.8, 1.85, 1.9, 1.95, 2.0, 2.05, 2.1, 2.15, 2.2, 2.25, 2.3, 2.35, 2.4, 2.45, 2.5, 2.55, 2.6, 2.65, 2.7, or 2.75 ng·hr/mL/mg.

In one embodiment, the immediate release product referenced for the Partial AUC calculations is PERCOCET (oxycodone and acetaminophen) in the fasted state and the following calculation was used to determine $AUC_{(0-(Tmax\ of\ IR\ product+2SD))}$:

oxycodone mean±SD=1.0h±0.89h; $T$max+2SD=2.8 hours

In such embodiment, the pharmaceutical composition, when orally administered to a subject, may produce a plasma profile characterized by an $AUC_{(0-2.8)}$ for oxycodone after a single dose from about 1.0 ng·hr/mL/mg to about 3.0 ng·hr/mL/mg, from about 1.50 ng·hr/mL/mg to about 2.5 ng·hr/mL/mg, or from about 1.75 ng·hr/mL/mg to about 2.25 ng·hr/mL/mg. In another embodiment, the $AUC_{(0-2.8)}$ for oxycodone may be about 1.25, 1.3, 1.35, 1.4, 1.45, 1.5, 1.55, 1.6, 1.65, 1.7, 1.75, 1.8, 1.85, 1.9, 1.95, 2.0, 2.05, 2.1, 2.15, 2.2, 2.25, 2.3, 2.35, 2.4, 2.45, 2.5, 2.55, 2.6, 2.65, 2.7, or 2.75 ng·hr/mL/mg.

In yet another embodiment, the pharmaceutical composition, when orally administered to a subject, may produce a plasma profile characterized by an $AUC_{(2.8-48)}$ for oxycodone after a single dose from about 7.5 ng·hr/mL/mg to about 15.0 ng·hr/mL/mg, from about 8.45 ng·hr/mL/mg to about 13.7 ng·hr/mL/mg, or from about 9.5 ng·hr/mL/mg to about 11.5 ng·hr/mL/mg. In another embodiment, the $AUC_{(2.8-48)}$ for oxycodone may be about 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, or 12.5 ng·hr/mL/mg.

In one embodiment, the immediate release product referenced for the Partial AUC calculations is PERCOCET (oxycodone and acetaminophen) in the fed state and the following calculation was used to determine $AUC_{(0-(Tmax\ of\ IR\ product+2SD))}$:

oxycodone mean±SD=1.9h±1.2h; $T$max+2SD=4.3 hours

In such embodiment, the pharmaceutical composition, when orally administered to a subject, may produce a plasma profile characterized by an $AUC_{(0-4.3)}$ for oxycodone after a single dose from about 1.5 ng·hr/mL/mg to about 5.5 ng·hr/mL/mg, from about 2.0 ng·hr/mL/mg to about 5.0 ng·hr/mL/mg, from about 2.5 ng·hr/mL/mg to about 4.5 ng·hr/mL/mg, or from about 3.0 ng·hr/mL/mg to about 4.0 ng·hr/mL/mg. In another embodiment, the $AUC_{(0-4.3)}$ for oxycodone may be about 1.5, 1.55, 1.6, 1.65, 1.7, 1.75, 1.8, 1.85, 1.9, 1.95, 2.0, 2.05, 2.1, 2.15, 2.2, 2.25, 2.3, 2.35, 2.4, 2.45, 2.5, 2.55, 2.6, 2.65, 2.7, 2.75, 2.8, 2.85, 2.9, 2.95, 3.0, 3.05, 3.1, 3.15, 3.2, 3.25, 3.3, 3.35, 3.4, 3.45, 3.5, 3.55, 3.6, 3.65, 3.7, 3.75, 3.8, 3.85, 3.9, 3.95, 4.0, 4.05, 4.1, 4.15, 4.2, 4.25, 4.3, 4.35, 4.4, 4.45, 4.5, 4.55, 4.6, 4.65, 4.7, 4.75, 4.8, 4.85, 4.9, 4.95, 5.0, 5.05, 5.1, 5.15, 5.2, 5.25, 5.3, 5.35, 5.4, 5.45, or 5.5 ng·hr/mL/mg.

In yet another embodiment, the pharmaceutical composition, when orally administered to a subject, may produce a plasma profile characterized by an $AUC_{(4.3-48)}$ for oxycodone after a single dose from about 5.0 ng·hr/mL/mg to about 15.0 ng·hr/mL/mg, from about 7.5 ng·hr/mL/mg to about 13.5 ng·hr/mL/mg, from about 9.0 ng·hr/mL/mg to about 12.0 ng·hr/mL/mg, or from about 9.5 ng·hr/mL/mg to about 11.5 ng·hr/mL/mg. In another embodiment, the $AUC_{(4.3-48)}$ for oxycodone may be about 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, or 15.0 ng·hr/mL/mg.

In one embodiment, the pharmaceutical composition, when orally administered to a subject in a fasted state, may produce a plasma profile characterized by an $AUC_{8-12hr}$ for oxycodone from about 3% to about 33% of the $AUC_{0-t}$, from about 10% to about 27% of the $AUC_{0-t}$, or from about 15% to about 22% of the $AUC_{0-t}$. In another embodiment, the pharmaceutical composition, when orally administered to a subject in a fed state, may produce a plasma profile characterized by an $AUC_{8-12hr}$ for oxycodone from about 5% to about 35% of the $AUC_{0-t}$, from about 12% to about 30% of the $AUC_{0-t}$, or from about 15% to about 25% of the $AUC_{0-t}$.

In an alternate embodiment, the pharmaceutical composition, when orally administered to a subject, may provide a mean half-life of oxycodone that ranges from about 3.5 hours to about 5.5 hours, or from about 4 hours to about 5 hours. In various embodiments, the mean half-life of oxycodone may be about 3.8, 4.0, 4.2, 4.4, 4.6, 4.8, 5.0, or 5.2 hours.

In yet another embodiment, the pharmaceutical composition, when orally administered to a subject, produces a plasma profile characterized by an abuse quotient for oxycodone from about 3 to about 5. In other embodiments, the abuse quotient for oxycodone may be about 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0.

Moreover, upon oral administration, the pharmaceutical composition disclosed herein may maintain a therapeutic plasma concentration of acetaminophen of at least about 2 mg/mL from about 1 hour to about 6 hours after administration. In another embodiment, the pharmaceutical composition may maintain a therapeutic plasma concentration of acetaminophen of at least about 2 mg/mL from about 0.75 hour to about 6.5 hours after administration. In yet another embodiment, the composition may maintain a plasma concentration of acetaminophen of at least about 1 mg/mL from about 0.5 hour to about 12 hours after administration.

In another embodiment, the pharmaceutical composition, when orally administered to a subject, may produce a plasma profile characterized by a mean $C_{max}$ for acetaminophen from about 4.0 ng/mL/mg to about 11.0 ng/mL/mg. In other embodiments, the mean $C_{max}$ for acetaminophen may be from about 4.0, 4.5, 5.0, 5.5, 6.0, 6.5, 7.0, 7.5, 8.0, 8.5, 9.0, 9.5, 10.0, 10.5, or 11.0 ng/mL/mg. Moreover, the mean $C_{max}$ for acetaminophen at steady state may range from about 6.0 ng/mL/mg to about 9.0 ng/mL/mg, from about 6.5 ng/mL/mg to about 8.5 ng/mL/mg, or from about 7.0 ng/mL/mg to about 8.0 ng/mL/mg.

In a further embodiment, the pharmaceutical composition, when orally administered to a subject, surprisingly may produce a blood plasma concentration profile characterized by a biphasic increase in blood plasma concentrations of acetaminophen. The biphasic absorption of acetaminophen may characterized by an initial rapid absorption resulting in first peak in plasma concentrations between about 0.5 hour and 2 hours, which contributes to the early onset on action, and a second peak in plasma concentrations between about 3 hours and 7 hours after administration of the composition, which contributes to the duration or maintenance of analgesia. In some instances, the second peak may correspond to the overall $C_{max}$ of the composition. The biphasic increase in blood plasma concentrations of acetaminophen is characterized by a plasma concentration-time profile for acetaminophen in which the slope of a line drawn between 0 hour and 2 hour is greater than the slope of a line drawn between about 2 hours and 5 hours. See FIG. 24.

This biphasic increase in acetaminophen levels resulting from the composition has several benefits. For example, the initial rapid rise in plasma levels produce quick onset of analgesia and the slower absorption provides maintenance of analgesia for an extended period of time.

In a further embodiment, the pharmaceutical composition, when orally administered to a subject, may produce a plasma profile characterized by a mean AUC for acetaminophen from about 35.0 ng·hr/mL/mg to about 80.0 ng·hr/mL/mg. In a further embodiment, the mean AUC for acetaminophen may range from about 35.0 ng·hr/mL/mg to about 60.0 ng·hr/mL/mg. In other embodiments, the mean AUC for acetaminophen may be about 35.0, 40.0, 45.0, 50.0, 55.0, 60.0, 65.0, 70.0, 75.0, or 80.0 ng·hr/mL/mg. Additionally, the mean AUC for acetaminophen at steady state may range from about 40.0 ng·hr/mL/mg to about 50.0 ng·hr/mL/mg, from about 35.0 ng·hr/mL/mg to about 45.0 ng·hr/mL/mg, or from about 37.0 ng·hr/mL/mg to about 42.0 ng·hr/mL/mg.

In yet another embodiment, the pharmaceutical composition when orally administered to a subject, may produce a plasma profile characterized by a median $T_{max}$ for acetaminophen from about 0.5 hours to about 6.0 hours. In another embodiment, the median $T_{max}$ for acetaminophen may be from about 1.0 hour to about 5.0 hours. In a further embodiment, the median $T_{max}$ for acetaminophen may range from about 0.5 hour to about 4.0 hours. In still another embodiment, the median $T_{max}$ for acetaminophen may range from about 0.75 to about 1.5 hours. In other embodiments, the median $T_{max}$ may be about 0.5, 0.6, 0.7, 0.8, 0.9, 1.0, 1.1, 1.2, 1.3, 1.4, 1.5, 1.6, 1.7 1.8, 1.9, 2.0, 2.2, 2.4, 2.6, 2.8, 3.0, 3.2, 3.4, 3.6, 3.8, 4.0, 4.2, 4.4, 4.6, 4.8, or 5.0 hours. Moreover, the median $T_{max}$ for acetaminophen at steady state may range from about 0.5 hour to about 1.0 hour, or from about 0.5 hour to about 0.75 hour.

In a further embodiment, the pharmaceutical composition, when orally administered to a subject, may produce a plasma profile characterized by a median $t_{lag}$ for acetaminophen from about 0 hour to about 0.5 hour. In an alternate embodiment, the median $t_{lag}$ for acetaminophen may be from about 0 hour to about 0.25 hour. In one embodiment, the median $t_{lag}$ for acetaminophen may be 0 hour. In another embodiment, the median $t_{lag}$ for acetaminophen may be 0.25 hour.

In one embodiment, the pharmaceutical composition, when orally administered to a subject, may produce a plasma profile characterized by various partial AUCs for acetaminophen. The partial AUCs for acetaminophen are calculated as described above for oxycodone. The pharmaceutical composition, when orally administered to a subject, may produce a plasma profile characterized by an $AUC_{0-1hr}$ for acetaminophen from about 1.25 ng·hr/mL/mg to about 3.25 ng·hr/mL/mg, from about 1.60 ng·hr/mL/mg to about 2.0 ng·hr/mL/mg, or from about 2.0 ng·hr/mL/mg to about 2.75 ng·hr/mL/mg. In another embodiment, the $AUC_{0-1hr}$ for acetaminophen may be about 1.25, 1.30, 1.40, 1.50, 1.55, 1.60, 1.65, 1.70, 1.75, 1.80, 1.85, 1.90, 1.95, 2.0, 2.05, 2.10, 2.15, 2.20, 2.25, 2.30, 2.35, 2.40, 2.45, 2.50, 2.55, 2.60, 2.65, 2.70, 2.75, 2.80, 2.85, or 2.90 or ng·hr/mL/mg.

In an additional embodiment, the pharmaceutical composition, when orally administered to a subject, may produce a plasma profile characterized by an $AUC_{0-2hr}$ for acetaminophen from about 4.25 ng·hr/mL/mg to about 8.75 ng·hr/mL/mg, from about 5.50 ng·hr/mL/mg to about 6.0 ng·hr/mL/mg, or from about 6.0 ng·hr/mL/mg to about 7.25 ng·hr/mL/mg. In another embodiment, the $AUC_{0-2hr}$ for acetaminophen may be about 4.25, 4.5, 4.75, 5.0, 5.25, 5.5, 5.75, 6.0, 6.25, 6.5, 6.75, 7.0, 7.25, 7.50, 7.75 or 8.0 ng·hr/mL/mg.

In a further embodiment, the pharmaceutical composition, when orally administered to a subject, may produce a plasma profile characterized by an $AUC_{0-4hr}$ for acetaminophen from about 10.0 ng·hr/mL/mg to about 20.0 ng·hr/mL/mg, from about 13.0 ng·hr/mL/mg to about 14.5 ng·hr/mL/mg, or from about 14.5 ng·hr/mL/mg to about 16.5 ng·hr/mL/mg. In another embodiment, the $AUC_{0-4hr}$ for acetaminophen may be about 10.0, 11.0, 12.0, 13.0, 13.5, 14.0, 14.5, 15.0, 15.5, 16.0, 16.5, or 17.0 ng·hr/mL/mg.

In yet another embodiment, the pharmaceutical composition, when orally administered to a subject, may produce a plasma profile characterized by an $AUC_{Tmax-t}$ for acetaminophen from about 20.0 ng·hr/mL/mg to about 40.0 ng·hr/mL/mg, from about 23.5 ng·hr/mL/mg to about 36.0 ng·hr/mL/mg, or from about 29.0 ng·hr/mL/mg to about 31.0 ng·hr/mL/mg. In another embodiment, the $AUC_{Tmax-t}$ for acetaminophen may be about 20.0, 21.0, 22.0, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5 or 36.0 ng·hr/mL/mg.

In yet another embodiment, the pharmaceutical composition, when orally administered to a subject, may produce a plasma profile characterized by an $AUC_{(0-(Tmax\ of\ IR\ product+2SD))}$ for acetaminophen after a single dose from about 5.0 ng·hr/mL/mg to about 13.0 ng·hr/mL/mg, from about 7.2 ng·hr/mL/mg to about 11.6 ng·hr/mL/mg, or from about 8.5 ng·hr/mL/mg to about 10.0 ng·hr/mL/mg. In another embodiment, the $AUC_{(0-(Tmax\ of\ IR\ product+2SD))}$ for acetaminophen may be about 5.0, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, or 12.0 ng·hr/mL/mg.

In one embodiment, the immediate release product referenced for the Partial AUC calculations is PERCOCET (oxycodone and acetaminophen) in the fasted state and the following calculation was used to determine $AUC_{(0-(Tmax\ of\ IR\ product+2SD))}$:

acetaminophen mean±SD=0.596h±0.529h; Tmax+2SD=1.65 hour

In such embodiment, the pharmaceutical composition, when orally administered to a subject, may produce a plasma profile characterized by an $AUC_{(0-1.7)}$ for acetaminophen after a single dose from about 5.0 ng·hr/mL/mg to about 13.0 ng·hr/mL/mg, from about 7.2 ng·hr/mL/mg to about 11.6 ng·hr/mL/mg, or from about 8.5 ng·hr/mL/mg to about 10.0 ng·hr/mL/mg. In another embodiment, the $AUC_{(0-1.7)}$ for acetaminophen may be about 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, or 12.0 ng·hr/mL/mg.

In still a further embodiment, the pharmaceutical composition, when orally administered to a subject, may produce a plasma profile characterized by an $AUC_{(1.7-48)}$ for acetaminophen after a single dose from about 25.0 ng·hr/mL/mg to about 75.0 ng·hr/mL/mg, from about 31.5 ng·hr/mL/mg to about 55.0 ng·hr/mL/mg, or from about 35.0 ng·hr/mL/mg to about 50.0 ng·hr/mL/mg. In another embodiment, the $AUC_{(1.7-48)}$ for acetaminophen may be about 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, 40.5, 41.0, 41.5, 42.0, 42.5, 43.0, 43.5, 44.0, 44.5, 45.0, 45.5, 46.0, 46.5, 47.0, 47.5, 48.0, 48.5, 49.0, 49.5, 50.0, 50.5, 51.0, 51.5, 52.0, 52.5, 53.0, 53.5, 54.0, 54.5, or 55.0 ng·hr/mL/mg.

In one embodiment, the immediate release product referenced for the Partial AUC calculations is PERCOCET (oxycodone and acetaminophen) in the fed state and the following calculation was used to determine $AUC_{(0-(Tmax\ of\ IR\ product+2SD))}$:

acetaminophen mean±SD=1.48h±0.875h; Tmax+2SD=3.2 hour

In such embodiment, the pharmaceutical composition, when orally administered to a subject, may produce a plasma profile characterized by an $AUC_{(0-3.2)}$ for acetaminophen after a single dose from about 7.0 ng·hr/mL/mg to about 21.0 ng·hr/mL/mg, from about 9.0 ng·hr/mL/mg to about 18.0 ng·hr/mL/mg, from about 10.0 ng·hr/mL/mg to about 16.0 ng·hr/mL/mg, or from about 12.0 ng·hr/mL/mg to about 15.0 ng·hr/mL/mg. In another embodiment, the $AUC_{(0-3.2)}$ for acetaminophen may be about 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, 15.0, 15.1, 15.2, 15.3, 15.4, 15.5, 15.6, 15.7, 15.8, 15.9, 16.0, 16.1, 16.2, 16.3, 16.4, 16.5, 16.6, 16.7, 16.8, 16.9, 17.0, 17.1, 17.2, 17.3, 17.4, 17.5, 17.6, 17.7, 17.8, 17.9, 18.0, 18.1, 18.2, 18.3, 18.4, 18.5, 18.6, 18.7, 18.8, 18.9, 19.0, 19.1, 19.2, 19.3, 19.4, 19.5, 19.6, 19.7, 19.8, 19.9, 20.0, 20.1, 20.2, 20.3, 20.4, 20.5, 20.6, 20.7, 20.8, 20.9, or 21.0 ng·hr/mL/mg.

In still a further embodiment, the pharmaceutical composition, when orally administered to a subject, may produce a plasma profile characterized by an $AUC_{(3.2-48)}$ for acetaminophen after a single dose from about 15.0 ng·hr/mL/mg to about 75.0 ng·hr/mL/mg, from about 25.0 ng·hr/mL/mg to about 55.0 ng·hr/mL/mg, from about 27.5 ng·hr/mL/mg to about 45.0 ng·hr/mL/mg, or from about 30.0 ng·hr/mL/mg to about 40.0 ng·hr/mL/mg. In another embodiment, the $AUC_{(3.2-48)}$ for acetaminophen may be about 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, 40.5, 41.0, 41.5, 42.0, 42.5, 43.0, 43.5, 44.0, 44.5, 45.0, 45.5, 46.0, 46.5, 47.0, 47.5, 48.0, 48.5, 49.0, 49.5, 50.0, 50.5, 51.0, 51.5, 52.0, 52.5, 53.0, 53.5, 54.0, 54.5, 55.0, 55.5, 56.0, 56.5, 57.0, 57.5, 58.0, 58.5, 59.0, 59.5, 60.0, 60.5, 61.0, 61.5, 62.0, 62.5, 63.0, 63.5, 64.0, 64.5, 65.0, 65.5, 66.0, 66.5, 67.0, 67.5, 68.0, 68.5, 69.0, 69.5, 70.0, 70.5, 71.0, 71.5, 72.0, 72.5, 73.0, 73.5, 74.0, 74.5, or 75.0 ng·hr/mL/mg.

In one embodiment, the pharmaceutical composition, when orally administered to a subject, may produce a plasma profile characterized by an $AUC_{0-12hr}$ for acetaminophen from about 20.0 ng·hr/mL/mg to about 60.0 ng·hr/mL/mg, from about 30 ng·hr/mL/mg to about 50 ng·hr/mL/mg, from about 35 to about 45 ng·hr/mL/mg, or from about 37.5 ng·hr/mL/mg to about 42.5 ng·hr/mL/mg. In another embodiment, the pharmaceutical composition, when orally administered to a subject, may produce a plasma profile characterized by an $AUC_{0-12hr}$ for acetaminophen from about 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, 40.5, 41.0, 41.5, 42.0, 42.5, 43.0, 43.5, 44.0, 44.5, 45.0, 45.5, 46.0, 46.5, 47.0, 47.5, 48.0, 48.5, 49.0, 49.5, 50.0, 50.5, 51.5, 52.0, 52.5, 53.0, 53.5, 54.0, 54.5, or 55.0. In a further embodiment, at $AUC_{0-12hr}$ between about 70%-95%, about 75%-92%, or about 77%-90% of the acetaminophen has been cleared. In still another embodiment, about 80% of the acetaminophen has been cleared.

In another embodiment, the pharmaceutical composition, when orally administered to a subject, may produce a plasma profile characterized by an $AUC_{1-12hr}$ for acetaminophen from about 15.0 ng·hr/mL/mg to about 55.0 ng·hr/mL/mg, from about 25.0 ng·hr/mL/mg to about 45.0 ng·hr/mL/mg, or from about 30.0 to about 40.0 ng·hr/mL/mg. In another embodiment, the pharmaceutical composition, when orally administered to a subject, may produce a plasma profile characterized by an $AUC_{1-12hr}$ for acetaminophen from about 15, 16, 17, 18, 19, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, 40.5, 41.0, 41.5, 42.0, 42.5, 43.0, 43.5, 44.0, 44.5, 45.0, 45.5, 46.0, 46.5, 47.0, 47.5, 48.0, 48.5, 49.0, 49.5, or 50.0 ng·hr/mL/mg.

In yet another embodiment, the pharmaceutical composition, when orally administered to a subject, may produce a plasma profile characterized by an $AUC_{12-36hr}$ for acetaminophen from about 5.0 ng·hr/mL/mg to about 25.0 ng·hr/mL/mg, from about 7.5 ng·hr/mL/mg to about 20.0 ng·hr/mL/mg, or from about 10.0 ng·hr/mL/mg to about 15.0. In other embodiments, the pharmaceutical composition, when orally administered to a subject, may produce a plasma profile characterized by an $AUC_{12-36hr}$ for acetaminophen from about 5.0, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, or 15.0 ng·hr/mL/mg.

In another embodiment, the pharmaceutical composition, when orally administered to a subject, may produce a plasma profile characterized by an $AUC_{8-12hr}$ for acetaminophen from about 1.5 ng·hr/mL/mg to about 15.5 ng·hr/mL/mg, from about 2 ng·hr/mL/mg to about 12.25 ng·hr/mL/mg, from about 3.5 ng·hr/mL/mg to about 10 ng·hr/mL/mg, or from about 4.5 ng·hr/mL/mg to about 6.5 ng·hr/mL/mg. In other embodiments, the pharmaceutical composition, when orally administered to a subject, may produce a plasma profile characterized by an $AUC_{8-12hr}$ for acetaminophen from about 1.5, 1.75, 2.0, 2.25, 2.5, 2.75, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, or 12.0 ng·hr/mL/mg.

In one embodiment, the pharmaceutical composition, when orally administered to a subject, may produce a plasma profile characterized by an $AUC_{(0-3hr)}$ for acetaminophen from about 5 ng·hr/mL/mg to about 30 ng·hr/mL/mg, from about 10 ng·hr/mL/mg to about 20 ng·hr/mL/mg, or from about 13 ng·hr/mL/mg to about 17 ng·hr/mL/mg. In other embodiments, the pharmaceutical composition, when orally administered to a subject, may produce a plasma profile characterized by an $AUC_{(0-3hr)}$ for acetaminophen from about 5.0, 6.0, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, 15.0, 15.1, 15.2, 15.3, 15.4, 15.5, 15.6, 15.7, 15.8, 15.9, 16.0, 16.1, 16.2, 16.3, 16.4, 16.5, 16.6, 16.7, 16.8, 16.9, 17.0, 17.1, 17.2, 17.3, 17.4, 17.5, 17.6, 17.7, 17.8, 17.9, 18.0, 18.1, 18.2, 18.3, 18.4, 18.5, 18.6, 18.7, 18.8, 18.9, 19.0, 19.1, 19.2, 19.3, 19.4, 19.5, 19.6, 19.7, 19.8, 19.9, or 20.0 ng·hr/mL/mg.

In another embodiment, the pharmaceutical composition, when orally administered to a subject, may produce a plasma profile characterized by an $AUC_{(3-36hr)}$ for acetaminophen from about 20 ng·hr/mL/mg to about 50 ng·hr/mL/mg, from about 20 ng·hr/mL/mg to about 40 ng·hr/mL/mg, or from about 25 ng·hr/mL/mg to about 35 ng·hr/mL/mg. In other embodiments, the pharmaceutical composition, when orally administered to a subject, may produce a plasma profile characterized by an $AUC_{(3-36hr)}$ for acetaminophen from about 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 31.5, 32, 32.5, 33, 33.5, 34, 34.5, 35, 35.5, 36, 36.5, 37, 37.5, 38, 38.5, 39, 39.5, 40, 40.5, 41, 41.5, 42, 42.5, 43, 43.5, 44, 44.5, 45, 45.5, 46, 46.5, 47, 47.5, 48, 48.5, 49, 49.5, or 50 ng·hr/mL/mg.

In one embodiment, the pharmaceutical composition, when orally administered to a subject, may produce a plasma profile characterized by an $AUC_{0-12hr}$ for acetaminophen from about 50% to about 90% of the $AUC_{0-t}$, from about 55% to about 85% of the $AUC_{0-t}$, or from about 75% to about 85% of the $AUC_{0-t}$. In other embodiments, the pharmaceutical composition, when orally administered to a subject, may produce a plasma profile characterized by an $AUC_{0-12hr}$ for acetaminophen that is about 50%, 55%, 60%, 65%, 70%, 75%, 76%, 77%, 78%, 79%, 80%, 81%, 82%, 83%, 84% or 85% of the $AUC_{0-t}$.

In one embodiment, the pharmaceutical composition, when orally administered to a subject, may produce a plasma profile characterized by an $AUC_{1-12hr}$ for acetaminophen from about 40% to about 90% of the $AUC_{0-t}$, from about 55% to about 85% of the $AUC_{0-t}$, or from about 60% to about 75% of the $AUC_{0-t}$. In other embodiments, the pharmaceutical composition, when orally administered to a subject, may produce a plasma profile characterized by an $AUC_{1-12hr}$ for acetaminophen of about 40%, 45%, 50%, 55%, 60%, 61%, 62%, 63%, 64%, 65%, 66%, 67%, 68%, 69%, 70%, 71%, 72%, 73%, 74%, 75%, 76%, 77%, 78%, 79%, or 80% of the $AUC_{0-t}$.

In one embodiment, the pharmaceutical composition, when orally administered to a subject, may produce a plasma profile characterized by an $AUC_{12-36hr}$ for acetaminophen from about 10% to about 40% of the $AUC_{0-t}$, from about 15% to about 35% of the $AUC_{0-t}$, or from about 20% to about 30% of the $AUC_{0-t}$. In other embodiments, the pharmaceutical composition, when orally administered to a subject, may produce a plasma profile characterized by an $AUC_{12-36hr}$ for acetaminophen of about 10%, 12%, 14%, 16%, 18%, 20%, 21%, 22%, 23%, 24%, 25%, 26%, 27%, 28%, 29%, or 30% of the $AUC_{0-t}$.

In one embodiment, the pharmaceutical composition, when orally administered to a subject, may produce a plasma profile characterized by an $AUC_{8-12hr}$ for acetaminophen from about 5% to about 30% of the $AUC_{0-t}$, from about 7% to about 25% of the $AUC_{0-t}$, or from about 10% to about 20% of the $AUC_{0-t}$. In other embodiments, the pharmaceutical composition, when orally administered to a subject, may produce a plasma profile characterized by an $AUC_{8-12hr}$ for acetaminophen of about 5%, 6%, 7%, 8%, 9%, 10%, 11%, 12%, 13%, 14%, 15%, 16%, 17%, 18%, 19%, 20%, 21%, 22%, 23%, 24%, or 25% of the $AUC_{0-t}$.

In an alternate embodiment, the pharmaceutical composition, when orally administered to a subject, may have a mean half-life of acetaminophen that ranges from about 2 hours to about 10 hours, or from about 3 hours to about 6 hours. In another embodiment, the pharmaceutical composition, when orally administered to a subject, may have a mean half-life of acetaminophen that ranges from about 3 hours to about 5 hours. In still another embodiment, the pharmaceutical composition, when orally administered to a subject, may have a mean half-life of acetaminophen that ranges from about 4 hours to about 5 hours. In various embodiments, the mean half-life of acetaminophen may be about 2.5, 3.0, 3.5, 4.0, 4.5, 5.0, 5.5, 6.0, 6.5, 6.0, 7.0, 7.5, or 8 hours. In additional embodiments, the pharmaceutical composition, when orally administered to a subject, has a mean observed half-life of acetaminophen that is more than the mean half-life of commercially available immediate release acetaminophen products.

In another embodiment, upon administration of the pharmaceutical composition to a subject, the composition may provide at least about 4 hours to about 12 hours of drug delivery to the upper gastrointestinal tract, which includes the duodenum, jejunum, and ileum of the small intestine. In another embodiment, the composition may provide at least about 6 hours of drug delivery to the upper gastrointestinal tract. In yet a further embodiment, the composition may provide at least about 8 hours of drug delivery to the upper gastrointestinal tract. In yet a further embodiment, the composition may provide at least about 9 hours, or at least about 10 hours of drug delivery to the upper gastrointestinal tract.

In yet another embodiment, upon administration of the pharmaceutical composition to a subject, APAP undergoes presystemic metabolism in the gut and/or liver allowing only a fraction of the drug to reach the systemic circulation. The fraction of drug that is originally absorbed prior to presystemic metabolism is referred to as the fraction absorbed and denoted "Fab." This is different from the fraction bioavailable "F," which is the fraction that reaches the systemic circulation after the metabolism in the gut and liver.

Figure 27A:
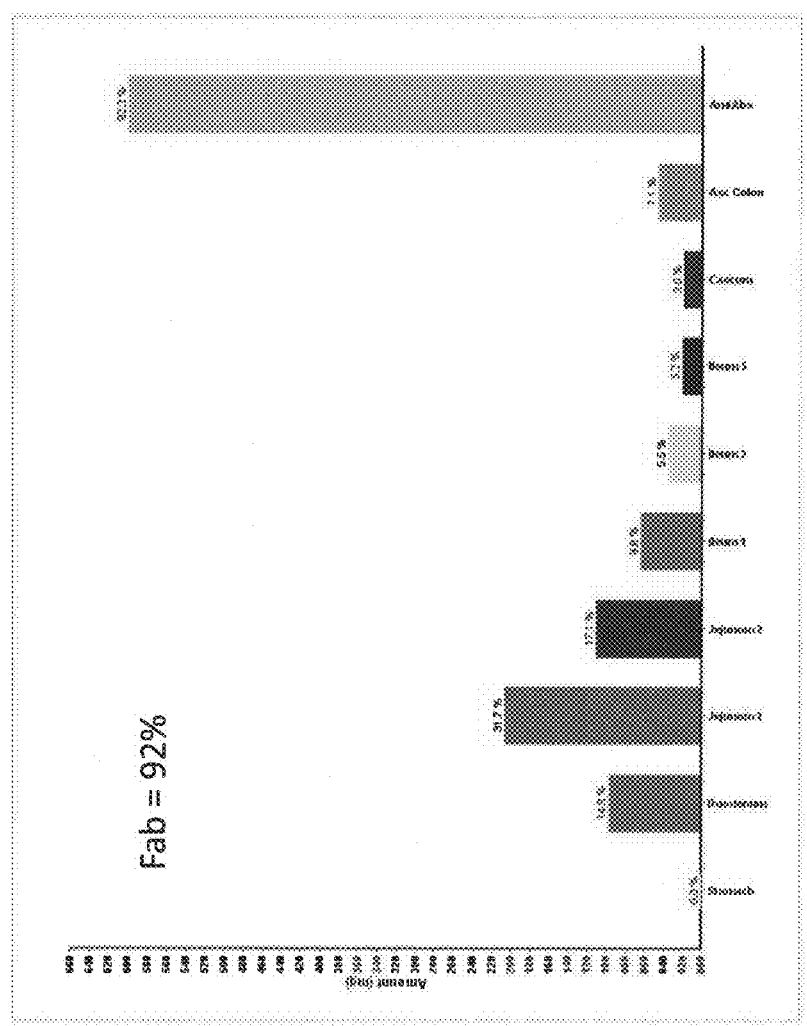
FIG. 27A is a bar graph depicting the simulated fractional absorption of acetaminophen in the upper GIT of a human subject after treatment of a 7.5 mg oxycodone/325 mg acetaminophen immediate release formulation.
Figure 27B:
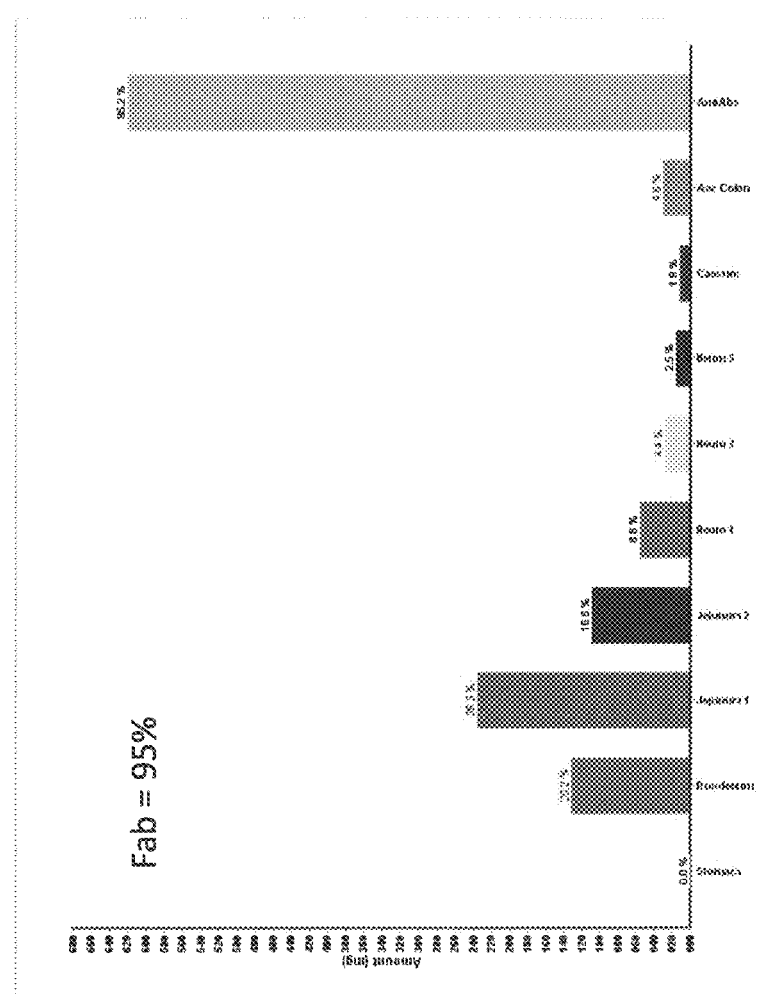
FIG. 27B is a bar graph depicting the simulated fractional absorption of acetaminophen in the upper GIT of a human subject after treatment of a 7.5 mg oxycodone/325 mg acetaminophen immediate release formulation, wherein the formulation's transit time from the stomach through ileum 3 has been doubled.
Figure 27C:
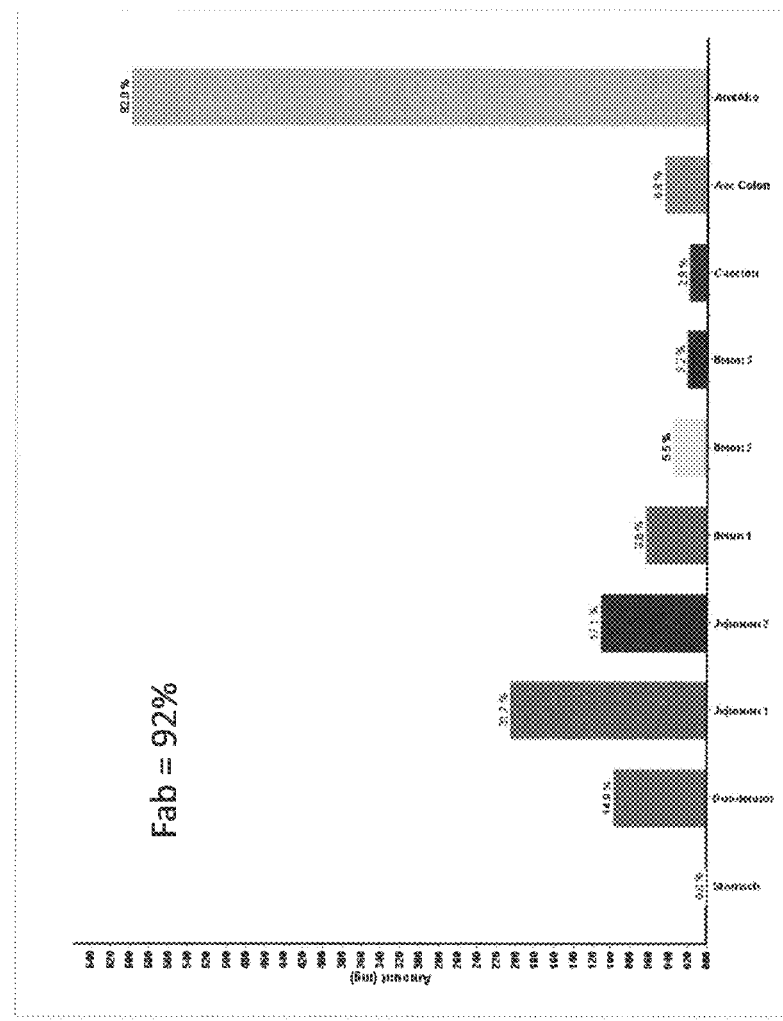
FIG. 27C is a bar graph depicting the simulated fractional absorption of acetaminophen in the upper GIT of a human subject after treatment of a 7.5 mg oxycodone/325 mg acetaminophen immediate release formulation, wherein the formulation's transit time in the stomach has been increased by two hours.

In another embodiment, 60-90% of the acetaminophen in the pharmaceutical composition, which is available for absorption into the systemic circulation, is absorbed in the upper gastrointestinal tract. In still another embodiment, 60-85% of acetaminophen in the pharmaceutical composition, which is available for absorption into the systemic circulation, is absorbed in the duodenum and jejunum. See FIG. 27. Greater than 50% absorption of acetaminophen in the upper gastrointestinal tract is beneficial to a human subject because acetaminophen is poorly absorbed in the stomach and well absorbed in the small intestine and particularly, the upper segment of the gastrointestinal tract. It is therefore critical that acetaminophen is available in upper small intestine for its absorption. In one embodiment acetaminophen is released in stomach and reaches quickly into upper part of the small intestine for the absorption to take place.

In another embodiment, when about 60% to about 75% of the acetaminophen is released from the dosage form in the stomach within 2 hours following oral administration, about 10% to about 25% of the total amount of the acetaminophen in the dosage form, which is available for absorption into the systemic circulation, is absorbed in the duodenum, about 25% to about 40% is absorbed in the proximal jejunum (noted as "jejunum 1" in FIG. 27), about 15% to about 20% is absorbed in the distal jejunum (noted as "jejunum 2" in FIG. 27), and about 5% to about 15% is absorbed in the ileum.

In another embodiment, when about 70% to about 90% of the acetaminophen is released from the dosage form in the stomach within 4 hours following oral administration, about 10% to about 25% of the total amount of the acetaminophen in the dosage form, which is available for absorption into the systemic circulation, is absorbed in the duodenum, about 25% to about 40% is absorbed in the proximal jejunum (noted as "jejunum 1" in FIG. 27), about 15% to about 20% is absorbed in the distal jejunum (noted as "jejunum 2" in FIG. 27), and about 5% to about 15% is absorbed in the ileum.

In yet another embodiment, when at least about 55% of the total amount of the acetaminophen is released from the dosage form in the stomach within 1 hour after oral administration and when at least about 60% of the acetaminophen is released in the stomach after 2 hours, about 15% to about 20% of the total amount of the acetaminophen in the dosage form, which is available for absorption into the systemic circulation, is absorbed in the duodenum, about 30% to about 37% is absorbed in the proximal jejunum, about 15% to about 18% is absorbed in the distal jejunum, and about 8% to about 10% is absorbed in the ileum.

In still another embodiment, upon administration of the pharmaceutical composition to a subject, the opioid undergoes presystemic metabolism in the gut and/or liver allowing only a fraction of the drug to reach the systemic circulation. The fraction of drug that is originally absorbed prior to pre-systemic metabolism is referred to as the fraction absorbed and denoted "Fab." In one embodiment, the opioid is oxycodone. This is different from the fraction bioavailable "F," which is the fraction that reaches the systemic circulation after metabolism in the gut and liver.

Figure 28A:
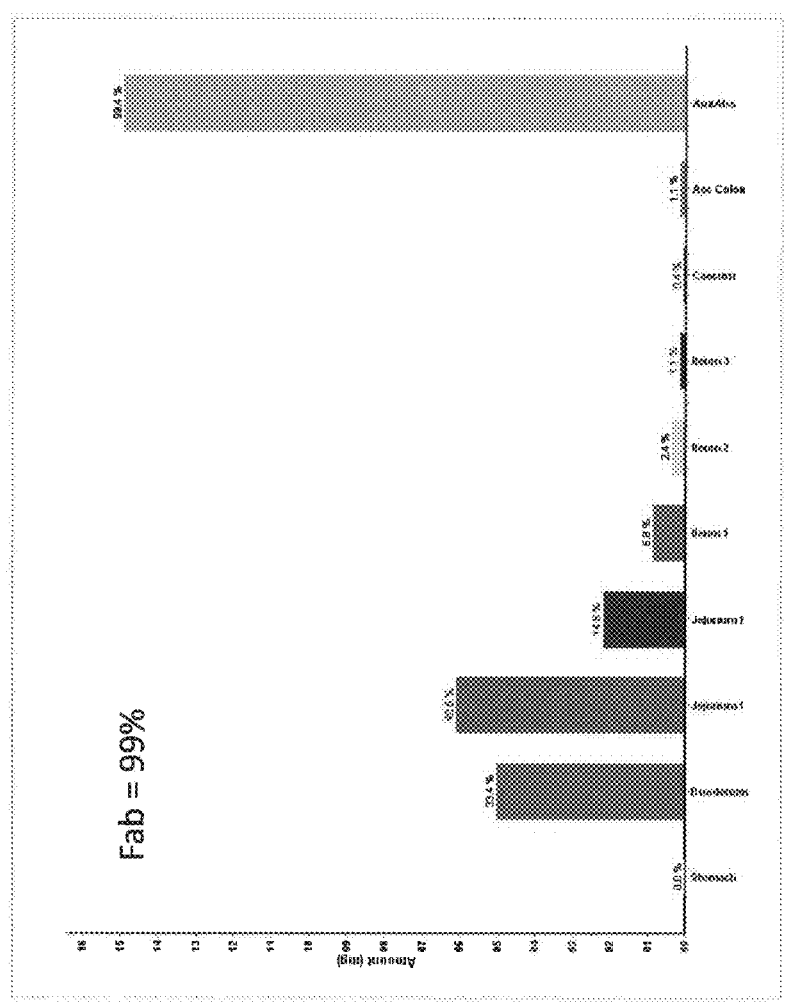
FIG. 28A is a bar graph depicting the simulated fractional absorption of oxycodone in the upper GIT of a human subject after treatment of a 7.5 mg oxycodone/325 mg acetaminophen immediate release formulation.
Figure 28B:
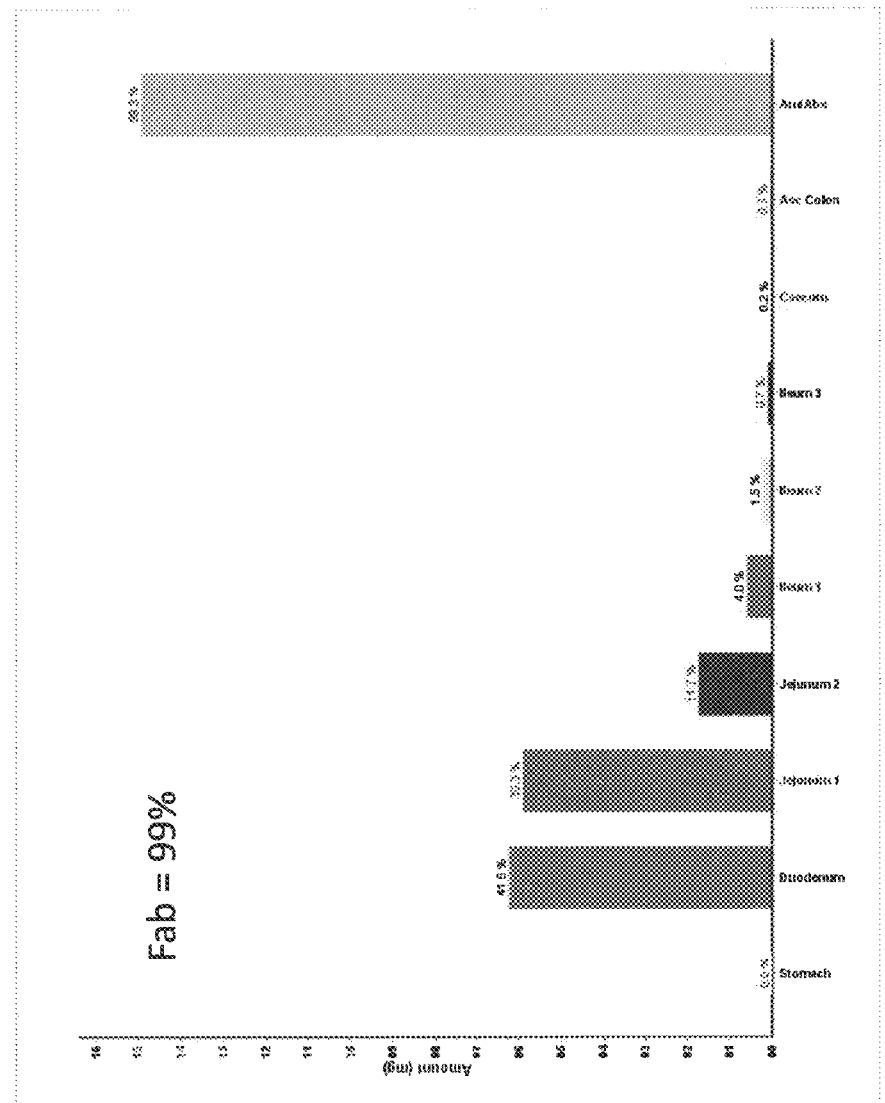
FIG. 28B is a bar graph depicting the simulated fractional absorption of oxycodone in the upper GIT of a human subject after treatment of a 7.5 mg oxycodone/325 mg acetaminophen immediate release formulation, wherein the formulation's transit time from the stomach through ileum 3 has been doubled.
Figure 28C:
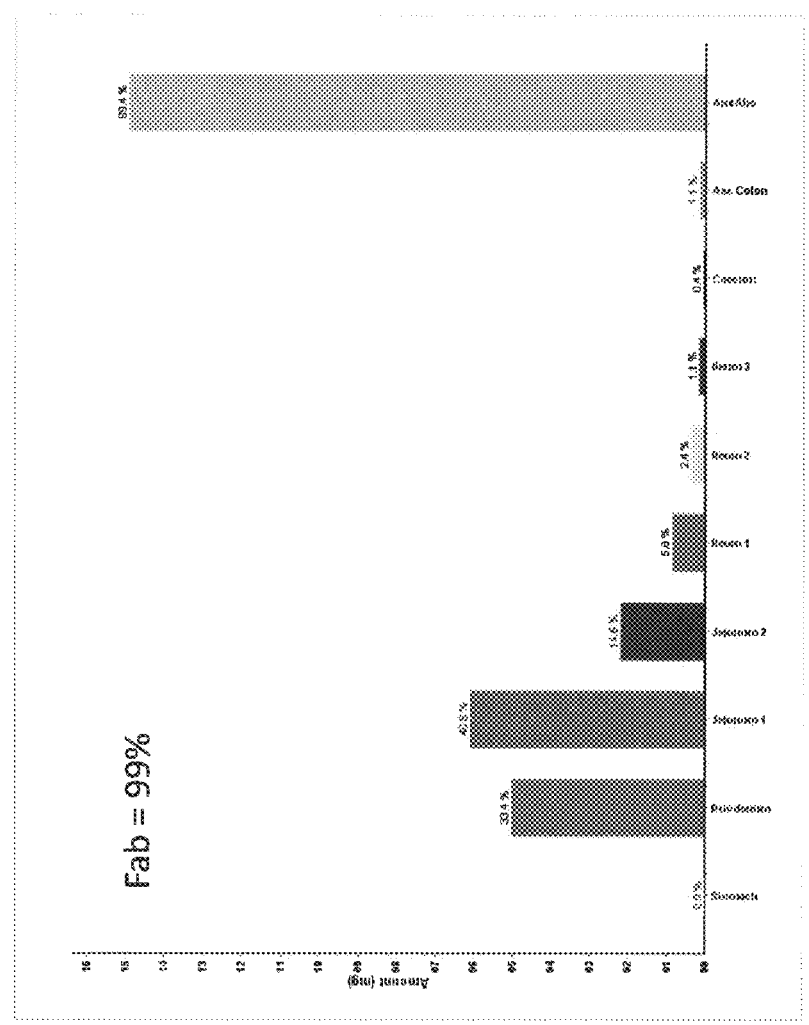
FIG. 28C is a bar graph depicting the simulated fractional absorption of oxycodone in the upper GIT of a human subject after treatment of a 7.5 mg oxycodone/325 mg acetaminophen immediate release formulation, wherein the formulation's transit time in the stomach has been increased by two hours.

In a further embodiment, 70-95% of the oxycodone in the pharmaceutical composition, which is available for absorption into the systemic circulation, is absorbed in the upper gastrointestinal tract. In still another embodiment, 80-95% of oxycodone in the pharmaceutical composition, which is available for absorption into the systemic circulation, is absorbed in the duodenum and jejunum. See FIG. 28.

In one embodiment, the composition releases the opioid and other API in the stomach to optimize drug absorption in the duodenum and jejunum. For example, when about 25% to about 50% of oxycodone is released from the dosage form in the stomach within 1 hour following oral administration, about 10% to about 45% of the total amount of the oxycodone in the dosage form, which is available for absorption into the systemic circulation, is absorbed in the duodenum, about 25% to about 50% is absorbed in the proximal jejunum (noted as "jejunum 1" in FIG. 28), about 7% to about 20% is absorbed in the distal jejunum (noted as "jejunum 2" in FIG. 28), and about 2% to about 15% is absorbed in the ileum.

In another embodiment, when about 45% to about 65% of oxycodone is released from the dosage form in the stomach within 2 hours following oral administration, about 10% to about 50% of the total amount of the oxycodone in the dosage form, which is available for absorption into the systemic circulation, is absorbed in the duodenum, about 25% to about 55% is absorbed in the proximal jejunum (noted as "jejunum 1" in FIG. 28), about 5% to about 25% is absorbed in the distal jejunum (noted as "jejunum 2" in FIG. 28), and about 2% to about 15% is absorbed in the ileum.

In another embodiment, when about 60% to about 85% of oxycodone is released from the dosage form in the stomach within 4 hours following oral administration, about 10% to about 55% of the total amount of the oxycodone in the dosage form, which is available for absorption into the systemic circulation, is absorbed in the duodenum, about 30% to about 60% is absorbed in the proximal jejunum (noted as "jejunum 1" in FIG. 28), about 10% to about 30% is absorbed in the distal jejunum (noted as "jejunum 2" in FIG. 28), and about 2% to about 20% is absorbed in the ileum.

In yet another embodiment, when at least 25% of the total amount of the oxycodone is released from the dosage form in the stomach within 1 hour after oral administration and when at least 45% of the oxycodone is released in the stomach after 2 hours, about 30% to about 45% of the total amount of oxycodone in the dosage form, which is available for absorption into the systemic circulation, is absorbed in the duodenum, about 37% to about 43% is absorbed in the proximal jejunum (noted as "jejunum 1" in FIG. 28), about 10% to about 15% is absorbed in the distal jejunum (noted as "jejunum 2" in FIG. 28), and about 2% to about 8% is absorbed in the ileum.

In another embodiment, about 90% to about 100% of the IR dose of acetaminophen is released within about 15 minutes, 30 minutes, 45 minutes or 60 minutes after oral administration. In one embodiment, the dosage form provides a dissolution profile wherein about 20% to about 65%, about 35% to about 55% or about 40% to about 50% of the ER dose of acetaminophen remains in the ER layer between about 1 and 2 hours after administration. In one embodiment, not more than 50% of the ER dose of acetaminophen is released within about the first hour. In a further embodiment, not more than 45% or not more than 40% of the ER dose of acetaminophen is released within about the first hour. In another embodiment, not more than 85% of the ER dose of acetaminophen is released within about 4 hours. In yet another embodiment, not less than 50% is released after about 6 hours. In yet another embodiment, not less than 60% is released after about 6 hours. In one embodiment, the ER dose of acetaminophen is released over a time period of about 6 to 12, about 8 to 10, or about 9 to 10 hours in vitro. In another embodiment, the ER dose of acetaminophen is released over a time period of about 7 hours, 8 hours, 9 hours, 10 hours, 11 hours or 12 hours in vitro. In another embodiment, at least 90% or 95% of the ER dose of acetaminophen is released over a time period of about 7 hours, 8 hours, 9 hours, 10 hours, 11 hours or 12 hours in vitro.

In one embodiment, the pharmaceutical compositions disclosed herein rapidly achieve therapeutic plasma drug levels of oxycodone and acetaminophen similar to an immediate release product, which provides an early onset of action within about the first 5 minutes, 10 minutes, 15 minutes, 20 minutes, 25 minutes, 30 minutes, 35 minutes, 40 minutes, 45 minutes, 50 minutes, 55 minutes or 60 minutes after administration of the composition, but unlike an immediate release product, the pharmaceutical composition is able to maintain those therapeutic plasma drug levels of oxycodone and acetaminophen over an extended period of time (e.g., up to 12 hours). Currently, there is no pharmaceutical composition available comprising oxycodone and acetaminophen which is able to provide a patient with quick onset of analgesia and maintenance of analgesia for an extended period of time.

In yet another embodiment, upon average, within one hour of administration to a subject, the pharmaceutical composition achieves a Cmax for acetaminophen. The Cmax achieved by the pharmaceutical composition disclosed herein is comparable to the Cmax obtained from a commercially-available immediate release product containing acetaminophen formulated at half the strength of the commercially-available immediate release product. The acetaminophen continues to be released from the pharmaceutical composition at a rate less than the clearance rate for the acetaminophen, so that the acetaminophen levels fall smoothly until all of the acetaminophen is absorbed. Stated another way, the acetaminophen released by the pharmaceutical composition is eliminated by the body faster than it is being absorbed. The absorption of the acetaminophen released from the pharmaceutical composition is complete in about 8 to about 10 hours so that for one half life of acetaminophen the blood supply reaching the subject's liver via the portal vein contains no additional amounts of acetaminophen beyond the amounts present in the subject's general circulation.

These additional amounts of acetaminophen delivered to the liver from the subject's portal vein are frequently caused by the absorption of acetaminophen in the subject's gastrointestinal tract. Indeed, blood from the subject's intestines passes through the liver and then on to the general circulation. When acetaminophen is undergoing absorption, blood containing acetaminophen from the absorption process passes through the subject's liver prior to entering the general circulation where the acetaminophen is diluted by the distribution and clearance processes. The metabolism of these higher acetaminophen concentrations in blood coming into the subject's liver is termed the "first pass effect." Hence, the absorption process for acetaminophen taxes a subject's metabolic systems in the liver due to these higher "first pass" concentrations. Once the absorption process is complete, the concentration of acetaminophen in the blood reaching the subject's liver through the portal vein will be the same concentration of acetaminophen as found in blood throughout the rest of the subject's body. Thus, the pharmaceutical compositions disclosed herein provide a Cmax comparable to a commercially-available immediate-release acetaminophen product (dosed at half strength) while providing a less taxing burden on the subject's metabolic systems in the liver because the acetaminophen released by the pharmaceutical composition is eliminated by the subject's body faster than it is being absorbed. This results in decreased levels of acetaminophen in a subject's liver as compared to an immediate release dosage form of acetaminophen dosed every 6 hours.

(h) Exemplary Compositions

In one embodiment, the pharmaceutical composition for extended release of oxycodone and acetaminophen comprises at least one extended release portion comprising acetaminophen, oxycodone or a combination thereof, and at least one extended release component; and at least one immediate release portion comprising oxycodone, acetaminophen or combinations thereof. In yet another embodiment, the pharmaceutical composition comprises an immediate release portion comprising oxycodone and acetaminophen and an extended release portion comprising oxycodone, acetaminophen and an extended release component. In still yet another embodiment, the composition comprises two extended release portions, each comprising an extended release component and one of the oxycodone or the acetaminophen, and an immediate release portion comprising the oxycodone and the acetaminophen. In another embodiment, the composition comprises two extended release portions, each comprising an extended release component and one of oxycodone or acetaminophen, and two immediate release portions, each comprising one of oxycodone or acetaminophen. In one embodiment, the extended release component comprises at least one extended release polymer. In another one embodiment, the extended release polymer comprises a polyethylene oxide. The molecular weight of the polyethylene oxide may be from about 500,000 Daltons to about 10,000,000 Daltons.

In another embodiment, the pharmaceutical composition may comprise from about 5 mg to about 30 mg of oxycodone and from about 250 mg to about 1300 mg of acetaminophen. In one exemplary embodiment, the pharmaceutical composition may comprise about 15 mg of oxycodone and about 650 mg of acetaminophen. In another exemplary embodiment, the composition may comprise about 15 mg of oxycodone and about 500 mg of acetaminophen. In yet another exemplary embodiment, the composition may comprise about 15 mg of oxycodone and about 325 mg of acetaminophen. In a further embodiment, the composition may comprise about 30 mg of oxycodone and about 500 mg of acetaminophen. In yet another exemplary embodiment, the pharmaceutical composition may comprise about 7.5 mg of oxycodone about 325 mg of acetaminophen. In still another exemplary embodiment, the pharmaceutical composition may comprise about 10 mg of oxycodone about 325 mg of acetaminophen. In a further exemplary embodiment, the pharmaceutical composition may comprise about 20 mg of oxycodone about 650 mg of acetaminophen. In another exemplary embodiment, the composition may comprise about 30 mg of oxycodone and about 650 mg of acetaminophen. In yet another exemplary embodiment, the composition may comprise about 22.5 mg of oxycodone and about 925 mg of acetaminophen.

In a further embodiment, a single dosage form of the pharmaceutical composition disclosed herein (e.g., one tablet) will provide a subject with approximately the same therapeutic benefit and pharmacokinetic profile as either two dosage forms (e.g., two tablets) of the composition formulated at half the strength, or three dosage forms (e.g., three tablets) of the composition formulated at a third of the strength. In yet another exemplary embodiment, the pharmaceutical composition comprising 15 mg of oxycodone and 650 mg of acetaminophen in a single dosage form (e.g., one tablet) will provide a subject with approximately the same therapeutic benefit and pharmacokinetic profile as two dosage forms of the pharmaceutical composition formulated at half the strength (e.g., each tablet comprising 7.5 mg of oxycodone and 325 mg of acetaminophen). In still another exemplary embodiment, the pharmaceutical composition comprising 15 mg of oxycodone and 650 mg of acetaminophen in a single dosage form (e.g., one tablet) will provide a subject with approximately the same therapeutic benefit and pharmacokinetic profile as three dosage forms of the pharmaceutical composition formulated at a third of the strength (e.g., each tablet comprising 5 mg of oxycodone and about 216.7 mg of acetaminophen). In yet another embodiment, the pharmaceutical composition comprising 15 mg of oxycodone and 325 mg of acetaminophen in a single dosage form (e.g., one tablet) taken together with another tablet comprising 7.5 mg of oxycodone and 325 mg of acetaminophen in a single dosage form will provide a subject with approximately the same therapeutic benefit and pharmacokinetic profile as a single tablet comprising 22.5 mg of oxycodone and 650 mg of acetaminophen. In still another exemplary embodiment, the pharmaceutical composition comprising 15 mg of oxycodone and 325 mg of acetaminophen in a single dosage form (e.g., one tablet) taken together with another tablet comprising 15 mg of oxycodone and 325 mg of acetaminophen in a single dosage form will provide a subject with approximately the same therapeutic benefit and pharmacokinetic profile as a single tablet configuration totaling 30 mg of oxycodone and 650 mg of acetaminophen. In yet a further exemplary embodiment, a pharmaceutical composition comprising 21 mg of oxycodone and 650 mg of acetaminophen in a single dosage form (e.g., one tablet) will provide a subject with approximately the same therapeutic benefit and pharmacokinetic profile as two dosage forms of the pharmaceutical composition formulated at half the strength (e.g., each tablet comprising 10.5 mg of oxycodone and 325 mg of acetaminophen). In yet another exemplary embodiment, a pharmaceutical composition comprising 22.5 mg of oxycodone and 925 mg of acetaminophen in a single dosage form (e.g., one tablet) will provide a subject with approximately the same therapeutic benefit and pharmacokinetic profile as three dosage forms of the pharmaceutical composition formulated at a third of the strength (e.g., each tablet comprising 7.5 mg of oxycodone and 325 mg of acetaminophen).

In yet another embodiment, the at least one extended release portion of the composition may comprise from about 40% to about 60% (w/w) of the total amount of acetaminophen in the composition and from about 70% to about 80% (w/w) of the total amount of oxycodone in the composition, whereas the at least one immediate release portion may comprise from about 40% to about 60% (w/w) of the total amount of acetaminophen in the composition and from about 20% to about 30% (w/w) of the total amount of oxycodone in the composition. In still another embodiment, the at least one extended release portion may comprise about 50% (w/w) of the total amount of acetaminophen in the composition and about 75% (w/w) of the total amount of oxycodone in the composition; and the at least one immediate release portion may comprise about 50% (w/w) of total amount of acetaminophen in the composition and about 25% (w/w) of the total amount of oxycodone in the composition.

In another embodiment, an extended release portion of the composition may comprise, by weight of such extended release portion, from about 30% to about 50% of the extended release polymer, from about 20% to about 40% of acetaminophen, and from about 0.5% to about 2% of oxycodone; and an immediate release portion may comprise, by weight of such immediate release portion, from about 70% to about 80% acetaminophen and from about 0.5% to about 1% of oxycodone.

In yet another embodiment, the pharmaceutical composition may comprise from about 7.5 mg to about 30 mg of oxycodone and from about 325 mg to about 650 mg of acetaminophen, wherein the at least one immediate release portion may comprise about 25% (w/w) of the total amount of oxycodone in the composition and about 50% (w/w) of the total amount of acetaminophen in the composition, and the at least one extended release portion may comprise about 75% (w/w) of the total amount of oxycodone in the composition, about 50% (w/w) of the total amount of acetaminophen in the composition, and about 35% to about 45%, by weight of the at least one extended release portion, of an extended release polymer comprising a polyethylene oxide.

Other exemplary formulations are set forth in Charts 1-2 below:

CHART 1

Representative Oxycodone/Acetaminophen Formulations.

| | | Formulation No. | | | | | | | | | |
|---|---|---|---|---|---|---|---|---|---|---|---|
| | | 1 | 2 | 3 | 4 | 5 | 6 | 7 | 8 | 9 | 10 |
| Immediate Release Layer | APAP | 185.3 | 175.0 | 180.0 | 160.4 | 200.0 | 193.4 | 118.8 | 162.5 | 139.0 | 150.0 |
| | Oxycodone hydrochloride | 1.100 | 1.75 | 2.00 | 2.50 | 1.25 | 1.00 | 2.75 | 1.875 | 1.75 | 1.875 |
| | Microcrystalline cellulose | 23.0 | 17.0 | 19.0 | 27.0 | 16.0 | 18.0 | 18.0 | 14.0 | 21.0 | 24.0 |
| | Pregelatinized starch | 0.05 | 0.15 | 0.25 | 0.10 | 0.05 | 0.30 | 0.20 | 0.25 | 0.15 | 0.20 |
| | Citric Acid Anhydrous | 0.08 | 0.08 | 0.08 | 0.11 | 0.11 | 0.14 | 0.07 | 0.13 | 0.15 | 0.17 |
| | EDTA disodium salt, dihydrate | 0.087 | 0.106 | 0.075 | 0.03 | 0.050 | 0.055 | 0.033 | 0.025 | 0.045 | 0.018 |
| | Hydroxypropyl cellulose | 14.1 | 17.8 | — | — | 17.3 | — | 16.7 | 16.1 | 21.5 | — |
| | Hypromellose | 2.5 | — | 3.2 | — | — | — | — | — | 8.9 | 19.5 |
| | Hydroxypropyl methyl cellulose | — | — | 21.7 | 18.3 | — | 19.3 | — | — | — | 3.0 |
| | Croscarmellose sodium | 10.0 | 11.0 | 11.5 | 11.5 | 13.0 | 14.5 | 14.5 | 12.5 | 14.0 | 12.5 |
| | Silicon dioxide | 0.97 | 0.75 | 1.14 | 1.02 | 1.10 | 1.03 | 0.88 | 1.05 | 0.93 | 2.30 |
| | Magnesium stearate | 1.5 | 1.0 | 1.0 | 0.5 | 2.0 | 2.0 | 2.0 | 0.5 | 1.5 | 2.5 |
| Extended Release Layer | APAP | 185.3 | 150.0 | 145.0 | 155.2 | 125.0 | 100.5 | 146.9 | 162.5 | 207.4 | 150.0 |
| | Oxycodone hydrochloride | 6.900 | 5.75 | 5.50 | 5.00 | 6.25 | 6.50 | 7.25 | 5.625 | 4.75 | 6.625 |
| | Microcrystalline cellulose | 175.4 | 180.0 | 302.2 | 275.0 | 214.8 | 250.0 | 245.7 | 203.6 | 288.3 | 200.5 |
| | Pregelatinized starch | 0.60 | 0.60 | 0.70 | 0.70 | 0.70 | 0.75 | 0.75 | 0.75 | 0.85 | 0.85 |
| | Citric Acid Anhydrous | 0.24 | 0.16 | 0.24 | 0.22 | 0.33 | 0.28 | 0.07 | 0.38 | 0.45 | 0.34 |
| | EDTA disodium salt, dihydrate | 0.160 | 0.085 | 0.095 | 0.055 | 0.130 | 0.065 | 0.065 | 0.075 | 0.130 | 0.125 |
| | Hydroxypropyl cellulose | 30.0 | 275.8 | 95.5 | 210.6 | 13.2 | 40.7 | 32.9 | 9.6 | — | — |
| | Polyox N12K | 292.8 | — | — | — | 287.7 | — | — | — | 155.5 | — |
| | Polyox 1105 | — | — | 244.2 | — | — | — | 275.5 | 321.8 | — | 189.2 |
| | Hydroxypropyl methyl cellulose | — | 103.2 | — | 134.2 | — | 182.2 | — | — | 155.5 | 210.2 |
| | Silicon Dioxide | 1.8 | 1.3 | 1.5 | 2.3 | 2.4 | 3.0 | 3.5 | 3.6 | 2.0 | 2.5 |
| | Magnesium Stearate | 7.5 | 8.0 | 7.4 | 8.1 | 7.5 | 10.2 | 9.9 | 7.2 | 10.3 | 10.3 |

| | | Formulation No. | | | | | | | | | |
|---|---|---|---|---|---|---|---|---|---|---|---|
| | | 11 | 12 | 13 | 14 | 15 | 16 | 17 | 18 | 19 | 20 |
| Immediate Release Layer | APAP | 300.0 | 150.0 | 200.0 | 150.0 | 100.0 | 160.0 | 190.0 | 75.0 | 90.0 | 125.0 |
| | Oxycodone hydrochloride | 2.00 | 1.00 | 1.50 | 3.50 | 2.75 | 1.25 | 1.25 | 2.50 | 1.75 | 3.00 |
| | Microcrystalline cellulose | 21.5 | 18.5 | 25.3 | 35.0 | 15.7 | 27.1 | 9.9 | 13.9 | 24.2 | 16.9 |
| | Pregelatinized starch | 0.03 | 0.30 | 0.25 | 0.27 | 0.08 | 0.35 | 0.75 | 0.09 | 0.15 | 0.26 |
| | Citric Acid Anhydrous | 0.12 | 0.08 | 0.09 | 0.16 | 0.07 | 0.24 | 0.14 | 0.26 | 0.15 | 0.20 |
| | EDTA disodium salt, dihydrate | 0.04 | 0.175 | 0.1 | 0.06 | 0.1 | 0.09 | 0.06 | 0.08 | 0.063 | 0.09 |
| | Hydroxypropyl cellulose | — | 21.5 | 1.8 | 9.8 | 14.8 | — | 20.8 | 19.2 | 25.4 | — |
| | Hypromellose | 2.5 | — | — | — | — | — | — | — | 10.3 | 22.5 |
| | Hydroxypropyl methyl cellulose | 16.3 | 11.4 | 17.5 | 8.7 | — | 29.3 | — | — | — | 4.4 |
| | Croscarmellose sodium | 6.8 | 11.0 | 12.8 | 7.9 | 19.0 | 9.6 | 13.3 | 15.6 | 15.1 | 14.7 |
| | Silicon dioxide | 0.86 | 0.80 | 2.25 | 1.24 | .95 | 1.34 | 0.80 | 1.66 | 0.79 | 2.37 |
| | Magnesium stearate | 1.75 | 1.0 | 0.75 | 0.6 | 0.5 | 2.5 | 1.9 | 0.8 | 1.2 | 2.8 |
| Extended Release Layer | APAP | 150.0 | 150.0 | 125.0 | 75.0 | 100.0 | 165.0 | 135.0 | 225.0 | 210.0 | 150.0 |
| | Oxycodone hydrochloride | 8.00 | 6.50 | 6.00 | 6.50 | 3.25 | 6.25 | 6.25 | 5.00 | 6.25 | 5.50 |
| | Microcrystalline cellulose | 182.2 | 197.6 | 300.4 | 269.6 | 210.0 | 275.5 | 283.2 | 310.2 | 240.8 | 210.0 |
| | Pregelatinized starch | 0.75 | 0.73 | 0.46 | 0.89 | 0.55 | 0.78 | 0.55 | 0.65 | 0.67 | 0.64 |
| | Citric Acid Anhydrous | 0.25 | 0.36 | 0.38 | 0.34 | 0.37 | 0.23 | 0.14 | 0.40 | 0.70 | 0.70 |
| | EDTA disodium salt, | 0.23 | 0.09 | 0.14 | 0.06 | 0.183 | 0.035 | 0.049 | 0.03 | 0.105 | 0.075 |

CHART 1-continued

Representative Oxycodone/Acetaminophen Formulations.

|  |  |  |  |  |  |  |  |  |  |  |
|---|---|---|---|---|---|---|---|---|---|---|
| dihydrate |  |  |  |  |  |  |  |  |  |  |
| Hydroxypropyl cellulose | 34.7 | 321.9 | 88.4 | 212.9 | 11.9 | 37.7 | 34.2 | 17.4 | — | — |
| Polyox N12K | — | — | 252.4 | — | 290.3 | — | 248.2 | 279.2 | 175.2 | — |
| Polyox 1105 | 275.8 | — | — | — | — | — | — | — | — | 224.5 |
| Hydroxypropyl methyl cellulose | — | 101.1 | — | 110.5 | — | 192.1 | — | — | 140.9 | 185.6 |
| Silicon Dioxide | 1.3 | 1.3 | 1.2 | 2.4 | 2.1 | 3.2 | 4.0 | 4.0 | 2.0 | 3.8 |
| Magnesium Stearate | 5.7 | 9.4 | 6.6 | 5.5 | 7.7 | 9.4 | 6.4 | 5.2 | 9.9 | 7.2 |

|  |  | Formulation No. |  |  |  |  |  |  |  |  |  |
|---|---|---|---|---|---|---|---|---|---|---|---|
|  |  | 21 | 22 | 23 | 24 | 25 | 26 | 27 | 28 | 29 | 30 |
| Immediate Release Layer | APAP | 185.3 | 175.0 | 180.0 | 160.4 | 200.0 | 193.4 | 118.8 | 162.5 | 139.0 | 150.0 |
|  | Oxycodone hydrochloride | 1.100 | 1.75 | 2.00 | 2.50 | 1.25 | 1.00 | 2.75 | 1.875 | 1.75 | 1.875 |
|  | Microcrystalline cellulose | 23.0 | 17.0 | 19.0 | 27.0 | 16.0 | 18.0 | 18.0 | 14.0 | 21.0 | 24.0 |
|  | Pregelatinized starch | 0.05 | 0.15 | 0.25 | 0.10 | 0.05 | 0.30 | 0.20 | 0.25 | 0.15 | 0.20 |
|  | Citric Acid Anhydrous | 0.08 | 0.08 | 0.08 | 0.11 | 0.11 | 0.14 | 0.07 | 0.13 | 0.15 | 0.17 |
|  | EDTA disodium salt, dihydrate | 0.087 | 0.106 | 0.075 | 0.03 | 0.050 | 0.055 | 0.033 | 0.025 | 0.045 | 0.018 |
|  | Hydroxypropyl cellulose | 14.1 | 17.8 | — | — | 17.3 | — | 16.7 | 16.1 | 21.5 | — |
|  | Hypromellose | 2.5 | — | 3.2 | — | — | — | — | — | 8.9 | 19.5 |
|  | Hydroxypropyl methyl cellulose | — | — | 21.7 | 18.3 | — | 19.3 | — | — | — | 3.0 |
|  | Croscarmellose sodium | 10.0 | 11.0 | 11.5 | 11.5 | 13.0 | 14.5 | 14.5 | 12.5 | 14.0 | 12.5 |
|  | Silicon dioxide | 0.97 | 0.75 | 1.14 | 1.02 | 1.10 | 1.03 | 0.88 | 1.05 | 0.93 | 2.30 |
|  | Magnesium stearate | 1.5 | 1.0 | 1.0 | 0.5 | 0.5 | 2.0 | 2.0 | 0.5 | 1.5 | 2.5 |
| Extended Release Layer | APAP | 185.3 | 150.0 | 145.0 | 155.2 | 125.0 | 100.5 | 146.9 | 162.5 | 207.4 | 150.0 |
|  | Oxycodone hydrochloride | 6.900 | 5.75 | 5.50 | 5.00 | 6.25 | 6.50 | 7.25 | 5.625 | 4.75 | 6.625 |
|  | Microcrystalline cellulose | 175.4 | 180.0 | 302.2 | 275.0 | 214.8 | 250.0 | 245.7 | 203.6 | 288.3 | 200.5 |
|  | Pregelatinized starch | 0.60 | 0.60 | 0.70 | 0.70 | 0.70 | 0.75 | 0.75 | 0.75 | 0.85 | 0.85 |
|  | Citric Acid Anhydrous | 0.24 | 0.16 | 0.24 | 0.22 | 0.33 | 0.28 | 0.07 | 0.38 | 0.45 | 0.34 |
|  | EDTA disodium salt, dihydrate | 0.160 | 0.085 | 0.095 | 0.055 | 0.130 | 0.065 | 0.065 | 0.075 | 0.130 | 0.125 |
|  | Hydroxypropyl cellulose | 30.0 | 275.8 | 95.5 | 210.6 | 13.2 | 40.7 | 32.9 | 9.6 | — | — |
|  | Polyox N60K | 292.8 | — | — | — | 287.7 | — | — | — | 155.5 | — |
|  | Polyox 205 | — | — | 244.2 | — | — | — | 275.5 | 321.8 | — | 189.2 |
|  | Hydroxypropyl methyl cellulose | — | 103.2 | — | 134.2 | — | 182.2 | — | — | 155.5 | 210.2 |
|  | Silicon Dioxide | 1.8 | 1.3 | 1.5 | 2.3 | 2.4 | 3.0 | 3.5 | 3.6 | 2.0 | 2.5 |
|  | Magnesium Stearate | 7.5 | 8.0 | 7.4 | 8.1 | 7.5 | 10.2 | 9.9 | 7.2 | 10.3 | 10.3 |

|  |  | Formulation No. |  |  |  |  |  |  |  |  |  |
|---|---|---|---|---|---|---|---|---|---|---|---|
|  |  | 31 | 32 | 33 | 34 | 35 | 36 | 37 | 38 | 39 | 40 |
| Immediate Release Layer | APAP | 300.0 | 150.0 | 200.0 | 150.0 | 100.0 | 160.0 | 190.0 | 75.0 | 90.0 | 125.0 |
|  | Oxycodone hydrochloride | 2.00 | 1.00 | 1.50 | 3.50 | 2.75 | 1.25 | 1.25 | 2.50 | 1.75 | 3.00 |
|  | Microcrystalline cellulose | 21.5 | 18.5 | 25.3 | 35.0 | 15.7 | 27.1 | 9.9 | 13.9 | 24.2 | 16.9 |
|  | Pregelatinized starch | 0.03 | 0.30 | 0.25 | 0.27 | 0.08 | 0.35 | 0.75 | 0.09 | 0.15 | 0.26 |
|  | Citric Acid Anhydrous | 0.12 | 0.08 | 0.09 | 0.16 | 0.07 | 0.24 | 0.14 | 0.26 | 0.15 | 0.20 |
|  | EDTA disodium salt, dihydrate | 0.04 | 0.175 | 0.1 | 0.06 | 0.1 | 0.09 | 0.06 | 0.08 | 0.063 | 0.09 |
|  | Hydroxypropyl cellulose | — | 21.5 | 1.8 | 9.8 | 14.8 | — | 20.8 | 19.2 | 25.4 | — |
|  | Hypromellose | 2.5 | — | — | — | — | — | — | — | 10.3 | 22.5 |
|  | Hydroxypropyl methyl cellulose | 16.3 | 11.4 | 17.5 | 8.7 | — | 29.3 | — | — | — | 4.4 |
|  | Croscarmellose sodium | 6.8 | 11.0 | 12.8 | 7.9 | 19.0 | 9.6 | 13.3 | 15.6 | 15.1 | 14.7 |
|  | Silicon dioxide | 0.86 | 0.80 | 2.25 | 1.24 | .95 | 1.34 | 0.80 | 1.66 | 0.79 | 2.37 |
|  | Magnesium stearate | 1.75 | 1.0 | 0.75 | 0.6 | 0.5 | 2.5 | 1.9 | 0.8 | 1.2 | 2.8 |
| Extended Release Layer | APAP | 150.0 | 150.0 | 125.0 | 75.0 | 100.0 | 165.0 | 135.0 | 225.0 | 210.0 | 150.0 |
|  | Oxycodone hydrochloride | 8.00 | 6.50 | 6.00 | 6.50 | 3.25 | 6.25 | 6.25 | 5.00 | 6.25 | 5.50 |
|  | Microcrystalline cellulose | 182.2 | 197.6 | 300.4 | 269.6 | 210.0 | 275.5 | 283.2 | 310.2 | 240.8 | 210.0 |
|  | Pregelatinized starch | 0.75 | 0.73 | 0.46 | 0.89 | 0.55 | 0.78 | 0.55 | 0.65 | 0.67 | 0.64 |
|  | Citric Acid Anhydrous | 0.25 | 0.36 | 0.38 | 0.34 | 0.37 | 0.23 | 0.14 | 0.40 | 0.70 | 0.70 |
|  | EDTA disodium salt, dihydrate | 0.23 | 0.09 | 0.14 | 0.06 | 0.183 | 0.035 | 0.049 | 0.03 | 0.105 | 0.075 |
|  | Hydroxypropyl cellulose | 34.7 | 321.9 | 88.4 | 212.9 | 11.9 | 37.7 | 34.2 | 17.4 | — | — |
|  | Polyox N60K | — | 45.5 | 249.9 | 24.3 | 282.0 | 49.8 | 200.1 | 240.1 | 186.8 | — |
|  | Polyox 205 | 268.4 | — | 53.6 | 70.2 | — | — | — | 36.3 | 10.4 | 259.3 |
|  | Hydroxypropyl methyl cellulose | — | 90.5 | — | 65.4 | — | 192.1 | — | — | 127.3 | 142.0 |
|  | Silicon Dioxide | 1.3 | 1.3 | 1.2 | 2.4 | 2.1 | 3.2 | 4.0 | 4.0 | 2.0 | 3.8 |
|  | Magnesium Stearate | 5.7 | 9.4 | 6.6 | 5.5 | 7.7 | 9.4 | 6.4 | 5.2 | 9.9 | 7.2 |

CHART 1-continued

Representative Oxycodone/Acetaminophen Formulations.

| | | Formulation No. | | | | | | | | | |
|---|---|---|---|---|---|---|---|---|---|---|---|
| | | 41 | 42 | 43 | 44 | 45 | 46 | 47 | 48 | 49 | 50 |
| Immediate Release Layer | APAP | 185.3 | 175.0 | 180.0 | 160.4 | 200.0 | 193.4 | 118.8 | 162.5 | 139.0 | 150.0 |
| | Oxycodone hydrochloride | 1.100 | 1.75 | 2.00 | 2.50 | 1.25 | 1.00 | 2.75 | 1.875 | 1.75 | 1.875 |
| | Microcrystalline cellulose | 23.0 | 17.0 | 19.0 | 27.0 | 16.0 | 18.0 | 18.0 | 14.0 | 21.0 | 24.0 |
| | Pregelatinized starch | 0.05 | 0.15 | 0.25 | 0.10 | 0.05 | 0.30 | 0.20 | 0.25 | 0.15 | 0.20 |
| | Citric Acid Anhydrous | 0.08 | 0.08 | 0.08 | 0.11 | 0.11 | 0.14 | 0.07 | 0.13 | 0.15 | 0.17 |
| | EDTA disodium salt, dihydrate | 0.087 | 0.106 | 0.075 | 0.03 | 0.050 | 0.055 | 0.033 | 0.025 | 0.045 | 0.018 |
| | Hydroxypropyl cellulose | 14.1 | 17.8 | — | — | 17.3 | — | 16.7 | 16.1 | 21.5 | — |
| | Hypromellose | 2.5 | — | 3.2 | — | — | — | — | — | 8.9 | 19.5 |
| | Hydroxypropyl methyl cellulose | — | — | 21.7 | 18.3 | — | 19.3 | — | — | — | 3.0 |
| | Croscarmellose sodium | 10.0 | 11.0 | 11.5 | 11.5 | 13.0 | 14.5 | 14.5 | 12.5 | 14.0 | 12.5 |
| | Silicon dioxide | 0.97 | 0.75 | 1.14 | 1.02 | 1.10 | 1.03 | 0.88 | 1.05 | 0.93 | 2.30 |
| | Magnesium stearate | 1.5 | 1.0 | 1.0 | 0.5 | 0.5 | 2.0 | 2.0 | 0.5 | 1.5 | 2.5 |
| Extended Release Layer | APAP | 185.3 | 150.0 | 145.0 | 155.2 | 125.0 | 100.5 | 146.9 | 162.5 | 207.4 | 150.0 |
| | Oxycodone hydrochloride | 6.900 | 5.75 | 5.50 | 5.00 | 6.25 | 6.50 | 7.25 | 5.625 | 4.75 | 6.625 |
| | Microcrystalline cellulose | 175.4 | 180.0 | 302.2 | 275.0 | 214.8 | 250.0 | 245.7 | 203.6 | 288.3 | 200.5 |
| | Pregelatinized starch | 0.60 | 0.60 | 0.70 | 0.70 | 0.70 | 0.75 | 0.75 | 0.75 | 0.85 | 0.85 |
| | Citric Acid Anhydrous | 0.24 | 0.16 | 0.24 | 0.22 | 0.33 | 0.28 | 0.07 | 0.38 | 0.45 | 0.34 |
| | EDTA disodium salt, dihydrate | 0.160 | 0.085 | 0.095 | 0.055 | 0.130 | 0.065 | 0.065 | 0.075 | 0.130 | 0.125 |
| | Hydroxypropyl cellulose | 30.0 | 275.8 | 95.5 | 210.6 | 13.2 | 40.7 | 32.9 | 9.6 | — | — |
| | Polyox N-750 | 292.8 | — | — | — | 287.7 | — | — | — | 155.5 | — |
| | Polyox 301 | — | — | 244.2 | — | — | — | 275.5 | 321.8 | — | 189.2 |
| | Hydroxypropyl methyl cellulose | — | 103.2 | — | 134.2 | — | 182.2 | — | — | 155.5 | 210.2 |
| | Silicon Dioxide | 1.8 | 1.3 | 1.5 | 2.3 | 2.4 | 3.0 | 3.5 | 3.6 | 2.0 | 2.5 |
| | Magnesium Stearate | 7.5 | 8.0 | 7.4 | 8.1 | 7.5 | 10.2 | 9.9 | 7.2 | 10.3 | 10.3 |

| | | Formulation No. | | | | | | | | | |
|---|---|---|---|---|---|---|---|---|---|---|---|
| | | 51 | 52 | 53 | 54 | 55 | 56 | 57 | 58 | 59 | 60 |
| Immediate Release Layer | APAP | 300.0 | 150.0 | 200.0 | 150.0 | 100.0 | 160.0 | 190.0 | 75.0 | 90.0 | 125.0 |
| | Oxycodone hydrochloride | 2.00 | 1.00 | 1.50 | 3.50 | 2.75 | 1.25 | 1.25 | 2.50 | 1.75 | 3.00 |
| | Microcrystalline cellulose | 21.5 | 18.5 | 25.3 | 35.0 | 15.7 | 27.1 | 9.9 | 13.9 | 24.2 | 16.9 |
| | Pregelatinized starch | 0.03 | 0.30 | 0.25 | 0.27 | 0.08 | 0.35 | 0.75 | 0.09 | 0.15 | 0.26 |
| | Citric Acid Anhydrous | 0.12 | 0.08 | 0.09 | 0.16 | 0.07 | 0.24 | 0.14 | 0.26 | 0.15 | 0.20 |
| | EDTA disodium salt, dihydrate | 0.04 | 0.175 | 0.1 | 0.06 | 0.1 | 0.09 | 0.06 | 0.08 | 0.063 | 0.09 |
| | Hydroxypropyl cellulose | — | 21.5 | 1.8 | 9.8 | 14.8 | — | 20.8 | 19.2 | 25.4 | — |
| | Hypromellose | 2.5 | — | — | — | — | — | — | — | 10.3 | 22.5 |
| | Hydroxypropyl methyl cellulose | 16.3 | 11.4 | 17.5 | 8.7 | — | 29.3 | — | — | — | 4.4 |
| | Croscarmellose sodium | 6.8 | 11.0 | 12.8 | 7.9 | 19.0 | 9.6 | 13.3 | 15.6 | 15.1 | 14.7 |
| | Silicon dioxide | 0.86 | 0.80 | 2.25 | 1.24 | .95 | 1.34 | 0.80 | 1.66 | 0.79 | 2.37 |
| | Magnesium stearate | 1.75 | 1.0 | 0.75 | 0.6 | 0.5 | 2.5 | 1.9 | 0.8 | 1.2 | 2.8 |
| Extended Release Layer | APAP | 150.0 | 150.0 | 125.0 | 75.0 | 100.0 | 165.0 | 135.0 | 225.0 | 210.0 | 150.0 |
| | Oxycodone hydrochloride | 8.00 | 6.50 | 6.00 | 6.50 | 3.25 | 6.25 | 6.25 | 5.00 | 6.25 | 5.50 |
| | Microcrystalline cellulose | 182.2 | 197.6 | 300.4 | 269.6 | 210.0 | 275.5 | 283.2 | 310.2 | 240.8 | 210.0 |
| | Pregelatinized starch | 0.75 | 0.73 | 0.46 | 0.89 | 0.55 | 0.78 | 0.55 | 0.65 | 0.67 | 0.64 |
| | Citric Acid Anhydrous | 0.25 | 0.36 | 0.38 | 0.34 | 0.37 | 0.23 | 0.14 | 0.40 | 0.70 | 0.70 |
| | EDTA disodium salt, dihydrate | 0.23 | 0.09 | 0.14 | 0.06 | 0.183 | 0.035 | 0.049 | 0.03 | 0.105 | 0.075 |
| | Hydroxypropyl cellulose | 34.7 | 321.9 | 88.4 | 212.9 | 11.9 | 37.7 | 34.2 | 17.4 | — | — |
| | Polyox N-750 | 63.4 | 30.1 | 125.9 | 100.3 | 149.2 | 63.2 | 150.5 | 140.3 | 94.3 | — |
| | Polyox 301 | 210.4 | — | 175.8 | 60.7 | 175.8 | — | 160.5 | 149.7 | 100.8 | 194.6 |
| | Hydroxypropyl methyl cellulose | — | 128.3 | — | 65.4 | — | 227.7 | — | — | 127.3 | 142.0 |
| | Silicon Dioxide | 1.3 | 1.3 | 1.2 | 2.4 | 2.1 | 3.2 | 4.0 | 4.0 | 2.0 | 3.8 |
| | Magnesium Stearate | 5.7 | 9.4 | 6.6 | 5.5 | 7.7 | 9.4 | 6.4 | 5.2 | 9.9 | 7.2 |

*All weights in mg.

CHART 2

Additional Oxycodone/Acetaminophen Formulations.

| | | 61 | 62 | 63 | 64 | 65 | 66 | 67 | 68 | 69 | 70 |
|---|---|---|---|---|---|---|---|---|---|---|---|
| Immediate Release Layer | APAP | 250.0 | 250.0 | 250.0 | 250.0 | 250.0 | 250.0 | 325.0 | 325.0 | 162.5 | 162.5 |
| | Oxycodone hydrochloride | 3.75 | 3.75 | 3.75 | 7.5 | 7.5 | 7.5 | 3.75 | 3.75 | 2.5 | 3.75 |
| | Microcrystalline cellulose | 23.72 | 23.72 | 23.72 | 32.42 | 32.42 | 32.42 | 28.10 | 28.10 | 15.50 | 18.40 |
| | Pregelatinized starch | 0.50 | 0.50 | 0.50 | 1.00 | 1.00 | 1.00 | 0.50 | 0.50 | 0.33 | 0.50 |
| | Citric Acid Anhydrous | 0.25 | 0.25 | 0.25 | 0.50 | 0.50 | 0.50 | 0.25 | 0.25 | 0.17 | 0.25 |
| | EDTA disodium salt, dihydrate | 0.05 | 0.05 | 0.05 | 0.10 | 0.10 | 0.10 | 0.05 | 0.05 | 0.033 | 0.05 |
| | Hydroxypropyl cellulose | 25.23 | 25.23 | 25.23 | 26.43 | 26.43 | 26.43 | 32.24 | 32.23 | 16.32 | 16.72 |
| | Croscarmellose sodium | 19.21 | 19.21 | 19.21 | 20.13 | 20.13 | 20.13 | 12.09 | 25.087 | 12.70 | 13.01 |
| | Silicon dioxide | 1.63 | 1.63 | 1.63 | 1.70 | 1.70 | 1.70 | 2.09 | 2.09 | 1.06 | 1.08 |
| | Magnesium stearate | 0.81 | 0.81 | 0.81 | 0.85 | 0.85 | 0.85 | 1.045 | 1.045 | 0.53 | 0.54 |
| Extended Release Layer | APAP | 250.0 | 250.0 | 250.0 | 250.0 | 250.0 | 250.0 | 325.0 | 325.0 | 162.5 | 162.5 |
| | Oxycodone hydrochloride | 11.25 | 11.25 | 11.25 | 22.5 | 22.5 | 22.5 | 11.25 | 11.25 | 7.5 | 11.25 |
| | Microcrystalline cellulose | 175.24 | 103.74 | 103.74 | 159.62 | 88.12 | 88.12 | 23.85 | 23.85 | 201.02 | 195.80 |
| | Pregelatinized starch | 1.50 | 1.50 | 1.50 | 3.00 | 3.00 | 3.00 | 1.50 | 1.50 | 1.00 | 1.50 |
| | Citric Acid Anhydrous | 0.75 | 0.75 | 0.75 | 1.50 | 1.50 | 1.50 | 0.75 | 0.75 | 0.50 | 0.75 |
| | EDTA disodium salt, dihydrate | 0.15 | 0.15 | 0.15 | 0.30 | 0.30 | 0.30 | 0.15 | 0.15 | 0.10 | 0.15 |
| | Hydroxypropyl cellulose | 15.13 | 15.13 | 15.13 | 17.11 | 17.11 | 17.11 | — | 19.16 | 9.91 | 10.57 |
| | Polyox 1105 | 250.25 | 321.75 | — | 250.25 | 321.75 | — | 321.02 | 321.02 | 321.75 | 321.75 |
| | Polyox N60K | — | — | 321.75 | — | — | 321.75 | — | — | — | — |
| | Silicon Dioxide | 3.58 | 3.58 | 3.58 | 3.58 | 3.58 | 3.58 | 3.57 | 3.57 | 3.58 | 3.58 |
| | Magnesium Stearate | 7.15 | 7.15 | 7.15 | 7.15 | 7.15 | 7.15 | 7.13 | 7.13 | 7.15 | 7.15 |

*All weights in mg.

III. METHODS FOR PREPARING SOLID DOSAGE FORMS OF THE PHARMACEUTICAL COMPOSITION

Another aspect of the disclosure provides methods for preparing solid dosage forms of the pharmaceutical composition that provide extended release of oxycodone and acetaminophen. Solid dosage compositions in the form of tablets may be produced using any suitable method known in the art including but not limited to wet granulation, dry granulation, direct compression, and combinations thereof.

Granulation is a manufacturing process which increases the size and homogeneity of active pharmaceutical ingredients and excipients that comprise a solid dose composition. The granulation process, which is often referred to as agglomeration, changes important physical characteristics of the dry composition, with the aim of improving manufacturability and, thereby, product quality, as well as providing desired release kinetics. Wet granulation is by far the more prevalent agglomeration process utilized within the pharmaceutical industry. Most wet granulation procedures follow some basic steps; the active agent(s) and excipients are mixed together, and a binder solution is prepared and added to the powder mixture to form a wet mass. The moist particles are then dried and sized by milling or by screening through a sieve. In some cases, the wet granulation is "wet milled" or sized through screens before the drying step. The wet granulation process may be a high shear granulation process or a fluid bed granulation process. Several methods of granulation are described in co-pending application U.S. application Ser. No. 13/166,770, filed Jun. 22, 2011, which is incorporated herein by reference in its entirety.

After granulation and drying of the resultant particles, batches are characterized with respect to properties such as final Loss on Drying (LOD), bulk density, tap density, and particle size. Loss on Drying (LOD) typically is determined after each granulation using the Moisture Analyzer. Several 1 g samples may be taken and loaded into the moisture analyzer. The samples may be run for 5 minutes at a temperature of 105° C. In another embodiment, the samples may be run at 105° C. until there is no weight fluctuation in order to determine the LOD.

Bulk and tap densities may be determined as follows. A graduated cylinder is filled with a certain amount of material (e.g., 30-40 g or 82-88 g), and the volume recorded to determine the material bulk density. Tap density can be determined with a help of a Tap Density Tester by exposing the material to 100 taps per test and recording the new volume.

Particle size determination generally is performed immediately after granulation, after sieving through 20 mesh screen to remove agglomerates. Particle diameter may be determined with a sieve-type particle diameter distribution gauge using sieves with openings of 30, 40, 60, 80, 120, and 325 mesh. Fractions may be weighed on a Mettler balance to estimate size distribution. This provides determination of the quantitative ratio by particle diameter of composition comprising extended release particles. Sieve analysis according to standard United States Pharmacopoeia methods (e.g., USP-23 NF 18), may be done such as by using a Meinzer II Sieve Shaker.

In one embodiment, the method for preparing dosage forms of the pharmaceutical composition may comprise wet granulating a first mixture comprising oxycodone, acetaminophen, and a binder to produce a first granulation mixture. The wet granulation process may be a fluid bed granulation process. In additional embodiments, the first mixture may further comprise at least one additional excipient selected from the group consisting of fillers, lubricants, antioxidants, chelating agents, and color agents. The first granulation mixture may be blended with an extended release polymer and one or more excipients, as listed above, to form at least one extended release portion of a dosage form. In certain embodiments, the extended release polymer may be a polyethylene oxide.

In another embodiment, the method further comprises wet granulating a second mixture comprising oxycodone, acetaminophen, and a binder to form a second granulation mixture. The wet granulation process may be a fluid bed granulation process. In some embodiments, the second mixture may further comprise at least one additional excipient selected from the group consisting of fillers, lubricants, disintegrants, antioxidants, chelating agents, and color agents. The second granulation mixture may be blended with one or more excipients, as listed above, to form an immediate release portion of a dosage form.

In an additional embodiment, the method may further comprise compressing the at least one extended release portion and the at least one immediate release portion into a tablet. The tablet may be a bilayer tablet. The tablet may be coated with a tablet coating.

In another embodiment, the method may comprise granulating via a high shear wet granulation process a mixture comprising oxycodone and at least one excipient to form oxycodone particles. The oxycodone particles may be dried at a suitable temperature. The oxycodone particles comprising oxycodone may be granulated via a fluid bed granulation process with acetaminophen, a binder, and an optional excipient to form the granulation mixture. The granulation mixture may be blended with an extended release polymer and at least one excipient to form an extended release portion of a solid dosage form.

In a further embodiment, the method may further comprise granulating via a fluid bed granulation process oxycodone particles comprising oxycodone with acetaminophen, a binder, and an optional excipient to form another granulation mixture. This granulation mixture may be blended with one or more excipients to form an immediate release portion of a solid dosage form.

In an additional embodiment, the method may further comprise compressing the at least one extended release portion comprising oxycodone particles and the at least one immediate release portion comprising oxycodone particles into a tablet. In one embodiment, the method comprises compressing one extended release portion comprising the oxycodone particles and one immediate release portion comprising the oxycodone particles into a bilayer tablet. The tablet may be coated with a tablet coating.

In another embodiment, wet granulation of either mixture may produce particles with a bulk density ranging from about 0.30 to 0.40 grams/milliliter (g/mL). In other aspects, the wet granulation may produce particles with a tap density ranging from about 0.35 g/mL to about 0.45 g/mL. In other embodiments, the wet granulation may produce particles, wherein at least about 50% of the particles have a size greater than 125 microns. In still other embodiments, the wet granulation may produce particles wherein about 20% to about 65% of the particles have a size greater than about 125 microns and less than about 250 microns.

Tablets generally are characterized with respect to disintegration and dissolution release profiles as well as tablet hardness, friability, and content uniformity.

In vitro dissolution profiles for the tablets may be determined using a USP Type II apparatus, with a paddle speed of either about 100 rpm or 150 rpm, in 0.1 N HCl, at 37° C. Samples of 5 ml at each time-point may be taken without media replacement at 0.08, 0.25, 0.5, 1, 2, 4, 6, 8 and 12 hours, for example. In some embodiments, the dissolution profiles may be determined at varying pH values, such as at a pH of about 3.0, 3.5, 4.0, 4.5, 5.0, 5.5, 6.0 or 6.5. The fluid used may be, for example, HCl, phosphate buffer, or simulated gastric fluid. The resulting cumulative dissolution profiles for the tablets are based upon a theoretical percent active added to the compositions.

A tablet preferably disintegrates before it dissolves. A disintegration tester measures the time it takes a tablet to break apart in solution. The tester suspends tablets in a solution bath for visual monitoring of the disintegration rate. Both the time to disintegration and the disintegration consistency of all tablets may be measured. The disintegration profile may be determined in a USP Disintegration Tester in 0.1 N HCl of pH 1.2. The fluid used may be, for example, HCl, phosphate buffer, or simulated gastric fluid. Samples, 1-5 ml at each time-point, may be taken, for example, without media replacement at 0.5, 1, 2, 3, 4, 5, 6, 7 and 8 hours. The resulting cumulative disintegration profiles are based upon a theoretical percent active added to the pharmaceutical compositions.

After tablets are formed by compression, it is desired that the tablets have a strength of at least 9-25 Kiloponds (kp), or at least about 12-20 kp. A hardness tester generally is used to determine the load required to diametrically break the tablets (crushing strength) into two equal halves. The fracture force may be measured using a Venkel Tablet Hardness Tester, using standard USP protocols.

Friability is a well-known measure of a tablet's resistance to surface abrasion that measures weight loss in percentage after subjecting the tablets to a standardized agitation procedure. Friability properties are especially important during any transport of the dosage form as any fracturing of the final dosage form may result in a subject receiving less than the prescribed medication. Friability may be determined using a Roche Friability Drum according to standard USP guidelines which specifies the number of samples, the total number of drum revolutions, and the drum rpm to be used. Friability values of from 0.8 to 1.0% generally are regarded as constituting the upper limit of acceptability.

The prepared tablets generally are tested for content uniformity to determine if they meet the pharmaceutical requirement of an acceptance value of 15 or less. Each tablet may be placed in a solution of 60% methanol/40% isopropanol and stirred at room temperature until the tablet disintegrates. The solution containing the dissolved tablet may be further diluted in 90% water/10% isopropanol/0.1 heptafluorobutyric acid and generally is analyzed by HPLC.

IV. METHOD FOR REDUCING THE RISK OF ACETAMINOPHEN-INDUCED HEPATIC DAMAGE

The present disclosure also provides methods for reducing the risk of acetaminophen-induced hepatic damage in a subject being treated for pain with a dosage regimen that comprises administering to the subject at least two consecutive doses of a pharmaceutical composition comprising oxycodone and acetaminophen. The method comprises administering a first dose of a pharmaceutical composition comprising at least one extended release portion comprising the acetaminophen, the oxycodone or a combination thereof, and an extended release component to the subject, wherein the composition maintains a therapeutic blood plasma concentration of oxycodone of at least 5 ng/mL from about 0.75 hours to about 10 hours after administration of the composition, and wherein at least about 90% of the acetaminophen is released from the composition by about 8 hours after administration of the composition such that, by about 10 hours after administration of the composition, acetaminophen has a blood plasma concentration that is less than about 30% of acetaminophen's maximum plasma concentration. The method further comprises administering a second dose of the pharmaceutical composition to the subject at about 12 hours after administration of the first dose.

Avoiding toxic intermediate formation is an important strategy in addressing product safety. Indeed, acetaminophen is absorbed from the stomach and small intestine and primarily metabolized by conjugation in the liver to non-toxic, water-soluble compounds that are eliminated in the urine. When the maximum daily dose ("MDD") is exceeded over a prolonged period, metabolism by conjugation becomes saturated, and excess acetaminophen is oxidatively metabolized by the CYP enzymes (CYP2E1, 1A2, 2A6, 3A4) to a reactive metabolite, N-acetyl-p-benzoquinone-imine (NAPQI). NAPQI has an extremely short half-life, and rapidly conjugates with available glutathione, which acts as a sulfhydryl donor. The reduced NAPQI is then renally excreted. The liver plays a central role in the turnover of glutathione in the body. Given that toxicity due to NAPQI formation occurs via necrosis of the liver following the formation of toxic adducts, minimizing glutathione depletion and enhancing glutathione regeneration in the liver is an important concern.

Human erythrocyte data resulting from hepatic turnover demonstrate a time-delayed response to redox and free radical insults via glutathione depletion and regeneration. The hepatic dynamics of glutathione formation and depletion in animal data using hepatic models can also be reviewed. In Swiss mice, the dynamics of glutathione depletion was investigated in detail for acetaminophen doses ranging from (100 mg/kg to 600 mg/kg) in work done by Brzeznicka and Piotrowski (1989). Under one embodiment of the present invention, the intended dosage for patients with acute pain is 1.3 g/day of acetaminophen. Assuming a subject's weight of 70 kg, this is $1.229 \times 10$ moles/kg/day in human subjects. In Swiss mice, 400 mg/kg and 600 mg/kg are $2.65 \times 10^{-3}$ moles/kg/day and $3.97 \times 10^{-3}$ moles/kg/day, respectively, resulting in a 22-fold and a 32-fold safety exposure ratio, as compared with human levels. The bioequivalence level is 95%. Brzeiznicka and Piotrowski report that circulating hepatic GSH changes in mice began within 15 min after acetaminophen administration, and depletion followed a pattern that was strictly dose dependent, reaching a minimum GSH level 2 hrs after injection for the all dose groups, rebounding to initial levels between hours 8 and 12. Taken together, these results support the hypothesis that exposing subjects to the lower end of the therapeutic window of acetaminophen may provide benefit in terms of the patient's ability to regenerate physiologically protective levels of glutathione. Thus, the pharmaceutical formulations disclosed herein, which are designed to allow for a two hour break in acetaminophen exposure in each twelve hour exposure window allows for restorative hepatic regeneration of the subject's glutathione levels during that period when the acetaminophen concentrations are at their lowest or absent, while still preserving the considerable benefits of the potentiating effects of combination analgesia.

As mentioned above, acetaminophen is primarily metabolized via conjugation reactions, e.g., glucuronidation and sulfation, in the liver to nontoxic, water-soluble compounds that are rapidly eliminated from the body. A small proportion of acetaminophen is metabolized by the cytochrome P450 system to the reactive metabolite, NAPQI. Generally, this toxic metabolite is rapidly detoxified by conjugation to glutathione to form a non-toxic metabolite that is renally excreted. However, if the conjugation pathways become saturated and more acetaminophen is metabolized via the cytochrome P450 pathway, the pool of available glutathione may become depleted. With insufficient glutathione to bind to and inactivate NAPQI, this toxic metabolite is able to react with the sulfhydryl groups of cellular proteins initiating a cascade of cellular damage, which may lead to liver necrosis, and, ultimately, liver failure.

The method disclosed herein addresses the problem of depleted stores of glutathione by providing a period of time during the later part of the dosing interval during which the release of acetaminophen is low because most of the acetaminophen has already been released from the composition. The period of time during which the release of acetaminophen is low is called the acetaminophen "time-off" period. As a consequence of this acetaminophen time-off period, the plasma levels of acetaminophen fall to sufficiently low levels such that the metabolic burden on the liver is reduced, thereby allowing the depleted stores of glutathione to be replenished via the continuous glutathione manufacturing pathway comprising the glutathione synthase pathway. Because the levels of glutathione are able to be restored before the next dose, the risk of acetaminophen-induced hepatic damage is significantly reduced.

Additionally, the acetaminophen time-off period provided by the compositions disclosed herein may provide an added and beneficial precaution for any subject undergoing acetaminophen therapy to avoid an inadvertent reduction in glutathione stores and any potential acetaminophen-induced hepatic damage. In particular, the acetaminophen time-off period provided by the compositions disclosed herein may be especially useful during chronic administration of analgesic compositions comprising acetaminophen. The subject may be at increased risk for developing acetaminophen-induced hepatic damage because of frequent and regular user of alcohol (i.e., ethanol), concurrent administration of acetaminophen from another source (e.g., an over-the-counter medication), poor diet, and/or compromised liver function.

In general, the compositions disclosed herein are formulated such that the rate of release of acetaminophen is high during the first several hours of the dosing interval and the rate of release of acetaminophen is low during the last several hours of the dosing interval. More specifically, the compositions are formulated to release from about 40% to about 65% of the acetaminophen in about 30 minutes, from about 55% to about 80% of the acetaminophen in about 2 hours, from about 65% to about 92% of the acetaminophen in about 4 hours, and from about 67% to about 95% of the acetaminophen in about 8 hours, wherein the dosing interval is about 12 hours. In another, the compositions are formulated to release from about 45% to about 60% of the acetaminophen in about 30 minutes, from about 57% to about 75% of the acetaminophen in about 2 hours, from about 67% to about 90% of the acetaminophen in about 4 hours, and from about 70% to about 95% of the acetaminophen in about 8 hours, wherein the dosing interval is about 12 hours. In yet another embodiment, during the final 4 hours of a 12 hour dosing interval, only about 5% of the acetaminophen remains to be released from the composition.

The subject may be a mammal, and in certain embodiments, the subject may be a human. In various embodiments, the at least two consecutive doses of the analgesic composition may be administered to the subject at 8 hour intervals, 10 hour intervals, 12 hour intervals, 18 hour intervals, or 24 hour intervals.

The method for reducing the risk of acetaminophen-induced hepatic damage disclosed herein may further comprise administering additional doses of the pharmaceutical composition at regular dosing intervals, such as e.g., at 12 hour intervals. During the latter part of each dosing interval, therefore, the acetaminophen time-off period allows depleted stores of glutathione to be replenished, thereby reducing the risk of acetaminophen-induced hepatic damage in subjects being treated for pain with a composition comprising acetaminophen.

V. METHOD FOR TREATING PAIN

Also provided is a method for treating pain in a subject in need of such treatment with a pharmaceutical composition that comprises oxycodone and acetaminophen, wherein the method comprises administering an effective amount of any of the pharmaceutical compositions disclosed herein. The method comprises orally administering to the subject an effective amount of a pharmaceutical composition comprising at least one extended release portion comprising oxycodone, acetaminophen and combination thereof, and an extended release component, wherein the composition maintains a therapeutic plasma concentration of oxycodone of at least about 5 ng/mL from about 0.75 hour to about 10 hours after administration of the composition, and wherein at least about 90% of the acetaminophen is released from the composition by about 8 hours after administration of the composition such that, by about 10 hours after administration of the composition, acetaminophen has a blood plasma concentration that is less than about 30% of acetaminophen's maximum plasma concentration.

In some embodiments, the subject may be suffering from or diagnosed with chronic pain. In yet another embodiment, the subject may be suffering from or diagnosed with acute pain. In still another embodiment, the subject may be suffering from or diagnosed with moderate to severe acute pain. In yet other embodiments, the subject may be suffering from or diagnosed with both chronic and acute pain. The subject may be a mammal, and in certain embodiments, the subject may be a human.

In one embodiment, the effective amount of a pharmaceutical composition may be 15 mg of oxycodone and 650 mg of acetaminophen. For example, one solid dosage form comprising 15 mg of oxycodone and 650 mg of acetaminophen may be administered. Alternatively, two solid dosage forms with each comprising 7.5 mg of oxycodone and 325 mg of acetaminophen may be administered. In another embodiment, the effective amount of a pharmaceutical composition may be 7.5 mg of oxycodone and 325 mg of acetaminophen, wherein one solid dosage form comprising 7.5 mg of oxycodone and 325 mg of acetaminophen may be administered. In yet another embodiment, the effective amount of a pharmaceutical composition may be 20 mg of oxycodone and 650 mg of acetaminophen. For example, one solid dosage form comprising 20 mg of oxycodone and 650 mg of acetaminophen may be administered. Alternatively, two solid dosage forms with each comprising 10 mg of oxycodone and 325 mg of acetaminophen may be administered. In another embodiment, the effective amount of a pharmaceutical composition may be 10 mg of oxycodone and 325 mg of acetaminophen, wherein one solid dosage form comprising 10 mg of oxycodone and 325 mg of acetaminophen may be administered. In still yet another embodiment, the effective amount of a pharmaceutical composition may be 30 mg of oxycodone and 650 mg of acetaminophen. For example, one solid dosage form comprising 30 mg of oxycodone and 650 mg of acetaminophen may be administered. Alternatively, two solid dosage forms with each comprising 15 mg of oxycodone and 325 mg of acetaminophen may be administered. In another embodiment, the effective amount of a pharmaceutical composition may be 15 mg of oxycodone and 325 mg of acetaminophen, wherein one solid dosage form comprising 15 mg of oxycodone and 325 mg of acetaminophen may be administered.

The dosing intervals of the effective amount of the pharmaceutical composition can and will vary. For example, an effective amount of the pharmaceutical composition may be administered once a day, twice a day, or three times a day. In another embodiment, an effective amount of the pharmaceutical composition may be administered twice a day.

In general, therapeutic plasma concentrations of oxycodone and acetaminophen are attained within about 5 minutes, 10 minutes, 15 minutes, 20 minutes, 25 minutes, 30 minutes, 35 minutes, 40 minutes, 45 minutes, 50 minutes, 55 minutes, or 60 minutes after administration of the first dose of the pharmaceutical composition. Accordingly, depending upon the severity of the pain, onset on analgesia may be attained within about 5 minutes, 10 minutes, 15 minutes, 20 minutes, 25 minutes, 30 minutes, 35 minutes, 40 minutes, 45 minutes, 50 minutes, 55 minutes, or 60 minutes after administration of the composition. Onset of analgesia may be measured by the double stopwatch method or other pain assessments as described in Example 12 below. Generally, analgesia or pain relief will be maintained throughout the duration of the dosing interval. For example, in one embodiment, analgesia or pain relief will be maintained for 12 hours. Upon administration of the next dose of the pharmaceutical composition, therefore, analgesia or pain relief may be maintained. Accordingly, analgesia or pain relief will be maintained as long as therapeutic amounts of the pharmaceutical composition are administered at regular dosing intervals. Moreover, pain relief may be managed such that no break-through episodes of pain occur.

In some embodiments, an effective amount of the pharmaceutical composition may be administered to a subject in a fed state. In general, a fed state is defined as having consumed food within about 30 min prior to administration of the pharmaceutical composition. The food may be a high fat meal, a low fat meal, a high calorie meal, or a low calorie meal. In other embodiments, an effective amount of the pharmaceutical composition may be administered to a subject in a fasted state. In general, a fasted state is defined as not having ingested food for at least 10 hours prior to administration of the pharmaceutical composition. In some embodiments, the pharmaceutical composition may be administered to a subject who has fasted for at least 10 hours prior to the first dose and who fasts for at least one hour prior to administration of subsequent doses. In other embodiments, the pharmaceutical composition may be administered to a subject who has fasted for at least 1 hour, 2 hours, 3 hours, 4 hours, 5 hours, 6 hours, 7 hours, 8 hours, 9 hours, or 10 hours prior to administration of each dose.

The method of the present invention is useful for treating numerous pain states that are currently being treated with conventional immediate release compositions comprising acetaminophen and oxycodone. These and additional pain states include, by way of illustration and not limitation, headache pain, pain associated with migraine, neuropathic pain selected from the group consisting of diabetic neuropathy, HIV sensory neuropathy, post-herpetic neuralgia, post-thoracotomy pain, trigeminal neuralgia, radiculopathy, neuropathic pain associated with chemotherapy, reflex sympathetic dystrophy, back pain, peripheral neuropathy, entrapment neuropathy, phantom limb pain, and complex regional pain syndrome, dental pain, pain associated with a surgical procedure and or other medical intervention, bone cancer pain, joint pain associated with psoriatic arthritis, osteoarthritic pain, rheumatoid arthritic pain, juvenile chronic arthritis associated pain, juvenile idiopathic arthritis associated pain, Spondyloarthropathies (such as ankylosing spondylitis (Mb Bechterew) and reactive arthritis (Reiter's syndrome) associated pain), pain associated with psoriatic arthritis, gout pain, pain associated with pseudogout (pyrophosphate arthritis), pain associated with systemic lupus erythematosus (SLE), pain associated with systemic sclerosis (scleroderma), pain associated with Behcet's disease, pain associated with relapsing polychondritis, pain associated with adult Still's disease, pain associated with transient regional osteoporosis, pain associated with neuropathic arthropathy, pain associated with sarcoidosis, arthritic pain, rheumatic pain, joint pain, osteoarthritic joint pain, rheumatoid arthritic joint pain, juvenile chronic arthritis associated joint pain, juvenile idiopathic arthritis associated joint pain, Spondyloarthropathies (such as ankylosing spondylitis (Mb Bechterew) and reactive arthritis (Reiter's syndrome) associated joint pain), gout joint pain, joint pain associated with pseudogout (pyrophosphate arthritis), joint pain associated with systemic lupus erythematosus (SLE), joint pain associated with systemic sclerosis (scleroderma), joint pain associated with Behcet's disease, joint pain associated with relapsing polychondritis, joint pain associated with adult Still's disease, joint pain associated with transient regional osteoporosis, joint pain associated with neuropathic arthropathy, joint pain associated with sarcoidosis, arthritic joint pain, rheumatic joint pain, acute pain, acute joint pain, chronic pain, chronic joint pain, inflammatory pain, inflammatory joint pain, mechanical pain, mechanical joint pain, pain associated with the fibromyalgia syndrome (FMS), pain associated with polymyalgia rheumatica, monarticular joint pain, polyarticular joint pain, nociceptive pain, psychogenous pain, pain of unknown etiology, pain mediated by IL-6, IL-6 soluble receptor, or IL-6 receptor, pain associated with a surgical procedure in a patient with a clinical diagnosis of OA, pain like static allodynia, pain like dynamic allodynia, and/or pain associated with Crohn's disease.

Having described the invention in detail, it will be apparent that modifications and variations are possible without departing from the scope of the invention defined in the appended claims.

EXAMPLES

The following examples are included to demonstrate certain embodiments of the invention. Those of skill in the art should, however, in light of the present disclosure, appreciate that modifications can be made in the specific embodiments that are disclosed and still obtain a like or similar result without departing from the spirit and scope of the invention, therefore all matter set forth is to be interpreted as illustrative and not in a limiting sense.

Example 1

In Vitro Dissolution of Controlled-Release Bilayer Tablets

Control-release bilayer tablets were prepared containing 15 mg of oxycodone and 500 mg of acetaminophen (APAP), or 30 mg of oxycodone and 500 mg APAP. (See selected examples from Chart No. 2.) The ER layer contained 75% of the total amount of oxycodone in the tablet, 50% of the total amount of APAP in the tablet, and either 35% w/w POLYOX® 1105 (for fast release), 45% w/w POLYOX® 1105 (for medium release), or 45% w/w POLYOX® N60K (for slow release). The IR layer contained 25% of the total amount of oxycodone in the tablet and 50% of the total amount of APAP in the tablet.

Dissolution profiles for the three above-described compositions were determined in USP Type II apparatus. Six tablets of each composition were weighed, placed in a sinker, and dropped into an equilibrated dissolution bath vessel that contained 900 mL of (helium sparged) 0.1 N HCl that was heated to 37° C.±0.5° C. The mixture was stirred at 150±6 rpm and the temperature was maintained at 37° C.±0.5° C. for 12 hr. The bath vessel was covered with a low evaporation vessel cover. Samples (5 mL) were removed at 0.25, 0.5, 1, 2, 4, 6, 8, and 12 hours. Each sample was filtered through a 0.45 µm filter and analyzed by HPLC using standard procedures.

Figure 2:
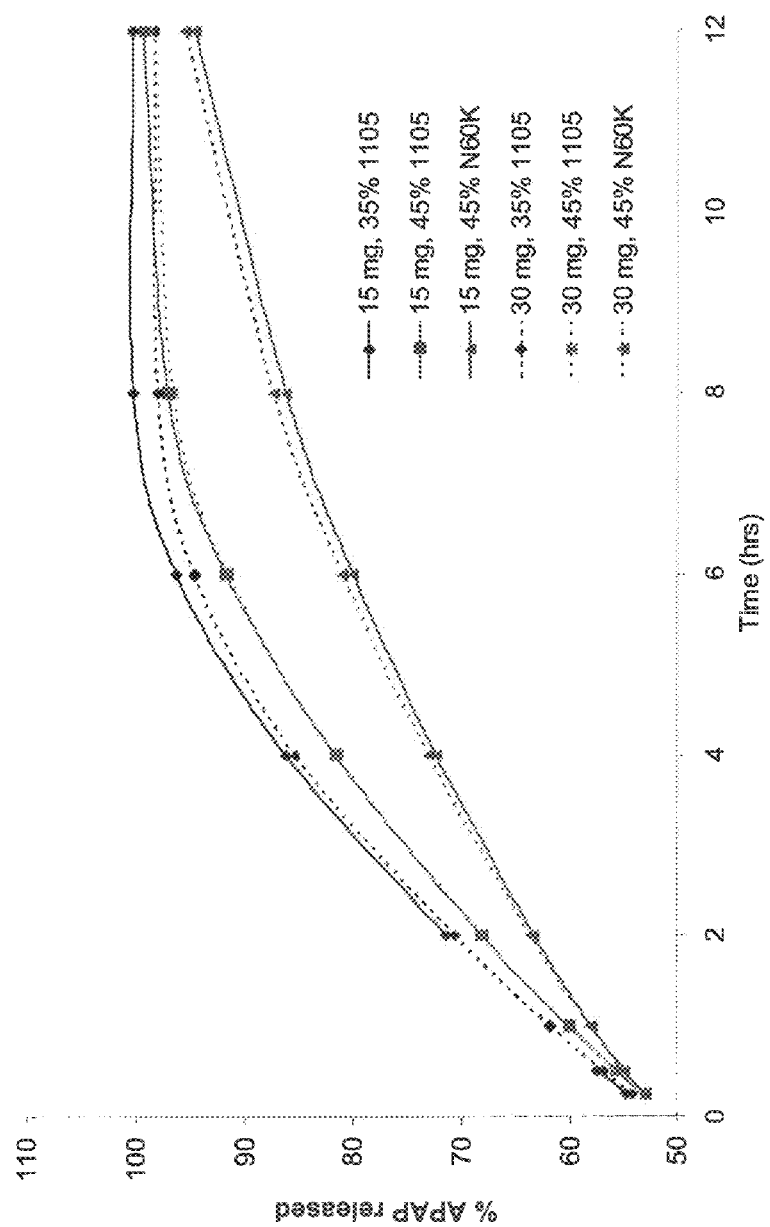
FIG. 2 shows the in vitro release profile of acetaminophen from oxycodone-acetaminophen bilayer tablets comprising either 15 or 30 mg of oxycodone, 500 mg of acetaminophen (APAP), and either 35 wt % POLYOX® 1105, 45 wt % POLYOX® 1105, or 45 wt % POLYOX® N60K, as indicated.

The cumulative release of oxycodone and APAP from 15 mg oxycodone/500 mg APAP tablets is presented in Table 1. Table 2 presents the cumulative release of oxycodone and APAP from 30 mg oxycodone/500 mg APAP (30/500) tablets. FIG. 1 presents the release profile of oxycodone from the 15/500 and 30/500 tablets. The dissolution profile of APAP from the 15/500 and 30/500 tablets is shown in FIG. 2. The release of oxycodone and APAP from the fast release and medium release tablets was essentially linear during the first half of the 12 hour time period but then plateaued during the last half of the 12 hour time period. The release of oxycodone and APAP from the slow release tablets was essentially linear during the entire 12 hour time period.

TABLE 1

Cumulative Release - 15 mg oxycodone/500 mg APAP Tablets

| | Oxycodone (%) | | | APAP (%) | | |
|---|---|---|---|---|---|---|
| Time (hr) | Fast | Medium | Slow | Fast | Medium | Slow |
| 0.25 | 27.56 | 25.70 | 25.68 | 54.78 | 53.06 | 53.01 |
| 0.5 | 34.33 | 31.31 | 30.39 | 57.55 | 55.73 | 54.89 |
| 1.0 | — | 40.85 | 37.81 | — | 60.03 | 58.03 |
| 2.0 | 59.88 | 55.67 | 49.50 | 71.42 | 68.16 | 63.27 |
| 4.0 | 83.46 | 77.94 | 67.43 | 86.17 | 81.55 | 72.31 |
| 6.0 | 97.48 | 92.12 | 80.53 | 96.19 | 91.62 | 79.97 |
| 8.0 | 101.26 | 99.26 | 90.20 | 100.16 | 96.96 | 86.06 |
| 12.0 | 101.57 | 101.23 | 99.36 | 100.10 | 99.16 | 94.41 |

TABLE 2

Cumulative Release - 30 mg oxycodone/500 mg APAP Tablets

| | Oxycodone (%) | | | APAP (%) | | |
|---|---|---|---|---|---|---|
| Time (hr) | Fast | Medium | Slow | Fast | Medium | Slow |
| 0.25 | 31.65 | 30.27 | 29.78 | 54.17 | 52.97 | 52.97 |
| 0.5 | 37.55 | 35.91 | 34.42 | 56.96 | 55.64 | 54.97 |
| 1.0 | 47.18 | 45.21 | 41.12 | 61.81 | 60.19 | 58.15 |
| 2.0 | 62.51 | 59.63 | 52.40 | 70.60 | 68.04 | 63.61 |
| 4.0 | 84.72 | 80.44 | 70.01 | 85.28 | 81.56 | 73.04 |
| 6.0 | 96.97 | 93.98 | 82.49 | 94.57 | 91.42 | 80.94 |
| 8.0 | 100.23 | 99.63 | 91.78 | 97.91 | 96.48 | 87.26 |
| 12.0 | 100.57 | 101.13 | 99.60 | 98.09 | 98.14 | 95.25 |

The cumulative in vitro release of oxycodone and APAP from 7.5 mg oxycodone/325 mg APAP medium release tablets is presented in Table 3. The ER layer of these tablets contained 5.625 mg of oxycodone, 162.5 mg of APAP, and 45% (w/w) POLYOX® 1105, and the IR layer contained 1.875 mg of oxycodone and 162.5 mg of APAP. (See selected example from Chart 1.) The dissolution profile was determined essentially as described above, except that samples were collected at 0.08 hour (~5 min) in addition to the later time points.

TABLE 3

Cumulative Release 7.5 mg oxycodone/325 mg APAP Tablets

| Time (hr) | Oxycodone (%) | | APAP (%) | |
|---|---|---|---|---|
| | Mean (%) | % RSD (%) | Mean (%) | % RSD (%) |
| 0.08 | 26.6 | 4.3 | 49.0 | 3.4 |
| 0.25 | 31.5 | 4.2 | 51.3 | 3.1 |
| 0.5 | 37.5 | 2.7 | 53.8 | 2.9 |
| 1.0 | 45.9 | 1.6 | 58.2 | 2.5 |
| 2.0 | 60.1 | 1.7 | 66.0 | 2.3 |
| 4.0 | 81.4 | 1.1 | 78.7 | 1.7 |
| 6.0 | 95.4 | 1.4 | 88.4 | 1.9 |
| 8.0 | 101.8 | 0.9 | 93.9 | 1.4 |
| 12.0 | 103.2 | 1.2 | 94.9 | 1.1 |

Figure 3:
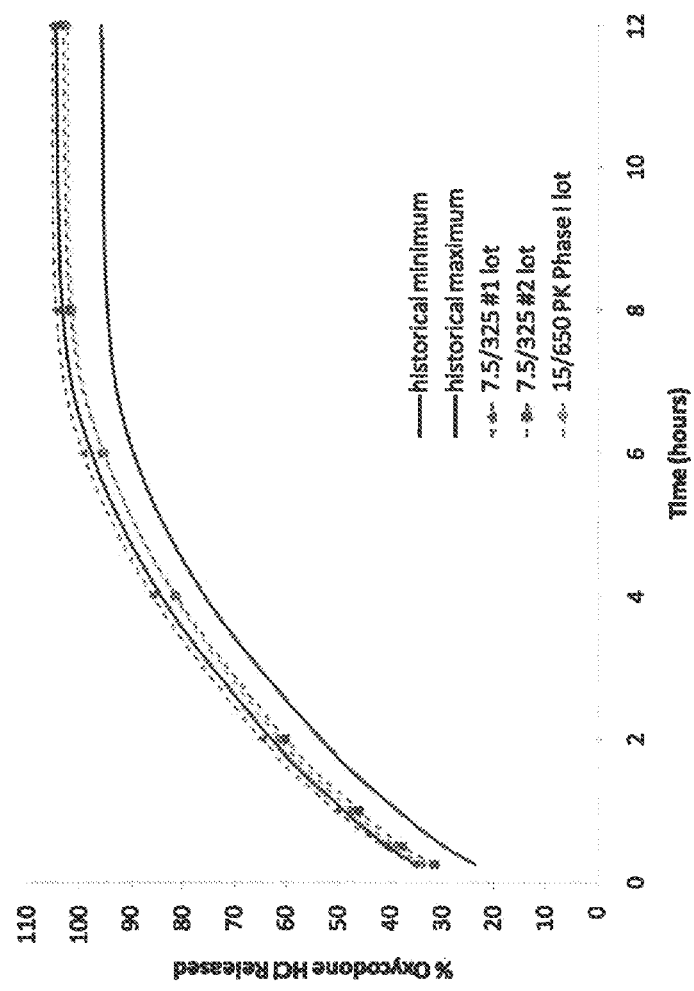
FIG. 3 presents the in vitro release profile of oxycodone from bilayer tablets comprising 7.5 mg of oxycodone and 325 mg of acetaminophen, and bilayer tablets comprising 15 mg of oxycodone and 650 mg of acetaminophen, as indicated.
Figure 4:
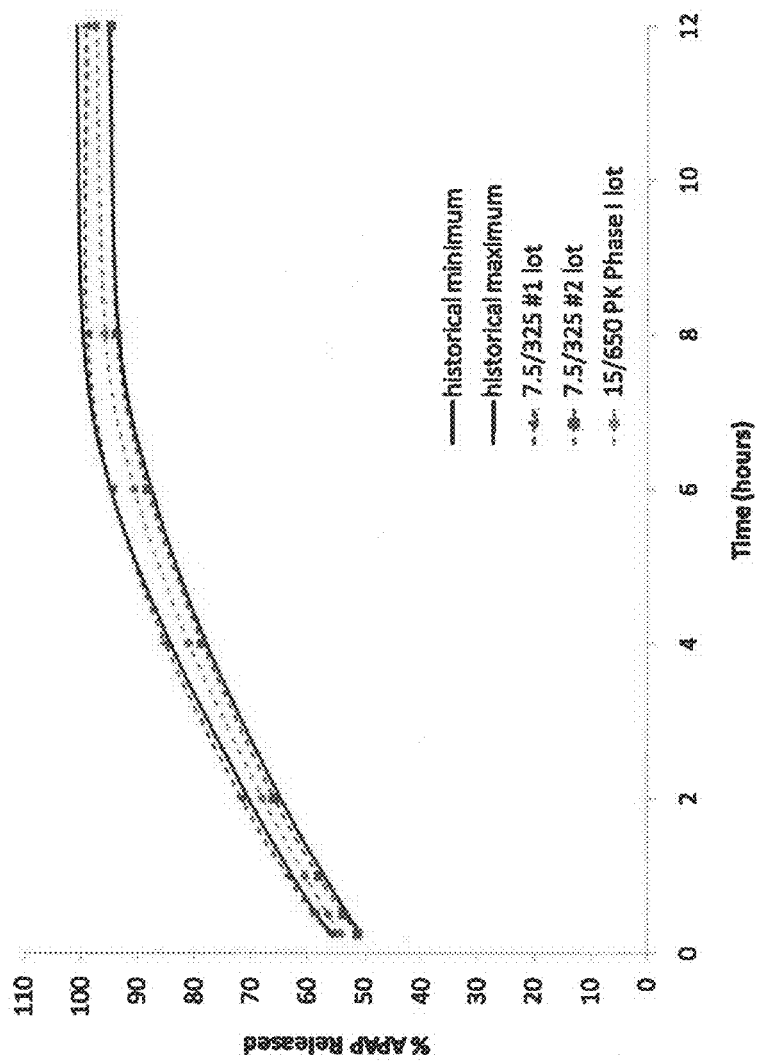
FIG. 4 presents the in vitro release profile of acetaminophen from bilayer tablets comprising 7.5 mg of oxycodone and 325 mg of acetaminophen, and bilayer tablets comprising 15 mg of oxycodone and 650 mg of acetaminophen, as indicated.

FIG. 3 and FIG. 4 present the percentage of oxycodone and APAP, respectively, released from two different lots of 7.5/325 tablets as compared to 15/650 tablets (see Example 28 for the dissolution data of the 15 mg oxycodone/650 acetaminophen tablets). The dissolution profiles were similar among all the tablets.

The release of oxycodone and APAP from each layer was analyzed by determining the calculated release from the ER layer and actual release from the total composition. For this, the tablets contained 7.5 mg of oxycodone HCl and 325 mg of APAP (i.e., the ER layer contained 5.625 mg of oxycodone HCl, 162.5 mg of APAP, and 45% (w/w) POLYOX® 1105; and the IR layer contained 1.875 mg of oxycodone HCl and 162.5 mg of APAP). The dissolution profile was determined essentially as described above. The calculated cumulative release of oxycodone HCl from the ER layer and the total tablet is presented in Table 4, and the calculated cumulative release of APAP from the ER layer and the total tablet is presented in Table 5. These data show that essentially all of the 1.875 mg of oxycodone HCl in the IR layer was released within about 5 minutes and essentially all of the 162.5 mg of APAP in the IR layer was released within about 15 minutes.

TABLE 4

Split Release of Oxycodone 7.5 mg oxycodone/325 mg APAP Tablets

| Time (hr) | Total (%) | Total (mg) | ER (%) | ER (mg) |
|---|---|---|---|---|
| 0.08 | 26.6 | 2.00 | 2.1 | 0.12 |
| 0.25 | 31.5 | 2.36 | 8.7 | 0.49 |
| 0.5 | 37.5 | 2.81 | 16.7 | 0.94 |
| 1.0 | 45.9 | 3.44 | 27.9 | 1.57 |
| 2.0 | 60.1 | 4.51 | 46.8 | 2.63 |
| 4.0 | 81.4 | 6.11 | 75.2 | 4.23 |
| 6.0 | 95.4 | 7.16 | 93.9 | 5.28 |
| 8.0 | 101.8 | 7.64 | 102.4 | 5.76 |
| 12.0 | 103.2 | 7.74 | 104.3 | 5.87 |

TABLE 5

Split Release of APAP 7.5 mg oxycodone/325 mg APAP Tablets

| Time (hr) | Total (%) | Total (mg) | ER (%) | ER (mg) |
|---|---|---|---|---|
| 0.08 | 49.0 | 159.25 | 0.0 | 0.00 |
| 0.25 | 51.3 | 166.73 | 2.6 | 4.22 |
| 0.5 | 53.8 | 174.85 | 7.6 | 12.35 |
| 1.0 | 58.2 | 189.15 | 16.4 | 26.65 |
| 2.0 | 66.0 | 214.50 | 32.0 | 52.00 |
| 4.0 | 78.7 | 255.78 | 57.4 | 93.28 |
| 6.0 | 88.4 | 287.30 | 76.8 | 124.80 |
| 8.0 | 93.9 | 305.18 | 87.8 | 142.68 |
| 12.0 | 94.9 | 308.43 | 89.8 | 145.93 |

Example 2

Clinical Pharmacokinetic Analysis of Controlled-Release 15 mg Oxycodone/500 mg Acetaminophen Bilayer Tablets—Single Dose An open-label, single dose, four-period crossover study was conducted to evaluate the pharmacokinetics (PK) and bioavailability of three controlled-release bilayer tablets comprising 15 mg oxycodone (OC) and 500 mg APAP as compared to a commercially available immediate-release tablet containing 7.5 mg oxycodone/325 mg acetaminophen. The three controlled release formulations—fast, medium, and slow—are described above. (See selected examples from Chart No. 2.) One tablet of each of the controlled-release bilayer formulations was administered to the test subjects under fed conditions. One tablet of the commercially available immediate-release tablet containing 7.5 mg oxycodone/325 mg acetaminophen was administered every 6 hours (Q6h) for two doses under fed conditions. The test subjects were about 40 normal, healthy male subjects between 21-45 years of age.

Subjects were randomly assigned to Treatments A, B, C, and D using a four-period, eight-sequence, crossover design as follows:
  Treatment A: One (1) tablet of 15 mg OC/500 mg APAP, Fast Release administered orally under fed conditions.
  Treatment B: One (1) tablet of 15 mg OC/500 mg APAP, Medium Release administered orally under fed conditions.
  Treatment C: One (1) tablet of 15 mg OC/500 mg APAP, Slow Release administered orally under fed conditions.
  Treatment D: One (1) tablet of a commercially available immediate-release tablet containing 7.5 mg oxycodone/325 mg administered orally Q6h for two (2) doses under fed conditions.

The crossover design allowed for within-subject comparisons among the test formulations with differing release profiles. Subjects received each of the study drug treatments (A-D) separated by at least a 7-day interval between the start of each period at Hour 0. During each period, subjects remained in the clinical facility from the time of check-in (on the day prior to dosing) until discharge on Day 3 (after the 48 hour blood draw).

Physical examinations, electrocardiograms and clinical laboratory tests were performed at screening and at the conclusion of the study (or early termination). Vital sign measurements (including pulse oximetry) and adverse events were monitored during the study. Subjects were administered a 50 mg naltrexone tablet 12 hours prior to Hour 0 dosing, at Hour 0, and 12 hours post-dose to block the effects and potential risks of oxycodone. After a 10 hour overnight fast, subjects were served a standardized FDA high-fat breakfast to be consumed in 30 minutes or less prior to Hour 0 dosing for the first oral dosage. All subjects in each period were served a standardized meal to be consumed in 30 minutes or less prior to Hour 6. Only subjects randomized to Treatment D were administered the second oral dosage of the commercially available immediate-release tablet containing 7.5 mg oxycodone/325 mg acetaminophen at Hour 6 in each period.

Blood was drawn at designated times for PK analysis. Samples (6 mL in pre-chilled vacuum blood collection tubes, containing K2EDTA as the anticoagulant) were taken pre-dose (up to 60 minutes prior to dose), 10 min, 20 min, 30 min, 40 min and 1, 2, 3, 4, 5, 6, 6.5, 7, 8, 9, 10, 12, 16, 18, 20, 24, 36 and 48 hours post-dose. The collected plasma samples were analyzed for the active pharmaceutical ingredients (APIs), i.e., oxycodone and acetaminophen, using validated liquid chromatography/tandem mass spectrometry (LC-MS/MS) assays.

The following PK parameters were calculated for oxycodone and acetaminophen using standard non-compartmental methods:

area under the plasma concentration curve to last quantifiable concentration $AUC_{(0-t)}$ area under the plasma concentration curve to infinite time $AUC_{(0-inf)}$ maximum observed plasma concentration ($C_{max}$)

time observed maximum plasma concentration ($t_{max}$)

lag time ($t_{lag}$)

apparent first-order terminal elimination rate constant ($k_{el}$)

apparent plasma terminal elimination half-life ($t_{1/2}$)

Parametric general linear model (GLM) methodology was used in the analysis of all pharmacokinetic parameters. The SAS GLM procedure was used to perform analysis of variance (ANOVA) on each pharmacokinetic parameter with sequence, treatment, period, and subjects nested within sequences, as sources of variation. For each formulation, least squares means and the associated standard errors were obtained using the LSMEANS option. All treatment pairwise comparisons were performed, without adjustment for multiplicity. AUC and $C_{max}$ were dose-adjusted for comparative purposes for acetaminophen and the commercially available immediate-release tablet containing 7.5 mg oxycodone/325 mg acetaminophen.

The pharmacokinetic data for oxycodone and APAP are presented in Tables 6-8 and 9-11, respectively.

TABLE 6

Oxycodone Pharmacokinetics (15/500)

| | Fast Release Formulation | | | | Commercially available immediate-release tablet |
|---|---|---|---|---|---|
| | | LSM | 90% CI | | |
| Parameter | Mean (% CV) | Ratio | Lower | Upper | Mean (% CV) |
| $C_{max}$ (ng/mL) | 18.803 (21) | 82.92 | 78.02 | 88.12 | 22.428 (20) |
| $C_{1\ hr}$ (ng/mL) | 6.891 (77) | 72.79 | 49.02 | 108.1 | 10.226 (65) |
| $C_{2\ hr}{}^a$ (ng/mL) | 12.355 (32) | 80.74 | 71.2 | 91.56 | 14.94 (26) |
| $AUC_{0-t}$ (ng · hr/mL) | 209.949 (26) | 89.73 | 86.52 | 93.06 | 229.788 (22) |
| $AUC_{0-inf}$ (ng · hr/mL) | 211.8 (25) | 89.95 | 86.77 | 93..24 | 231.421 (22) |
| $AUC_{0-1\ hr}$ (ng · hr/mL) | 2.565 (104) | 61.32 | 37.64 | 99.92 | 4.334 (80) |
| $AUC_{0-2\ hr}{}^b$ (ng · hr/mL) | 12.189 (53) | 70.16 | 55.97 | 87.95 | 16.917 (46) |
| $AUC_{0-4\ hr}{}^c$ (ng · hr/mL) | 41.3 (29) | 88.76 | 80.61 | 97.73 | 45.699 (24) |
| $T_{max}$ (hr) | 4.954 (34) | na | na | na | 7.954 (22) |
| $T_{lag}$ (hr) | 0.31 (68) | na | na | na | 0.219 (77) |
| $T_{1/2}$ (hr) | 4.584 (17) | na | na | na | 4.495 (14) |
| $K_{el}$ (1/hr) | 0.155 (16) | na | na | na | 0.157 (13) |

$^a$Concentration at the median $T_{max}$ for commercially-available immediate release tablet
$^b$AUC from zero the median $T_{max}$ for commercially-available immediate release tablet
$^c$AUC from the zero to the median $T_{max}$ + 2SD for commercially-available immediate release tablet

TABLE 7

Oxycodone Pharmacokinetics (15/500)

| | Medium Release Formulation | | | | Commercially-available immediate release tablet |
|---|---|---|---|---|---|
| | Mean | | 90% CI | | Mean |
| Parameter | (% CV) | LSM Ratio | Lower | Upper | (% CV) |
| $C_{max}$ (ng/mL) | 18.266 (25) | 80.87 | 76.09 | 85.95 | 22.428 (20) |
| $C_{1\ hr}$ (ng/mL) | 7.364 (81) | 67.62 | 45.75 | 99.95 | 10.226 (65) |
| $C_{2\ hr}{}^a$ (ng/mL) | 12.388 (45) | 79.04 | 69.69 | 89.64 | 14.94 (26) |

TABLE 7-continued

Oxycodone Pharmacokinetics (15/500)

| | Medium Release Formulation | | | | Commercially-available immediate release tablet |
|---|---|---|---|---|---|
| | Mean | | 90% CI | | Mean |
| Parameter | (% CV) | LSM Ratio | Lower | Upper | (% CV) |
| $AUC_{0-t}$ (ng · hr/mL) | 217.188 (23) | 94.19 | 90.82 | 97.68 | 229.788 (22) |
| $AUC_{0-inf}$ (ng · hr/mL) | 218.545 (23) | 94.09 | 90.77 | 97.54 | 231.421 (22) |
| $AUC_{0-1\ hr}$ (ng · hr/mL) | 3.248 (118) | 64.69 | 39.93 | 104.8 | 4.334 (80) |
| $AUC_{0-2\ hr}{}^b$ (ng · hr/mL) | 13.124 (70) | 71.74 | 57.22 | 89.96 | 16.917 (46) |
| $AUC_{0-4\ hr}{}^c$ (ng · hr/mL) | 42.101 (43) | 88.61 | 80.47 | 97.58 | 45.699 (24) |
| $T_{max}$ (hr) | 5.31 (38) | na | na | na | 7.954 (22) |
| $T_{lag}$ (hr) | 0.264 (64) | na | na | na | 0.219 (77) |
| $T_{1/2}$ (hr) | 4.557 (16) | na | na | na | 4.495 (14) |
| $K_{el}$ (1/hr) | 0.156 (16) | na | na | na | 0.157 (13) |

[a] Concentration at the median $T_{max}$ for commercially-available immediate release tablet
[b] AUC from zero the median $T_{max}$ for commercially-available immediate release tablet
[c] AUC from the zero to the median $T_{max}$ + 2SD for commercially-available immediate release tablet

TABLE 8

Oxycodone Pharmacokinetics (15/500)

| | Slow Release Formulation | | | | Commercially-available immediate release tablet |
|---|---|---|---|---|---|
| | Mean | LSM | 90% CI | | Mean |
| Parameter | (% CV) | Ratio | Lower | Upper | (% CV) |
| $C_{max}$ (ng/mL) | 17.403 (25) | 76.75 | 72.21 | 81.58 | 22.428 (20) |
| $C_{1\ hr}$ (ng/mL) | 7.601 (79) | 69.63 | 47.08 | 102.97 | 10.226 (65) |
| $C_{2\ hr}{}^a$ (ng/mL) | 11.237 (39) | 73.55 | 64.84 | 83.43 | 14.94 (26) |
| $AUC_{0-t}$ (ng · hr/mL) | 222.096 (25) | 95.62 | 92.2 | 99.18 | 229.788 (22) |
| $AUC_{0-inf}$ (ng · hr/mL) | 223.553 (25) | 95.61 | 92.22 | 99.11 | 231.421 (22) |
| $AUC_{0-1\ hr}$ (ng · hr/mL) | 2.893 (112) | 57.34 | 35.37 | 92.95 | 4.334 (80) |
| $AUC_{0-2\ hr}{}^b$ (ng · hr/mL) | 12.312 (66) | 68.63 | 54.72 | 86.08 | 16.917 (46) |
| $AUC_{0-4\ hr}{}^c$ (ng · hr/mL) | 38.842 (35) | 83.46 | 75.78 | 91.92 | 45.699 (24) |
| $T_{max}$ (hr) | 5.655 (27) | na | na | na | 7.954 (22) |
| $T_{lag}$ (hr) | 0.299 (74) | na | na | na | 0.219 (77) |
| $T_{1/2}$ (hr) | 4.647 (19) | na | na | na | 4.495 (14) |
| $K_{el}$ (1/hr) | 0.154 (18) | na | na | na | 0.157 (13) |

[a] Concentration at the median $T_{max}$ for commercially-available immediate release tablet
[b] AUC from zero the median $T_{max}$ for commercially-available immediate release tablet
[c] AUC from the zero to the median $T_{max}$ + 2SD for commercially-available immediate release tablet

TABLE 9

Acetaminophen Pharmacokinetics (15/500)

| | Fast Release Formulation | | | | Commercially-available immediate release tablet* |
|---|---|---|---|---|---|
| | Mean | LSM | 90% CI | | Mean |
| Parameter | (% CV) | Ratio | Lower | Upper | (% CV) |
| $C_{max}$ (ng/mL) | 2612 (26) | 94.46 | 87.25 | 102.26 | 2721 (22) |
| $C_{1\ hr}$ (ng/mL) | 1627 (66) | 113.22 | 84.91 | 150.98 | 1516 (58) |
| $C_{2\ hr}{}^a$ (ng/mL) | 2248 (30) | 118.49 | 107.61 | 130.48 | 1841 (20) |
| $AUC_{0-t}$ (ng · hr/mL) | 21944 (27) | 98.78 | 95.91 | 101.75 | 21962 (22) |
| $AUC_{0-inf}$ (ng · hr/mL) | 23090 (27) | 98.73 | 95.85 | 101.7 | 23104 (21) |
| $AUC_{0-1\ hr}$ (ng · hr/mL) | 823 (96) | 105.42 | 68.75 | 161.64 | 814 (82) |
| $AUC_{0-2\ hr}{}^b$ (ng · hr/mL) | 2761 (52) | 106.73 | 86.55 | 131.62 | 2492 (47) |
| $AUC_{0-4\ hr}{}^c$ (ng · hr/mL) | 7006 (28) | 119.91 | 110.42 | 130.2 | 5726 (22) |
| $T_{max}$ (hr) | 2.328 (58) | na | na | na | 6.971 (34) |
| $T_{lag}$ (hr) | 0.276 (81) | na | na | na | 0.219 (98) |

TABLE 9-continued

Acetaminophen Pharmacokinetics (15/500)

| Parameter | Fast Release Formulation | | | | Commercially-available immediate release tablet* |
|---|---|---|---|---|---|
| | Mean (% CV) | LSM Ratio | 90% CI Lower | 90% CI Upper | Mean (% CV) |
| $T_{1/2}$ (hr) | 5.235 (35) | na | na | na | 6.461 (66) |
| $K_{el}$ (1/hr) | 0.145 (28) | na | na | na | 0.137 (39) |

*Dose Normalized to 500 mg
[a] Concentration at the median $T_{max}$ for commercially-available immediate release tablet
[b] AUC from zero the median $T_{max}$ for commercially-available immediate release tablet
[c] AUC from the zero to the median $T_{max}$ + 2SD for commercially-available immediate release tablet

TABLE 10

Acetaminophen Pharmacokinetics (15/500)

| Parameter | Medium Release Formulation | | | | Commercially-available immediate release tablet* |
|---|---|---|---|---|---|
| | Mean (% CV) | LSM Ratio | 90% CI Lower | 90% CI Upper | Mean (% CV) |
| $C_{max}$ (ng/mL) | 2720 (22) | 99.19 | 91.61 | 107.39 | 2721 (22) |
| $C_{1\,hr}$ (ng/mL) | 1831 (54) | 121.62 | 91.51 | 161.65 | 1516 (58) |
| $C_{2\,hr}{}^{a}$ (ng/mL) | 2170 (23) | 116.69 | 105.96 | 128.51 | 1841 (20) |
| $AUC_{0-t}$ (ng·hr/mL) | 22184 (22) | 100.68 | 97.74 | 103.7 | 21962 (22) |
| $AUC_{0-inf}$ (ng·hr/mL) | 23554 (22) | 101.39 | 98.43 | 104.44 | 23104 (21) |
| $AUC_{0-1\,hr}$ (ng·hr/mL) | 974 (85) | 124.39 | 81.52 | 189.79 | 814 (82) |
| $AUC_{0-2\,hr}{}^{b}$ (ng·hr/mL) | 2974 (47) | 117.9 | 95.58 | 145.43 | 2492 (47) |
| $AUC_{0-4\,hr}{}^{c}$ (ng·hr/mL) | 7122 (23) | 123.98 | 114.17 | 134.64 | 5726 (22) |
| $T_{max}$ (hr) | 2.069 (66) | na | na | na | 6.971 (34) |

TABLE 10-continued

Acetaminophen Pharmacokinetics (15/500)

| Parameter | Medium Release Formulation | | | | Commercially-available immediate release tablet* |
|---|---|---|---|---|---|
| | Mean (% CV) | LSM Ratio | 90% CI Lower | 90% CI Upper | Mean (% CV) |
| $T_{lag}$ (hr) | 0.218 (77) | na | na | na | 0.219 (98) |
| $T_{1/2}$ (hr) | 5.696 (33) | na | na | na | 6.461 (66) |
| $K_{el}$ (1/hr) | 0.133 (29) | na | na | na | 0.137 (39) |

*Dose Normalized to 500 mg
[a] Concentration at the median $T_{max}$ for commercially-available immediate release tablet
[b] AUC from zero the median $T_{max}$ for commercially-available immediate release tablet
[c] AUC from the zero to the median $T_{max}$ + 2SD for commercially-available immediate release tablet

TABLE 11

Acetaminophen Pharmacokinetics (15/500)

| Parameter | Slow Release Formulation | | | | Commercially-available immediate release tablet* |
|---|---|---|---|---|---|
| | Mean (% CV) | LSM Ratio | 90% CI Lower | 90% CI Upper | Mean (% CV) |
| $C_{max}$ (ng/mL) | 2521 (18) | 93.6 | 86.44 | 101.35 | 2721 (22) |
| $C_{1\,hr}$ (ng/mL) | 1766 (51) | 126.26 | 94.96 | 167.87 | 1516 (58) |
| $C_{2\,hr}{}^{a}$ (ng/mL) | 2113 (18) | 116.18 | 105.48 | 127.96 | 1841 (20) |
| $AUC_{0-t}$ (ng·hr/mL) | 21947 (25) | 99.61 | 96.7 | 102.61 | 21962 (22) |
| $AUC_{0-inf}$ (ng·hr/mL) | 23279 (25) | 100.47 | 97.53 | 103.49 | 23104 (21) |
| $AUC_{0-1\,hr}$ (ng·hr/mL) | 872 (83) | 115.25 | 75.49 | 175.95 | 814 (82) |
| $AUC_{0-2\,hr}{}^{b}$ (ng·hr/mL) | 2811 (43) | 116.49 | 94.42 | 143.73 | 2492 (47) |
| $AUC_{0-4\,hr}{}^{c}$ (ng·hr/mL) | 6828 (19) | 120.68 | 111.11 | 131.07 | 5726 (22) |
| $T_{max}$ (hr) | 2.184 (59) | na | na | na | 6.971 (34) |
| $T_{lag}$ (hr) | 0.253 (86) | na | na | na | 0.219 (98) |
| $T_{1/2}$ (hr) | 5.366 (32) | na | na | na | 6.461 (66) |
| $K_{el}$ (1/hr) | 0.141 (28) | na | na | na | 0.137 (39) |

*Dose Normalized to 500 mg
[a] Concentration at the median $T_{max}$ for commercially-available immediate release tablet
[b] AUC from zero the median $T_{max}$ for commercially-available immediate release tablet
[c] AUC from the zero to the median $T_{max}$ + 2SD for commercially-available immediate release tablet The pharmacokinetic parameters for the medium release 15/500 formulation and the commercially-available immediate release tablet are shown in Table 12.

TABLE 12

Pharmacokinetic Profile (Mean ± SD) of Oxycodone/APAP versus commercially-available immediate release tablet (N = 29)

| Dosage | $C_{max}$ (ng/mL) | $AUC_{0-t}$ (ng · hr/mL) | $AUC_{0-inf}$ (ng · hr/mL) | $T_{max}$ (hr) | $K_{el}$ (1/hr) | $t_{1/2}$ (hr) |
|---|---|---|---|---|---|---|
| Oxycodone | | | | | | |
| 15 mg OC/500 mg APAP | 18.3 ± 4.6 | 217 ± 49.2 | 219 ± 49.5 | 5.3 ± 2.0 | 0.156 ± 0.024 | 4.6 ± 0.7 |
| Commercially-available immediate release tablet (7.5 mg OC/325 mg APAP) | 22.4 ± 4.5* | 230 ± 49.8 | 231 ± 50.0 | 8.0 ± 1.7* | 0.157 ± 0.020 | 4.5 ± 0.6 |
| Acetaminophen | | | | | | |
| 15 mg OC/500 mg APAP | 2720 ± 608 | 221184 ± 4804 | 23554 ± 5234 | 2.1 ± 1.4 | 0.133 ± 0.039 | 5.7 ± 1.9 |
| Commercially-available immediate release tablet[a] (7.5 mg OC/325 mg APAP) | 2721 ± 584* | 21962 ± 4772 | 23104 ± 4882 | 7.0 ± 2.4* | 0.137 ± 0.054 | 6.5 ± 4.3 |

*Most values occurred after the second dose.
[a]AUC and $C_{max}$ dose-normalized to 500 mg for APAP.

Figure 5:
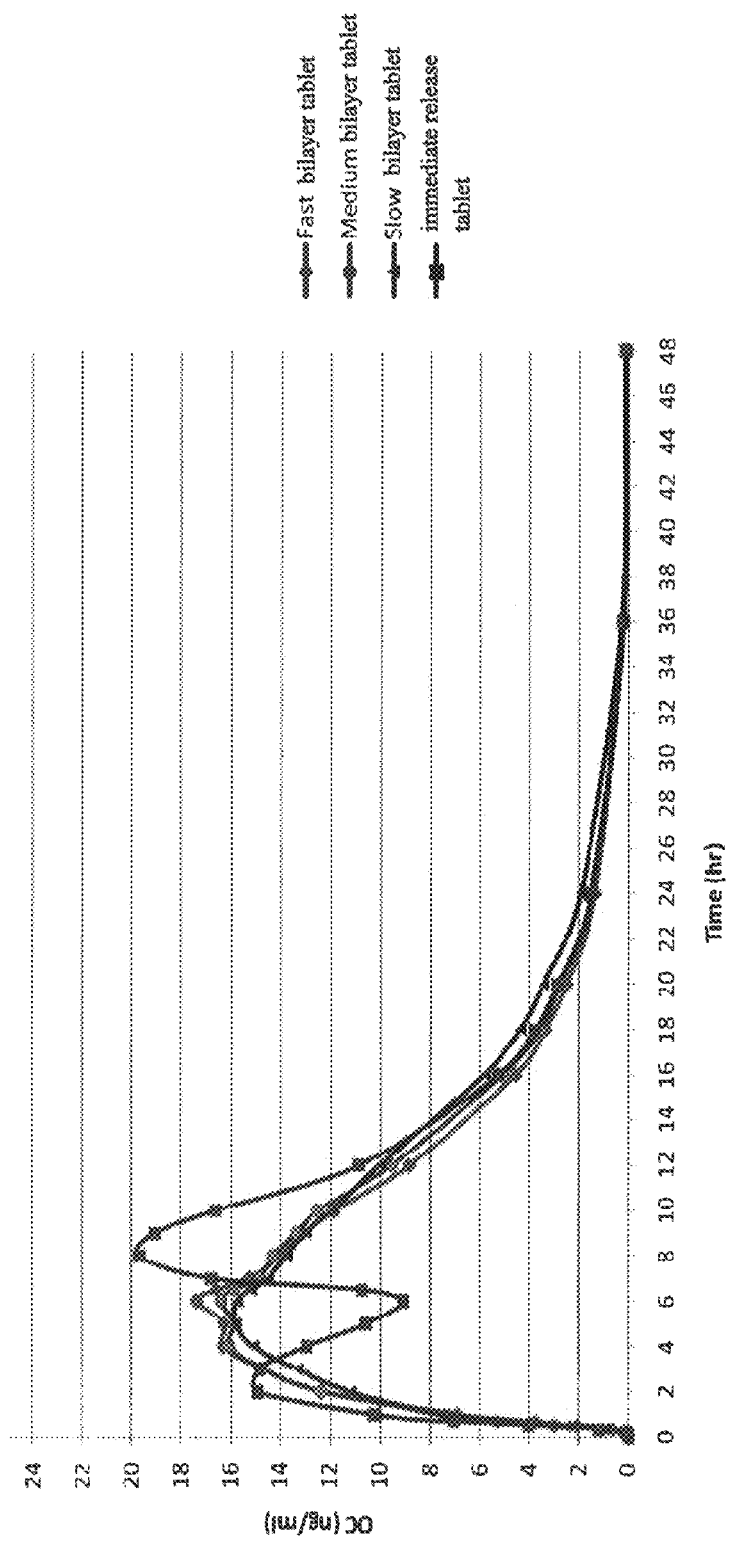
FIG. 5 is a graphical representation of the mean plasma oxycodone concentrations as a function of time after administration of a single dose of bilayer tablet comprising 15 mg oxycodone/500 mg acetaminophen and having fast, medium, or slow release properties as compared to an immediate release 7.5 oxycodone/325 acetaminophen tablet administered twice at a 6 hr interval.
Figure 6:
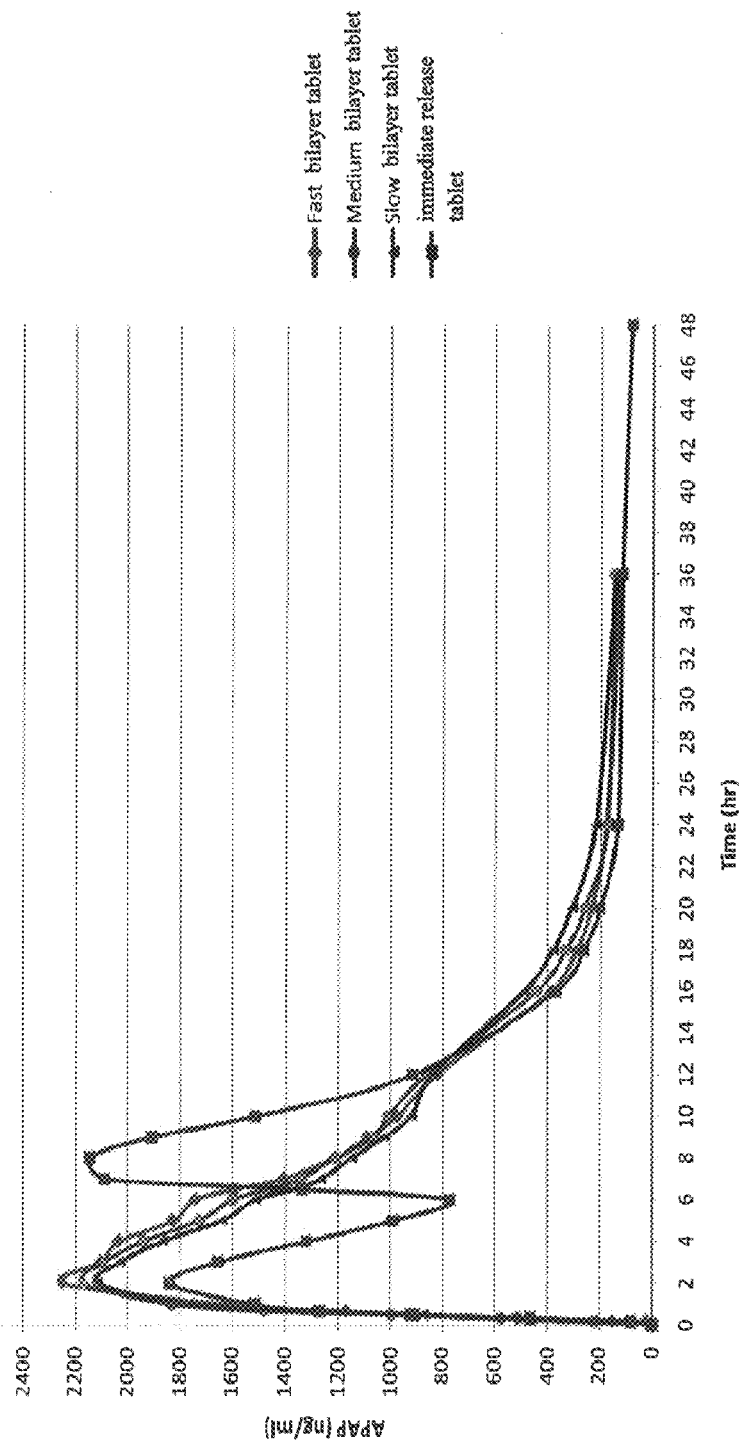
FIG. 6 is a graphical representation of the mean plasma acetaminophen concentrations as a function of time after administration of a single dose of bilayer tablet comprising 15 mg oxycodone/500 mg acetaminophen and having fast, medium, or slow release properties as compared to an immediate release 7.5 oxycodone/325 acetaminophen tablet administered twice at a 6 hr interval. The immediate release 7.5 oxycodone/325 acetaminophen tablet dose was normalized.

The oxycodone mean plasma concentration as a function of time after administration of 15/500 tablets is shown in Table 13 and FIG. 5. The APAP mean plasma concentration over time after administration of 15/500 tablets is shown in Table 14 and FIG. 6.

TABLE 13

Time Course of Oxycodone Plasma Concentration (ng/mL)

| Time (hr) | Mean Fast | SEM | Mean Medium | SEM | Mean Slow | SEM | Mean commercially-available immediate release tablet | SEM |
|---|---|---|---|---|---|---|---|---|
| 0 | 0 | 0 | 0 | 0 | 0 | 0 | 0 | 0 |
| 0.17 | 0 | 0 | 0.13 | 0.11 | 0.06 | 0.02 | 0.03 | 0.03 |
| 0.33 | 0.65 | 0.29 | 1.08 | 0.44 | 0.93 | 0.41 | 1.16 | 0.36 |
| 0.5 | 2.09 | 0.55 | 2.98 | 0.95 | 2.55 | 0.96 | 4.03 | 0.9 |
| 0.67 | 3.74 | 0.91 | 5.29 | 1.25 | 4.15 | 1.1 | 7.04 | 0.93 |
| 1 | 6.89 | 0.98 | 7.36 | 1.11 | 7.6 | 1.24 | 10.23 | 1.11 |
| 2 | 12.36 | 0.74 | 12.39 | 1.04 | 11.24 | 0.73 | 14.94 | 0.81 |
| 3 | 14.77 | 0.82 | 14.73 | 0.91 | 13.35 | 0.53 | 14.84 | 0.62 |
| 4 | 16.33 | 0.8 | 16.1 | 0.82 | 15.12 | 0.44 | 12.95 | 0.58 |
| 5 | 16.28 | 0.67 | 15.89 | 0.81 | 15.83 | 0.41 | 10.58 | 0.8 |
| 6 | 17.4 | 0.72 | 16.43 | 0.81 | 15.76 | 0.41 | 9.1 | 0.67 |
| 6.5 | 16.59 | 0.64 | 15.89 | 0.72 | 15.22 | 0.96 | 10.76 | 0.7 |
| 7 | 15.28 | 0.58 | 14.83 | 0.69 | 14.49 | 1.43 | 16.84 | 0.69 |
| 8 | 14.02 | 0.6 | 14.29 | 0.64 | 13.77 | 0.85 | 19.7 | 0.7 |
| 9 | 13.13 | 0.57 | 13.39 | 0.55 | 13 | 0.78 | 19.08 | 0.65 |
| 10 | 11.9 | 0.64 | 12.52 | 0.53 | 11.92 | 0.68 | 16.63 | 0.57 |
| 12 | 8.86 | 0.6 | 9.59 | 0.49 | 10.04 | 0.59 | 10.88 | 0.53 |

TABLE 14

Time Course of Acetaminophen Plasma Concentration (ng/mL)

| Time (hr) | Mean Fast | SEM | Mean Medium | SEM | Mean Slow | SEM | Mean commercially-available immediate release tablet | SEM |
|---|---|---|---|---|---|---|---|---|
| 0 | 0 | 0 | 0 | 0 | 0 | 0 | 0 | 0 |
| 0.17 | 31 | 18 | 284 | 151 | 220 | 88 | 107 | 47 |
| 0.33 | 673 | 210 | 751 | 221 | 678 | 197 | 607 | 173 |
| 0.5 | 1216 | 266 | 1299 | 275 | 1133 | 248 | 1181 | 229 |
| 0.67 | 1624 | 301 | 1922 | 301 | 1647 | 252 | 1653 | 255 |
| 1 | 2116 | 258 | 2380 | 239 | 2296 | 217 | 1971 | 210 |
| 2 | 2922 | 160 | 2821 | 123 | 2747 | 93 | 2393 | 90 |
| 3 | 2736 | 129 | 2719 | 90 | 2636 | 94 | 2150 | 65 |
| 4 | 2643 | 120 | 2524 | 103 | 2424 | 110 | 1717 | 71 |
| 5 | 2376 | 112 | 2246 | 121 | 2130 | 118 | 1290 | 59 |
| 6 | 2263 | 100 | 2080 | 143 | 1965 | 107 | 1006 | 58 |
| 6.5 | 2068 | 93 | 1903 | 126 | 1774 | 102 | 1742 | 212 |
| 7 | 1830 | 80 | 1744 | 116 | 1644 | 98 | 2749 | 232 |
| 8 | 1577 | 81 | 1573 | 103 | 1495 | 93 | 2790 | 114 |
| 9 | 1416 | 79 | 1407 | 88 | 1330 | 80 | 2482 | 111 |
| 10 | 1286 | 82 | 1314 | 84 | 1198 | 71 | 1968 | 105 |
| 12 | 1069 | 89 | 1131 | 86 | 1089 | 66 | 1188 | 82 |

Example 3

Figure 7:
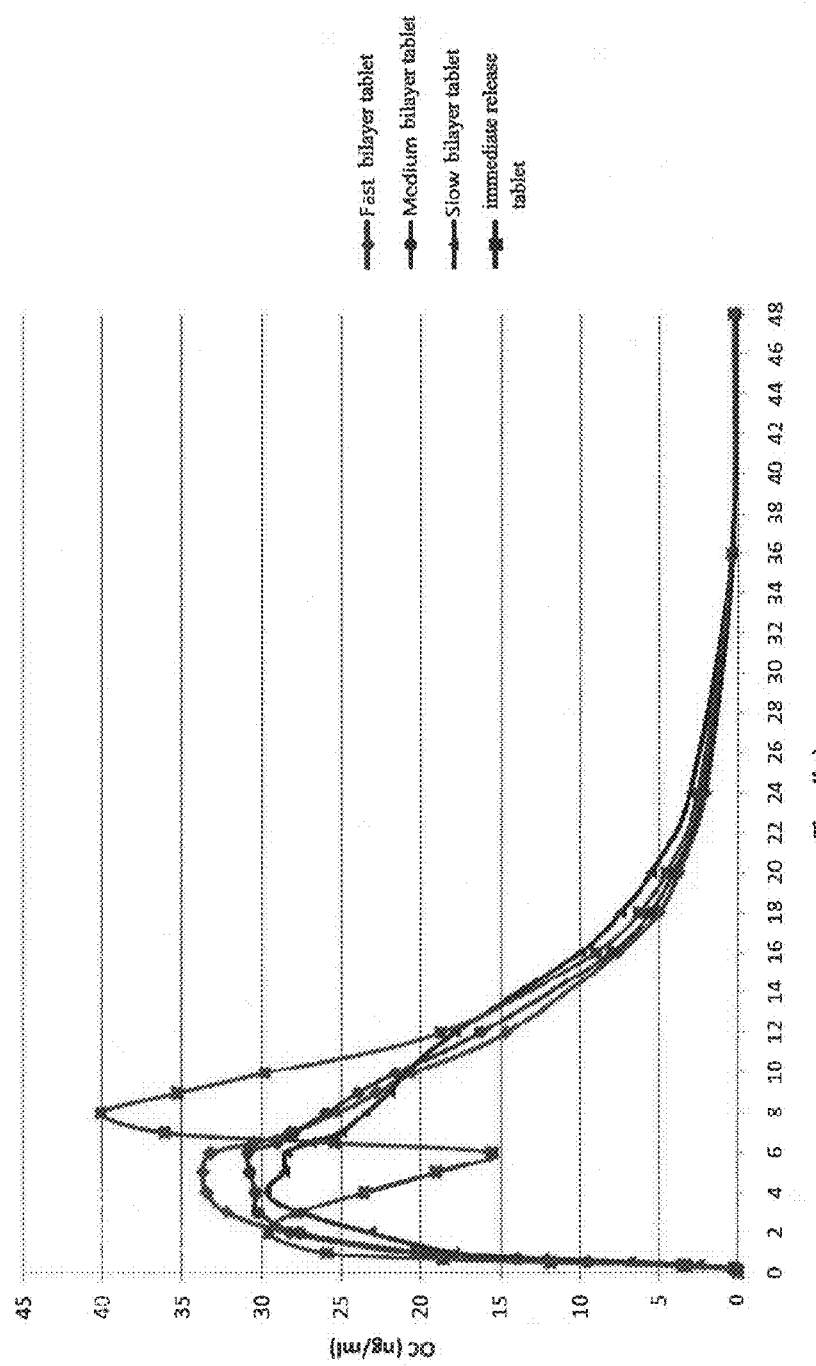
FIG. 7 is a graphical representation of the mean plasma oxycodone concentrations as a function of time after administration of a single dose of bilayer tablet comprising 30 mg oxycodone/500 mg acetaminophen and having fast, medium, or slow release properties as compared to an immediate release 7.5 oxycodone/325 acetaminophen tablet administered twice at a 6 hr interval. The immediate release 7.5 oxycodone/325 acetaminophen tablet dose was normalized.
Figure 8:
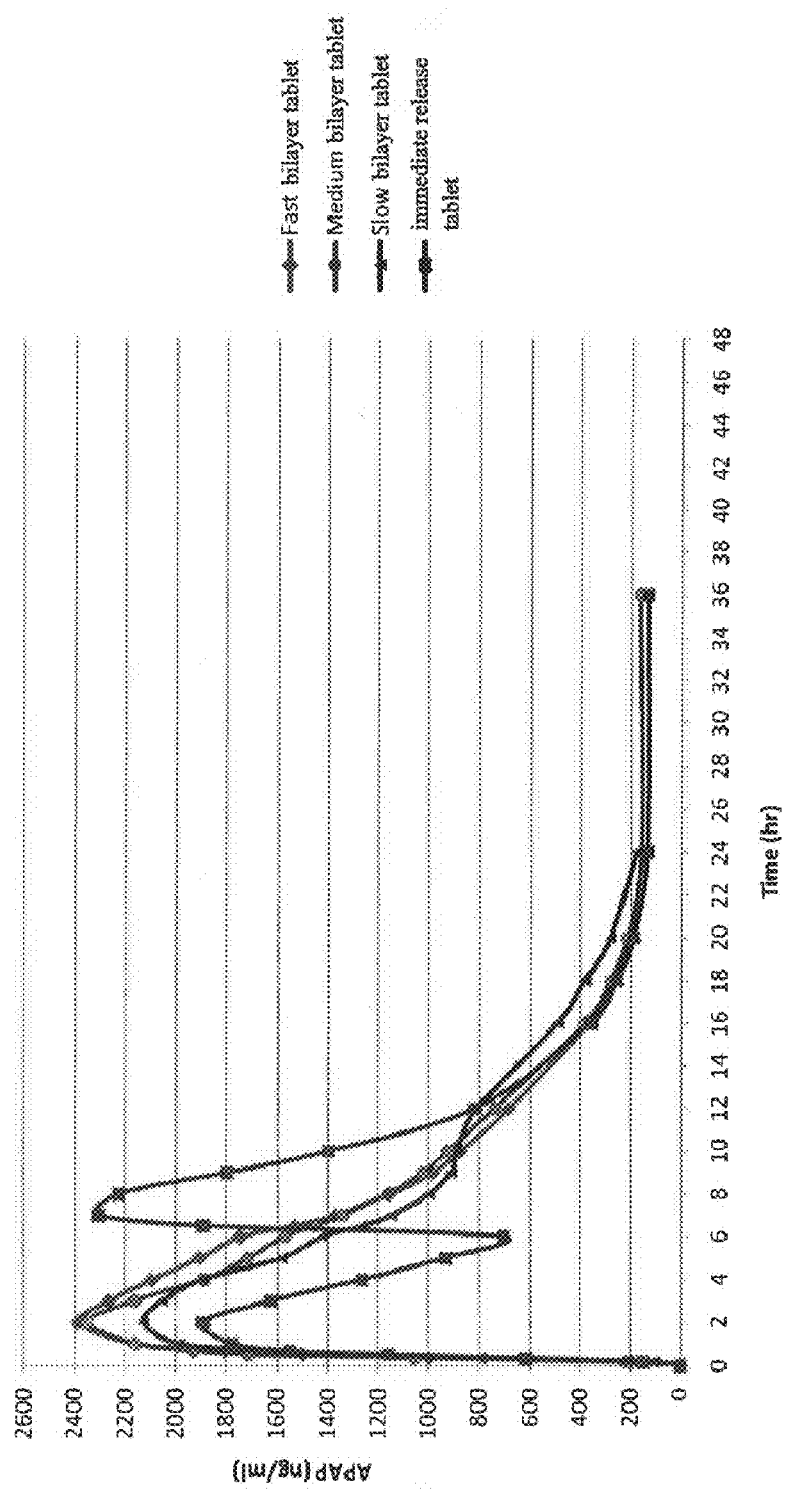
FIG. 8 is a graphical representation of the mean plasma acetaminophen concentrations as a function of time after administration of a single dose of bilayer tablet comprising 30 mg oxycodone/500 mg acetaminophen and having fast, medium, or slow release properties as compared to an immediate release 7.5 oxycodone/325 acetaminophen tablet administered twice at a 6 hr interval. The immediate release 7.5 oxycodone/325 acetaminophen tablet dose was normalized.

Clinical Pharmacokinetic Analysis of Controlled-Release 30 mg Oxycodone/500 mg Acetaminophen Bilayer Tablets—Single Dose A single dose, four-period crossover study was conducted essentially as described in Example 2, except the controlled-release bilayer tablets contained 30 mg oxycodone and 500 mg APAP. (See selected examples from Chart No. 2.) Tables 15-17 and 18-20 present the PK data for oxycodone and APAP, respectively. The plasma concentrations of oxycodone and APAP are presented in FIG. 7 and FIG. 8, respectively.

TABLE 15

Oxycodone Pharmacokinetics (30/500)

| | Fast Release Formulation | | | | Commercially-available immediate release tablet |
|---|---|---|---|---|---|
| | Mean | LSM | 90% CI | | Mean |
| Parameter | (% CV) | Ratio | Lower | Upper | (% CV) |
| $C_{max}$ (ng/mL) | 39.159 (28) | 82.17 | 75.96 | 88.9 | 47.597 (26) |
| $C_{1\ hr}$ (ng/mL) | 20.462 (74) | 77.25 | 54.37 | 109.76 | 25.911 (67) |
| $C_{2\ hr}^{a}$ (ng/mL) | 28.221 (39) | 95.18 | 83.82 | 108.08 | 29.579 (32) |
| $AUC_{0-t}$ (ng · hr/mL) | 393.952 (30) | 92.84 | 89.3 | 96.53 | 425.978 (29) |
| $AUC_{0-inf}$ (ng · hr/mL) | 396.135 (29) | 92.4 | 88.94 | 95.99 | 430.196 (29) |
| $AUC_{0-1\ hr}$ (ng · hr/mL) | 9.106 (100) | 71.09 | 46.05 | 109.76 | 11.55 (93) |
| $AUC_{0-2\ hr}^{b}$ (ng · hr/mL) | 33.448 (61) | 82.59 | 67.9 | 100.46 | 39.295 (53) |
| $AUC_{0-4\ hr}^{c}$ (ng · hr/mL) | 96.47 (38) | 101.27 | 91.51 | 112.06 | 93.706 (29) |
| $AUC_{4\ hr-t}^{d}$ | 395.522 (29) | 92.4 | 88.95 | 95.99 | 429.507 (29) |
| $T_{max}$ (hr) | 4.057 (51) | na | na | na | 6.948 (33) |
| $T_{lag}$ (hr) | 0.213 (107) | na | na | na | 0.184 (66) |
| $T_{1/2}$ (hr) | 4.398 (15) | na | na | na | 4.32 (15) |
| $K_{el}$ (1/hr) | 0.161 (15) | na | na | na | 0.164 (16) |

[a]Concentration at the median $T_{max}$ for commercially-available immediate release tablet
[b]AUC from zero the median $T_{max}$ for commercially-available immediate release tablet
[c]AUC from the zero to the median $T_{max}$ + 2SD for commercially-available immediate release tablet

TABLE 16

Oxycodone Pharmacokinetics (30/500)

| | Medium Release Formulation | | | | Commercially-available immediate release tablet |
|---|---|---|---|---|---|
| | Mean | LSM | 90% CI | | Mean |
| Parameter | (% CV) | Ratio | Lower | Upper | (% CV) |
| $C_{max}$ (ng/mL) | 36.731 (30) | 77.14 | 71.27 | 83.48 | 47.597 (26) |
| $C_{1\ hr}$ (ng/mL) | 19.758 (70) | 86.12 | 60.48 | 122.62 | 25.911 (67) |
| $C_{2\ hr}^{a}$ (ng/mL) | 27.655 (39) | 93.53 | 82.31 | 106.28 | 29.579 (32) |
| $AUC_{0-t}$ (ng · hr/mL) | 396.026 (29) | 94.17 | 90.55 | 97.92 | 425.978 (29) |
| $AUC_{0-inf}$ (ng · hr/mL) | 398.084 (29) | 93.68 | 90.16 | 97.34 | 430.196 (29) |
| $AUC_{0-1\ hr}$ (ng · hr/mL) | 8.988 (85) | 93.06 | 60.12 | 144.04 | 11.55 (93) |
| $AUC_{0-2\ hr}^{b}$ (ng · hr/mL) | 32.695 (56) | 86.02 | 70.64 | 104.74 | 39.295 (53) |
| $AUC_{0-4\ hr}^{c}$ (ng · hr/mL) | 91.998 (36) | 98.13 | 88.63 | 108.65 | 93.706 (29) |
| $AUC_{4\ hr-t}^{d}$ | 397.436 (29) | 93.68 | 90.16 | 97.34 | 429.507 (29) |
| $T_{max}$ (hr) | 4.523 (51) | na | na | na | 6.948 (33) |
| $T_{lag}$ (hr) | 0.207 (95) | na | na | na | 0.184 (66) |
| $T_{1/2}$ (hr) | 4.369 (14) | na | na | na | 4.32 (15) |
| $K_{el}$ (1/hr) | 0.162 (14) | na | na | na | 0.164 (16) |

[a]Concentration at the median $T_{max}$ for commercially-available immediate release tablet
[b]AUC from zero the median $T_{max}$ for commercially-available immediate release tablet
[c]AUC from the zero to the median $T_{max}$ + 2SD for commercially-available immediate release tablet

TABLE 17

Oxycodone Pharmacokinetics (30/500)

| Parameter | Slow Release Formulation | | | | Commercially-available immediate release tablet |
|---|---|---|---|---|---|
| | Mean (% CV) | LSM Ratio | 90% CI Lower | 90% CI Upper | Mean (% CV) |
| $C_{max}$ (ng/mL) | 32.976 (29) | 68.96 | 63.74 | 74.6 | 47.597 (26) |
| $C_{1\,hr}$ (ng/mL) | 17.897 (74) | 73.61 | 52.01 | 104.18 | 25.911 (67) |
| $C_{2\,hr}{}^a$ (ng/mL) | 23.183 (33) | 78.42 | 69.06 | 89.05 | 29.579 (32) |
| $AUC_{0-t}$ (ng·hr/mL) | 399.623 (26) | 94.5 | 90.9 | 98.25 | 425.978 (29) |
| $AUC_{0-inf}$ (ng·hr/mL) | 401.362 (26) | 93.88 | 90.36 | 97.52 | 430.196 (29) |
| $AUC_{0-1\,hr}$ (ng·hr/mL) | 7.643 (96) | 69.93 | 45.52 | 107.44 | 11.55 (93) |
| $AUC_{0-2\,hr}{}^b$ (ng·hr/mL) | 28.183 (59) | 71.58 | 58.85 | 87.06 | 39.295 (53) |
| $AUC_{0-4\,hr}{}^c$ (ng·hr/mL) | 82.171 (36) | 86.17 | 77.87 | 95.35 | 93.706 (29) |
| $AUC_{4\,hr-t}{}^d$ | 400.56 (26) | 93.85 | 90.34 | 97.49 | 429.507 (29) |
| $T_{max}$ (hr) | 3.96 (48) | na | na | na | 6.948 (33) |
| $T_{lag}$ (hr) | 0.201 (78) | na | na | na | 0.184 (66) |
| $T_{1/2}$ (hr) | 4.418 (17) | na | na | na | 4.32 (15) |
| $K_{el}$ (1/hr) | 0.161 (17) | na | na | na | 0.164 (16) |

$^a$Concentration at the median $T_{max}$ for commercially-available immediate release tablet
$^b$AUC from zero the median $T_{max}$ for commercially-available immediate release tablet
$^c$AUC from the zero to the median $T_{max}$ + 2SD for commercially-available immediate release tablet

TABLE 18

Acetaminophen Pharmacokinetics (30/500)

| Parameter | Fast Release Formulation | | | | Commercially-available immediate release tablet |
|---|---|---|---|---|---|
| | Mean (% CV) | LSM Ratio | 90% CI Lower | 90% CI Upper | Mean (% CV) |
| $C_{max}$ (ng/mL) | 3138 (32) | 101.52 | 91.58 | 122.53 | 3085 (29) |
| $C_{1\,hr}$ (ng/mL) | 2163 (59) | 130.98 | 101.04 | 169.78 | 1777 (59) |
| $C_{2\,hr}{}^a$ (ng/mL) | 2386 (32) | 125.37 | 113.22 | 138.82 | 1892 (28) |
| $AUC_{0-t}$ (ng·hr/mL) | 21742 (26) | 98.53 | 95.07 | 102.13 | 21897 (23) |
| $AUC_{0-inf}$ (ng·hr/mL) | 22798 (26) | 99.02 | 95.5 | 102.66 | 22881 (23) |
| $AUC_{0-1\,hr}$ (ng·hr/mL) | 1260 (85) | 122.71 | 85.05 | 177.03 | 1005 (80) |
| $AUC_{0-2\,hr}{}^b$ (ng·hr/mL) | 3534 (53) | 120.52 | 100.69 | 144.26 | 2839 (48) |
| $AUC_{0-4\,hr}{}^c$ (ng·hr/mL) | 8038 (33) | 130.54 | 119.98 | 142.02 | 6041 (27) |
| $AUC_{4\,hr-t}{}^d$ | 14707 (32) | 86.22 | 82.35 | 90.27 | 16720 (26) |
| $T_{max}$ (hr) | 1.908 (69) | na | na | na | 3.615 (54) |
| $T_{lag}$ (hr) | 0.236 (106) | na | na | na | 0.178 (90) |
| $T_{1/2}$ (hr) | 4.798 (26) | na | na | na | 5.3 (43) |
| $K_{el}$ (1/hr) | 0.153 (25) | na | na | na | 0.152 (36) |

* Dose Normalized to 500 mg
$^a$Concentration at the median $T_{max}$ for commercially-available immediate release tablet
$^b$AUC from zero the median $T_{max}$ for commercially-available immediate release tablet
$^c$AUC from the zero to the median $T_{max}$ + 2SD for commercially-available immediate release tablet

TABLE 19

Acetaminophen Pharmacokinetics (30/500)

| | Medium Release Formulation | | | | Commercially-available immediate release tablet |
|---|---|---|---|---|---|
| | Mean | LSM | 90% CI | | Mean |
| Parameter | (% CV) | Ratio | Lower | Upper | (% CV) |
| $C_{max}$ (ng/mL) | 2940 (38) | 93.8 | 84.57 | 104.03 | 3085 (29) |
| $C_{1\,hr}$ (ng/mL) | 2161 (56) | 139.29 | 107.29 | 180.84 | 1777 (59) |
| $C_{2\,hr}{}^a$ (ng/mL) | 2349 (27) | 125.86 | 113.61 | 139.44 | 1892 (28) |
| $AUC_{0-t}$ (ng · hr/mL) | 21822 (26) | 99.42 | 95.9 | 103.06 | 21897 (23) |
| $AUC_{0-inf}$ (ng · hr/mL) | 23107 (26) | 100.76 | 97.16 | 104.49 | 22881 (23) |
| $AUC_{0-1\,hr}$ (ng · hr/mL) | 1342 (81) | 155.89 | 107.81 | 225.4 | 1005 (80) |
| $AUC_{0-2\,hr}{}^b$ (ng · hr/mL) | 3596 (52) | 129.14 | 107.79 | 154.73 | 2839 (48) |
| $AUC_{0-4\,hr}{}^c$ (ng · hr/mL) | 7880 (32) | 130.08 | 119.51 | 141.59 | 6041 (27) |
| $AUC_{4\,hr-t}{}^d$ | 15040 (29) | 88.93 | 84.92 | 93.13 | 16720 (26) |
| $T_{max}$ (hr) | 1.724 (62) | na | na | na | 5.615 (54) |
| $T_{lag}$ (hr) | 0.19 (114) | na | na | na | 0.178 (90) |
| $T_{1/2}$ (hr) | 6.116 (63) | na | na | na | 5.3 (43) |
| $K_{el}$ (1/hr) | .0139 (37) | na | na | na | 0.152 (36) |

* Dose Normalized to 500 mg
[a] Concentration at the median $T_{max}$ for commercially-available immediate release tablet
[b] AUC from zero the median $T_{max}$ for commercially-available immediate release tablet
[c] AUC from the zero to the median $T_{max}$ + 2SD for commercially-available immediate release tablet

TABLE 20

Acetaminophen Pharmacokinetics (30/500)

| | Slow Release Formulation | | | | Commercially-available immediate release tablet |
|---|---|---|---|---|---|
| | Mean | LSM | 90% CI | | Mean |
| Parameter | (% CV) | Ratio | Lower | Upper | (% CV) |
| $C_{max}$ (ng/mL) | 2734 (33) | 88.33 | 79.68 | 97.91 | 3085 (29) |
| $C_{1\,hr}$ (ng/mL) | 1989 (53) | 120.26 | 93.05 | 155.44 | 1777 (59) |
| $C_{2\,hr}{}^a$ (ng/mL) | 2131 (25) | 112.77 | 101.84 | 124.86 | 1892 (28) |
| $AUC_{0-t}$ (ng · hr/mL) | 21272 (23) | 97.1 | 93.68 | 100.64 | 21897 (23) |
| $AUC_{0-inf}$ (ng · hr/mL) | 22504 (22) | 98.45 | 94.95 | 102.07 | 22881 (23) |
| $AUC_{0-1\,hr}$ (ng · hr/mL) | 1092 (76) | 120.91 | 84.15 | 173.72 | 1005 (80) |
| $AUC_{0-2\,hr}{}^b$ (ng · hr/mL) | 3152 (45) | 112.74 | 94.19 | 134.94 | 2839 (48) |
| $AUC_{0-4\,hr}{}^c$ (ng · hr/mL) | 7217 (26) | 119.31 | 109.5 | 129.61 | 6041 (27) |
| $AUC_{4\,hr-t}{}^d$ | 15227 (26) | 90.59 | 86.52 | 94.85 | 16720 (26) |
| $T_{max}$ (hr) | 1.897 (56) | na | na | na | 5.615 (54) |
| $T_{lag}$ (hr) | 0.196 (79) | na | na | na | 0.178 (90) |
| $T_{1/2}$ (hr) | 4.843 (27) | na | na | na | 5.3 (43) |
| $K_{el}$ (1/hr) | 0.152 (24) | na | na | na | 0.152 (36) |

* Dose Normalized to 500 mg
[a] Concentration at the median $T_{max}$ for commercially-available immediate release tablet
[b] AUC from zero the median $T_{max}$ for commercially-available immediate release tablet
[c] AUC from the zero to the median $T_{max}$ + 2SD for commercially-available immediate release tablet The pharmacokinetic parameters for the medium release 30/500 formulation and the commercially-available immediate release tablet are shown in Table 21.

TABLE 21

Pharmacokinetic Profile (Mean ± SD) of Oxycodone/APAP versus Commercially-available immediate release tablet (N = 29)

| Dosage | $C_{max}$ (ng/mL) | $AUC_{0-t}$ (ng · hr/mL) | $AUC_{0-inf}$ (ng · hr/mL) | $T_{max}$ (hr) | $K_{el}$ (1/hr) | $t_{1/2}$ (hr) |
|---|---|---|---|---|---|---|
| Oxycodone | | | | | | |
| 30 mg OC/500 mg APAP | 36.7 ± 10.9 | 396 ± 116 | 398 ± 115 | 4.5 ± 2.3 | 0.162 ± 0.023 | 4.4 ± 0.6 |
| Commercially-available immediate release tablet[a] (7.5 mg OC/325 mg APAP) | 47.6 ± 12.3* | 426 ± 125 | 430 ± 124 | 6.9 ± 2.3* | 0.164 ± 0.026 | 4.3 ± 0.6 |
| Acetaminophen | | | | | | |
| 30 mg OC/500 mg APAP | 2940 ± 1105 | 21822 ± 5630 | 23107 ± 5927 | 1.7 ± 1.1 | 0.139 ± 0.052 | 6.1 ± 3.9 |
| Commercially-available immediate release tablet[a] (7.5 mg OC/325 mg APAP) | 3085 ± 899* | 21897 ± 5125 | 22881 ± 5362 | 5.6 ± 3.0* | 0.152 ± 0.055 | 5.3 ± 2.3 |

*Most values occurred after the second dose.
[a]AUC and Cmax dose-normalized to 30 mg for OC and 500 mg for APAP.

Example 4

Clinical Pharmacokinetic Analysis of Controlled-Release 15 mg Oxycodone/650 mg Acetaminophen Bilayer Tablets—Single Dose The following study evaluated the bioavailability, pharmacokinetics, dose-proportionality, and safety of 1 or 2 tablets of 15 mg of a composition comprising OC/650 mg APAP (1 dose) (see selected example from Chart No. 1) compared to 1 tablet of the commercially-available immediate release tablet under fed conditions. The ER layer contained 75% of the total amount of the oxycodone in the tablet, 50% of the total amount of APAP in the tablet, and 45% (w/w) POLYOX® 1105. The IR layer contained 25% of the total amount of oxycodone in the tablet and 50% of the total amount of APAP. This study was conducted in 42 male and female healthy subjects.

Figure 9:
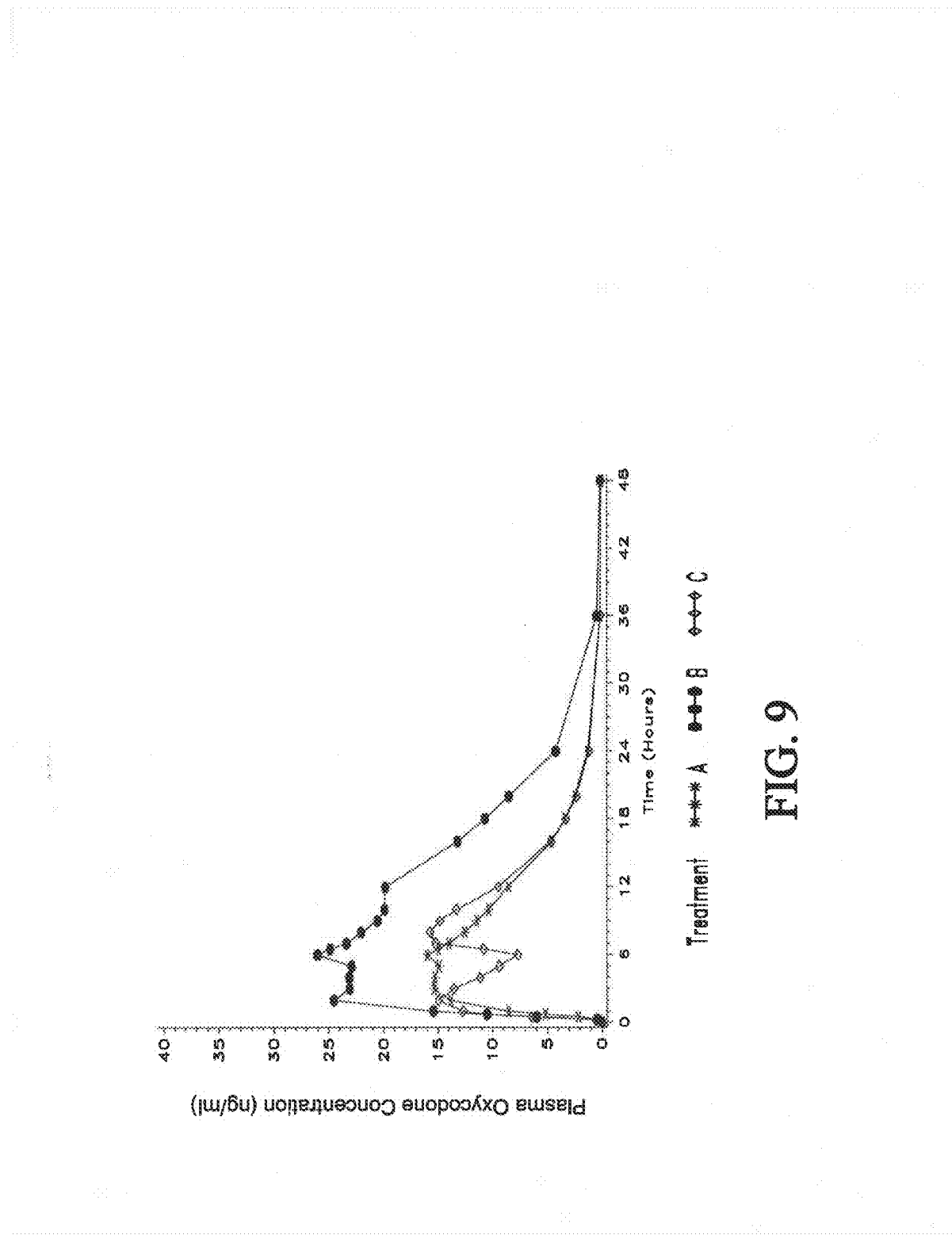
FIG. 9 shows the mean plasma concentrations of oxycodone versus time by treatment. Treatment A was one tablet of 15 mg oxycodone/650 mg acetaminophen administered orally under fed conditions. Treatment B was two tablets of 15 mg oxycodone/650 mg acetaminophen administered orally one at a time under fed conditions. Treatment C was one tablet of an immediate release 7.5 oxycodone/325 acetaminophen tablet administered orally every 6 hours for 2 doses under fed conditions.

PK parameters for oxycodone are presented in Table 22. Plasma concentrations of OC for the 1 tablet dosing configuration of 15/650 showed a median $t_{lag}$ of 0.25 hours, while there was no lag time for plasma concentrations of OC for the 2 tablet dosing configuration of 15/650 and the commercially-available immediate release tablet under fed conditions. As illustrated in FIG. 9 demonstrating the plasma concentrations of oxycodone versus time of treatment (i.e., Treatment A was one tablet of 15 mg oxycodone/650 mg acetaminophen administered orally under fed conditions; Treatment B was two tablets of 15 mg oxycodone/650 mg acetaminophen administered orally one at a time under fed conditions; and Treatment C was one tablet of the commercially-available immediate release tablet (7.5 mg oxycodone/325 mg acetaminophen) administered orally every 6 hours for 2 doses under fed conditions). Plasma concentrations of OC rose rapidly after administration of 15/650 formulation in a similar fashion to commercially-available immediate release tablet. Peak plasma levels of OC for the 15/650 tablets, however, were biphasic. Peak levels were observed at about 2-3 hours and about 6 hours for the 1 or 2 tablet dosing configuration of the 15/650 formulation. In contrast, the peak plasma level of OC for the commercially-available immediate release tablet was about 7-8 hours after the initial dose of the commercially-available immediate release tablet (~1-2 hr after the second dose). Mean plasma concentrations of OC from 15/650 formulations were detectable through 48 hours following all treatments and $t_{1/2}$ was about 4 hours across all treatments.

TABLE 22

Pharmacokinetic Parameter Estimates (Mean ± SD) of Oxycodone Following Administration of 15 mg Oxycodone/650 mg APAP versus Commercially-available immediate release tablet

| Dosage | $C_{max}$ (ng/mL) | $AUC_{0-t}$ (ng · hr/mL) | $AUC_{0-inf}$ (ng · hr/mL) | $T_{max}{}^a$ (hr) | $T_{lag}{}^a$ (hr) | $t_{1/2}$ (hr) |
|---|---|---|---|---|---|---|
| One tablet (N = 25) Treatment A | 17.68 (4.42) | 199.60 (59.52) | 201.6 (59.27) | 3.00 (1.00-12.45) | 0.25 (0.00-0.75) | 4.18 (0.77) |
| Two tablets (N = 25) Treatment B | 29.18 (6.53) | 414.73 (109.87) | 417.41[b] (112.17) | 5.00 (1.00-12.00) | 0.00 (0.00-0.50) | 4.11[b] (0.67) |
| Commercially-available | 20.34 (4.81) | 199.63 (60.53) | 201.76 (60.24) | 7.00 (0.50-9.00) | 0.00 (0.00-1.00) | 4.08 (0.64) |

TABLE 22-continued

Pharmacokinetic Parameter Estimates (Mean ± SD) of Oxycodone
Following Administration of 15 mg Oxycodone/650 mg APAP versus
Commercially-available immediate release tablet

| Dosage | $C_{max}$ (ng/mL) | $AUC_{0-t}$ (ng · hr/mL) | $AUC_{0-inf}$ (ng · hr/mL) | $T_{max}^a$ (hr) | $T_{lag}^a$ (hr) | $t_{1/2}$ (hr) |
|---|---|---|---|---|---|---|
| immediate release tablet (7.5 mg OC/325 mg APAP (N = 25) Treatment C | | | | | | |

[a] $T_{max}$ and $t_{lag}$ median (minimum-maximum)
[b] N = 24

Figure 10:
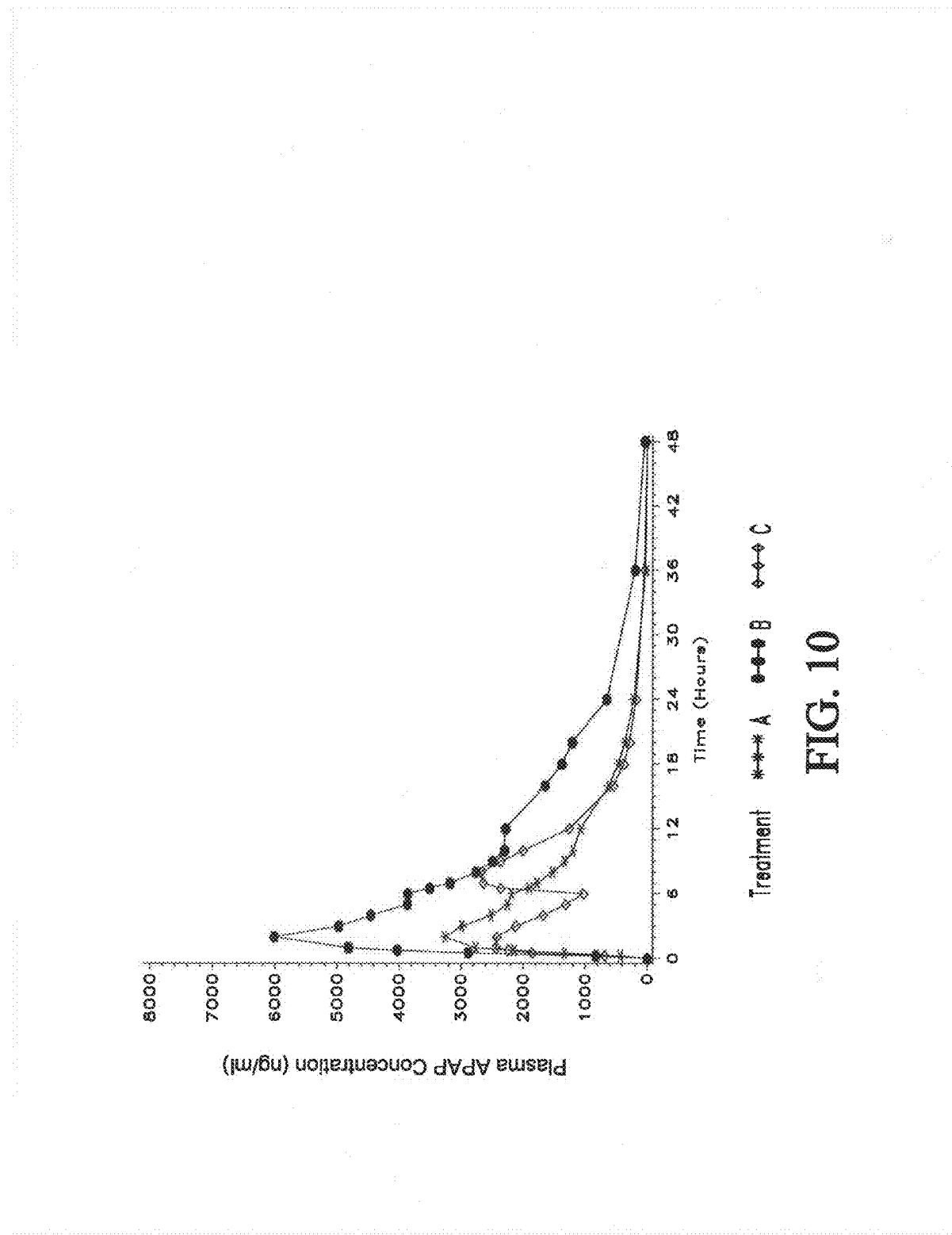
FIG. 10 presents the mean plasma concentrations of acetaminophen versus time by treatment. Treatment A was one tablet of 15 mg oxycodone/650 mg acetaminophen administered orally under fed conditions. Treatment B was two tablets of 15 mg oxycodone/650 mg acetaminophen administered orally one at a time under fed conditions. Treatment C was one tablet of an immediate release 7.5 oxycodone/325 acetaminophen tablet administered orally every 6 hours for 2 doses under fed conditions.

PK parameters for APAP are presented in Table 23. Plasma concentrations of APAP for the 1 tablet dosing configuration of 15/650 showed a median $t_{lag}$ of 0.25 hour, while there was no lag in the appearance of APAP in plasma for the 2 tablet dosing configuration of 15/650 and the commercially-available immediate release tablet. Plasma concentrations of APAP rose rapidly after administration of the 15/650 formulations, similar to that observed with RDL. (See FIG. 10). Peak plasma levels of APAP following administration of the 1 tablet and 2 tablet dosing configurations of 15/650 were observed at approximately 2 hours (with a shoulder peak at 5-6 hours) after dosing compared with 1 hour after the second dose of the commercially-available immediate release tablet. Mean plasma concentrations of APAP were detectable through 36 hours following all treatments and the mean $t_{1/2}$ was approximately 6 to 8 hours across treatment groups.

TABLE 23

Pharmacokinetic Parameter Estimates (Mean ± SD) of
APAP Following Administration of 15 mg Oxycodone/650 mg
APAP versus Commercially-available immediate release tablet

| Dosage | $C_{max}$ (ng/mL) | $AUC_{0-t}$ (ng · hr/mL) | $AUC_{0-inf}$ (ng · hr/mL) | $T_{max}^a$ (hr) | $T_{lag}^a$ (hr) | $t_{1/2}$ (hr) |
|---|---|---|---|---|---|---|
| One tablet (N = 25) | 3822 (874) | 30239 (5673) | 32194[c] (6437) | 2.00 (0.50-4.00) | 0.25 (0.00-1.00) | 6.17[c] (2.22) |
| Two tablets (N = 25) | 6941 (1989) | 64783 (15017) | 67600[d] (14655) | 2.00 (0.50-5.00) | 0.00 (0.00-0.50) | 7.67[d] (4.06) |
| Commercially-available immediate release tablet (7.5 mg OC/325 mg APAP (N = 25) | 3629 (841) | 30137 (6426) | 30802[c] (6697) | 6.50 (0.50-9.00) | 0.00 (0.00-1.00) | 5.89[c] (2.63) |

[a] $T_{max}$ and $t_{lag}$ median (minimum-maximum)
[c] N = 21
[d] N = 23

Example 5

Clinical Pharmacokinetic Analysis of
Controlled-Release 15 mg Oxycodone/650 mg
Acetaminophen Bilayer Tablets—Multiple Doses The following study evaluated the steady state bioavailability, pharmacokinetics, and safety of a 15 mg OC/650 mg APAP composition administered (see selected example from Chart No. 2) orally as 1 tablet (Treatment A) or 2 tablets (Treatment B) every 12 hours (9 doses) compared to 2 tablets of the commercially-available immediate release tablet (2×7.5 mg OC/325 mg APAP) (Treatment C) dosed every 6 hours for 4.5 days (18 doses) under fed conditions with 48 male and female subjects in equal distribution.

Figure 11:
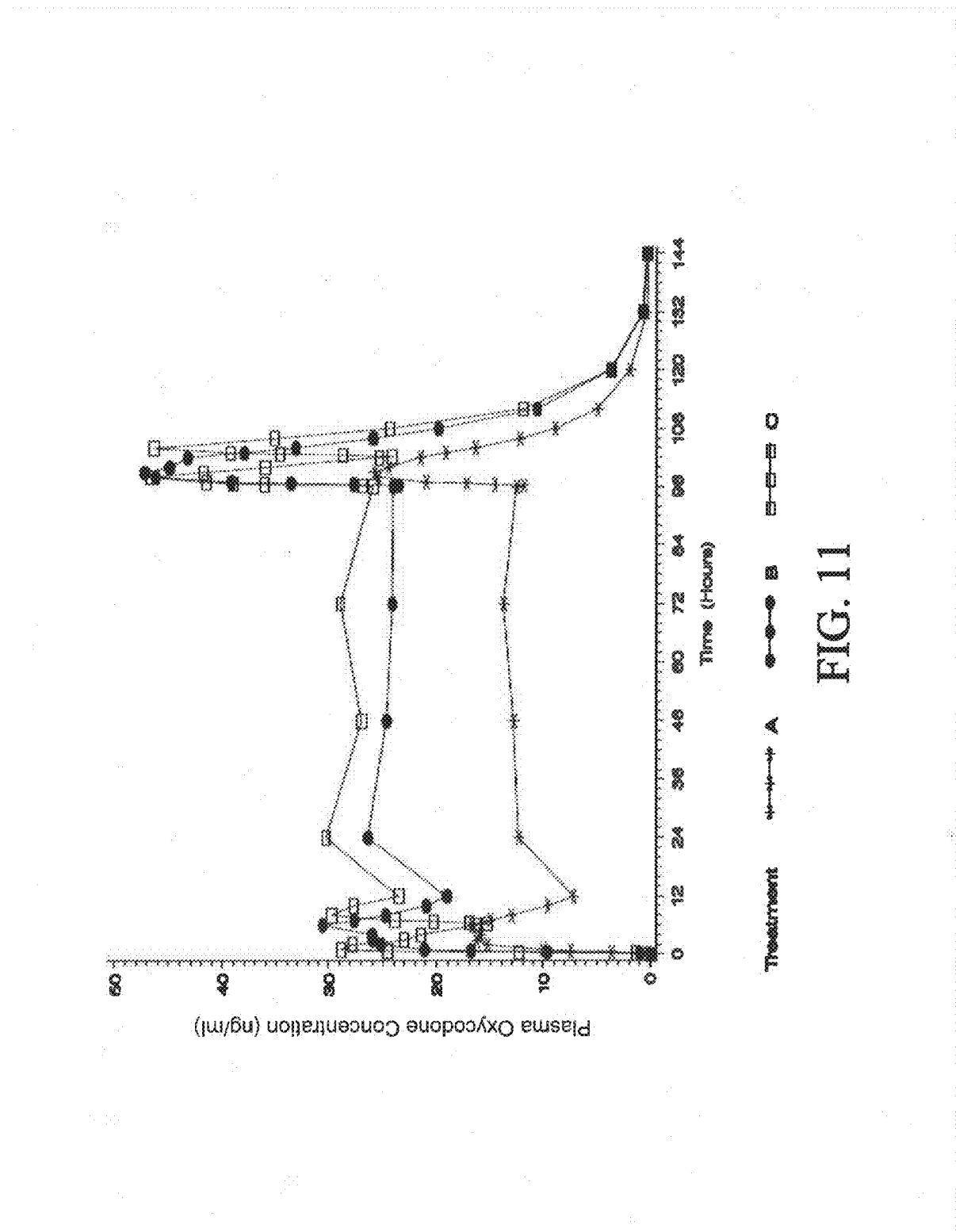
FIG. 11 shows the mean plasma concentrations of oxycodone versus time by treatment. Treatment A was one tablet of 15 mg oxycodone/650 mg acetaminophen administered orally every 12 hours for 4.5 days (9 doses) under fed conditions. Treatment B was two tablets of 15 mg oxycodone/650 mg acetaminophen administered orally one at a time every 12 hours for 4.5 days (9 doses) under fed conditions. Treatment C was two tablets of an immediate release 7.5 oxycodone/325 acetaminophen tablet administered orally every 6 hours for 4.5 days (18 doses) under fed conditions.

The pharmacokinetic (PK) parameters of OC are presented in Table 24. The PK behavior of OC on Study Day 1 was similar to that observed in the single dose study (see Table 22). There was a slight lag (median tlag 0.25 hr) in the appearance of OC following the 1 tablet dose of 15 mg OC/650 mg APAP. No lag was observed following dosing with 2 tablets of 15 mg OC/650 mg APAP or the commercially-available immediate release tablet. Peak plasma levels were observed at 4 and 6 hours after administration of 1 and 2 tablets of the 15/650 formulation, respectively, and at 1.5 hours after the second dose of the commercially-available immediate release tablet. (See FIG. 11). Minimum (trough) plasma concentrations ($C_{min}$) of OC achieved steady-state levels by Day 2 for 15/650 formulations and by Day 3 for the commercially-available immediate release tablet.

TABLE 24

Oxycodone Pharmacokinetic Parameters

| Dosage | $C_{max}$ (ng/mL) | $AUC_{0-t}$ (ng · hr/mL) | $T_{max}$[a] (hr) | $T_{lag}$[a] (hr) | $t_{1/2}$ (hr) |
|---|---|---|---|---|---|
| A: One tablet Day 1 (N = 20) | 18.79 (5.00) | 149.68[c] (37.92) | 4.00 (2.00-8.00) | 0.25 (0.00-0.50) | Day 1 |
| B: Two tablets Day 1 (N = 20) | 33.57 (8.41) | 280.45[c] (62.61) | 5.93 (1.00-11.92) | 0.00 (0.00-0.25) | Day 1 |
| C: Commercially-available immediate release tablet (7.5 mg OC/325 mg APAP) Day 1 (N = 20) | 36.02 (10.52) | 278.60[c] (67.17) | 7.50 (0.75-11.92) | 0.00 (0.00-0.33) | Day 1 |
| A: One tablet Day 5 (N = 20) | 27.26 (6.33) | 223.10[c] (59.45) | 3.00 (1.00-5.92) | Day 5 | 6.06[d] (1.91) |
| B: Two tablets Day 5 (N = 20) | 50.70 (10.95) | 433.37[c] (93.21) | 3.00 (2.00-7.00) | Day 5 | 6.35 (1.89) |
| C: Commercially-available immediate release tablet (7.5 mg OC/325 mg APAP) Day 5 (N = 20) | 52.41 (12.40) | 435.70[c] (98.68) | 2.00 (0.50-8.02) | Day 5 | 5.93[d] (1.68) |

[a] $T_{max}$ and $t_{lag}$ median (minimum-maximum)
[c] Day 1 - $AUC_{0-12 h}$; Day 5 - $AUC_{0-12 h}$ss
[d] N = 19

On Day 5 of the study, the maximum plasma OC concentration at steady-state ($C_{max}^{ss}$) was 27.3 ng/mL following 4.5 days of dosing with 1 tablet of 15 mg OC/650 mg APAP administered every 12 hours. $C_{max}^{ss}$ following 2 tablets of 15 mg OC/650 mg APAP administered every 12 hours or the commercially-available immediate release tablet administered Q6 hours for 4.5 days were 50.7 ng/mL and 52.4 ng/mL, respectively. Median $T_{max}^{ss}$ was observed at 3 hours following 1 tablet or 2 tablets of 15/650 and at 2 hours following the first daily dose of the commercially-available immediate release tablet.

Figure 12:
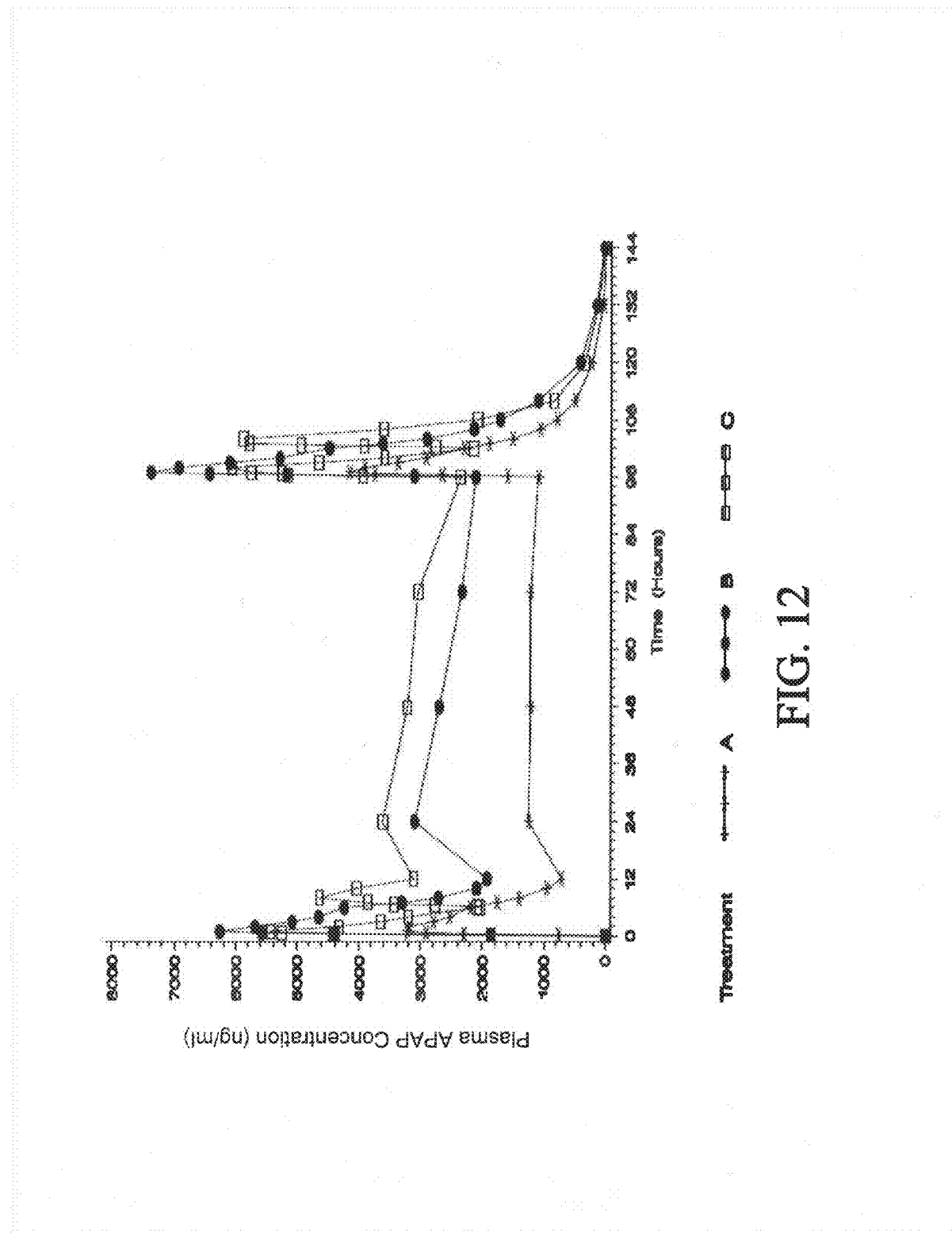
FIG. 12 shows the mean plasma concentrations of acetaminophen versus time by treatment. Treatment A was one tablet of 15 mg oxycodone/650 mg acetaminophen administered orally every 12 hours for 4.5 days (9 doses) under fed conditions. Treatment B was two tablets of 15 mg oxycodone/650 mg acetaminophen administered orally one at a time every 12 hours for 4.5 days (9 doses) under fed conditions. Treatment C was two tablets of an immediate release 7.5 oxycodone/325 acetaminophen tablet administered orally every 6 hours for 4.5 days (18 doses) under fed conditions.

PK parameters for APAP are presented in Table 25. Acetaminophen was rapidly absorbed following a single dose of 1 or 2 tablets of 15/650 and in a similar fashion to the commercially-available immediate release tablet (see FIG. 12). There was no lag in plasma concentrations following any of the three dosing regimens. Peak APAP plasma concentrations were observed at 1 hour after administration of 1 or 2 tablets of 15/650 and at 0.9 hours after the first dose of the commercially-available immediate release tablet on Day 1. After a single administration of 15/650, $C_{max}$ for APAP was proportional with respect to the amount of APAP in 1 or 2 tablets of 15/650 (i.e., 1 tablet—3942 ng/mL; 2 tablets—7536 ng/mL). Minimum (trough) concentrations ($C_{min}$) of APAP achieved steady-state levels by Day 2 for 1 tablet of 15/650, by Day 4 for 2 tablets of 15/650 and by the second dose on Day 1 for the commercially-available immediate release tablet.

TABLE 25

Acetaminophen Pharmacokinetic Parameters

| Dosage | $C_{max}$ (ng/mL) | $AUC_{0-t}$ (ng · hr/mL) | $T_{max}$[a] (hr) | $T_{lag}$[a] (hr) | $t_{1/2}$ (hr) |
|---|---|---|---|---|---|
| A: One tablet Day 1 (N = 20) | 3942 (1168) | 22928[g] (7331) | 1.00 (0.50-5.93) | 0.00 (0.00-0.28) | Day 1 |
| B: Two tablets Day 1 (N = 20) | 7536 (2205) | 44254[g] (13885) | 1.00 (0.28-4.00) | 0.00 (0.00-0.25) | Day 1 |
| C: Commercially-available immediate release tablet (7.5 mg OC/325 mg APAP) Day 1 (N = 20) | 6757 (1949) | 43634[g] (12357) | 0.90 (0.32-11.92) | 0.00 (0.00-0.25) | Day 1 |
| A: One tablet Day 5 (N = 20) | 4635 (1330) | 26968[g] (9134) | 1.00 (0.50-3.00) | Day 5 | 7.06 (2.24) |

TABLE 25-continued

Acetaminophen Pharmacokinetic Parameters

| Dosage | $C_{max}$ (ng/mL) | $AUC_{0-t}$ (ng · hr/mL) | $T_{max}$[a] (hr) | $T_{lag}$[a] (hr) | $t_{1/2}$ (hr) |
|---|---|---|---|---|---|
| B: Two tablets Day 5 (N = 20) | 8206 (2666) | 50221[g] (18415) | 1.00 (0.30-4.00) | Day 5 | 7.46 (1.85) |
| C: Commercially-available immediate release tablet (7.5 mg OC/325 mg APAP) Day 5 (N = 20) | 7433 (1979) | 50678[g] (15565) | 1.50 (0.25-8.02) | Day 5 | 6.79[h] (2.47) |

[a] $T_{max}$ and $t_{lag}$ median (minimum-maximum)
[g] Day 1 - $AUC_{0-12\ h}$; Day 5 - $AUC_{0-12\ h}^{ss}$
[h] N = 17

On Day 5 of the study, median $T_{max}^{ss}$ for APAP was observed at 1 hour following 1 or 2 tablets of 15/650 and at 1.5 hours following the first daily dose of the commercially-available immediate release tablet on Day 5. Maximum plasma APAP concentration at steady-state ($C_{max}^{ss}$) was 4635 ng/mL following 4.5 days of dosing with 1 tablet of 15/650 every 12 hours (Table 25). $C_{max}^{ss}$ following 2 tablets of 15/650 administered every 12 hours and for the commercially-available immediate release tablet administered Q6 hours for 4.5 days were 8206 and 7433 ng/mL, respectively.

Example 6

Clinical Pharmacokinetic Analysis of Controlled-Release 15 mg Oxycodone/650 mg Acetaminophen Bilayer Tablets Under Fed and Fasted Conditions Two open-label, randomized, two-period crossover studies were conducted to evaluate the effect of food on the pharmacokinetics, bioavailability and safety of the 15 mg oxycodone/650 mg APAP composition (see selected example from Chart No. 2) using a 1 tablet or 2 tablet dosing configuration in normal, healthy subjects. Studies were conducted in 48 subjects under fed (FDA high fat breakfast) or fasted conditions.

Figure 13:
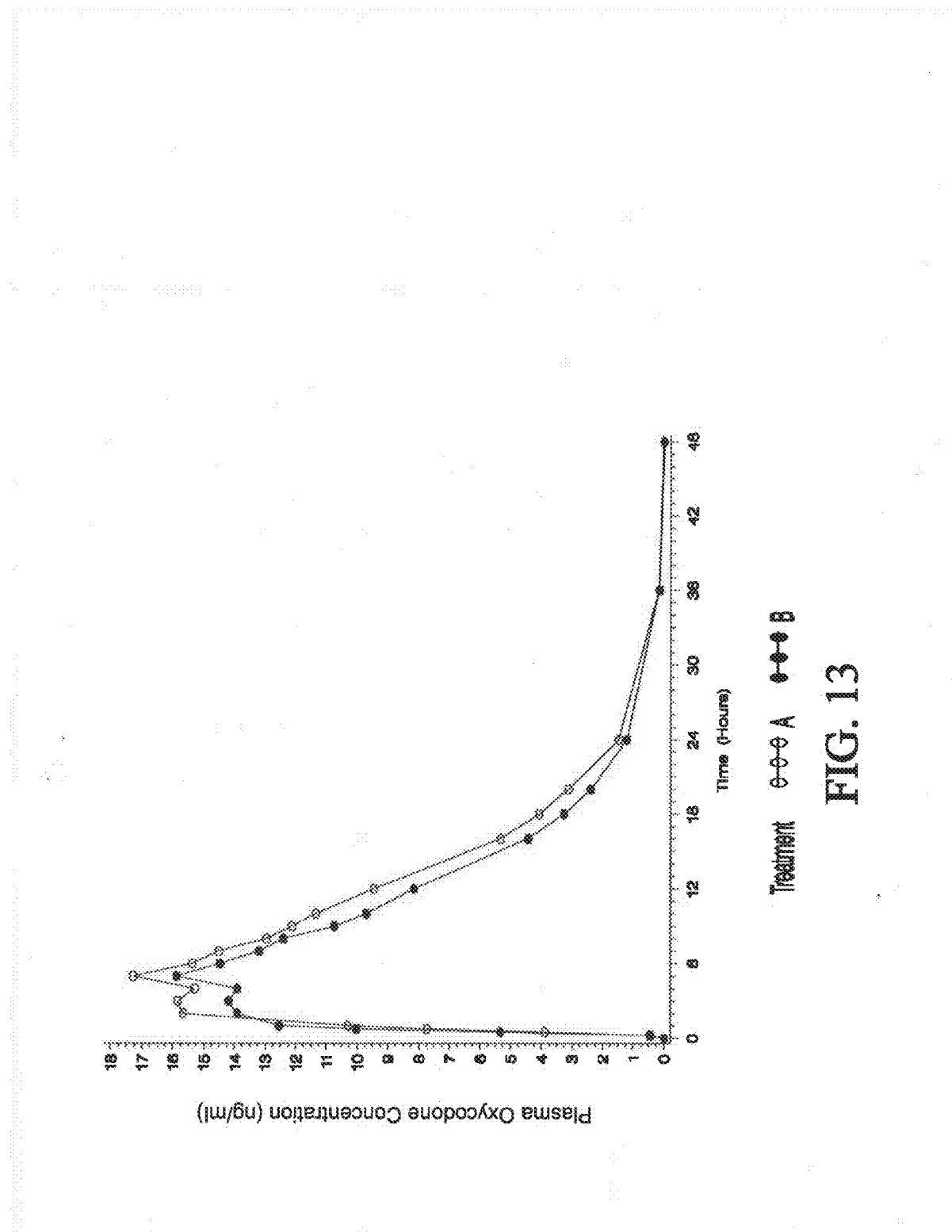
FIG. 13 presents the mean plasma concentrations of oxycodone versus time by treatment following oral administration of one tablet of 15 mg oxycodone/650 mg acetaminophen. Treatment A was under fed conditions. Treatment B was under fasted conditions.
Figure 14:
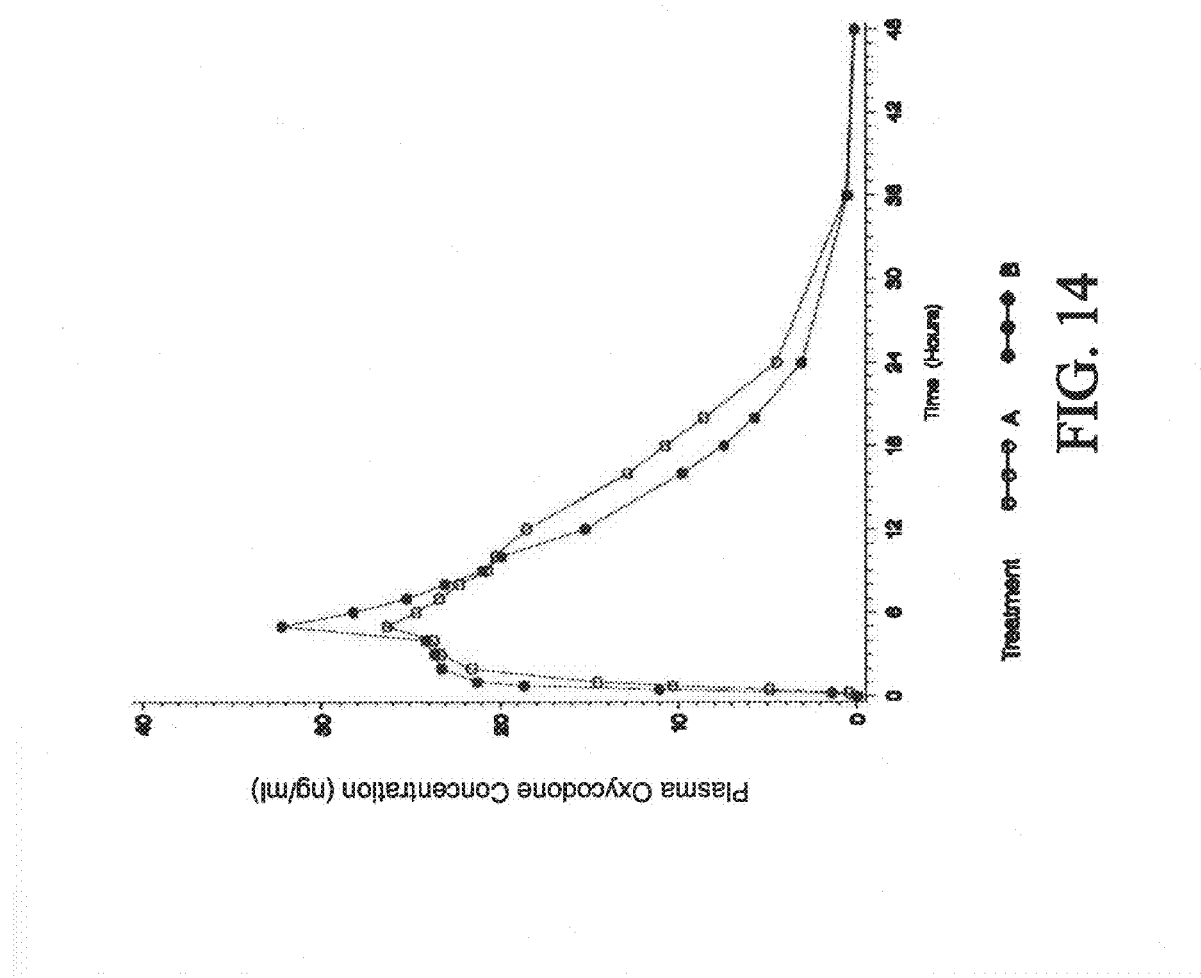
FIG. 14 shows the mean plasma concentrations of oxycodone versus time by treatment following oral administration of two tablets of 15 mg oxycodone/650 mg acetaminophen. Treatment A was under fed conditions. Treatment B was under fasted conditions.
Figure 15:
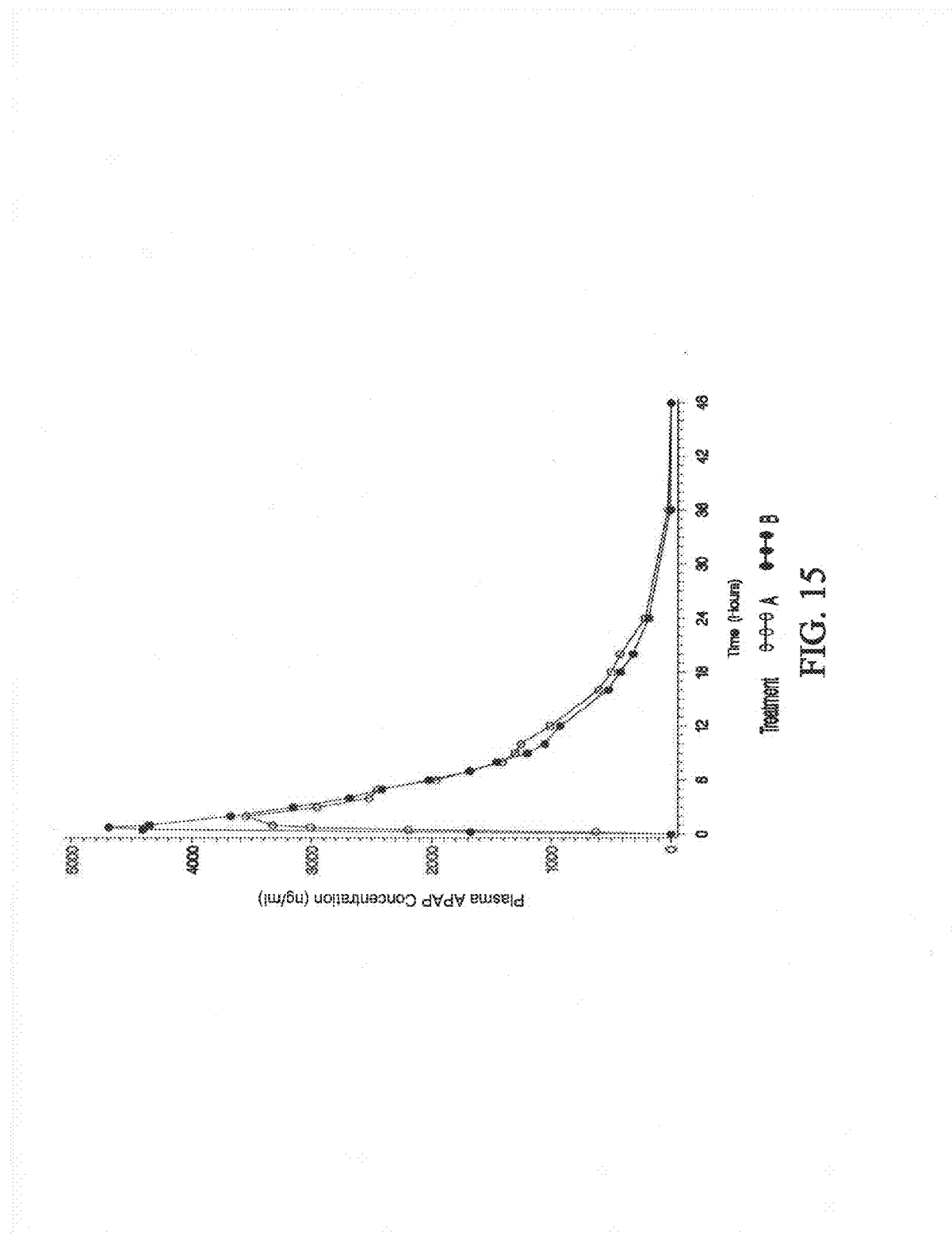
FIG. 15 presents the mean plasma concentrations of acetaminophen versus time by treatment following oral administration of one tablet of 15 mg oxycodone/650 mg acetaminophen. Treatment A was under fed conditions. Treatment B was under fasted conditions.
Figure 16:
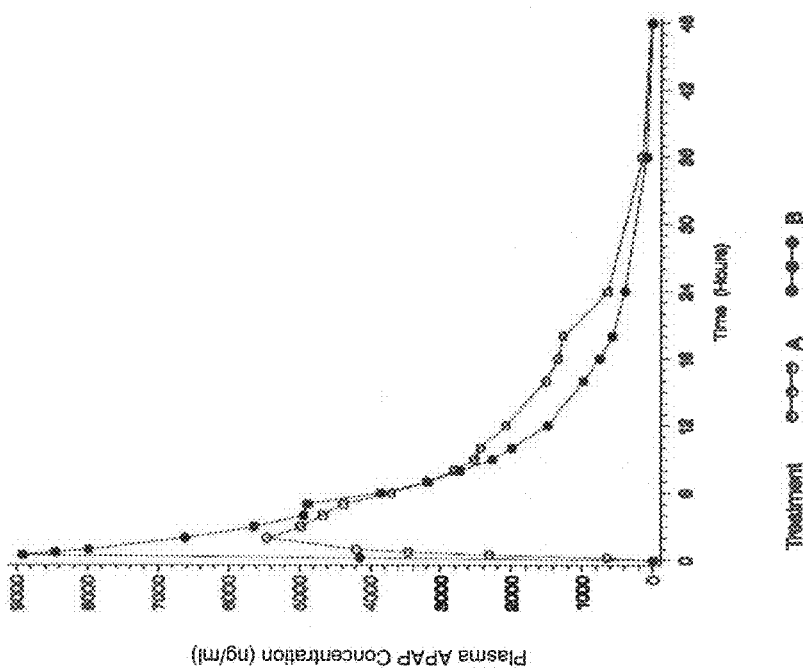
FIG. 16 shows mean plasma concentrations of acetaminophen versus time by treatment following oral administration of two tablets of 15 mg oxycodone/650 mg acetaminophen. Treatment A was under fed conditions. Treatment B was under fasted conditions.

Tables 26 and 27 present the pharmacokinetic data for oxycodone (OC) and APAP, respectively. FIGS. 13 and 14 present the plasma concentration of OC following administration of one tablet and two tablets, respectively, under fed (Treatment A) or fasted (Treatment B) conditions. FIGS. 15 and 16 present the plasma concentration of APAP following administration of one tablet and two tablets, respectively, under fed (Treatment A) or fasted (Treatment B) conditions.

TABLE 26

Oxycodone Pharmacokinetics (15/650)

| Dose | State (N) | $C_{max}$ (ng/mL) | $AUC_{0-t}$ (ng · hr/mL) | $AUC_{0-inf}$ (ng · hr/mL) | $T_{max}$[a] (hr) | $t_{lag}$[a] (hr) | $t_{1/2}$ (hr) |
|---|---|---|---|---|---|---|---|
| One tablet | fed (28) | 19.03 (4.20) | 219.23 (55.99) | 221.06 (55.88) | 5.00 (1.00-12.00) | 0.25 (0.00-0.50) | 3.94 (0.69) |
| Two tablets | fed (17) | 30.58 (6.57) | 414.01 (104.76) | 415.88 (104.86) | 5.00 (0.75-12.00) | 0.25 (0.00-0.27) | 4.42 (0.97) |
| One tablet | fasted (28) | 18.31 (4.67) | 196.51 (53.04) | 198.33 (52.82) | 3.50 (0.50-10.00) | 0.00 (0.00-0.25) | 4.25 (0.59) |
| Two tablets | fasted (17) | 33.69 (7.45) | 390.33 (145.27) | 392.15 (145.81) | 5.00 (2.00-5.20) | 0.00 (0.00-0.25) | 4.80 (1.07) |

[a] $T_{max}$ and $t_{lag}$ median (minimum-maximum)

Plasma concentrations (Table 26; FIGS. 13 and 14) of OC rose rapidly with the median $T_{max}$ observed at about 4 to 5 hr under both fed and fasted conditions for both the 1- and 2-tablet dose configurations. OC plasma levels were biphasic—with a first peak at about 3 hours and a second peak at about 5 hours. The $C_{max}$ values (at 5 hours) for OC under fed (1 and 2 tablets, 19.0 and 30.6 ng/mL) conditions were equivalent to those observed under fasted (1 and 2 tablets, 18.3 and 33.7 ng/mL) conditions for both the 1 tablet and 2 tablet dosing configurations.

TABLE 27

Acetaminophen Pharmacokinetics (15/650)

| Dose | State (N) | $C_{max}$ (ng/mL) | $AUC_{0-t}$ (ng · hr/mL) | $AUC_{0-inf}$ (ng · hr/mL) | $T_{max}^a$ (hr) | $t_{lag}^a$ (hr) | $t_{1/2}$ (hr) |
|---|---|---|---|---|---|---|---|
| One tablet | fed (28) | 4374 (1286) | 31480 (9316) | 32552 (9489) | 1.00 (0.50, 5.00) | 0.00 (0.00-0.50) | 4.65 (1.26) |
| Two tablets | fed (17) | 6341 (1698) | 62904 (19294) | 68839[b] (19826) | 2.00 (0.75-6.00) | 0.00 (0.00-0.25) | 7.02[b] (1.77) |
| One tablet | fasted (28) | 5511 (2095) | 31876 (103339) | 33860 (10731) | 0.75 (0.25, 5.00) | 0.00 (0.00-0.25) | 5.19[e] (1.50) |
| Two tablets | fasted (17) | 10428 (3529) | 61164 (16552) | 65281 (15711) | 0.75 (0.25-5.00) | 0.00 (0.00-0.00) | 5.6 (1.49) |

[a] $T_{max}$ and $t_{lag}$ median (minimum-maximum)
[b] N = 12
[e] N = 27
[f] N = 13

Plasma concentrations (Table 27; FIGS. 15 and 16) of APAP rose rapidly following 1 tablet dosed under fed and fasted conditions with similar $T_{max}$ values (1.0 hour and 0.8 hour). $T_{max}$ was observed sooner following 2 tablets given under fasted conditions (0.8 hour) than under fed conditions (2 hours). Plasma concentrations of APAP were lower under fed conditions than under fasted conditions with fed $C_{max}$ values of 4374 ng/mL (1 tablet) and 6341 ng/mL (2 tablets) and fasted $C_{max}$ values of 5511 ng/mL (1 tablet) and 10,428 ng/mL (2 tablets). Nevertheless, the peak concentrations demonstrate that there was only a slight, minimal food effect on the absorption of APAP, which is consistent with that observed for other oxycodone and acetaminophen products. Thus, there is no meaningful food effect seen with this composition, and as such, the composition can to be administered without regard to food.

Example 7

Abuse Potential of Controlled-Release Formulations

It has long been theorized that the desirability of a drug of abuse is related to the speed with which it reaches maximum concentration in the plasma of the user. Basic science and clinical observation suggest that a shortened time to maximum plasma concentration ($t_{max}$) and a heightened maximum plasma concentration ($C_{max}$) would increase the euphoric effects conferred by a drug. The abuse quotient (AQ) is a relatively new concept that attempts to predict the abuse potential of drugs. The AQ refers to the two PK parameters expressed as a ratio: $AQ = C_{max}/t_{max}$. The abuse potential of a drug increases as the value of the AQ increases, either by heightening $C_{max}$ or shortening $t_{max}$.

Table 28 presents the AQs for various extended release formulations disclosed herein (see, e.g., selected examples from Chart Nos. 1 and 2) and several commercially available formulations.

TABLE 28

Abuse Quotient

| Formulation | $C_{max}$ (ng/mL) | $t_{max}$ (hr) | AQ |
|---|---|---|---|
| 15/500 - Fast | 18.8 | 4.95 | 3.80 |
| 15/500 - Medium | 18.27 | 5.31 | 3.44 |
| 15/500 - Slow | 17.4 | 5.66 | 3.07 |
| 15/650 - 1 tablet | 17.68 | 3.90 | 4.53 |
| 15/650 - 2 tablets | 14.59* | 5.03 | 2.90 |
| 7.5/325 - 1 tablet | 16.82 | 3.71 | 4.53 |

TABLE 28-continued

Abuse Quotient

| Formulation | $C_{max}$ (ng/mL) | $t_{max}$ (hr) | AQ |
|---|---|---|---|
| 7.5/325 - 2 tablets | 16.39 | 3.17 | 5.17 |
| PERCOCET (oxycodone and acetaminophen) | 22.43 | 2.16 | 10.38 |
| Oxycontin | 17.35 | 3.54 | 4.90 |
| OxyER | 19.61 | 4.11 | 4.77 |

*dose normalized to 15 mg

Example 8

Ethanol Release Testing at a 150 rpm Paddle Speed

To assess the potential for dose dumping, the in vitro dissolution of oxycodone and APAP from 7.5 mg OC/325 mg APAP tablets was tested in 0.1 N HCl containing 0%, 5%, 20%, or 40% v/v ethanol. The ER layer of the 7.5/325 tablets contained 5.625 mg of OC, 162.5 mg of APAP, and 45% (w/w) POLYOX® 1105, and the IR layer contained 1.875 mg of OC and 162.5 mg of APAP. (See selected example from Chart No. 1.) For each profile, twelve tablets were weighed, placed in a sinker, and dropped into an equilibrated USP Type II apparatus (paddles) that contained 900 mL of (helium sparged) 0.1 N HCl (containing either 0%, 5%, 20%, or 40% ethanol) heated to ~37° C. The mixture was stirred at ~150 rpm and the temperature was maintained at ~37° C. for 120 minutes. The bath vessel was covered with a low evaporation vessel cover. Samples were removed at 15, 30, 45, 60, 75, 90, 105, and 120 minutes. Each sample was filtered through a 0.45 μm filter and analyzed by HPLC using standard procedures.

Figure 17:
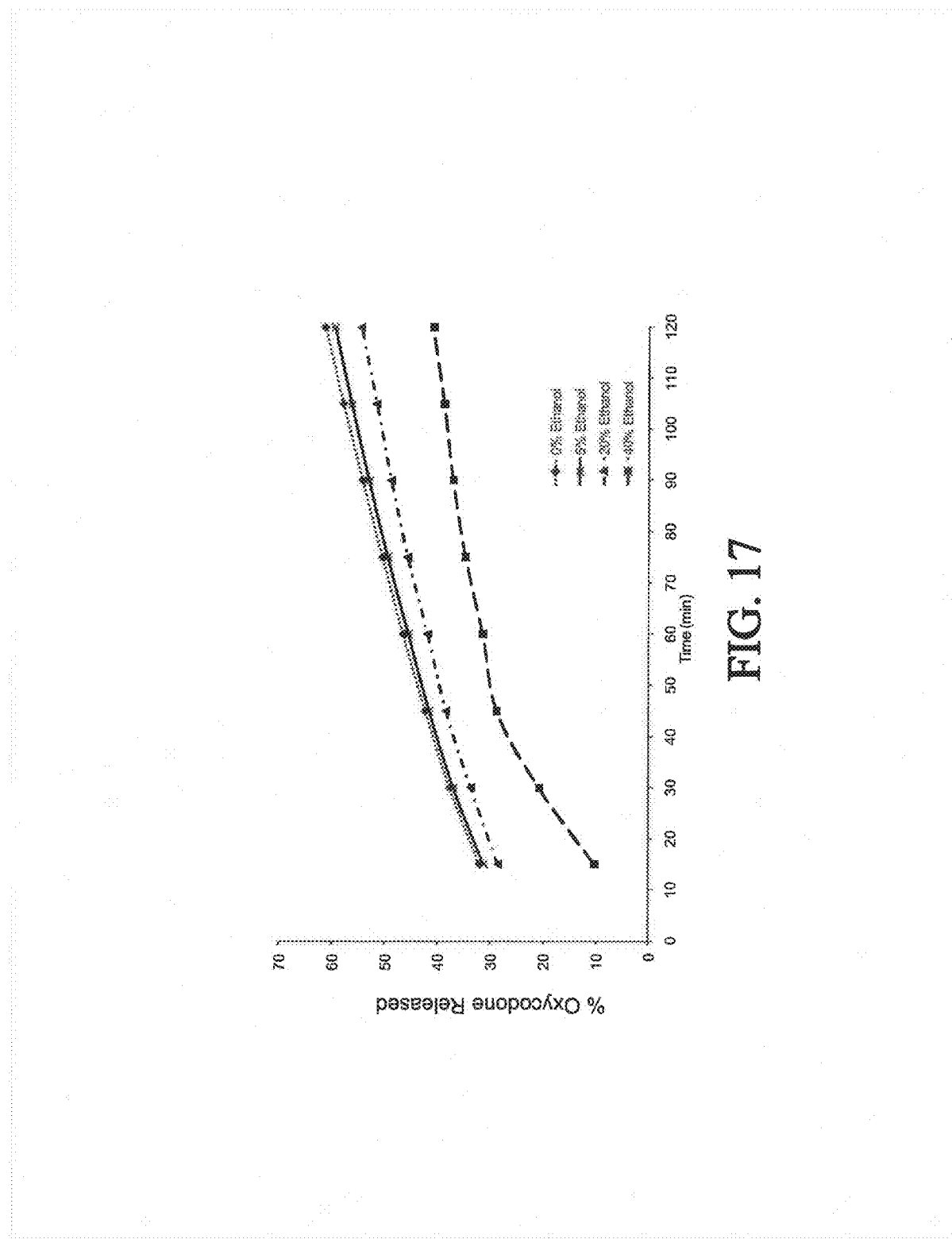
FIG. 17 illustrates the in vitro release of oxycodone from a bilayer tablet comprising 7.5 mg of oxycodone/325 mg of acetaminophen tested in 0.1 N HCl at a paddle speed of 150 rpm containing 0%, 5%, 20%, or 40% ethanol. Plotted is the percent of oxycodone released over a period of 2 hours.
Figure 18:
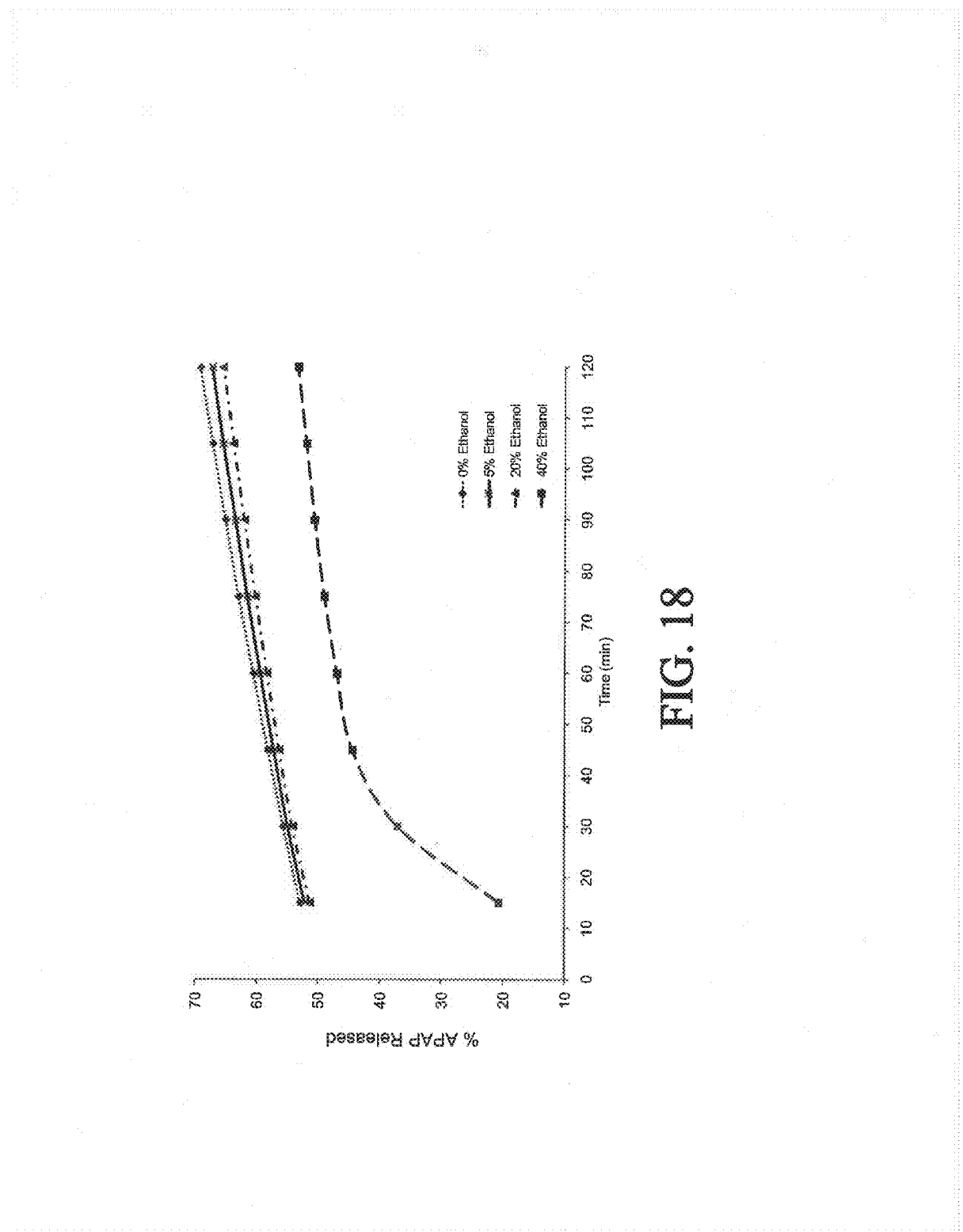
FIG. 18 presents the in vitro release of acetaminophen from a bilayer tablet comprising 7.5 mg of oxycodone/325 mg of acetaminophen tested in 0.1 N HCl at a paddle speed of 150 rpm containing 0%, 5%, 20%, or 40% ethanol. Plotted is the percent of acetaminophen released over a 2 hour period.

Tables 29, 30, 31, and 32 present the percent release of OC and APAP in the presence of 0%, 5%, 20%, and 40% ethanol, respectively. FIG. 17 presents dissolution profiles for OC and FIG. 18 presents dissolution profiles for APAP in the presence of 0%, 5%, 20%, and 40% ethanol. These data reveal that, for both OC and APAP, the dissolution in 5%, 20%, or 40% ethanol was either comparable or slower than the dissolution in 0% ethanol, indicating no dose dumping for this formulation.

TABLE 29

Percent Release in 0% Ethanol

| Time (Min) | OC Mean | OC RSD | OC Minimum | OC Maximum | APAP Mean | APAP RSD | APAP Minimum | APAP Maximum |
|---|---|---|---|---|---|---|---|---|
| 15 | 32.0 | 2.7 | 31.1 | 33.4 | 52.9 | 2.7 | 50.6 | 56.0 |
| 30 | 37.6 | 2.4 | 36.5 | 39.2 | 55.6 | 2.5 | 53.5 | 58.6 |
| 45 | 42.3 | 2.6 | 40.9 | 44.4 | 58.1 | 2.5 | 56.0 | 61.1 |
| 60 | 46.5 | 2.5 | 45.0 | 48.7 | 60.5 | 2.4 | 58.4 | 63.5 |
| 75 | 50.4 | 2.5 | 48.7 | 52.5 | 62.9 | 2.4 | 60.8 | 65.9 |
| 90 | 54.1 | 2.4 | 52.1 | 56.2 | 65.0 | 2.3 | 62.9 | 68.0 |
| 105 | 57.7 | 2.1 | 55.6 | 59.8 | 67.1 | 2.3 | 65.0 | 70.1 |
| 120 | 61.1 | 2.2 | 58.9 | 63.5 | 69.1 | 2.2 | 66.9 | 72.1 |

TABLE 30

Percent Release in 5% Ethanol

| Time (Min) | OC Mean | OC RSD | OC Minimum | OC Maximum | APAP Mean | APAP RSD | APAP Minimum | APAP Maximum |
|---|---|---|---|---|---|---|---|---|
| 15 | 31.2 | 2.4 | 30.2 | 32.4 | 52.1 | 1.5 | 50.5 | 53.5 |
| 30 | 36.9 | 3.2 | 35.1 | 39.0 | 54.9 | 1.6 | 53.4 | 56.4 |
| 45 | 41.5 | 3.3 | 39.1 | 44.0 | 57.2 | 1.5 | 55.7 | 58.7 |
| 60 | 45.5 | 3.5 | 43.4 | 48.2 | 59.4 | 1.5 | 57.9 | 60.9 |
| 75 | 49.4 | 2.6 | 47.9 | 52.5 | 61.5 | 1.5 | 60.0 | 63.0 |
| 90 | 52.9 | 3.5 | 50.7 | 56.1 | 63.4 | 1.5 | 61.9 | 65.0 |
| 105 | 56.2 | 1.8 | 54.0 | 57.8 | 65.4 | 1.5 | 63.8 | 66.9 |
| 120 | 59.3 | 2.8 | 56.7 | 61.7 | 67.2 | 1.5 | 65.6 | 68.7 |

TABLE 31

Percent Release in 20% Ethanol

| Time (Min) | OC Mean | OC RSD | OC Minimum | OC Maximum | APAP Mean | APAP RSD | APAP Minimum | APAP Maximum |
|---|---|---|---|---|---|---|---|---|
| 15 | 28.5 | 4.1 | 26.5 | 30.3 | 51.3 | 2.9 | 48.2 | 53.1 |
| 30 | 33.6 | 3.3 | 32.3 | 35.7 | 54.1 | 2.3 | 51.3 | 55.7 |
| 45 | 38.3 | 2.8 | 35.7 | 39.9 | 56.3 | 2.2 | 53.7 | 58.0 |
| 60 | 41.8 | 3.6 | 38.1 | 44.1 | 58.3 | 2.1 | 55.6 | 59.9 |
| 75 | 45.6 | 3.0 | 43.4 | 48.8 | 60.2 | 2.0 | 57.7 | 61.8 |
| 90 | 48.7 | 3.3 | 46.1 | 52.0 | 62.0 | 2.0 | 59.4 | 63.6 |
| 105 | 51.4 | 3.0 | 49.1 | 53.7 | 63.7 | 1.9 | 61.1 | 65.2 |
| 120 | 54.3 | 2.7 | 51.3 | 56.7 | 65.4 | 1.9 | 62.9 | 66.8 |

TABLE 32

Percent Release in 40% Ethanol

| Time (Min) | OC Mean | OC RSD | OC Minimum | OC Maximum | APAP Mean | APAP RSD | APAP Minimum | APAP Maximum |
|---|---|---|---|---|---|---|---|---|
| 15 | 10.3 | 16.3 | 7.8 | 13.7 | 20.7 | 16.3 | 15.8 | 25.9 |
| 30 | 20.7 | 8.6 | 16.5 | 23.0 | 37.1 | 7.7 | 31.4 | 41.4 |
| 45 | 28.6 | 10.4 | 24.4 | 33.4 | 44.4 | 2.6 | 42.2 | 45.8 |
| 60 | 31.3 | 5.9 | 29.2 | 35.0 | 47.0 | 1.4 | 45.9 | 48.0 |
| 75 | 34.5 | 6.5 | 30.3 | 38.1 | 49.0 | 1.4 | 47.7 | 49.8 |
| 90 | 36.8 | 7.0 | 33.9 | 41.2 | 50.5 | 1.5 | 49.2 | 51.6 |
| 105 | 38.5 | 6.8 | 35.3 | 44.0 | 51.9 | 1.7 | 50.4 | 53.1 |
| 120 | 40.7 | 4.5 | 38.0 | 43.5 | 53.2 | 1.4 | 51.5 | 54.1 |

Example 9

Clinical Pharmacokinetic Analysis of an Extended Release Formulation of Oxycodone/Acetaminophen Administered Under Fed and Fasted Conditions An open-label, randomized, three-period crossover study was conducted to evaluate the pharmacokinetics (PK), bioavailability, and safety of two tablets of a multi-layer extended-release formulation (each tablet comprising 7.5 mg oxycodone hydrochloride/325 mg acetaminophen), administered as a single dose in normal, healthy subjects under fed (high-fat or low-fat meal) and fasted conditions (i.e., 10 hr fast).

This single center, open-label, randomized, 3-period, 6-sequence crossover study in normal, healthy subjects was designed to evaluate the effect of a high-fat and low-fat meal on the PK, bioavailability, and safety of a multilayer ER tablet formulation of 7.5 mg OC/325 mg APAP (see selected example from Chart No. 1). The formulation was orally administered as 2 tablets (15 mg OC/650 mg APAP total dose) under 2 types of fed (high-fat and low-fat) and fasted conditions. Forty-eight subjects were enrolled and 31 subjects completed the study. Only subjects that completed all 3 study periods have been included in the PK evaluation.

Following a 10 hour overnight fast, subjects randomized to Treatment A consumed an entire standardized FDA high-fat breakfast (approximately 1,000±100 calories and approximately 50% from fat); those receiving Treatment B consumed an entire low-fat breakfast (approximately 800±80 calories and approximately 25% to 30% from fat). Breakfasts were consumed within 30 minutes prior to Hour 0 study drug administration. Subjects who could not consume the entire breakfast in the allotted time were dropped from the study. Subjects randomized to Treatment C were administered study drug under fasted conditions following an overnight fast of at least 10 hours. No food was allowed for the first 4 hours postdose. Blood samples were collected pre-dose (up to 60 minutes prior to dose), and at 15 min, 30 min, 45 min and 1, 2, 3, 4, 5, 6, 7, 8, 9, 10, 12, 16, 18, 20, 24, 36 and 48 hours post-dose, and the resulting plasma samples were analyzed for OC and APAP using a validated liquid chromatography-tandem mass spectrometry assay with a linear range of 0.100 to 100 ng/mL for OC and 100 to 50,000 ng/mL for APAP. Pharmacokinetic parameters, as detailed above in Example 2, were determined.

Figure 19:
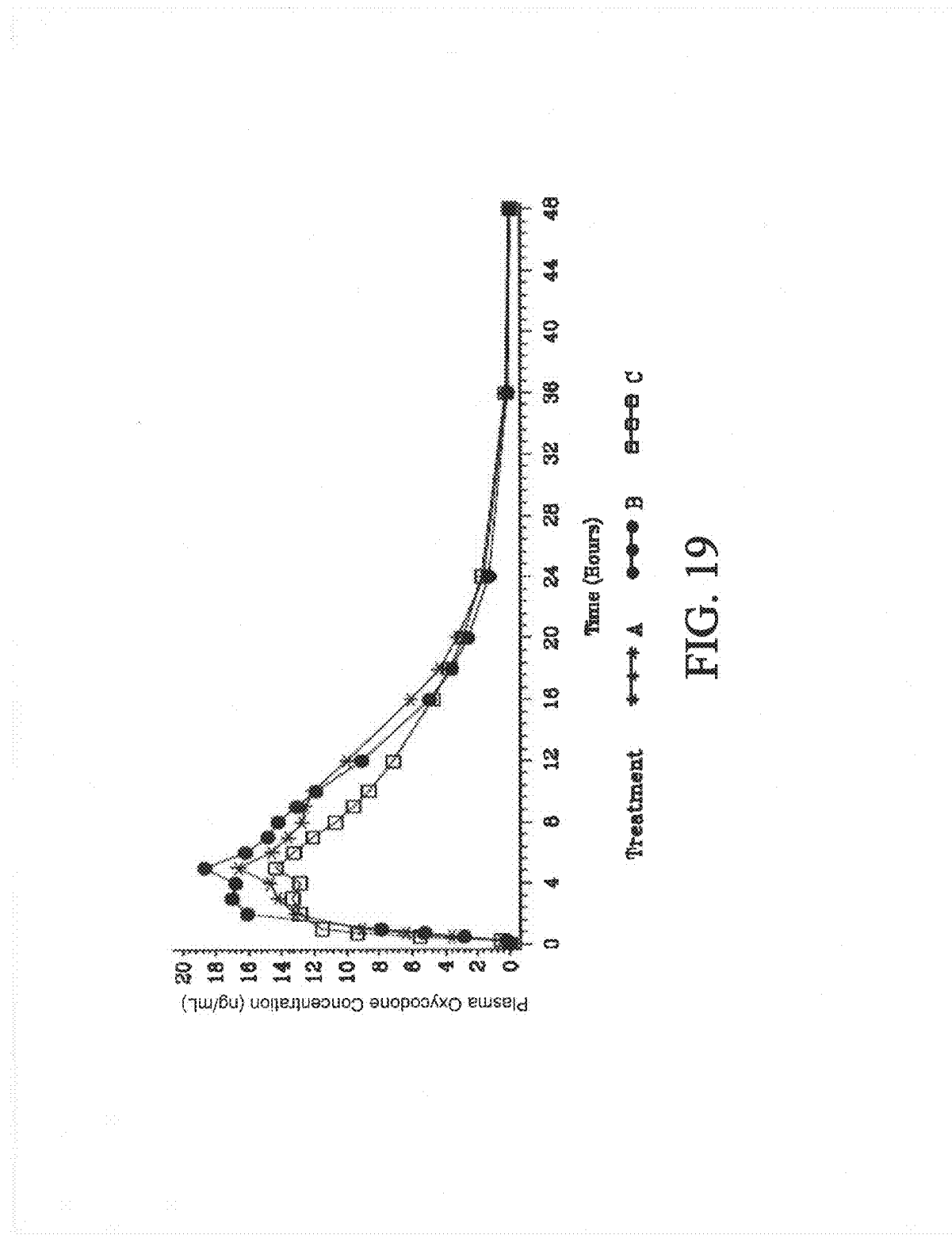
FIG. 19 shows the mean plasma concentrations of oxycodone as a function of time by treatment following oral administration of two tablets of 7.5 mg of oxycodone/325 mg of acetaminophen. Treatment A was under fed (high fat) conditions. Treatment B was under fed (low fat) conditions. Treatment C was under fasted conditions.

Tables 33 and 34 presents PK parameters for OC under the three treatment conditions, and FIG. 19 presents plasma OC concentration-time profiles for the treatments. Mean plasma concentration profiles of OC revealed that OC was rapidly absorbed under both fed (high and low fat meal) and fasted conditions. There was a slight lag (median 0.25 hours) when the formulation was administered after a meal (high and low fat). The median of the time of observed maximum plasma concentrations ($T_{max}$) were 4 hours and 3 hours after administration under low fat and fasted conditions, respectively. Median $T_{max}$ for OC under high fat conditions was significantly delayed, as compared to fasted conditions (5 hr vs. 3 hr; P<0.05). Average maximum plasma OC concentrations ($C_{max}$) were 19.94 ng/mL after a low fat breakfast, 17.90 ng/mL after a high fat breakfast, and 15.91 ng/mL under fasted conditions.

TABLE 33

Oxycodone Pharmacokinetic Estimates (2 tablets of 7.5/325)

| Parameter | Treatment A<br>High Fat<br>Mean (SD)<br>(N = 31) | Treatment B<br>Low Fat<br>Mean (SD)<br>(N = 31) | Treatment C<br>Fasted<br>Mean (SD)<br>(N = 31) |
|---|---|---|---|
| $AUC_{0-t}$ (ng · h/mL) | 219.41 (54.07) | 219.49 (57.29) | 190.70 (50.03) |
| $AUC_{0-inf}$ (ng · h/mL) | 221.00 (54.14) | 221.38 (56.95) | 192.63 (49.69) |
| $C_{max}$ (ng/mL) | 17.90 (4.25) | 19.94 (4.66) | 15.91 (3.43) |
| $T_{max}$ (h)[a] | 5.00 (1.00-12.00) | 4.00 (1.00-5.00) | 3.00 (0.75-8.00) |
| $K_{el}$ (1/h) | 0.1682 (0.0298) | 0.1693 (0.0321) | 0.1502 (0.0269) |
| $t_{lag}$ (h)[a] | 0.25 (0.00-1.00) | 0.25 (0.00-0.75) | 0.00 (0.00-0.25) |
| $t_{1/2}$ (h) | 4.26 (0.83) | 4.26 (0.91) | 4.76 (0.87) |

[a]Median (minimum-maximum).

A comparison of $C_{max}$ showed that OC concentrations were 12% and 25% higher when the formulation was given under high fat (Treatment A) and low fat (Treatment B) conditions, compared to fasted conditions (Treatment C; see Table 33). The $C_{max}$ for Treatment A was bioequivalent to both Treatments B (84%-96%) and C (105%-120%) as the 90% CIs for the geometric ratios were contained within 80% to 125% (see Table 34). The $C_{max}$ observed for Treatment B was not bioequivalent to Treatment C (117%-134%). AUCs were approximately 15% higher when the formulation was administered under fed conditions (high and low fat), as compared to fasted conditions (Table 33). AUC for both Treatments A and B (high fat and low fat) were bioequivalent to Treatment C (fasted; 111%-121% and 111%-120% for AUC0-t and 111%-120% and 110%-120% for AUC0-inf) (Table 34). The apparent plasma terminal elimination half-life (t½) for OC was similar when the formulation was administered under fed (4 hours) and fasted conditions (5 hours).

TABLE 34

Oxycodone Geometric LSMEANS Ratio (%)
(90% CI)

| Parameter | Treatment A/C<br>Fed (High<br>Fat)/Fasted | Treatment B/C<br>Fed (Low<br>Fat)/Fasted | Treatment A/B<br>Fed (High Fat)/<br>Fed (Low Fat) |
|---|---|---|---|
| $AUC_{0-inf}$<br>(ng · h/mL)[a] | 115.41<br>(110.63, 120.41) | 115.09<br>(110.38, 120.01) | 100.28<br>(96.18, 104.55) |
| $AUC_{0-t}$<br>(ng · h/mL)[a] | 115.85<br>(111.00, 120.90) | 115.30<br>(110.54, 120.27) | 100.47<br>(96.34, 104.79) |
| $C_{max}$ (ng/mL)[a] | 112.11<br>(104.61, 120.16) | 125.16<br>(116.88, 134.03) | 89.57<br>(83.67, 95.90) |

[a]N = 31.

Figure 20:
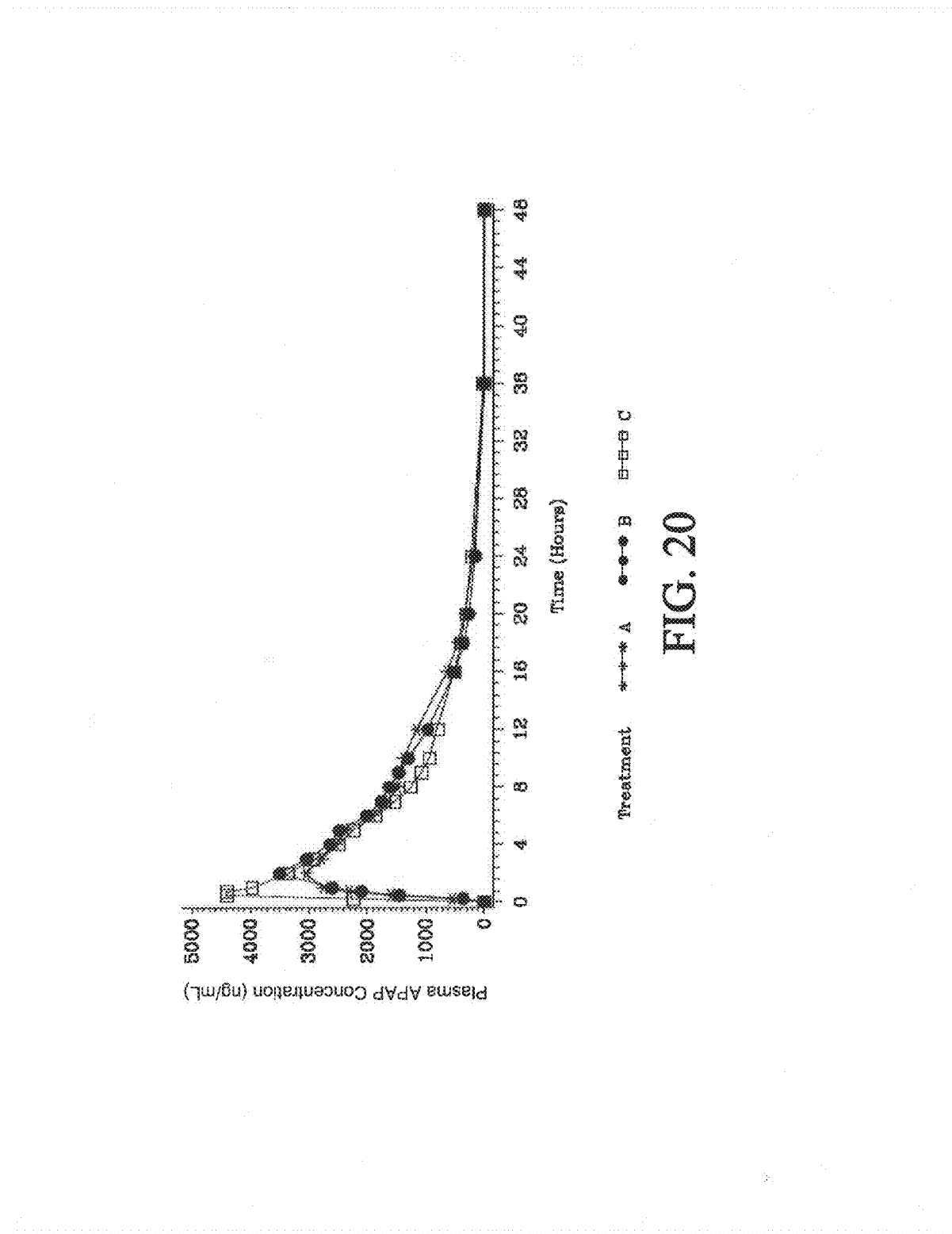
FIG. 20 presents the mean plasma concentrations of acetaminophen as a function of time by treatment following oral administration of two tablets of 7.5 mg of oxycodone/325 mg of acetaminophen. Treatment A was under fed (high fat) conditions. Treatment B was under fed (low fat) conditions. Treatment C was under fasted conditions.

PK parameters for APAP are presented in Tables 35 and 36 and the plasma APAP concentration-time profiles are presented in FIG. 20. APAP was rapidly absorbed following administration under fed (high and low fat meals) and fasted conditions. There was a slight lag when the formulation was administered after a low fat breakfast (median lag time [$t_{lag}$] 0.25 hours). There was no lag in the absorption of APAP when administered following a high fast breakfast or after fasting. The time to $C_{max}$ was significantly (P<0.05) longer when administered after a meal (high and low fat; median $T_{max}$=2 hours) than when administered under fasted conditions (median $T_{max}$=0.5 hour). Average $C_{max}$ values for APAP were lower after a high (3,775 ng/mL) and low fat (3,863 ng/mL) meal than when administered under fasted conditions (5,175 ng/mL). Geometric mean ratios for $C_{max}$ following Treatments A and B were 24% to 23% lower than for Treatment C (Table 36). The 90% CIs for $C_{max}$ following Treatment A (70%-82%) and Treatment B (72%-83%) with reference to fasted state were outside the bioequivalent range of 80%-125%. The AUCs for APAP were almost identical when the formulation was administered under high fat, low fat, or fasting conditions. (Comparison of geometric mean ratios of $AUC_{0-t}$ and $AUC_{0\ inf}$ for Treatments A (90% CI 97%-103% and 96%-102%) and B (90% CI 96%-101% and 94% to 100%) with those for Treatment C showed that treatments were bioequivalent. The $t_{1/2}$ for APAP after the formulation was administered after a high or low fat meal (5 hours) was slightly shorter than when administered under fasted conditions (7 hours).

TABLE 35

APAP Pharmacokinetic Estimates (2 tablets of 7.5/325)

| Parameter | Treatment A<br>Fed (High Fat)<br>Mean (SD)<br>(N = 31) | Treatment B<br>Fed (Low Fat)<br>Mean (SD)<br>(N = 31) | Treatment C<br>Fasted<br>Mean (SD)<br>(N = 31) |
|---|---|---|---|
| $AUC_{0-t}$ (ng · h/mL) | 29617.96 (7765.99) | 29346.82 (7869.75) | 29763.19 (7592.89) |
| $AUC_{0-inf}$ (ng · h/mL) | 31457.06 (7973.16)[a] | 30550.48 (8051.47) | 31807.70 (7923.30)[a] |
| $C_{max}$ (ng/mL) | 3774.52 (949.84) | 3862.90 (978.08) | 5175.48 (1731.31) |
| $T_{max}$ (h)[b] | 2.00 (0.50-5.00) | 2.00 (0.50-5.00) | 0.53 (0.23-5.00) |
| $K_{el}$ (1/h) | 0.1564 (0.0363)[a] | 0.1593 (0.0408) | 0.1146 (0.0360)[a] |

TABLE 35-continued

APAP Pharmacokinetic Estimates (2 tablets of 7.5/325)

| Parameter | Treatment A Fed (High Fat) Mean (SD) (N = 31) | Treatment B Fed (Low Fat) Mean (SD) (N = 31) | Treatment C Fasted Mean (SD) (N = 31) |
|---|---|---|---|
| $t_{lag}$ (h)[b] | 0.00 (0.00-1.00) | 0.25 (0.00-0.50) | 0.00 (0.00-0.25) |
| $t_{1/2}$ (h) | 4.66 (1.08)[a] | 4.71 (1.60) | 6.63 (1.99)[a] |

[a]N = 29
[b]Median (minimum-maximum).

TABLE 36

APAP Geometric LSMEANS Ratio (%) (90% CI)

| Parameter | Treatment A/C Fed (High Fat)/Fasted | Treatment B/C Fed (Low Fat)/Fasted | Treatment A/B Fed (High Fat)/Fed (Low Fat) |
|---|---|---|---|
| $AUC_{0-inf}$ (ng · h/mL)[a] | 98.60 (95.75, 101.54) | 96.56 (93.80, 99.39) | 102.12 (99.20, 105.11) |
| $AUC_{0-t}$ (ng · h/mL)[b] | 99.88 (97.31, 102.52) | 98.79 (96.27, 101.37) | 101.10 (98.54, 103.74) |
| $C_{max}$ (ng/mL)[b] | 76.00 (70.49, 81.94) | 77.18 (71.65, 83.13) | 98.48 (91.45, 106.05) |

[a]N = 27
[b]N = 31.

In summary, total exposure (AUC) for OC was slightly increased (by about 15%) when the formulation was administered with food (after high- or low-fat meal); however, AUCs for OC were equivalent between all treatments (high fat vs. fasted, low fat vs. fasted and high fat vs. low fat). Peak exposure ($C_{max}$) for OC was 12% and 25% higher under high fat and low-fat conditions, respectively, compared to fasted conditions. The $C_{max}$ for OC after a high-fat meal was bioequivalent to fasted conditions, as well as to low fat conditions, whereas the $C_{max}$ under low fat conditions was not equivalent to those under fasted conditions. The AUCs for APAP were equivalent between all treatments (high fat vs. fasted, low fat vs. fasted, and high fat vs. low fat). The peak exposure ($C_{max}$) for APAP was decreased by about 24% in fed (high- and low-fat) states as compared to the fasted state.

Example 10

Clinical Pharmacokinetic Analysis of an Extended Release Formulation of 7.5 mg Oxycodone/325 mg Acetaminophen—Single Dose An open-label, randomized, 3-period crossover study was performed to evaluate the single dose pharmacokinetic (PK) parameters, bioavailability, and safety of an extended-release formulation containing 7.5 mg OC/325 mg APAP (see selected example from Chart No. 1) in healthy subjects under fasted conditions. The PK and bioavailability of the extended-release formulation administered as 1 or 2 tablets were compared to the commercially-available immediate release tablet (immediate release 7.5 mg OC/325 mg APAP) administered as 1 or 2 tablets every 6 hours for 2 doses. This study was conducted in 48 male and female subjects, with equal gender distribution.

Figure 21:
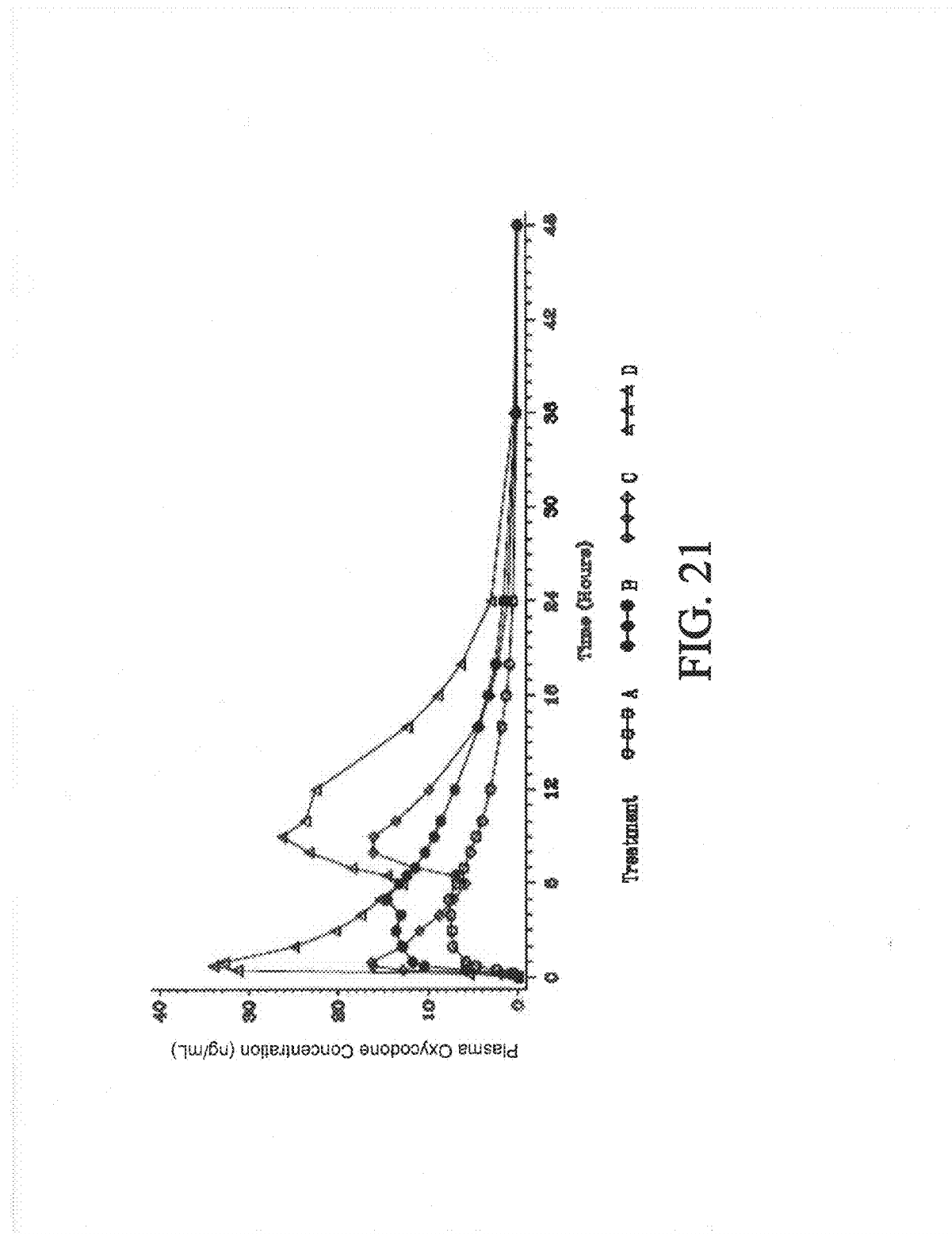
FIG. 21 shows the mean plasma concentrations of oxycodone versus time by treatment. Treatment A was one tablet of 7.5 mg oxycodone/325 mg acetaminophen administered orally under fasted conditions. Treatment B was two tablets of 7.5 mg oxycodone/325 mg acetaminophen administered orally under fasted conditions. Treatment C was one tablet of an immediate release 7.5 oxycodone/325 acetaminophen tablet administered orally every 6 hours for 2 doses under fasted conditions. Treatment D was two tablets of an immediate release 7.5 oxycodone/325 acetaminophen tablet administered orally every 6 hours for 2 doses under fasted conditions.

Pharmacokinetic parameter estimates for OC are presented in Table 37, and OC plasma concentration-time profiles are presented in FIG. 21. There was no lag in absorption of OC for the 1 and 2 tablet dosing configurations of the extended release formulation and the commercially-available immediate release tablet under fasted conditions. Plasma concentrations of OC rose rapidly after administration of the extended release formulation in a similar fashion to the commercially-available immediate release tablet, and peak plasma levels of OC were observed ($T_{max}$) at 4 and 3 hours for the 1 or 2 tablet dosing configuration of the extended release formulation compared with 7 hours after the initial dose of 1 tablet of the commercially-available immediate release tablet (1 hour after the second dose) and 0.75 hours after the initial dose of 2 tablets of the commercially-available immediate release tablet. Mean plasma concentrations of OC from the extended release formulation were detectable through 36 hours in most subjects following all treatments and $t_{1/2}$ was about 4 to 5 hours across all treatments. The extent of exposure ($AUC_{0-t}$ and $AUC_{0-inf}$) for the 2 tablet dosing configuration of the extended release formulation increased proportionally with dose compared with the 1-tablet dosing configuration of the extended release formulation.

TABLE 37

Oxycodone Pharmacokinetic Estimates (7.5/325)

| Parameter | Treatment A ER Formulation (1 tablet) Mean (SD) (N = 33) | Treatment B ER Formulation (2 tablets) Mean (SD) (N = 33) | Treatment C Commercially-available immediate release tablet (1 tablet twice) Mean (SD) (N = 33) | Treatment D Commercially-available immediate release tablet (2 tablets twice) Mean (SD) (N = 27) |
|---|---|---|---|---|
| $AUC_{0-t}$ (ng · h/mL) | 87.43 (24.59) | 185.98 (47.64) | 191.15 (53.43) | 401.23 (110.56) |
| $AUC_{0-inf}$ (ng · h/mL) | 89.85 (24.73)[b] | 187.71 (47.58) | 193.10 (53.22) | 403.04 (110.45) |

TABLE 37-continued

| | Oxycodone Pharmacokinetic Estimates (7.5/325) | | | |
|---|---|---|---|---|
| Parameter | Treatment A ER Formulation (1 tablet) Mean (SD) (N = 33) | Treatment B ER Formulation (2 tablets) Mean (SD) (N = 33) | Treatment C Commercially-available immediate release tablet (1 tablet twice) Mean (SD) (N = 33) | Treatment D Commercially-available immediate release tablet (2 tablets twice) Mean (SD) (N = 27) |
| $C_{max}$ (ng/mL) | 8.41 (2.06) | 16.39 (4.31) | 20.82 (5.98) | 41.24 (12.12) |
| $T_{max}$ (h)[a] | 4.00 (0.75-5.92) | 3.00 (0.75-6.50) | 7.38 (0.50-10.00) | 0.75 (0.50-12.00) |
| $t_{lag}$ (h)[a] | 0.00 (0.00-0.50) | 0.00 (0.00-0.52) | 0.00 (0.00-0.25) | 0.00 (0.00-0.25) |
| $t_{1/2}$ (h) | 4.50 (0.78)[b] | 4.87 (0.93) | 4.08 (0.89) | 4.34 (1.02) |
| $K_{el}$ (h$^{-1}$) | 0.1590 (0.0307)[b] | 0.1473 (0.0274) | 0.1770 (0.0352) | 0.1688 (0.0415) |

[a]Median (minimum-maximum).
[b]N = 32

No dose-dumping was observed in any subject receiving the ER formulation. The interindividual variability (CV %) for $C_{max}$ of OC after administration of 1 or 2 tablets of the ER formulation was comparable to 1 tablet of the commercially-available immediate release tablet and less than 29% for all 3 treatments. Similarly the interindividual variability (CV %) for AUC of OC was 28% or less for 1 and 2 tablets of the ER formulation and 1 tablet of the commercially-available immediate release tablet.

Figure 22:
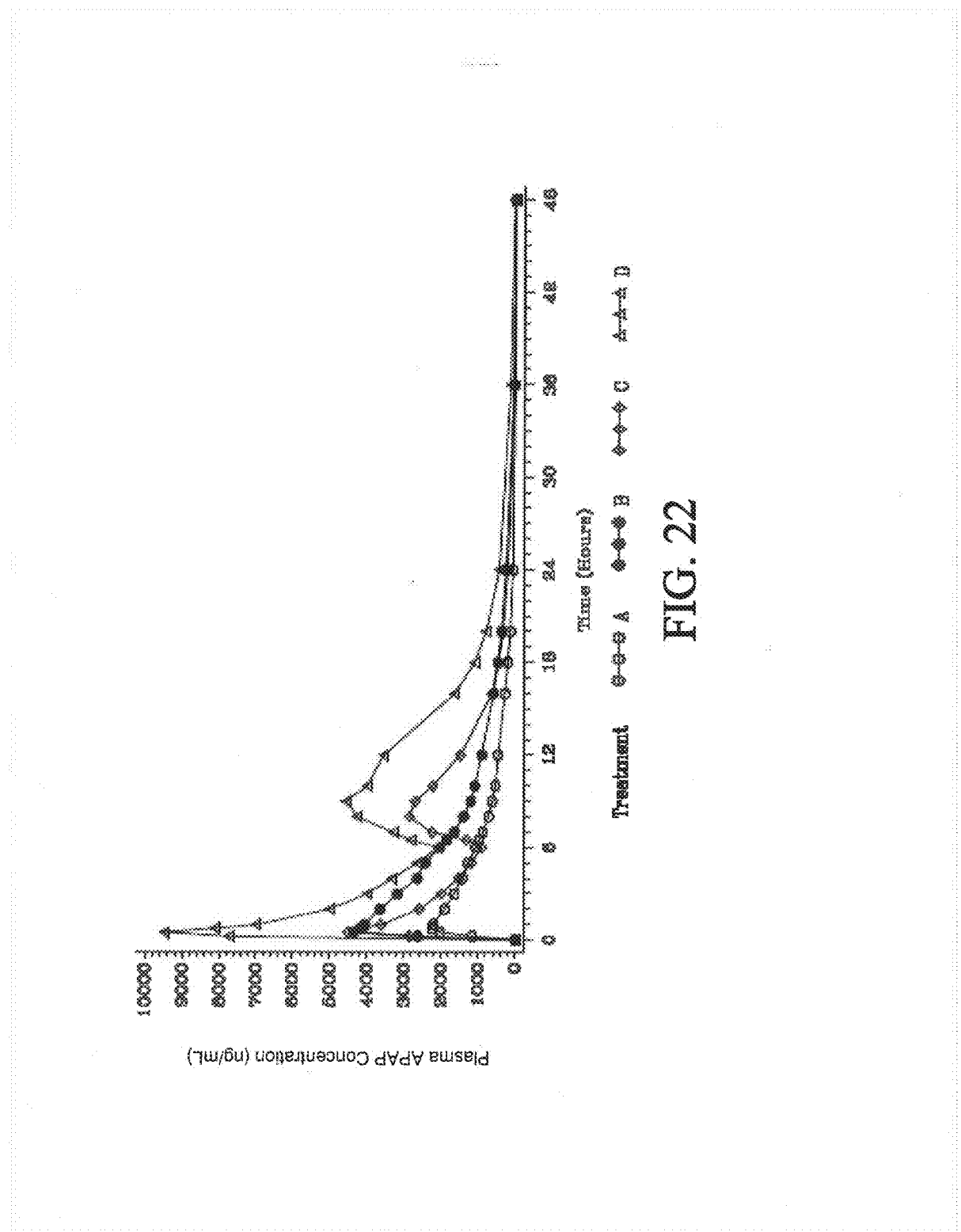
FIG. 22 presents the mean plasma concentrations of acetaminophen versus time by treatment. Treatment A was one tablet of 7.5 mg oxycodone/325 mg acetaminophen administered orally under fasted conditions. Treatment B was two tablets of 7.5 mg oxycodone/325 mg acetaminophen administered orally under fasted conditions. Treatment C was one tablet of an immediate release 7.5 oxycodone/325 acetaminophen tablet administered orally every 6 hours for 2 doses under fasted conditions. Treatment D was two tablets an immediate release 7.5 oxycodone/325 acetaminophen tablet administered orally every 6 hours for 2 doses under fasted conditions.

Table 38 presents APAP PK parameter estimates and FIG. 22 presents APAP plasma concentration-time profiles. The appearance of plasma concentrations of APAP for all dose configurations of the extended release formulation and the commercially-available immediate release tablet showed no lag. Plasma concentrations of APAP rose rapidly after administration of the extended release formulation, similar to that observed with the commercially-available immediate release tablet. Peak plasma levels of APAP following administration of the 1 tablet and 2 tablet dosing configurations of the extended release formulation were observed (median $T_{max}$) at 0.75 hours after dosing compared with 0.5 hours after the first dose of the commercially-available immediate release tablet (1 and 2 tablets). Mean plasma concentrations of APAP were detectable through 36 hours following all treatments and the mean $t_{1/2}$ was approximately 4 to 7 hours across treatment groups. The extent of exposure (AUC) to APAP following dosing with 1 and 2 tablets of the extended release formulation increased proportionally with dose.

TABLE 38

| | APAP Pharmacokinetic Estimates (7.5/325) | | | |
|---|---|---|---|---|
| Parameter | Treatment A ER Formulation (1 tablet) Mean (SD) (N = 33) | Treatment B ER Formulation (2 tablets) Mean (SD) (N = 33) | Treatment C Commercially-available immediate release tablet (1 tablet twice) Mean (SD) (N = 33) | Treatment D Commercially-available immediate release tablet (2 tablets twice) Mean (SD) (N = 27) |
| $AUC_{0-t}$ (ng · h/mL) | 15871 (4841) | 32665 (10894) | 33040 (9589) | 69837 (22945) |
| $AUC_{0-inf}$ (ng · h/mL) | 16995 (5073) | 34836 (11067)[b] | 34236 (10126)[b] | 71949 (24234)[c] |
| $C_{max}$ (ng/mL) | 2632 (918) | 5230 (2086) | 4878 (1545) | 10741 (4123) |
| $T_{max}$ (h)[a] | 0.75 (0.25-2.02) | 0.75 (0.25-4.00) | 0.50 (0.25-9.00) | 0.50 (0.25-12.00) |
| $t_{lag}$ (h)[a] | 0.00 (0.00-0.50) | 0.00 (0.00-0.25) | 0.00 (0.00-0.00) | 0.00 (0.00-0.00) |
| $t_{1/2}$ (h) | 5.33 (1.53) | 6.88 (2.15)[b] | 4.41 (1.16)[b] | 5.76 (1.47)[c] |
| $K_{el}$ (h$^{-1}$) | 0.1421 (0.0479) | 0.1103 (0.0337)[b] | 0.1669 (0.0411)[b] | 0.1291 (0.0368)[c] |

[a]Median (minimum-maximum).
[b]N = 32
[c]N = 25

No dose-dumping was observed in any subject receiving the ER formulation. The interindividual variability (CV %) for $C_{max}$ of APAP was slightly more after administration of 1 and 2 tablets of the ER formulation (35% and 40%, respectively) than for 1 tablet of the commercially-available immediate release tablet (32%). The interindividual variability (CV %) for AUC of APAP was less than 33% for all 3 treatments.

Both OC and APAP were rapidly absorbed under all conditions with no lag in plasma concentrations. Both OC and APAP levels were sufficiently high within 1 hour after administration of the extended release formulation. Peak exposure to OC was 18% to 21% lower for the ER formulation than for the commercially-available immediate release tablet (1 tablet Q6h). OC levels were sustained over the proposed 12 h dosing interval. By 12 hours after dosing with the extended release formulation, APAP plasma levels were less than 20% of $C_{max}$. Total exposure to both OC and APAP from the extended release formulation was equivalent to that of 1 tablet of the commercially-available immediate release tablet.

Figure 24:
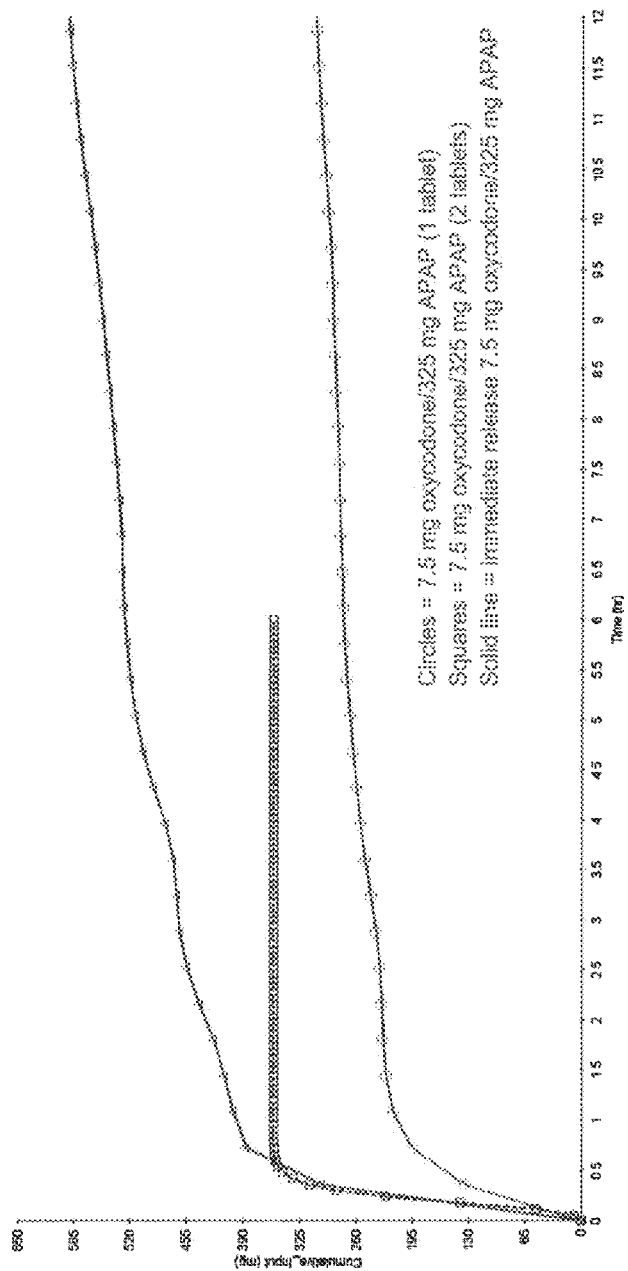
FIG. 24 presents a deconvolution plot of the biphasic absorption of acetaminophen from tablets of the 7.5 mg oxycodone/325 mg acetaminophen formulation. The cumulative amount of acetaminophen is plotted versus time. Circles represent one tablet of 7.5 mg oxycodone/325 mg acetaminophen; triangles represent two tablets of 7.5 mg oxycodone/325 mg acetaminophen; and squares represent the immediate release 7.5 oxycodone/325 acetaminophen product.

To further analyze the absorption of OC and APAP from the ER formulation, the plasma concentrations of OC and APAP following administration of 1 tablet of the ER formulation, 2 tablets of the ER formulation, and the commercially-available immediate release tablet were deconvolved using WinNonlin 5.2 (Pharsight). Deconvolution evaluates in vivo drug release and delivery based on data for a known drug input. Depending upon the type of reference input information available, the drug transport evaluated will be either a simple in vivo drug release (e.g., gastrointestinal release) or a composite form, typically consisting of an in vivo release followed by a drug delivery to the general systemic circulation. It can estimate the cumulative amount and fraction absorbed over time for the subjects, given PK profile data and dose. For a pure immediate release (IR) or an extended release (ER) formulation the cumulative absorption plot shows a monoexponential curve whereas for a bilayer formulation (IR+FER) a biexponential (rapid phase followed by slower phase) absorption curve will be observed. FIG. 23 and FIG. 24 present the deconvolution plots for OC and APAP, respectively. For each, there is an early rapid phase of absorption that is followed by a later slower phase of absorption from the ER formulation.

Figure 25:
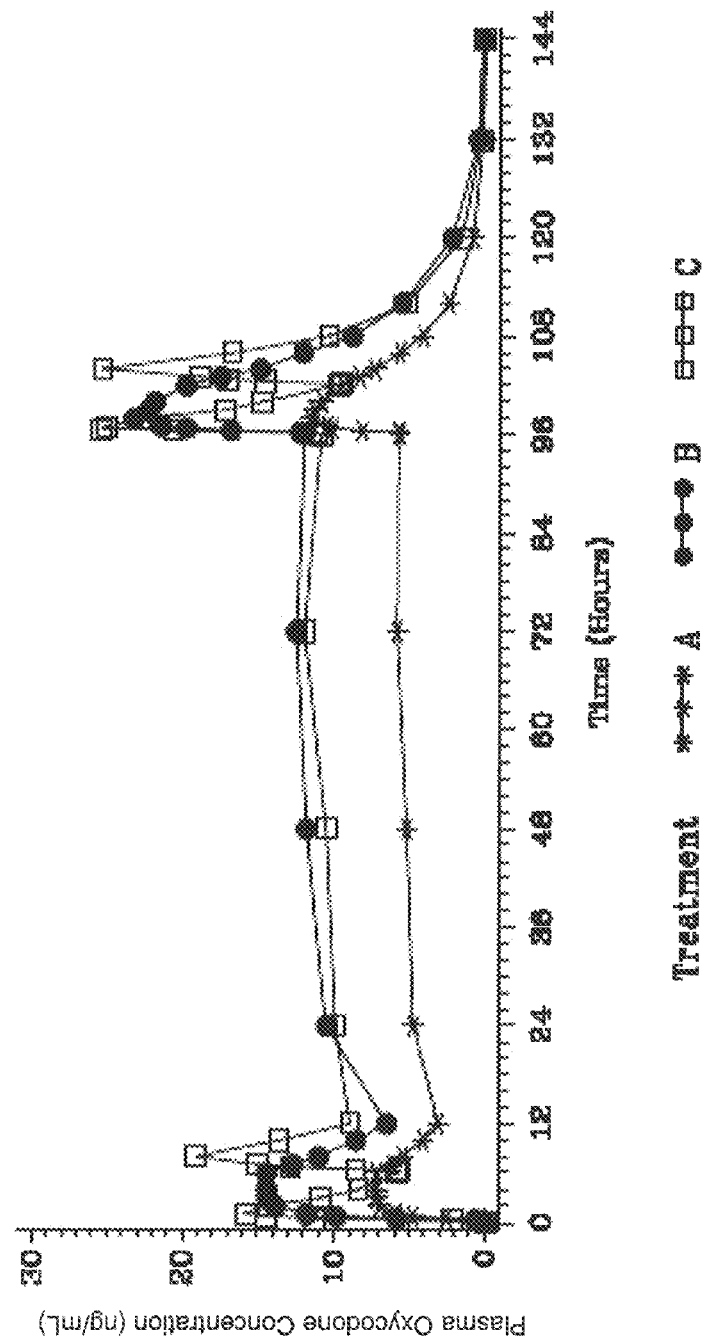
FIG. 25 shows the mean plasma concentrations of oxycodone versus time by treatment. Treatment A was one tablet of 7.5 mg oxycodone/325 mg acetaminophen administered orally every 12 hours for 4.5 days (9 doses) under fasted conditions. Treatment B was two tablets of 7.5 mg oxycodone/325 mg acetaminophen administered orally every 12 hours for 4.5 days (9 doses) under fasted conditions. Treatment C was one tablet of an immediate release 7.5 oxycodone/325 acetaminophen tablet administered orally every 6 hours for 4.5 days (18 doses) under fasted conditions.

Example 10). There was no lag (median $t_{lag}$ 0 hours) in the absorption of OC following administration of the ER formulation (1 or 2 tablets) and the commercially-available immediate release tablet, and no dose-dumping was observed for any subject. Peak plasma levels were observed at 3 hours after administration of 1 and 2 tablets of the ER formulation and at 1 hour after the second dose of the commercially-available immediate release tablet (FIG. 25). On Day 1, interindividual variability (% CV) in the $C_{max}$ for OC was slightly higher for 1 tablet (29%) than for 2 tablets (23%) of the ER formulation or the commercially-available immediate release tablet (up to 22%). The variability in the $AUC_{0-12hr}$ for OC was comparable between all 3 treatments (21% to 23%). Minimum (trough) plasma concentrations (Cmin) of OC achieved steady-state levels by Day 4 for 1 tablet of the ER formulation and the commercially-available immediate release tablet and by Day 3 for 2 tablets of the ER formulation. Trough levels of OC on Days 2 through 5 for 2 tablets of the ER formulation were comparable to those observed for the commercially-available immediate release tablet.

TABLE 39

Oxycodone Pharmacokinetic Estimates - Day 1

| Parameter | Treatment A ER Formulation (1 Tablet Q12h) Mean (SD) (N = 33) | Treatment B ER Formulation (2 Tablets Q12h) Mean (SD) (N = 33) | Treatment C Commercially-available immediate release tablet (1 Tablet Q6h) Mean (SD) (N = 33) |
|---|---|---|---|
| $AUC_{0-12\ h}$ (ng · h/mL) | 66.93 (15.14) | 135.89 (30.81) | 141.73 (29.78) |
| $C_{max}$ (ng/mL) | 8.34 (2.37) | 17.05 (3.97) | 21.93 (4.80) |
| $T_{max}$ (h)$^a$ | 3.00 (0.75-7.00) | 3.00 (0.50-5.92) | 7.00 (0.50-8.00) |
| $t_{lag}$ (h)$^a$ | 0.00 (0.00-0.50) | 0.00 (0.00-0.32) | 0.00 (0.00-0.25) |

$^a$Median (minimum-maximum).

Example 11

Clinical Pharmacokinetic Analysis of an Extended Release Formulation of 7.5 mg Oxycodone/325 mg Acetaminophen—Multiple Doses An open-label, randomized, 3-period crossover study was performed to evaluate the steady-state PK, bioavailability, and safety of the extended release formulation containing 7.5 mg OC/325 mg APAP in healthy subjects (see selected example from Chart No. 1). The PK and bioavailability of the ER formulation administered as 1 or 2 tablets every 12 hours for 4.5 days (9 doses) was compared to the commercially-available immediate release tablet (immediate release 7.5 mg OC/325 mg APAP) administered as 1 tablet every 6 hours for 4.5 days (18 doses) under fasted conditions (10 hours for the first dose on Days 1 and 5; at least 1 hour for all other doses). This study was conducted in 48 male and female subjects, with equal gender distribution.

The PK behavior of OC on Study Day 1 (see Table 39) was similar to that observed in the single dose study (see On Day 5 (see Table 40), steady state was achieved and the median $T_{max}^{ss}$ was observed at 2 hours following 1 tablet or 2 tablets of the ER formulation and at 30 min following the second daily dose of the commercially-available immediate release tablet. Maximum observed plasma concentrations at steady-state ($C_{max}^{ss}$) for OC for the 1 and 2 tablet dosing configurations of the ER formulation were not equivalent to the commercially-available immediate release tablet. On Day 5, interindividual variability (% CV) in $C_{max}^{ss}$ and $AUC_{0-12\ h}^{ss}$ for OC was comparable between all 3 treatments (up to 29%). The degree of fluctuation (DFL) in and the swing of plasma concentrations for the ER formulation over the last 12 hour dosing interval on Day 5 were 15% to 22% less than that observed for the commercially-available immediate release tablet.

TABLE 40

Oxycodone Pharmacokinetic Estimates - Day 5

| Parameter | Treatment A ER Formulation (1 Tablet Q12 h) Mean (SD) (N = 33) | Treatment B ER Formulation (2 Tablets Q12 h) Mean (SD) (N = 33) | Treatment C Commercially-available immediate release tablet (1 Tablet Q6 h) Mean (SD) (N = 33) |
|---|---|---|---|
| $AUC_{0-12\,h}^{ss}$ (ng · h/mL) | 102.36 (29.30) | 208.59 (59.28) | 208.93 (57.30) |
| $C_{av}^{ss}$ (ng/mL) | 8.53 (2.44) | 17.38 (4.94) | 17.41 (4.78) |
| $C_{max}^{ss}$ (ng/mL) | 12.67 (3.48) | 25.67 (7.49) | 30.50 (8.91) |
| $C_{min}^{ss}$ (ng/mL) | 4.06 (1.40) | 8.98 (3.52) | 8.78 (3.17) |
| DFL (%) | 101.72 (14.14) | 97.17 (18.80) | 126.83 (27.93) |
| Swing | 2.23 (0.64) | 2.03 (0.70) | 2.67 (0.92) |
| $T_{max}^{ss}$ (h)$^a$ | 2.00 (0.50-10.00) | 2.00 (0.50-7.00) | 6.50 (0.50-8.02) |
| $t_{1/2}$ (h)$^c$ | 5.46 (1.24) | 6.11 (1.46) | 5.47 (1.70)$^b$ |
| $K_{el}$ (1/h)$^c$ | 0.1326 (0.0269) | 0.1199 (0.0291) | 0.1387 (0.0418)$^b$ |

$^a$Median (minimum-maximum).
$^b$N = 32
$^c$Days 5 to 7.

Figure 26:
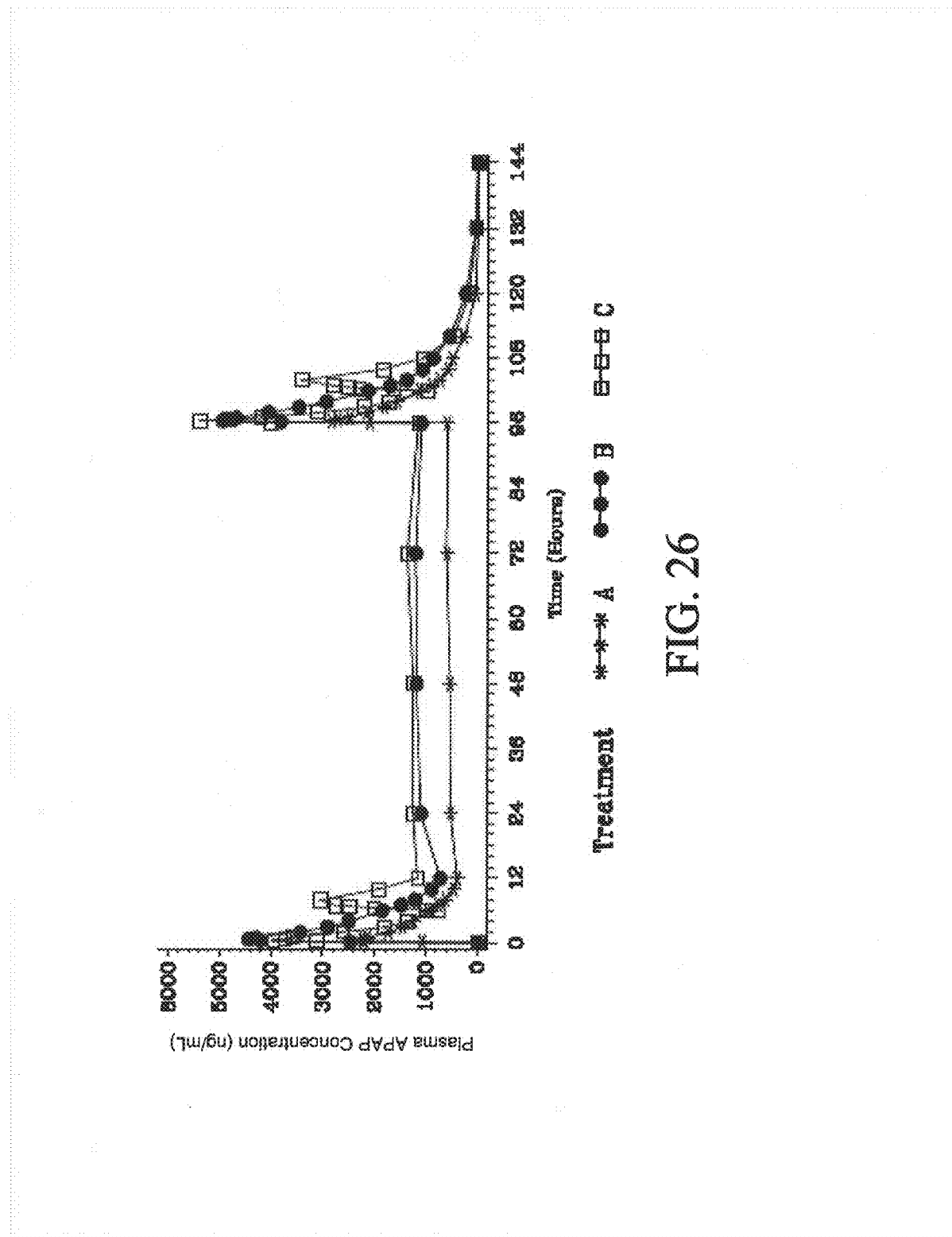
FIG. 26 presents the mean plasma concentrations of acetaminophen versus time by treatment. Treatment A was one tablet of 7.5 mg oxycodone/325 mg acetaminophen administered orally every 12 hours for 4.5 days (9 doses) under fasted conditions. Treatment B was two tablets of 7.5 mg oxycodone/325 mg acetaminophen administered orally every 12 hours for 4.5 days (9 doses) under fasted conditions. Treatment C was one tablet of an immediate release 7.5 oxycodone/325 acetaminophen tablet administered orally every 6 hours for 4.5 days (18 doses) under fasted conditions.

The PK behavior of APAP on Study Day 1 (see Table 41) was similar to that observed in the single dose study (see Example 10). Acetaminophen was rapidly absorbed following a single dose of 1 or 2 tablets of the ER formulation and in a similar fashion to the commercially-available immediate release tablet (FIG. 26). There was no lag in plasma concentrations following any of the 3 dosing regimens (median $t_{lag}$ 0 hours), and no dose-dumping was observed for any subject. Peak APAP plasma concentrations were observed 30 to 45 minutes after administration of 1 or 2 tablets of the ER formulation and at 30 minutes after the first dose of the commercially-available immediate release tablet on Day 1. The $C_{max}$ for APAP occurred following the first 325 mg dose of the commercially-available immediate release tablet, rather than after the second dose. Dose proportionality for $C_{max}$ and $AUC_{0-12h}$ was observed over the range of 325 mg to 650 mg APAP after a single administration of 1 or 2 tablets of the ER formulation. The $C_{min}$ of APAP achieved steady-state levels by Day 4 for 1 tablet and by Day 2 for 2 tablets of the ER formulation and for the commercially-available immediate release tablet. Trough levels of APAP on Days 2 through 5 for 2 tablets of the ER formulation were comparable to those observed for the commercially-available immediate release tablet. On Day 1, interindividual variability (% CV) in $C_{max}$ and $AUC_{0-12h}$ for APAP was comparable between all 3 treatments (31% or less).

On Day 5 of the study, median $T_{max}^{ss}$ for APAP was observed at 30 minutes following 1 or 2 tablets of the ER formulation and at 30 minutes following the first daily dose of the commercially-available immediate release tablet (see Table 42). Acetaminophen concentrations following administration of 325 mg or 650 mg APAP (1 or 2 tablets) Q12h were proportional to dose. The DFL in and swing of plasma APAP levels for the ER formulation were equivalent to the commercially-available immediate release tablet. On Day 5, interindividual variability (% CV) in $C_{max}^{ss}$ for APAP was slightly higher following administration of 2 tablets of the ER formulation (33%) than the % CV seen for 1 tablet of the ER formulation and the commercially-available immediate release tablet (~27%). Interindividual variability in $AUC_{0-12h}^{ss}$ for APAP was comparable between all 3 treatments (up to 27%).

TABLE 41

APAP Pharmacokinetic Estimates - Day 1

| Parameter | Treatment A ER Formulation (1 Tablet Q12 h) Mean (SD) (N = 33) | Treatment B ER Formulation (2 Tablets Q12 h) Mean (SD) (N = 33) | Treatment C Commercially-available immediate release tablet (1 Tablet Q6 h) Mean (SD) (N = 33) |
|---|---|---|---|
| $AUC_{0-12\,h}$ (ng · h/mL) | 12192 (3331) | 24141 (6436) | 24884 (6656) |
| $C_{max}$ (ng/mL) | 2631 (815) | 5245 (1473) | 5146 (1553) |
| $T_{max}$ (h)$^a$ | 0.55 (0.25-3.00) | 0.75 (0.25-2.00) | 0.50 (0.25-8.00) |
| $t_{lag}$ (h)$^a$ | 0.00 (0.00-0.25) | 0.00 (0.00-0.25) | 0.00 (0.00-0.00) |

$^a$Median (minimum-maximum).

TABLE 42

APAP Pharmacokinetic Estimates - Day 5

| Parameter | Treatment A ER Formulation (1 Tablet Q12 h) Mean (SD) (N = 33) | Treatment B ER Formulation (2 Tablets Q12 h) Mean (SD) (N = 33) | Treatment C Commercially-available immediate release tablet (1 Tablet Q6 h) Mean (SD) (N = 33) |
|---|---|---|---|
| $AUC_{0-12\,h}^{ss}$ (ng · h/mL) | 15307 (4092) | 28512 (7714) | 28719 (7023) |
| $C_{av}^{ss}$ (ng/mL) | 1276 (341) | 2376 (643) | 2393 (585) |
| $C_{max}^{ss}$ (ng/mL) | 3117 (840) | 5872 (1932) | 5968 (1639) |
| $C_{min}^{ss}$ (ng/mL) | 474.67 (163) | 870.42 (336) | 922.58 (321) |
| DFL (%) | 212.08 (52.29) | 218.06 (81.14) | 213.79 (50.53) |
| Swing | 5.95 (2.04) | 6.63 (3.61) | 5.94 (2.24) |
| $T_{max}^{ss}$ (h)$^a$ | 0.50 (0.25-3.00) | 0.50 (0.25-3.02) | 0.50 (0.25-8.02) |
| $t_{1/2}$ (h)$^c$ | 5.60 (1.35)$^b$ | 7.47 (2.89) | 5.74 (2.98)$^b$ |
| $K_{el}$ (1/h)$^c$ | 0.1308 (0.0317)$^b$ | 0.1026 (0.0292) | 0.1416 (0.0515)$^b$ |

$^a$Median (minimum-maximum).
$^b$N = 31
$^c$Days 5 to 7.

Both OC and APAP were rapidly absorbed under all conditions with no lag in plasma concentrations. Both OC and APAP levels were sufficiently high within 1 hour after administration of the ER formulation as a single dose and at steady-state. OC levels were sustained over the proposed 12 h dosing interval. Plasma APAP concentrations decreased to below 1,000 ng/mL between doses of the ER formulation, thus minimizing the chances of its accumulation and the possibility of hepatotoxicity. Total exposure to both OC and APAP from the ER formulation was equivalent to that of the commercially-available immediate release tablet.

Example 12

Clinical Evaluation of the Safety and Analgesic Efficacy of an Extended Release Formulation of Oxycodone and Acetaminophen for Acute Pain Pain relief for acute post-surgical pain requires immediate-release (IR) compounds acting within 1 hour of administration. These IR compounds, however, have a short half-life and require frequent administration; this is inconvenient to patients and leads to poor compliance. Such patients may benefit from an extended-release (ER) oral formulation of oxycodone hydrochloride (OC) and acetaminophen (APAP) that is designed to (1) provide the immediate-release of each drug to attain rapid therapeutic levels (within 1 hour of dosing) and (2) provide continuous release of each drug to maintain the plasma levels of each drug within therapeutic windows for sustained analgesia (up to 12 hours). Furthermore, combining analgesics with distinct mechanisms of action provides maximum efficacy while reducing the toxicity of each agent, as the amount of OC and APAP can remain within the lower, safer end of their therapeutic windows. This ER formulation may provide the advantages of both immediate and prolonged pain relief from two analgesic compounds, potentially offering greater convenience to patients and greater dosing compliance. Accordingly, a study may be conducted to demonstrate the efficacy of repeated doses of 15 mg OC/650 mg APAP versus placebo, and to determine the safety and tolerability of multiple oral doses of the OC/APAP formulation administered to subjects with acute postoperative, moderate to severe pain.

The study will be conducted in the following phases: 1) pre-treatment phase consisting of a) screening, b) surgery, and c) recovery/qualification periods; 2) double-blind phase consisting of a single dose period followed by a multiple-dose period which begins with the request of the 2nd dose of study medication, and; 3) a voluntary open-label extension phase.

The single dose period of the double-blind phase will evaluate the onset and duration of analgesia of a single dose of 15 mg OC/650 mg APAP (as two 7.5/325 tablets) versus placebo. The time from the initial dose of study medication to the onset of perceptible pain relief and to the onset of meaningful pain relief will be measured. The subject will provide additional pain assessments (e.g., pain intensity will be measured using the 11 point NPRS scale at regular intervals).

The multiple dose period of the double-blind phase will evaluate the analgesic effects of multiple doses of 15 mg OC/650 mg APAP versus placebo with subjects dosed regularly every 12 hours for 48 hours. The multiple dose period will begin upon administration of the second dose after the subject's request for additional pain relief. Pain relief and intensity will be among the data measured in this arm of the study.

After completion of study evaluations 48 hours after the 2nd dose of study medication, subjects will be encouraged to enter the open-label extension phase of the study. During this time they will be provided with doses of 15 mg OC/650 mg APAP to be taken Q12h until no longer needed, for up to 14 days. The open-label extension phase (starting 48 hours after the second dose) will evaluate the safety profile as determined by adverse events (AE) and evaluate subject satisfaction with analgesic effects.

Example 13

Clinical Evaluation of the Safety and Efficacy of an Extended Release Formulation of Oxycodone and Acetaminophen for Chronic Pain An open label safety study of doses of 15 mg OC/650 mg APAP administered at 12 hour intervals for up to 35 days in a patient population having pain associated with osteoarthritis (OA) of the knee or hip or chronic low back pain (CLBP) may be conducted. The primary objective of the study is to determine the safety and tolerability of doses of 15 mg OC/650 mg APAP for up to 35 days of use. Secondary objectives such as pain relief and changes in pain intensity will also be assessed.

Subjects enrolled in the study will be treated with 2 tablets of 7.5 mg OC/325 mg APAP every 12 hours (Q12h) for between 10 days and 35 days. Subjects will initially take 1 tablet of 7.5 mg OC/325 mg APAP under clinic supervision. Subjects will be observed for opioid tolerability symptoms. Subjects who experience opioid tolerability symptoms, or moderate to severe AEs, will be discontinued from the study. Subjects who do not experience opioid tolerability symptoms, or moderate to severe AEs, will be given a second tablet of 7.5 mg OC/325 mg APAP under clinic supervision. If subjects still do not experience opioid tolerability symptoms, or moderate to severe AEs, they will be sent home with supplies for dosing with 2 tablets of 7.5 mg OC/325 mg APAP Q12h for one week. If subjects do experience opioid tolerability symptoms, or moderate to severe AEs, they will be sent home with supplies for dosing with 1 tablet of 7.5 mg OC/325 mg APAP Q12h for one week.

Subjects that continue in the study beyond one week will continue to take 2 tablets Q12h for up to a total of 35 days, during which they will return to the clinic for subsequent assessments of safety and efficacy. After the Day 36 visit, subjects will be instructed to return to pre-study medication. Subjects whose pain subsides prior to the Day 36 visit, or who discontinue for other reasons will be instructed to return remaining study medication.

Example 14

Partial Areas Under the Curve for Oxycodone and Acetaminophen

Partial AUCs were calculated for a bilayer extended release tablet disclosed herein containing acetaminophen and oxycodone, and an immediate release acetaminophen and oxycodone tablet. Specifically, Partial AUCs were calculated for the acetaminophen and oxycodone tablets of (1) Treatment B of Example 10, (2) Treatment C of Example 9, and (3) Treatment D of Example 10. These results are summarized in Tables 43-46.

TABLE 43

Mean (SD) Parameter Estimates for Partial AUCs for Acetaminophen.

| Study | $AUC_{0-1.7\,h}$ (ng · h/mL) | $AUC_{1.7-48\,h}$ (ng · h/mL) | $AUC_{0-t}$ (ng · h/mL) |
| --- | --- | --- | --- |
| Treatment B (Ex. 10) | 6029 | 28435 | 32644 |
| Treatment C (Ex. 9) | 5854 | 25539 | 29741 |

TABLE 44

Additional Mean (SD) Parameter Estimates for Partial AUCs for Acetaminophen.

| Study | $AUC_{0-12\,h}$ (ng · h/mL) | $AUC_{1-12\,h}$ (ng · h/mL) | $AUC_{12-36\,h}$ (ng · h/mL) | $AUC_{8-12\,h}$ (ng · h/mL) | $AUC_{0-t}$ (ng · h/mL) |
| --- | --- | --- | --- | --- | --- |
| Treatment B (Ex. 10) | 25912 | 22615 | 7978 | 4401 | 32644 |
| Treatment C (Ex. 9) | 24102 | 20875 | 6854 | 3910 | 29741 |

TABLE 45

Percent of $AUC_{0-t}$ for Acetaminophen

| Study | $AUC_{0-12\,h}$ (dosing interval) | $AUC_{1-12\,h}$ ($T_{max}$ to end of dosing interval) | $AUC_{12-36\,h}$ (end of dosing interval to last concentration) | $AUC_{8-12\,h}$ |
| --- | --- | --- | --- | --- |
| Treatment B (Ex. 10) | 79% | 69% | 24% | 13% |
| Treatment C (Ex. 9) | 81% | 70% | 23% | 13% |

TABLE 46

Mean(SD) Parameter Estimates for Partial AUCs for Oxycodone.

| Study | $AUC_{0-2.8\,h}$ (ng · h/mL) | $AUC_{2.8-48\,h}$ (ng · h/mL) | $AUC_{0-t}$ (ng · h/mL) |
| --- | --- | --- | --- |
| Treatment B (Ex. 10) | 28.75 | 158.49 | 185.93 |
| Treatment C (Ex. 9) | 27.89 | 164.27 | 190.66 |

The bioequivalence determinations between two tablets of a pharmaceutical composition described herein, each containing 7.5 mg oxycodone and 325 mg acetaminophen and an immediate release tablet comprising 7.5 mg oxycodone and 325 mg acetaminophen can be found in Tables 47 and 48.

TABLE 47

Bioequivalence Determination for Acetaminophen

| Parameter | LSM Ratio | 90% CI Lower | 90% CI Upper |
| --- | --- | --- | --- |
| $Ln(AUC_{0-1.7\,h})$ | 101.97 | 82.90 | 125.43 |
| $Ln(AUC_{1.7-48\,h})$ | 91.15 | 80.58 | 103.11 |
| $Ln(AUC_{0-t})$ | 93.14 | 82.40 | 105.28 |

TABLE 48

Bioequivalence Determination for Oxycodone

| Parameter | LSM Ratio | 90% CI Lower | 90% CI Upper |
| --- | --- | --- | --- |
| $Ln(AUC_{0-2.8\,h})$ | 99.04 | 87.83 | 111.68 |
| $Ln(AUC_{2.8-48\,h})$ | 103.21 | 92.57 | 115.06 |
| $Ln(AUC_{0-t})$ | 102.19 | 92.34 | 113.09 |

Figure 29A:
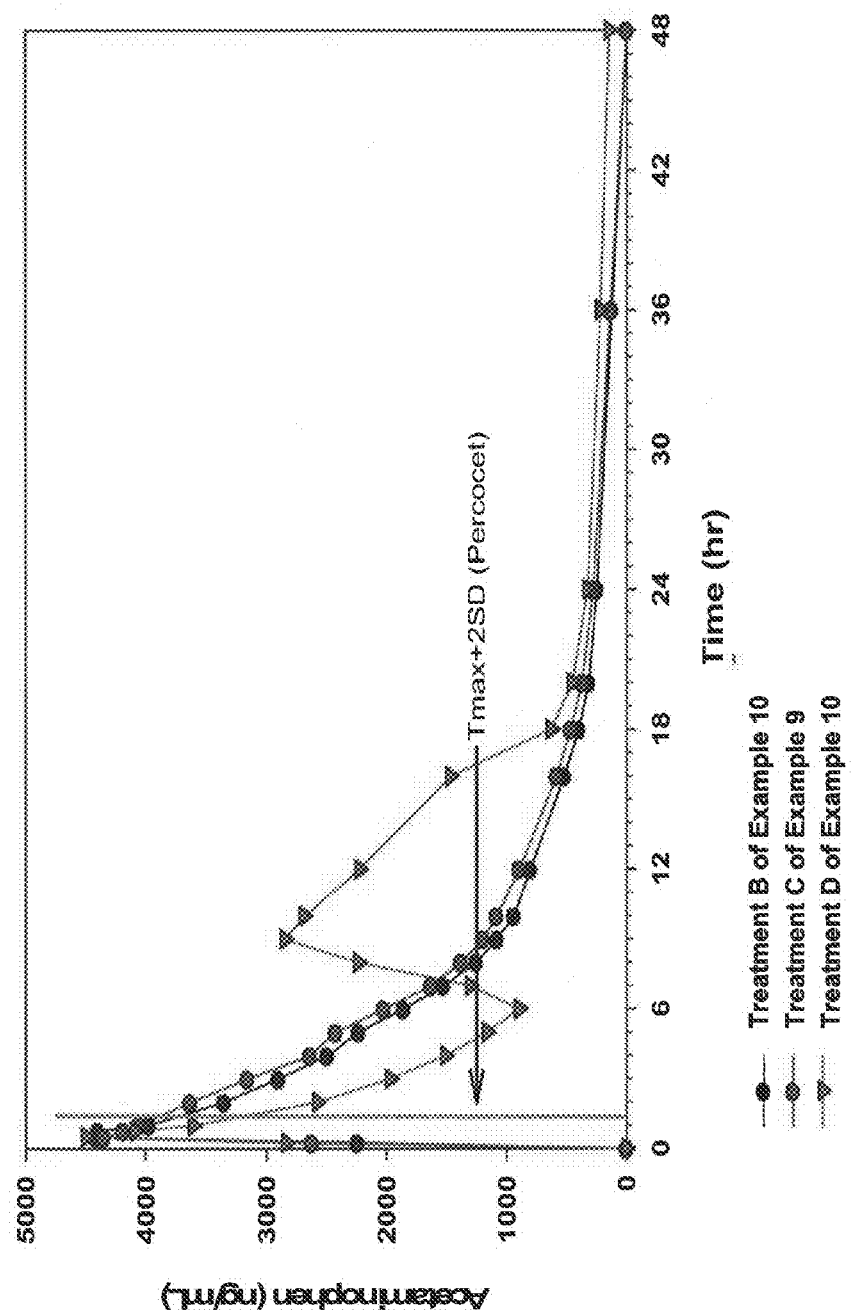
FIG. 29A presents the mean plasma concentrations and Partial AUCs of acetaminophen (e.g., $AUC_{0-1.7}h$ and AUC$_{1.7-48h}$) versus time by treatment: (1) Treatment B of Example 10, (2) Treatment C of Example 9, and (3) Treatment D of Example 10.
Figure 29B:
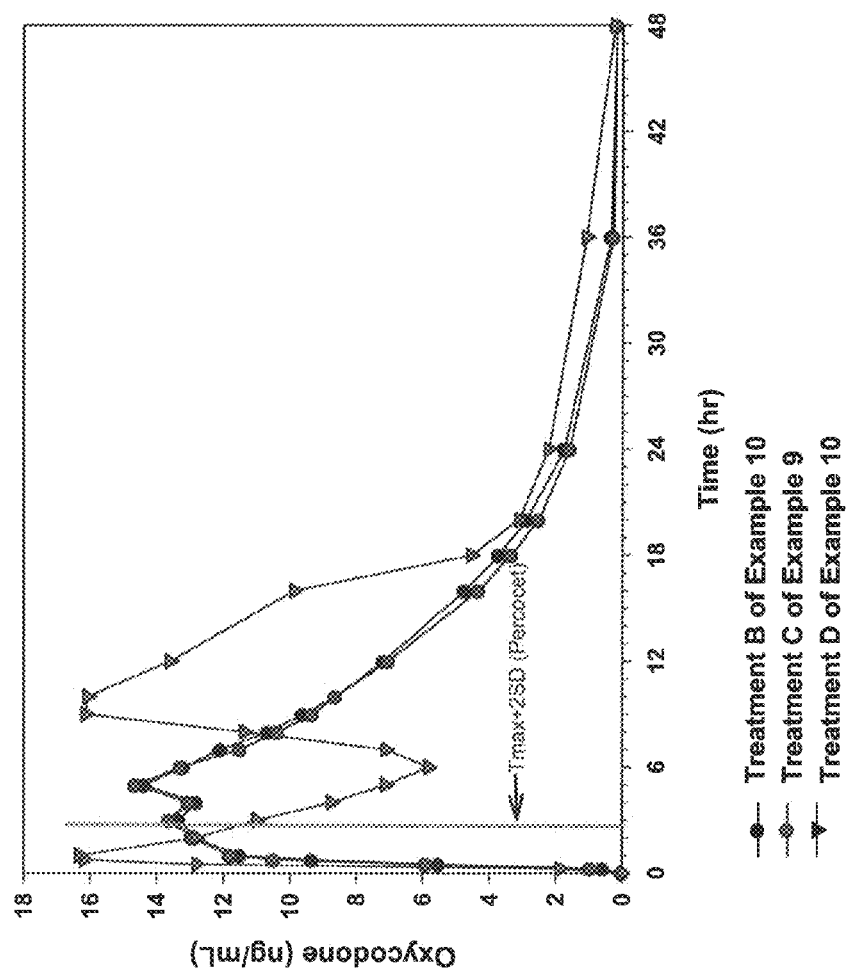
FIG. 29B presents the mean plasma concentrations and Partial AUCs of oxycodone (e.g., AUC$_{0-2.8}h$ and AUC$_{2.8-48h}$) versus time by treatment: (1) Treatment B of Example 10, (2) Treatment C of Example 9, and (3) Treatment D of Example 10.

The results demonstrate that the plasma concentrations of both oxycodone and acetaminophen rose rapidly with no lag time for a pharmaceutical composition of the present invention and an immediate release tablet comprising 7.5 mg oxycodone and 325 mg acetaminophen. See FIG. 29. Further, 30 minutes after administration of a dose of a pharmaceutical composition of the present invention (i.e., 2 tablets of 7.5 oxycodone/325 acetaminophen), oxycodone levels were within the therapeutic range (>5 ng/mL). Thus, an analgesic effect will be seen in opioid naïve patients. In addition, a pharmaceutical composition of the present invention was able to maintain oxycodone levels above 5 ng/mL for up to 12 hours after dosing, suggesting that the analgesic effect may extend to the next dosing cycle.

Concentrations of acetaminophen resulting from a dose of a pharmaceutical composition of the present invention (i.e., 2 tablets of 7.5 oxycodone/325 acetaminophen), decreased to less than 900 ng/mL (>17% of Cmax) by 12 hours after administration. This decreased concentration of acetaminophen at the end of the dosing cycle allows for sufficient acetaminophen or "APAP time off" between doses.

Oxycodone and acetaminophen levels from a pharmaceutical composition of the present invention (i.e., 2 tablets of 7.5 oxycodone/325 acetaminophen) declined at a similar rate to an immediate release tablet comprising 7.5 mg oxycodone and 325 mg acetaminophen, with a terminal elimination half-life of approximately 4 to 5 hours.

Example 15

Partial Areas Under the Curve for Oxycodone and Acetaminophen Administered with Food Partial AUCs were calculated for a bilayer extended release tablet disclosed herein containing acetaminophen and oxycodone, and an immediate release acetaminophen and oxycodone tablet. Specifically, Partial AUCs were calculated for the acetaminophen and oxycodone tablets of (1) Treatment A of Example 4, (2) Treatment A of Example 6 (one tablet), and (3) Treatment C of Example 4. These results are summarized in Tables 49-50.

TABLE 49

Mean (SD) Parameter Estimates for Partial AUCs for Acetaminophen.

| Study | $AUC_{0-3.2\,h}$ (ng · h/mL) | $AUC_{3.2-48\,h}$ (ng · h/mL) | $AUC_{0-t}$ (ng · h/mL) |
|---|---|---|---|
| Treatment A (Ex. 4) | 8042 | 23810 | 30245 |
| Treatment A (Ex. 6) (one tablet) | 9145 | 23319 | 31478 |

TABLE 50

Mean (SD) Parameter Estimates for Partial AUCs for Oxycodone.

| Study | $AUC_{0-4.3\,h}$ (ng · h/mL) | $AUC_{4.3-48\,h}$ (ng · h/mL) | $AUC_{0-t}$ (ng · h/mL) |
|---|---|---|---|
| Treatment A (Ex. 4) | 48.62 (15.99) | 152.57 (49.86) | 199.43 (59.47) |
| Treatment A (Ex. 6) (one tablet) | 53.29 (17.12) | 167.50 (51.83) | 219.20 (55.99) |

The bioequivalence determinations between the pharmaceutical composition described herein, containing 15 mg oxycodone and 650 mg acetaminophen and an immediate release product comprising 15 mg oxycodone and 650 mg acetaminophen can be found in Tables 51 and 52.

TABLE 51

Bioequivalence Determination for Acetaminophen

| Parameter | LSM Ratio | 90% CI Lower | 90% CI Upper |
|---|---|---|---|
| $Ln(AUC_{0-3.2\,h})$ | 114.46 | 96.21 | 136.16 |
| $Ln(AUC_{3.2-48\,h})$ | 94.62 | 83.31 | 107.47 |
| $Ln(AUC_{0-t})$ | 101.32 | 90.00 | 114.07 |

TABLE 52

Bioequivalence Determination for Oxycodone

| Parameter | LSM Ratio | 90% CI Lower | 90% CI Upper |
|---|---|---|---|
| $Ln(AUC_{0-4.3\,h})$ | 109.87 | 94.98 | 127.08 |
| $Ln(AUC_{4.3-48\,h})$ | 109.75 | 94.48 | 127.48 |
| $Ln(AUC_{0-t})$ | 110.53 | 97.39 | 125.44 |

Figure 30A:
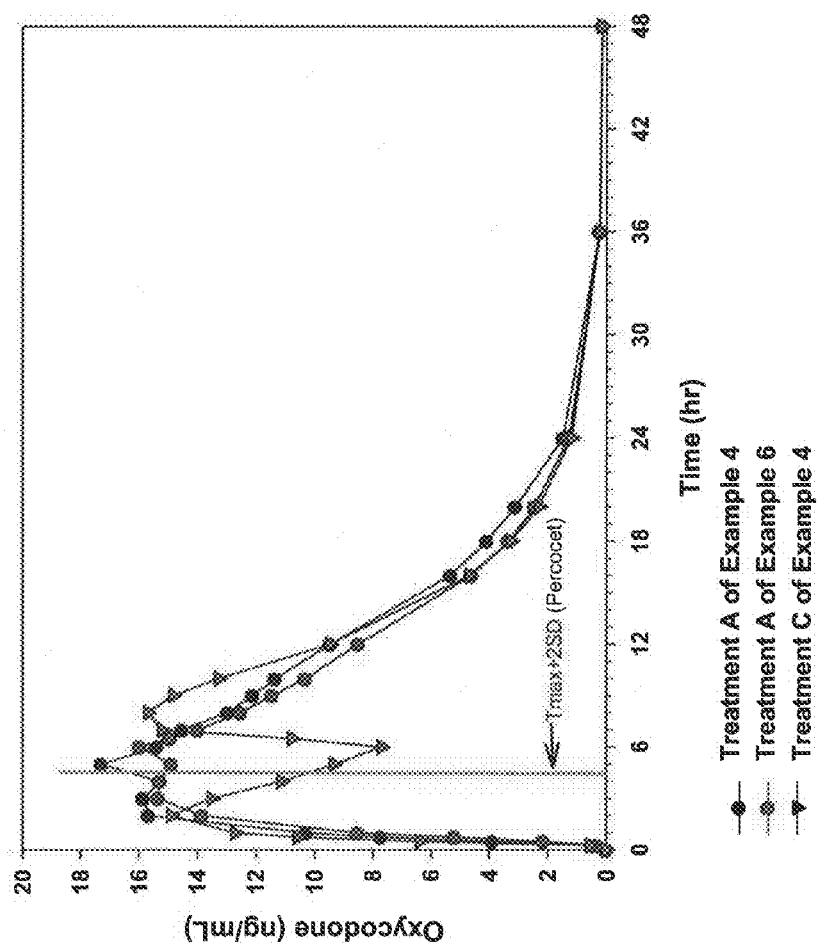
FIG. 30A presents the mean plasma concentrations and Partial AUCs of oxycodone versus time for Treatment A of Example 4, Treatment A of Example 6, and Treatment C of Example 4.
Figure 30B:
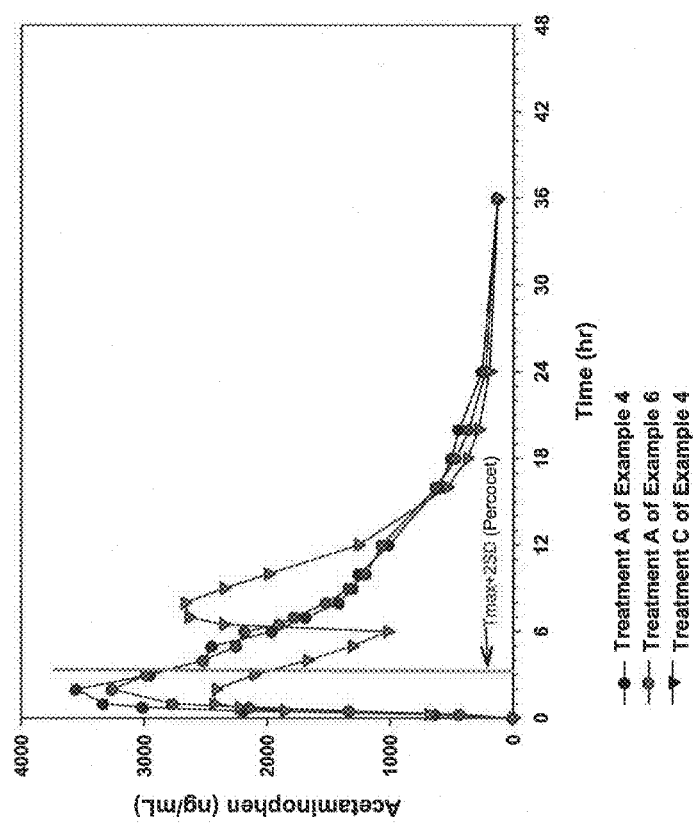
FIG. 30B presents the mean plasma concentrations and Partial AUCs of acetaminophen versus time for Treatment A of Example 4, Treatment A of Example 6, and Treatment C of Example 4.

Exposure to oxycodone and acetaminophen was comparable between Treatment A of Example 4 and Treatment A of Example 6 (one tablet). Thus, these results indicate that the release of oxycodone and acetaminophen is consistent across studies. Plasma concentration-time profiles are presented in FIGS. 30A and 30B.

The initial exposure to oxycodone ($AUC_{0-4.3}h$) was slightly outside the bioequivalence parameters established by the FDA (upper 90% CI 127%). The initial exposure to acetaminophen ($AUC_{0-3.2}h$) was outside of the FDA's bioequivalence parameters (upper 90% CI 136%).

The extended (sustained) exposure to oxycodone ($AUC_{4.3-48h}$) was slightly outside the FDA's limit for bioequivalence (upper 90% CI 127%). However, the extended exposure to acetaminophen ($AUC_{3.2-48h}$) and total exposure ($AUC_{0-t}$) for both oxycodone and acetaminophen was equivalent between studies.

Example 16

Mechanical Crushing into Powder Form

Drug abusers often tamper with extended release opioid-containing formulations by crushing the dosage form. This process generally serves several functions, including destroying the extended release properties of the dosage form and enabling the dosage form to be processed for unintended methods of administration, such as snorting or intravenous injection. Accordingly, comparative tamper resistance experiments were performed on a tablet dosage form of the pharmaceutical composition of the present invention containing 7.5 mg oxycodone HCl and 325 mg acetaminophen (see Chart 1) (the "product") and a commercially available immediate-release tablet containing 7.5 mg oxycodone/325 mg acetaminophen (the "comparator").

The product and comparator tablets were subjected to standard mechanical crushing by the following means: a hammer, a pill crusher, a mortar and pestle, a knife, two spoons, a utility knife, a blender, a coffee mill, and a coffee grinder. The success or failure of the particle size reduction was then visually assessed. In some cases, a sieving analysis was also utilized to quantitatively measure if significant particle size reduction occurred. Generally, drug abusers desire to crush pharmaceutical formulations into a fine powder, as this form is convenient for processing the tablet into a snortable or injectable form.

The results demonstrated that in most instances, the comparator was easily broken down into smaller pieces by each of the mechanical means listed above. Accordingly, in most instances, the comparator offered little tamper resistance as it could easily be mechanically crushed into a suitable powder. In contrast, the physical properties of the product tablet prevented the product tablet from being crushed into a fine powder. Indeed, in relation to the comparator, the product tablet was more difficult to break down using the methods listed above. Specifically, all of the mechanical methods described above were ineffective at producing a suitable powder from the product tablets except grinding in a mortar and pestle. Consequently, the product tablets offer improved protection from the mechanical crushing methods employed by drug abusers.

Example 17

Abuse Resistance Properties of Product Powders Produced by Grinding Using a Mortar and Pestle An in vitro dissolution test with human abuse liability ("HAL") predictions was conducted to determine the cumulative amount of drug released from intact and crushed tablets of the pharmaceutical compositions disclosed herein and a commercially-available immediate release oxycodone and acetaminophen tablet.

Figure 31:
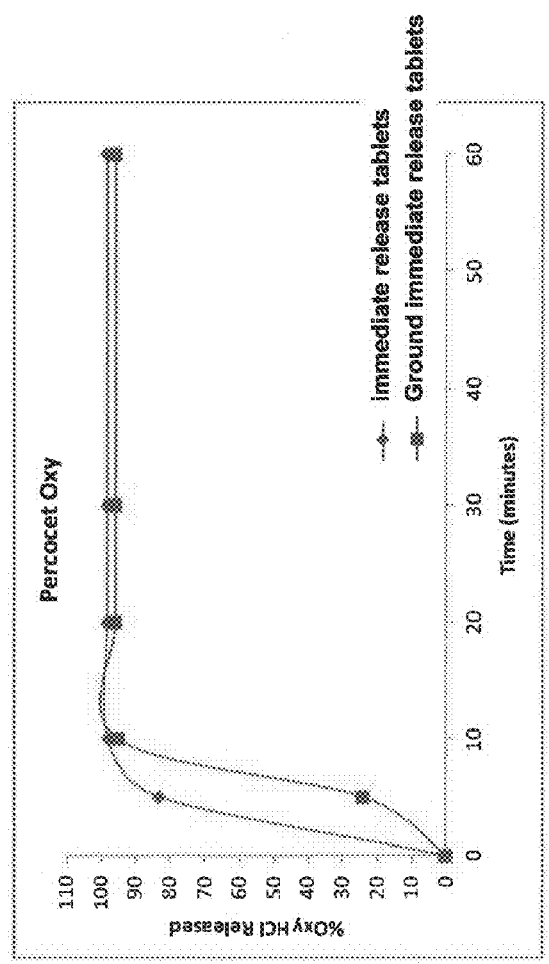
FIG. 31 presents oxycodone dissolution data from crushed and intact immediate release tablets containing 7.5 mg oxycodone and 325 mg acetaminophen.

Comparator tablets (the "comparator") containing a total of 7.5 mg of oxycodone HCl and a total of 325 mg acetaminophen were obtained. Six comparator tablets were ground with a mortar and pestle and placed into capsules, while six tablets were used as is (i.e., kept intact, but placed into capsules). Dissolution profiles for the intact and crushed tablets were determined in a USP type II apparatus. Six intact tablets and six crushed tablets were weighed, placed in a sinker, and dropped into an equilibrated dissolution bath vessel containing 900 mL of (helium sparged) 0.1 N HCl heated to 37° C.±0.5° C. The mixture was stirred at 100±4 rpm, and the temperature was maintained at 37° C.±0.5° C. for 12 hr. The bath vessel was covered with a low evaporation vessel cover. Samples (5 mL) were removed at 5 min, 10 min, 20 min, 30 min, and 60 min. Each sample was filtered through a 0.45 μm filter and analyzed by HPLC using standard procedures. The release profile of oxycodone HCl from intact and crushed comparator is shown in FIG. 31.

Figure 32A:
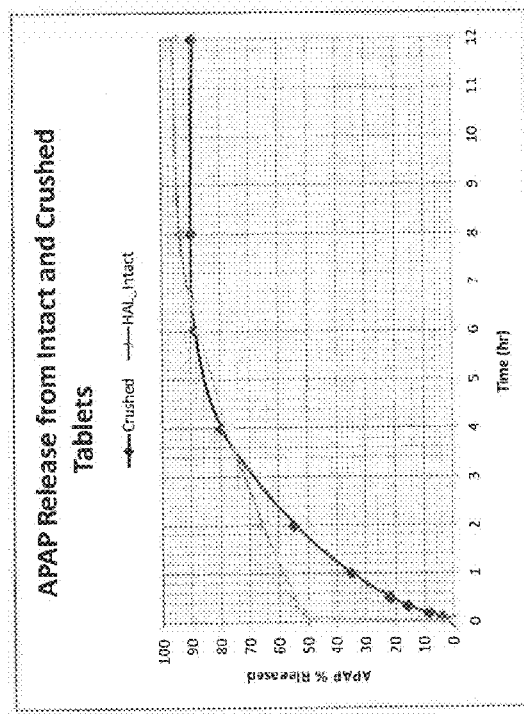
FIGS. 32A and 32B present acetaminophen dissolution data from crushed and intact pharmaceutical formulations described herein containing a total of 7.5 mg oxycodone and a total of 325 mg acetaminophen per tablet.
Figure 32B:
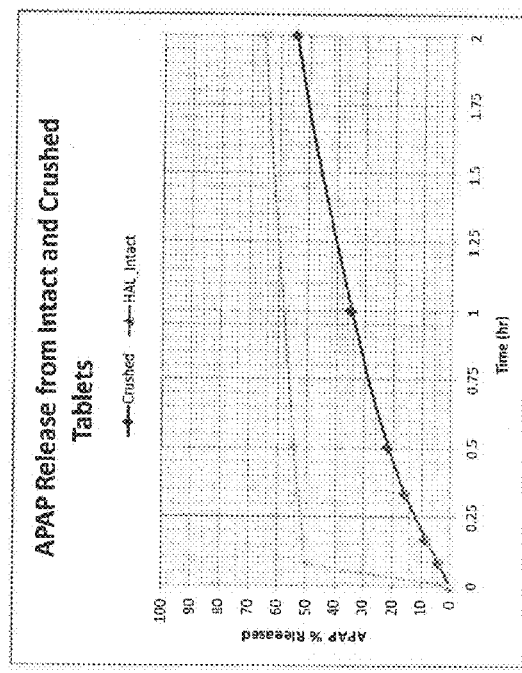
Figure 33A:
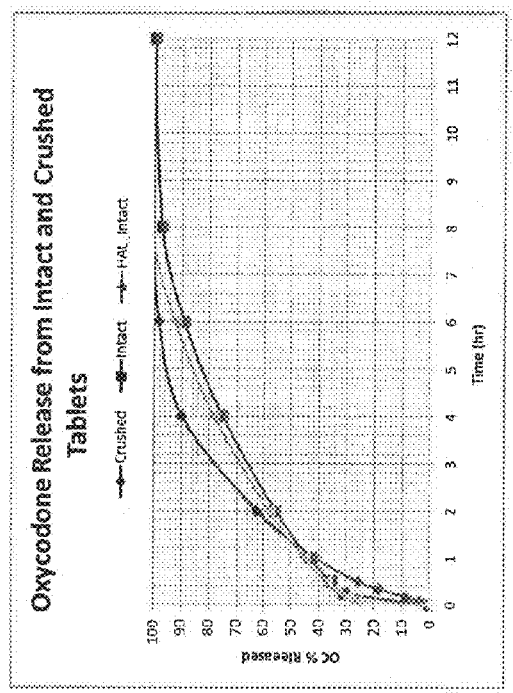
FIGS. 33A and 33B present oxycodone HCl dissolution data from crushed and intact pharmaceutical formulations described herein containing a total of 7.5 mg oxycodone and a total of 325 mg acetaminophen per tablet.
Figure 33B:
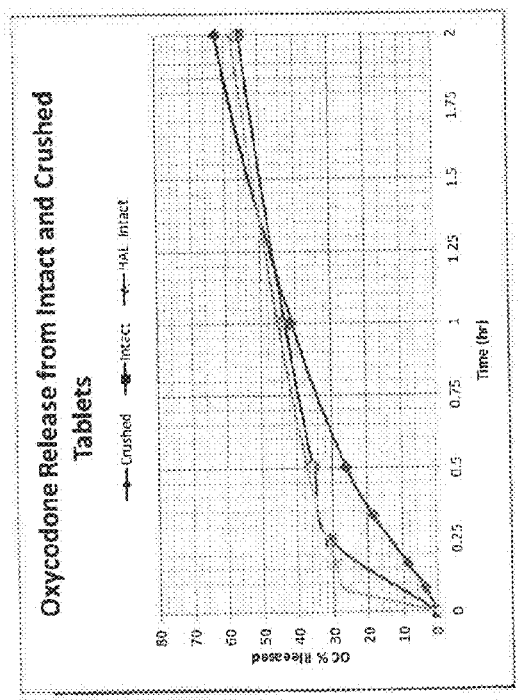

Bilayer formulations described herein were prepared, each containing a total of 7.5 mg of oxycodone HCl, a total of 325 mg of acetaminophen, and an extended release polymer. Six product tablets (as defined in Example 16) were ground with a mortar and pestle and placed into capsules, while twelve product tablets were used as is. The same dissolution method as described for the intact and crushed comparator above was used to obtain release profiles for intact and crushed product tablets. However, six of the intact product tablets (labeled as "Intact") were sampled (5 mL) at 0.25 hr, 0.5 hr, 1 hr, 2 hr, 4 hr, 6 hr, 8 hr, and 12 hr. The release profiles of acetaminophen and oxycodone HCl from the intact and crushed product tablets are shown in FIGS. 32 and 33, respectively. In these figures, "intact" refers to the intact product tablets sampled at 0.25 hr, 0.5 hr, 1 hr, 2 hr, 4 hr, 6 hr, 8 hr, and 12 hr. "HAL_Intact" refers to the intact product tablets sampled at the same time intervals as the crushed tablets, namely, 5 min, 10 min, 20 min, 30 min, 1 hr, 2 hr, 4 hr, 6 hr, 8 hr, 12 hr.

These results show that for release of oxycodone HCl from the comparator tablets, there is no substantial difference in the release profiles for crushed and intact tablets for abuse purposes. In each case, almost all of the oxycodone HCl was released in as little as ten minutes. In stark contrast, there are substantial differences in the release profiles for crushed and intact product tablets. The intact product tablets surprisingly exhibited a higher release rate of both active ingredients than the crushed product tablets in the first hour. This suggests that upon grinding the product tablets, the active ingredients in the immediate release portion are incorporated into the extended release portion, and the product tablet loses its immediate release characteristics. This feature may effectively negate a drug abuser's purpose for crushing the product tablet in the first place—to obtain an early onset of analgesia.

Predicted pharmacokinetic parameters were obtained for these in vitro release profiles for the crushed and intact products and comparator tablets by using in vitro in vivo correlation ("IVIVC") technique. These results, which are summarized in Table 53, demonstrate that the abuse quotients for the crushed and intact comparator tablets are orders of magnitude higher than the abuse quotients for the crushed and intact product tablets. This is consistent with the experimentally determined pharmacokinetic parameters from Example 10.

TABLE 53

Predicted pharmacokinetic parameters and abuse quotient for intact and crushed product and comparator tablets.

| Product | $C_{max}$ (ng/mL) | $T_{max}$ (hr) | Abuse Quotient (ng/mL · hr) |
|---|---|---|---|
| Predicted | | | |
| Comparator (intact) | 32.5 | 0.16 | 203.1 |
| Comparator (crushed) | 30.8 | 0.17 | 181.2 |
| Product (intact) | 17.5 | 6 | 2.9 |
| Product (crushed) | 20.6 | 4 | 5.2 |
| Experimental - see Example 10 | | | |
| Comparator (intact) | 41.6 | 0.7 | 59.4 |
| Product (intact) | 16.4 | 3.2 | 5.1 |

Example 18

Preconditioning the Tablets by Crisping

Drug abusers often precondition the tablet by a process known as crisping. This procedure is intended to remove some of the tablet fillers, making the drug easier to crush and insufflate or inject. Accordingly, an experiment was performed to determine a drug abuser's ability to crisp a tablet dosage form of the pharmaceutical composition of the present invention containing 7.5 mg oxycodone HCl and 325 mg acetaminophen (see Chart 1) (the "product") as compared to a commercially available immediate-release tablet containing 7.5 mg oxycodone/325 mg acetaminophen (the "comparator").

First, the product and comparator tablet were crushed into a powder and placed in a spoon. The spoon was then heated from underneath with an open flame. Once the powder began to caramelize and smoke, the heat was removed and the powder was mixed using a metal spatula. The spoon was again heated until the powder began to caramelize further. The heat was once again and removed, and the powder was allowed to cool. The resulting powders were then removed from the spoon and placed in a mortar and pestle for subsequent crushing. The comparator tablet resulted in a powder that could be easily crushed into a fine powder. Unlike the comparator tablet, the product tablet resulted in a sticky composition, rendering the product tablet unsuitable for grinding into a fine powder after the crisping process.

Example 19

Separation Studies

To determine the ease at which the immediate release (IR) and extended release (ER) layers of a bilayer form of the pharmaceutical composition disclosed herein could be tampered with, several attempts were made at separating the immediate release (IR) and extended release (ER) layers of the product (as defined in Example 18). Initially, a tablet dosage form of the pharmaceutical composition of the present invention was positioned with the inscribed side facing up and cut completely through vertically. Upon slicing the tablet, observations revealed no visual distinction between the IR and ER layers. The tablet was then re-oriented and sliced from several additional angles. However, no demarcation line was observed between the IR and ER layers. Consequently, a drug abuser could not visually distinguish the IR and ER layers of the pharmaceutical composition disclosed herein by simply cutting the dosage form.

Example 20

Injectability Studies

An injectability study was conducted to determine the extent to which crushed and dissolved tablets of the pharmaceutical composition disclosed herein containing 7.5 mg oxycodone/325 mg acetaminophen (the "product") could be drawn into a syringe for intravenous administration as compared to a commercially available immediate-release tablet containing 7.5 mg oxycodone/325 mg acetaminophen that had been crushed and dissolved (the "comparator"). Intravenous administration is a common practice used by drug abusers as a means to potentiate their drugs by administering the drug as one large bolus instead of a steady release over time. Two measurable entities were evaluated: the amount of useable fluid that was harvested through the process and the concentration of oxycodone in these aliquots. This study employed a standard 1 mL insulin syringe equipped with 22-, 26-, and 30-gauge needles, which are the typical sizes of needles used by intravenous drug users.

An intact product and comparator tablet were each ground in a mortar and pestle to yield a fine powder. The powder was then placed onto a tablespoon secured to a laboratory ring stand. 3 mL of deionized water was added to the spoon and was mixed into a slurry in an attempt to dissolve the active ingredient. To enhance solubility of the drug, a butane lighter was used to uniformly heat the bottom of the spoon. When the solution began to boil slightly, heat was removed and any liquid lost was replenished. A traditional insulin syringe (1 mL) with a makeshift cotton ball filter and the various gauge needles was used to extract the resulting liquid into the syringe.

Three types of cotton filters were evaluated for use in this procedure. The first filter was a small cotton plug placed between the needle hub and barrel of the syringe. This filter clogged for all three gauges when attempts were made to draw liquid into the syringe. The second filter was formed by inserting the tip of the syringe needle into the end of a Q-tip. This second filter also prevented an appreciable amount of fluid to be drawn into the syringe. The third filter was a small piece of cotton attached to the end of the needle. The third filter was chosen for further study because it was the only filter evaluated in which liquid could be drawn into the syringe for all three gauges without clogging the filter. The drawn liquid was collected, measured and quantified by LC/MS/MS analysis.

When water was mixed with the ground product tablet, the solid did not completely dissolve upon heating. Instead, a pasty material was produced that did not readily disperse when mixed. The product required almost constant mixing of the crushed powder and water with constant heating to produce a removable liquid. It was difficult to generate a homogeneous mixture of liquid that could be drawn into a syringe because the combined volume of the crushed product tablet and the 3 mL of water essentially filled the spoon to capacity. Additionally, with heating, it was necessary to replenish the evaporated water to maintain a constant slurry level in the spoon. Liquid samples were drawn from the bottom of the spoon with a 1 mL syringe with the cotton plug on the tip. This study demonstrated that only about 1 mL of liquid could consistently be drawn into the syringe, independent of needle size. The resulting liquid in the syringe was murky and not transparent due to particulate matter.

In contrast, a large portion of the comparator readily dissolved when mixed and heated in the tablespoon. The resulting liquid in the syringe therefore contained much less particulate matter than the liquid resulting from the product tablet.

These results indicate that injection is not a preferred form of drug diversion for the product tablets. When adding water to the ground tablets, the user may recover only a small portion of that liquid for use in a syringe. The product tablet tended to produce a semi-solid paste that interfered with liquid recovery through the syringe. The overall results indicate a recovery of less than 20% of the oxycodone in the product tablet.

Example 21

Snorting Studies

Another method of tampering and diversion is to grind a tablet into a fine powder and insufflate (snort) the powder. The inhaled powder is deposited inside the nasal passage, and the oxycodone is absorbed through the mucous membranes of the nasal passage. In order for the procedure to work efficiently, the powder must deposit as a thin layer onto the nasal tissue in the sinus cavity. A study was performed to estimate the effectiveness of this process using the pharmaceutical composition disclosed herein containing 7.5 mg oxycodone/325 mg acetaminophen (the "product") and a commercially available immediate-release tablet containing 7.5 mg oxycodone/325 mg acetaminophen (the "comparator").

Product tablet and a comparator tablet were ground in a mortar and pestle. 1 mL of water was added to each ground tablet, and the resulting combination was mixed in an attempt to produce a thin slurry, which mimics the interface between the nasal passage and the absorptive tissue. The product tablet formed a paste that tended to clump. The comparator produced a more fluid consistency. Consequently, the comparator produced a more effective coating for absorption of insufflated oxycodone in the nasal cavity than the product disclosed herein.

Example 22

Dose Dumping Studies

Dose dumping is the process of releasing the active ingredient(s) of an extended release pharmaceutical formulation in a short period of time in a manner in which the entire dosage, or a significant portion of the dosage, becomes available for absorption in the body. This is often achieved by ingesting tablets along with alcoholic beverages to enhance drug delivery. The alcohol serves as a means to act on either the coating of a tablet to help release the active ingredients or to promote greater absorption within the body. This method is employed by drug abusers as an attempt to potentiate analgesic drugs. Release of elevated quantities of drug can lead to increased euphoric effects but can also cause adverse effects, some of which may be fatal.

Two dissolution experiments were performed in a dose dumping study. The dissolutions were designed to examine the differences between intact pharmaceutical compositions disclosed herein containing 7.5 mg oxycodone/325 mg acetaminophen (the "product") and a commercially available immediate-release tablet containing 7.5 mg oxycodone/325 mg acetaminophen (the "comparator") when exposed to simulated gastric fluid dissolution media ("SGF"). The first dissolution was performed in 75 mL of SGF in the absence of vodka. The second dissolution was performed in 75 mL of a 50:50 mixture of SGF and 80-proof vodka. This was designed to measure the extent that the product and comparator may be abused by the simultaneous intake of alcohol. Both dissolutions were performed at room temperature and were mixed on a stir plate. Aliquots were removed at 0.25, 0.50, 1, 2 and 4 hours for quantification by LC/MS/MS, a summary of which is contained in Table 54 below.

TABLE 54

Mean percent recovery of oxycodone in (i) simulated gastrointestinal fluid and (ii) a solution containing 50% simulated gastric fluid and 50% 80-proof vodka.

| Fluid | Intact Tablet | 0.25 hr | 0.5 hr | 1 hr | 2 hr | 4 hr |
| --- | --- | --- | --- | --- | --- | --- |
| SGF | Product | 15% | 30% | 43% | 57% | 80% |
| SGF | Comparator | 104% | 102% | 105% | 102% | 100% |
| SGF:EtOH | Product | 12% | 23% | 35% | 46% | 62% |
| SGF:EtOH | Comparator | 101% | 101% | 103% | 100% | 102% |

At the end of the four hour dissolution, the product tablets were still visible but had lost their outer coating in SGF both in the presence and absence of vodka. Addition of ethanol to the SGF produced a slight decrease in the dissolution rate of the product tablet. Comparator tablets were dissolved in SGF both in the presence and absence of vodka after five minutes. Consequently, the product tablets were resistant to dose dumping when compared to the comparator tablets.

Example 23

Clinical Evaluation of the Relative Abuse Potential of an Extended Release Formulation of Oxycodone and Acetaminophen A study may be performed to assess the relative abuse potential of a bilayer, extended-release oral formulation disclosed herein containing 7.5 mg oxycodone/325 mg acetaminophen (see Chart One) versus an immediate release oxycodone HCl/acetaminophen tablet in non-dependent, recreational opioid users. The study will consist of a screening period, and in-clinic period, and a follow-up period.

The study will consist of seven treatment periods, each of which will involve a single treatment of one of the study medications followed by a wash-out period. Tests will be conducted to ensure that the subjects are not physically dependent on opioids, and that they can discriminate between the effects oxycodone versus the placebo. Upon completion, the study medications will be randomly administered as a single oral dose to each subject and consist of the following:

Group A: two tablets disclosed herein containing 7.5 mg oxycodone HCl and 325 mg acetaminophen each plus two placebo tablets disclosed herein plus four placebo immediate release capsules.

Group B: four tablets disclosed herein containing 7.5 mg oxycodone HCl and 325 mg acetaminophen each plus four placebo immediate release capsules.

Group C: two immediate release capsules containing 7.5 mg oxycodone HCl and 325 mg acetaminophen each plus two placebo immediate release capsules plus four placebo tablets disclosed herein.

Group D: four immediate release capsules containing 7.5 mg oxycodone HCl and 325 mg acetaminophen each plus four placebo tablets disclosed herein.

Group E: two crushed tablets disclosed herein containing 7.5 mg oxycodone HCl and 325 mg acetaminophen each placed in four capsules plus four placebo tablets disclosed herein.

Group F: two crushed immediate release tablets containing 7.5 mg oxycodone HCl and 325 mg acetaminophen each placed in two capsules plus two placebo immediate release capsules.

Group G: four placebo tablets disclosed herein plus four placebo immediate release capsules.

Subjects will receive seven treatments according to their treatment sequence, and doses will be separated.

Example 24

Varying Polyox Grades Comprising 25% by Weight of the Extended Release Portion of Bilayer Formulations Single layer tablet formulations containing only the extended release portion were prepared, each tablet containing a total of 9 mg of oxycodone HCl and a total of 250 mg of acetaminophen. Since these tablets contained only the extended release portion, they contained 50% of the total acetaminophen for the bilayer tablet and 60% of the total oxycodone HCl for the bilayer tablet. In a first formulation, POLYOX® 205 was employed as the extended release component in an amount of 25% by weight of the ER portion, and therefore, the tablet weight. In a second formulation, POLYOX® 1105 was employed as the extended release component in an amount of 25% by weight of the tablet of ER portion. In a third formulation, POLYOX® N-60K was employed as the extended release component in an amount of 25% by weight of the tablet or ER portion.

Dissolution profiles for the three above-described compositions were determined in USP Type II apparatus. Six tablets of each composition were weighed, placed in a sinker, and dropped into an equilibrated dissolution bath vessel containing 900 mL of (helium sparged) 0.1 N HCl heated to 37° C.±0.5° C. The mixture was stirred at 150±6 rpm, and the temperature was maintained at 37° C.±0.5° C. through 12 hr. The bath vessel was covered with a low evaporation vessel cover. Samples (5 mL) were removed at 0.25 hr, 0.5 hr, 1 hr, 2 hr, 4 hr, 6, hr, 8 hr, and 12 hr. The final time point for the Polyox 205 was 17 hrs; the final time point for the Polyox 1105 was 15 hrs; and the final time point for the Polyox N60k was 18 hrs and 40 minutes. Each sample was filtered through a 0.45 µm filter and analyzed by HPLC using standard procedures.

Figure 34:
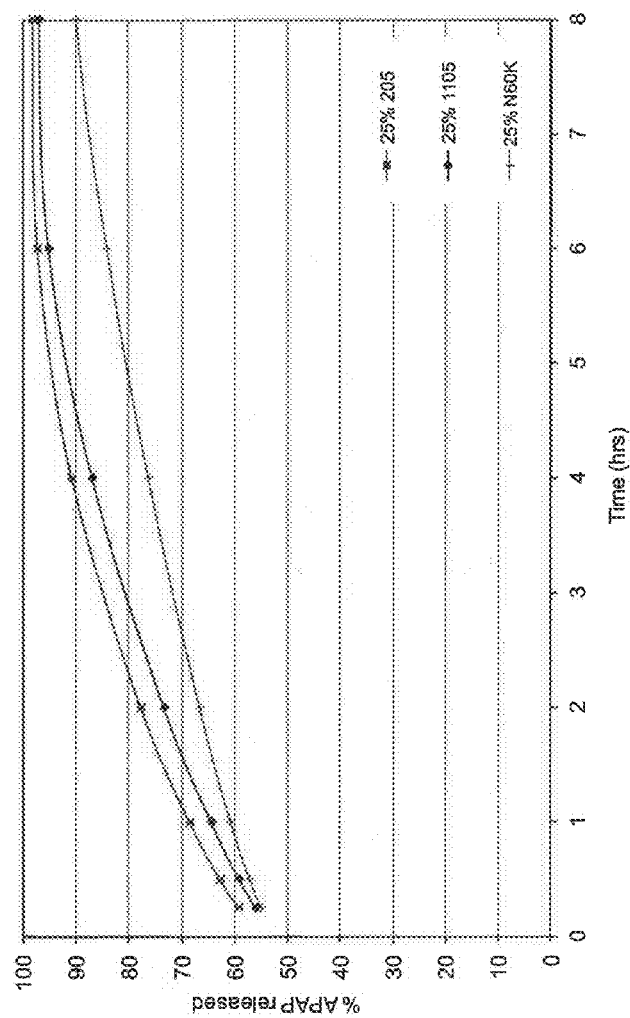
FIG. 34 presents acetaminophen dissolution data for three pharmaceutical formulations described herein. The dissolution data represents an extended release tablet with the immediate release data theoretically added. For each formulation, the tablet contained a total of 9 mg oxycodone HCl and a total of 250 mg acetaminophen. The three pharmaceutical formulations contained 25% by weight POLYOX® 205, 1105, and N-60K, respectively.
Figure 35:
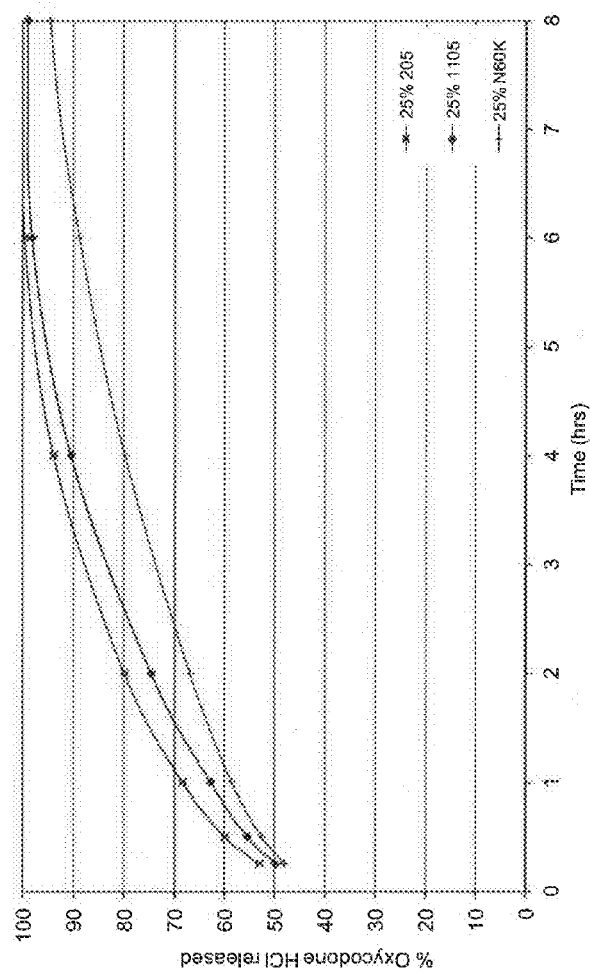
FIG. 35 presents oxycodone HCl dissolution data for the three pharmaceutical formulations described in FIG. 34.

The cumulative release profiles of acetaminophen and oxycodone from these compositions are shown in FIGS. 34 and 35, respectively. This data represents dissolution for the extended release portion with the immediate release data theoretically added. These figures demonstrate that as the average molecular weight of the POLYOX® extended release component increases, the rate of dissolution at each time point decreases. For example, the formulations containing POLYOX® 205, 1105, and N-60K had released about 59%, about 56%, and about 55% acetaminophen after 15 minutes, respectively; about 63%, about 59%, and about 57% acetaminophen after 30 minutes, respectively; about 69%, about 64%, and about 61% acetaminophen after 1 hr, respectively; about 78%, about 73%, and about 67% acetaminophen after 2 hr, respectively; about 91%, about 87%, and about 76% acetaminophen after 4 hr, respectively; about 97%, about 95%, and about 84% acetaminophen after 6 hr, respectively; and about 98%, about 97%, and about 90% acetaminophen after 8 hr, respectively.

The same general trend of a decreased release rate with a higher molecular weight POLYOX® grade was also observed for the oxycodone. For example, the formulations containing POLYOX® 205, 1105, and N-60K had released about 53%, about 50%, and about 48% oxycodone after 15 minutes, respectively; about 60%, about 56%, and about 53% oxycodone after 30 minutes, respectively; about 68%, about 63%, and about 59% oxycodone after 1 hr, respectively; about 80%, about 75%, and about 67% oxycodone after 2 hr, respectively; about 94%, about 91%, and about 80% oxycodone after 4 hr, respectively; about 100%, about 98%, and about 89% oxycodone after 6 hr, respectively; and about 100%, about 99%, and about 95% oxycodone after 8 hr, respectively.

Example 25

Varying Polyox Grades Comprising 45% by Weight of the Extended Release Portion of Bilayer Formulations Single layer formulations containing only the extended release portion described herein were prepared, each tablet containing a total of 9 mg of oxycodone HCl and a total of 250 mg of acetaminophen. Since these tablets contained only the extended release portion, they contained 50% of the total acetaminophen for a bilayer tablet and 60% of the total oxycodone HCl for a bilayer tablet. In a first formulation, POLYOX® 205 was employed as the extended release component in an amount of 45% by weight of the tablet or ER portion. In a second formulation, POLYOX® 1105 was employed as the extended release component in an amount of 45% by weight of the tablet or ER portion. In a third formulation, POLYOX® N-60K was employed as the extended release component in an amount of 45% by weight of the tablet or ER portion. The other excipients in the extended release portion were microcrystalline cellulose, spress B825, citric acid anhydrous, EDTA, hydroxypropyl cellulose, silicon dioxide, and magnesium stearate.

Dissolution profiles for the three above-described formulations were determined in USP Type II apparatus. Six tablets of each formulation were weighed, placed in a sinker, and dropped into an equilibrated dissolution bath vessel containing 900 mL of (helium sparged) 0.1 N HCl heated to 37° C.±0.5° C. The mixture was stirred at 150±6 rpm, and the temperature was maintained at 37° C.±0.5° C. through 12 hr. The bath vessel was covered with a low evaporation vessel cover. Samples (5 mL) were removed at 0.25 hr, 0.5 hr, 1 hr, 2 hr, 4 hr, 6, hr, 8 hr, and 12 hr. The final time point for the Polyox 205 was 17 hours; the final time point for Polyox 1105 was 17.5 hours; and the final time point for Polyox N60k was 23.5 hours. Each sample was filtered through a 0.45 µm filter and analyzed by HPLC using standard procedures.

Figure 36:
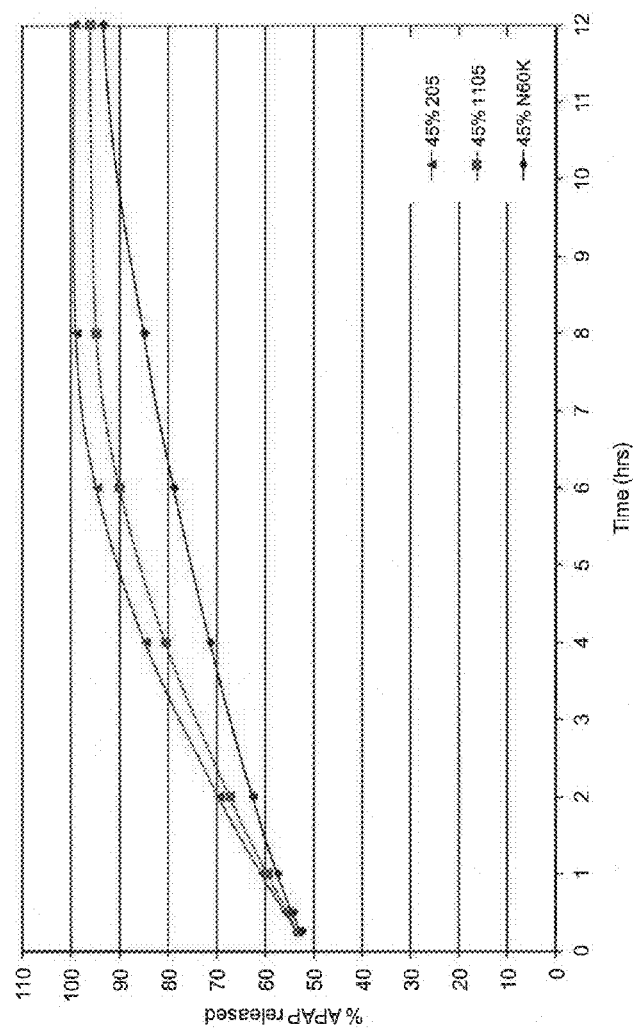
FIG. 36 presents acetaminophen dissolution data for three pharmaceutical formulations described herein. The dissolution data represents an extended release tablet with the immediate release data theoretically added. For each formulation, the tablet contained a total of 9 mg oxycodone HCl and a total of 250 mg acetaminophen. The three pharmaceutical formulations contained 45% by weight POLYOX® 205, 1105, and N-60K, respectively.
Figure 37:
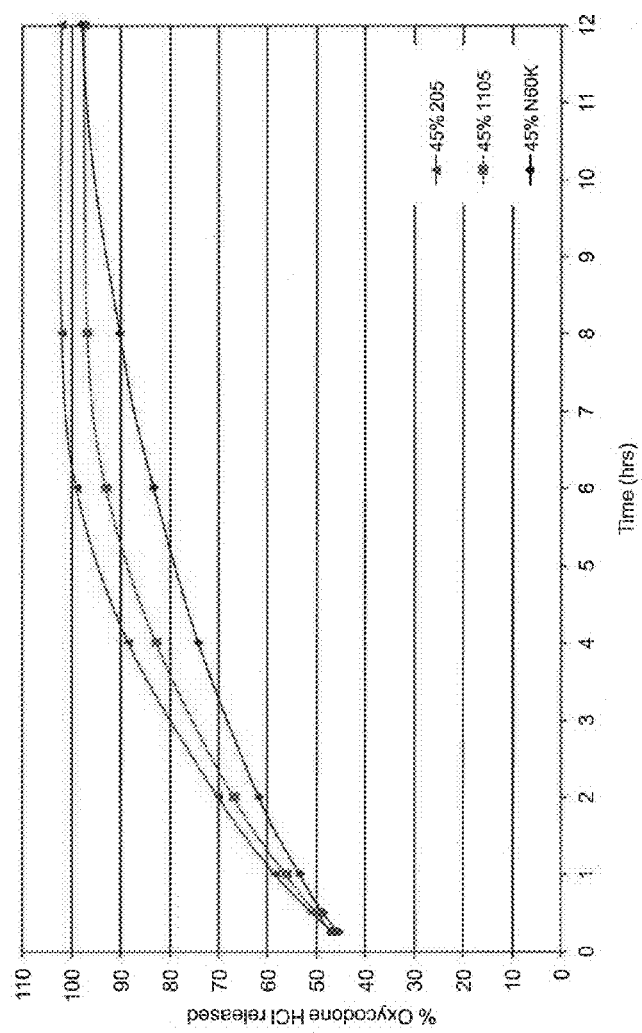
FIG. 37 presents oxycodone HCl dissolution data for the three pharmaceutical formulations described in FIG. 36.

The cumulative release profiles of acetaminophen and oxycodone from these compositions are shown in FIGS. 36 and 37, respectively. This data represents dissolution for the extended release portion with the immediate release data theoretically added. Consistent with the results of Example 24, the rate of dissolution at each time point decreases as the molecular weight of POLYOX® increases. For example, the formulations containing POLYOX® 205, 1105, and N-60K had released about 53%, about 53%, and about 53% acetaminophen after 15 minutes, respectively; about 56%, about 55%, and about 54% acetaminophen after 30 minutes, respectively; about 61%, about 60%, and about 57% acetaminophen after 1 hr, respectively; about 70%, about 67%, and about 63% acetaminophen after 2 hr, respectively; about 85%, about 81%, and about 71% acetaminophen after 4 hr, respectively; about 95%, about 90%, and about 79% acetaminophen after 6 hr, respectively; about 99%, about 95%, and about 85% acetaminophen after 8 hr, respectively; and about 99%, about 96% and about 93% acetaminophen after 12 hr.

The formulations containing POLYOX® 205, 1105, and N-60K also released about 47%, about 47%, and about 46% oxycodone after 15 minutes, respectively; about 51%, about 50%, and about 49% after 30 minutes, respectively; about 59%, about 56%, and about 53% oxycodone after 1 hr, respectively; about 70%, about 67%, and about 62% oxycodone after 2 hr, respectively; about 88%, about 83%, and about 74% oxycodone after 4 hr, respectively; about 99%, about 93%, and about 83% oxycodone after 6 hr, respectively; and about 100%, about 97%, and about 90% oxycodone after 8 hr, respectively.

Example 26

Varying the Concentrations of a Specific Polyox Grade in the Extended Release Portion of Bilayer Formulations The data from Examples 24 and 25 indicate that an increase in the amount of POLYOX® in the pharmaceutical composition retards the release of oxycodone and acetaminophen from the pharmaceutical composition. To confirm this observation, single layer extended release formulations described herein were prepared, each containing a total of 9 mg of oxycodone HCl and a total of 250 mg of acetaminophen. Since these tablets contained only the extended release portion, they contained 50% of the total acetaminophen for the bilayer tablet and 60% of the total oxycodone for the bilayer tablet. In a first formulation, POLYOX® 1105 was employed as the extended release component in an amount of 25% by weight of the tablet or ER portion. In a second formulation, POLYOX™ 1105 was employed as the extended release component in an amount of 35% by weight of the tablet or ER portion. In a third formulation, POLYOX™ 1105 was employed as the extended release component in an amount of 45% by weight of the tablet or ER portion. In a fourth formulation, POLYOX® 1105 was employed as the extended release component in an amount of 55% by weight of the tablet or ER portion. The amount of the microcrystalline cellulose in the four formulations was adjusted to account for the differing amounts of POLYOX® 1105 in each formulation. The other excipients in the extended release portion were B825, citric acid anhydrous, EDTA, hydroxypropyl cellulose, silicon dioxide, and magnesium stearate. However, the percentages for all the other excipients remained the same for each formulation, and were consistent with the percentages used in Example 25.

Dissolution profiles for the above-described formulations were determined in USP Type II apparatus. Six tablets of each formulation were weighed, placed in a sinker, and dropped into an equilibrated dissolution bath vessel containing 900 mL of (helium sparged) 0.1 N HCl heated to 37° C.±0.5° C. The mixture was stirred at 150±6 rpm, and the temperature was maintained at 37° C.±0.5° C. through 12 hr. The bath vessel was covered with a low evaporation vessel cover. Samples (5 mL) were removed at 0.25 hr, 0.5 hr, 1 hr, 2 hr, 4 hr, 6, hr, 8 hr, and 12 hr. The final time point for the 25%, 35%, 45%, and 55% formulations was 15 hr, 15 hr, 17.5 hr, and 17.5 hr, respectively. Each sample was filtered through a 0.45 µm filter and analyzed by HPLC using standard procedures.

Figure 38:
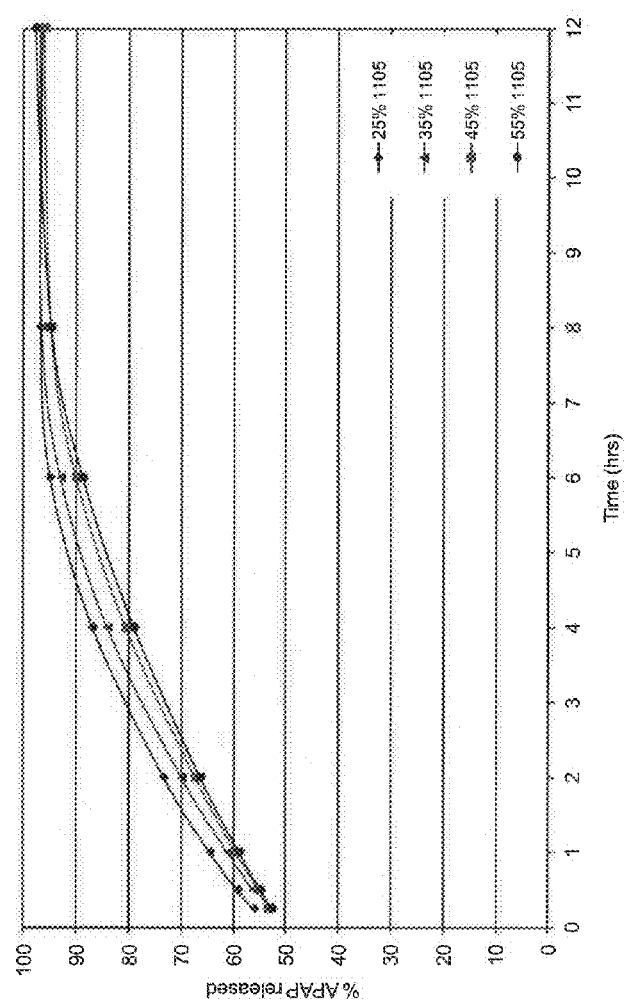
FIG. 38 presents acetaminophen dissolution data for four pharmaceutical formulations described herein. The dissolution data represents an extended release tablet with the immediate release data theoretically added. For each formulation, the tablet contained a total of 9 mg oxycodone HCl and a total of 250 mg acetaminophen. The four pharmaceutical compositions contained 25% by weight, 35% by weight, 45% by weight, and 55% by weight POLYOX® 1105, respectively.
Figure 39:
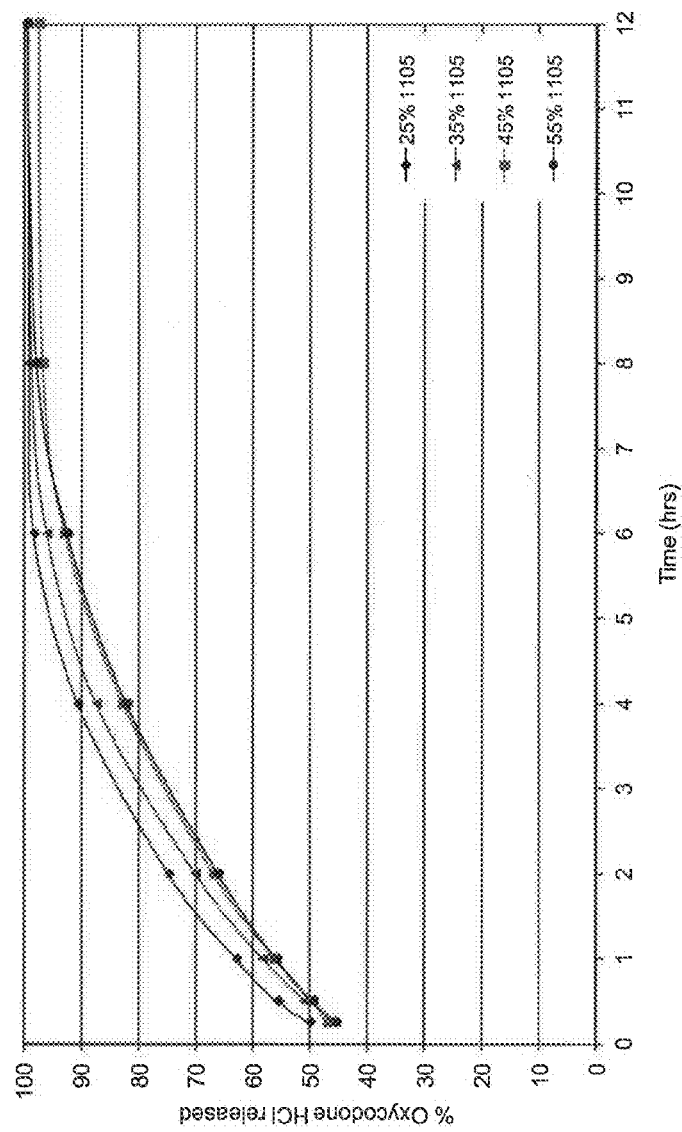
FIG. 39 presents oxycodone HCl dissolution data for the three pharmaceutical formulations described in FIG. 38.

The cumulative release profiles of acetaminophen and oxycodone from these compositions are shown in FIGS. 38 and 39, respectively. These profiles confirm that as the amount of POLYOX® 1105 used in the pharmaceutical formulations increase, the release rate of the acetaminophen and oxycodone generally decreases. For example, the formulations containing 25%, 45%, and 55% POLYOX® 1105 had released about 56%, about 53%, and about 53% acetaminophen after 15 minutes, respectively; about 59%, about 56%, about 55%, and about 55% acetaminophen after 30 minutes, respectively; about 64%, about 61%, about 60%, and about 59% acetaminophen after 1 hr, respectively; about 73%, about 70%, about 67%, and about 66% acetaminophen after 2 hr, respectively; about 87%, about 84%, about 81%, and about 79% acetaminophen after 4 hr, respectively; about 95%, about 93%, about 90%, and about 89% acetaminophen after 6 hr, respectively; about 97%, about 97%, about 95%, and about 95% acetaminophen after 8 hr, respectively; and about 97%, about 97%, about 96%, and about 98% acetaminophen after 12 hr, respectively.

Similar trends were observed for the cumulative release of oxycodone. However, there was no observable difference in the release of oxycodone from the formulations containing 45% and 55% POLYOX® 1105. For example, the formulations containing 25%, 45%, and 55% POLYOX® 1105 had released about 50%, about 47%, and about 45% oxycodone after 15 minutes, respectively; about 56%, about 51%, about 50%, and about 50% oxycodone after 30 minutes, respectively; about 63%, about 58%, about 56%, and about 56% oxycodone after 1 hr, respectively; about 75%, about 70%, about 67%, and about 66% oxycodone after 2 hr, respectively; about 91%, about 87%, about 83%, and about 82% oxycodone after 4 hr, respectively; about 98%, about 96%, about 93%, and about 93% oxycodone after 6 hr, respectively; about 99%, about 99%, about 97%, and about 98% oxycodone after 8 hr, respectively; and about 99%, about 100%, about 97%, and about 100% oxycodone after 12 hr, respectively.

Example 27

In Vitro Dissolution of Controlled-Release Bilayer Tablets Containing 7.5 mg Oxycodone and 325 mg Acetaminophen Performed at a 100 rpm Paddle Speed Three batches of bilayer formulations described herein were prepared, each containing a total of 7.5 mg of oxycodone HCl and a total of 325 mg of acetaminophen. 50% of the acetaminophen was contained in the immediate release portion, and the other 50% was contained in the ER layer. 25% of the oxycodone HCl was contained in the immediate release portion of the formulation, and the other 75% was contained in the ER layer. POLYOX® 1105 was employed as the extended release component in an amount of 45% by weight of the ER portion.

Dissolution profiles for the formulations of each batch were determined in a USP Type II apparatus. Twelve tablets from each batch were weighed, placed in a sinker, and dropped into an equilibrated dissolution bath vessel containing 900 mL of (helium sparged) 0.1 N HCl heated to 37° C.±0.5° C. The mixture was stirred at 100±4 rpm, and the temperature was maintained at 37° C.±0.5° C. for 12 hr. The bath vessel was covered with a low evaporation vessel cover. Samples (5 mL) were removed at 0.25 hr, 0.5 hr, 1 hr, 2 hr, 4 hr, 6, hr, 8 hr, and 12 hr. Each sample was filtered through a 0.45 µm filter and analyzed by HPLC using standard procedures.

The cumulative percent release of acetaminophen and oxycodone from each batch are described in Table 55.

TABLE 55

Release rate data of bilayer tablets (7.5 mg oxycodone HCl; 325 mg acetaminophen) using a 100 rpm dissolution method.

| Time | Oxycodone HCl | | | | Acetaminophen | | | |
|---|---|---|---|---|---|---|---|---|
| (Hours) | Mean (%) | RSD | Min (%) | Max (%) | Mean (%) | RSD | Min (%) | Max (%) |
| Batch 1 | | | | | | | | |
| 0.25 | 31.7 | 2.1 | 30.6 | 32.5 | 51.8 | 1.4 | 50.9 | 53.1 |
| 0.5 | 37.1 | 1.3 | 36.3 | 37.8 | 54.3 | 1.3 | 53.5 | 55.6 |
| 1.0 | 45.4 | 1.0 | 44.9 | 46.0 | 58.6 | 1.2 | 57.7 | 60.1 |
| 2.0 | 58.5 | 1.3 | 57.4 | 59.7 | 66.0 | 1.2 | 64.8 | 67.7 |
| 4.0 | 78.6 | 1.7 | 76.8 | 80.5 | 78.5 | 1.5 | 77.0 | 80.6 |

TABLE 55-continued

Release rate data of bilayer tablets (7.5 mg oxycodone HCl; 325 mg acetaminophen) using a 100 rpm dissolution method.

| Time | Oxycodone HCl | | | | Acetaminophen | | | |
|---|---|---|---|---|---|---|---|---|
| (Hours) | Mean (%) | RSD | Min (%) | Max (%) | Mean (%) | RSD | Min (%) | Max (%) |
| 6.0 | 92.2 | 1.8 | 90.0 | 94.7 | 88.0 | 1.6 | 86.0 | 90.3 |
| 8.0 | 99.5 | 1.8 | 97.4 | 102.7 | 93.8 | 1.5 | 91.8 | 96.3 |
| 12.0 | 101.7 | 1.4 | 99.7 | 104.3 | 96.1 | 1.0 | 94.9 | 98.2 |
| Batch 2 | | | | | | | | |
| 0.25 | 31.6 | 3.5 | 29.6 | 34.0 | 52.1 | 4.0 | 48.8 | 55.8 |
| 0.5 | 37.2 | 3.2 | 34.9 | 39.9 | 54.5 | 3.8 | 51.4 | 58.3 |
| 1.0 | 45.4 | 3.3 | 42.4 | 48.3 | 59.1 | 3.5 | 56.0 | 63.1 |
| 2.0 | 58.9 | 1.7 | 57.3 | 61.1 | 66.4 | 3.0 | 63.6 | 70.0 |
| 4.0 | 79.1 | 1.5 | 77.7 | 81.5 | 78.7 | 2.5 | 75.4 | 81.8 |
| 6.0 | 93.1 | 1.3 | 91.5 | 95.8 | 87.7 | 2.2 | 84.4 | 90.7 |
| 8.0 | 100.2 | 1.2 | 98.7 | 102.3 | 93.5 | 1.9 | 90.4 | 96.2 |
| 12.0 | 102.7 | 1.3 | 100.4 | 104.4 | 95.6 | 2.0 | 92.6 | 98.4 |
| Batch 3 | | | | | | | | |
| 0.25 | 30.4 | 1.6 | 29.3 | 31.0 | 52.2 | 2.3 | 49.6 | 54.2 |
| 0.5 | 35.7 | 1.6 | 34.2 | 36.7 | 54.6 | 2.3 | 52.0 | 56.6 |
| 1.0 | 43.5 | 1.8 | 42.0 | 45.1 | 58.6 | 2.2 | 56.0 | 60.8 |
| 2.0 | 56.1 | 1.9 | 54.4 | 58.0 | 65.5 | 2.1 | 63.1 | 68.0 |
| 4.0 | 75.4 | 1.8 | 73.3 | 77.6 | 77.3 | 2.0 | 74.8 | 80.0 |
| 6.0 | 88.9 | 1.7 | 86.1 | 91.4 | 86.5 | 2.2 | 83.7 | 90.1 |
| 8.0 | 97.0 | 1.5 | 94.7 | 99.8 | 93.0 | 2.1 | 90.1 | 96.8 |
| 12.0 | 100.4 | 1.1 | 98.7 | 102.4 | 96.5 | 1.6 | 93.2 | 98.3 |

Example 28

In Vitro Dissolution of Controlled-Release Bilayer Tablets Containing 15 mg Oxycodone and 650 mg Acetaminophen Performed at a 150 rpm Paddle Speed Bilayer formulations described herein were prepared, each containing a total of 15 mg of oxycodone HCl and a total of 650 mg of acetaminophen. 50% of the acetaminophen was contained in the immediate release portion, and the other 50% was contained in the ER layer. 25% of the oxycodone HCl was contained in the immediate release portion of the formulation, and the other 75% was contained in the ER layer. POLYOX® 1105 was employed as the extended release component in an amount of 45% by weight of the ER portion.

Dissolution profiles for the formulations were determined in a USP Type II apparatus. Six tablets were weighed, placed in a sinker, and dropped into an equilibrated dissolution bath vessel containing 900 mL of (helium sparged) 0.1 N HCl heated to 37° C.±0.55° C. The mixture was stirred at 150±6 rpm, and the temperature was maintained at 37° C.±0.5° C. for 12 hr. The bath vessel was covered with a low evaporation vessel cover. Samples (5 mL) were removed at 0.25 hr, 0.5 hr, 1 hr, 2 hr, 4 hr, 6, hr, 8 hr, and 12 hr. Each sample was filtered through a 0.45 µm filter and analyzed by HPLC using standard procedures.

The cumulative percent release of acetaminophen and oxycodone from each batch are described in Table 56.

TABLE 56

Release rate data of bilayer tablets (15 mg oxycodone HCl; 325 mg acetaminophen) using a 150 rpm dissolution method.

| Time (hr) | Oxycodone HCl (%) | Acetaminophen (%) |
|---|---|---|
| 0.25 | 33.7 | 54.4 |
| 0.50 | 39.0 | 56.5 |
| 1 | 47.4 | 60.6 |

TABLE 56-continued

Release rate data of bilayer tablets (15 mg oxycodone HCl; 325 mg acetaminophen) using a 150 rpm dissolution method.

| Time (hr) | Oxycodone HCl (%) | Acetaminophen (%) |
|---|---|---|
| 2 | 61.4 | 68.1 |
| 4 | 81.7 | 81.1 |
| 6 | 95.2 | 90.8 |
| 8 | 101.2 | 96.0 |
| 12 | 102.3 | 97.6 |

Example 29

Ethanol Release Testing at a 100 rpm Paddle Speed

Figure 40:
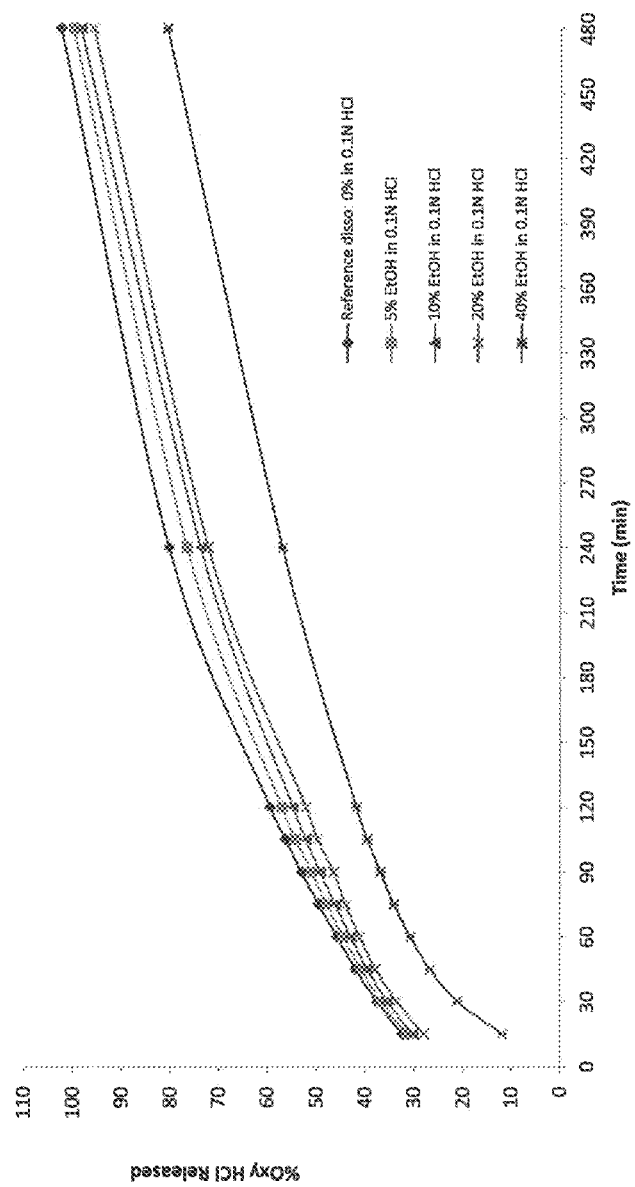
FIG. 40 presents the in vitro release of oxycodone from a bilayer tablet comprising 7.5 mg of oxycodone/325 mg of acetaminophen tested in 0.1 N HCl at a paddle speed of 100 rpm containing 0%, 5%, 20%, or 40% ethanol. Plotted is the percent of oxycodone released over a period of 8 hours.
Figure 41:
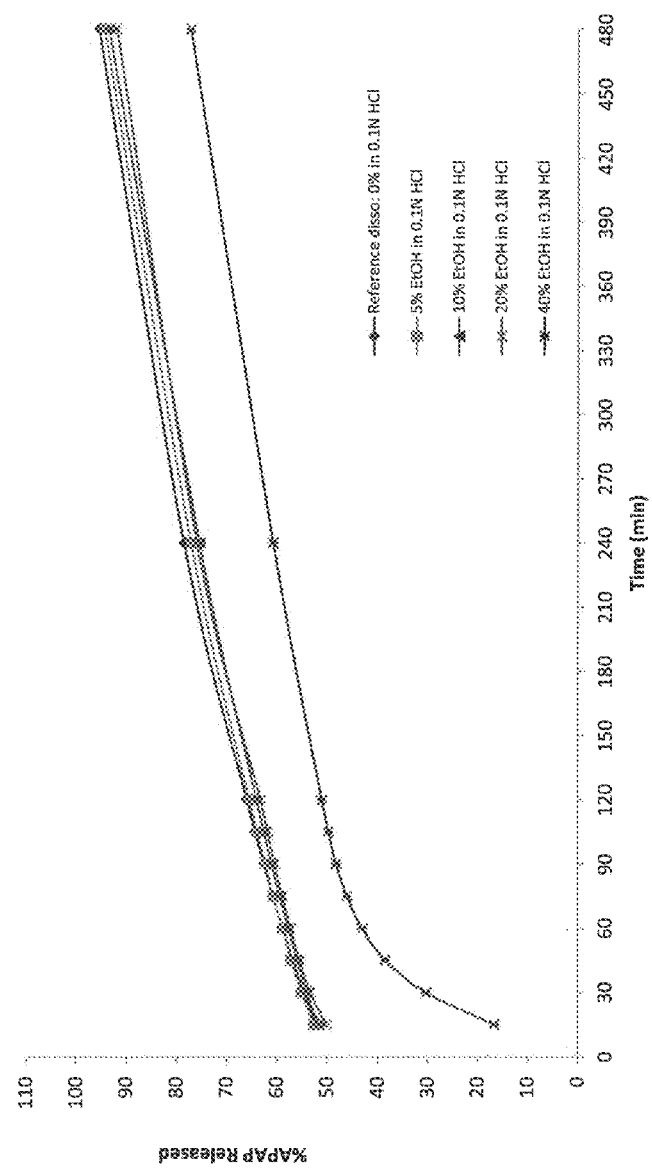
FIG. 41 presents the in vitro release of acetaminophen from a bilayer tablet comprising 7.5 mg of oxycodone/325 mg of acetaminophen tested in 0.1 N HCl at a paddle speed of 100 rpm containing 0%, 5%, 20%, or 40% ethanol. Plotted is the percent of acetaminophen released over a 8 hour period.

The ethanol release studies discussed above in Example 8 were repeated, except that the solutions were stirred at a paddle speed of 100 rpm and additional aliquots were sampled at 240 min and 480 min. Tables 57, 58, 59, 60, and 61 present the percent release of OC and APAP in the presence of 0%, 5%, 10%, 20%, and 40% ethanol, respectively. FIG. 40 presents dissolution profiles for OC and FIG. 41 presents dissolution profiles for APAP in the presence of 0%, 5%, 20%, and 40% ethanol. Like the results at a paddle speed of 150 rpm, these data reveal that, for both OC and APAP, the dissolution in 5%, 20%, or 40% ethanol was either comparable or slower than the dissolution in 0% ethanol, indicating no dose dumping for this formulation.

TABLE 57

Percent Release in 0% Ethanol

| | OC | | | | APAP | | | |
|---|---|---|---|---|---|---|---|---|
| Time (Min) | Mean | RSD | Min-imum | Max-imum | Mean | RSD | Min-imum | Max-imum |
| 15 | 32.5 | 3.7 | 31.5 | 36.0 | 52.2 | 1.6 | 50.7 | 53.4 |
| 30 | 37.6 | 2.5 | 36.6 | 39.9 | 54.6 | 1.4 | 53.2 | 55.7 |

TABLE 57-continued

Percent Release in 0% Ethanol

| Time (Min) | OC Mean | OC RSD | OC Minimum | OC Maximum | APAP Mean | APAP RSD | APAP Minimum | APAP Maximum |
|---|---|---|---|---|---|---|---|---|
| 45 | 42.1 | 2.7 | 40.9 | 44.8 | 56.8 | 1.4 | 55.3 | 57.9 |
| 60 | 45.8 | 2.1 | 44.6 | 48.1 | 58.8 | 1.4 | 57.4 | 59.8 |
| 75 | 49.6 | 2.3 | 48.2 | 52.2 | 60.8 | 1.4 | 59.2 | 61.8 |
| 90 | 53.1 | 2.4 | 51.7 | 55.8 | 62.6 | 1.4 | 60.9 | 63.8 |
| 105 | 56.3 | 2.4 | 54.8 | 59.3 | 64.3 | 1.4 | 62.6 | 65.6 |
| 120 | 59.5 | 2.5 | 57.6 | 63.0 | 66.0 | 1.4 | 64.2 | 67.3 |
| 240 | 80.3 | 2.5 | 77.3 | 84.9 | 78.6 | 1.8 | 76.3 | 80.6 |
| 480 | 102.4 | 1.8 | 100.5 | 107.2 | 95.5 | 1.6 | 92.6 | 97.7 |

TABLE 58

Percent Release in 5% Ethanol

| Time (Min) | OC Mean | OC RSD | OC Minimum | OC Maximum | APAP Mean | APAP RSD | APAP Minimum | APAP Maximum |
|---|---|---|---|---|---|---|---|---|
| 15 | 31.5 | 2.5 | 30.0 | 32.9 | 52.6 | 2.1 | 51.4 | 55.1 |
| 30 | 36.8 | 2.4 | 35.6 | 38.5 | 55.1 | 2.0 | 53.8 | 57.6 |
| 45 | 40.9 | 2.8 | 38.9 | 43.5 | 57.1 | 2.0 | 55.8 | 59.6 |
| 60 | 44.6 | 3.7 | 42.1 | 48.4 | 58.9 | 2.0 | 57.6 | 61.4 |
| 75 | 48.0 | 3.6 | 46.0 | 52.6 | 60.7 | 1.9 | 59.4 | 63.2 |
| 90 | 51.0 | 3.1 | 49.3 | 55.3 | 62.3 | 1.9 | 61.0 | 64.7 |
| 105 | 54.3 | 3.2 | 51.8 | 58.6 | 63.9 | 2.0 | 62.6 | 66.4 |
| 120 | 57.1 | 3.2 | 54.6 | 61.7 | 65.5 | 1.9 | 64.1 | 67.8 |
| 240 | 76.6 | 3.2 | 73.8 | 83.0 | 77.2 | 2.1 | 75.5 | 80.6 |
| 480 | 99.9 | 2.7 | 95.8 | 106.8 | 94.4 | 1.7 | 92.6 | 98.1 |

TABLE 59

Percent Release in 10% Ethanol

| Time (Min) | OC Mean | OC RSD | OC Minimum | OC Maximum | APAP Mean | APAP RSD | APAP Minimum | APAP Maximum |
|---|---|---|---|---|---|---|---|---|
| 15 | 30.3 | 3.1 | 28.9 | 32.1 | 51.7 | 1.8 | 50.1 | 53.4 |
| 30 | 35.6 | 3.3 | 33.7 | 37.3 | 54.1 | 1.9 | 52.4 | 55.8 |
| 45 | 39.6 | 2.6 | 37.6 | 40.9 | 56.0 | 1.9 | 54.3 | 57.8 |
| 60 | 43.1 | 2.6 | 41.2 | 44.7 | 57.8 | 1.9 | 56.1 | 59.5 |
| 75 | 46.2 | 2.3 | 44.1 | 47.5 | 59.5 | 1.8 | 57.7 | 61.1 |
| 90 | 49.3 | 2.1 | 47.3 | 50.6 | 61.1 | 1.8 | 59.3 | 62.8 |
| 105 | 52.2 | 2.2 | 50.1 | 53.6 | 62.6 | 1.8 | 60.9 | 64.2 |
| 120 | 54.8 | 2.3 | 52.8 | 56.4 | 64.1 | 1.8 | 62.3 | 65.6 |
| 240 | 73.8 | 2.2 | 70.8 | 76.1 | 75.5 | 1.7 | 73.4 | 77.4 |
| 480 | 98.4 | 2.1 | 94.7 | 101.1 | 93.5 | 1.6 | 91.0 | 95.9 |

TABLE 60

Percent Release in 20% Ethanol

| Time (Min) | OC Mean | OC RSD | OC Minimum | OC Maximum | APAP Mean | APAP RSD | APAP Minimum | APAP Maximum |
|---|---|---|---|---|---|---|---|---|
| 15 | 28.0 | 6.0 | 23.9 | 30.3 | 50.2 | 5.1 | 43.0 | 53.0 |
| 30 | 33.6 | 4.5 | 30.7 | 35.6 | 53.4 | 3.1 | 49.5 | 55.9 |
| 45 | 37.9 | 2.9 | 35.7 | 39.6 | 55.5 | 2.6 | 52.6 | 57.9 |
| 60 | 41.2 | 3.1 | 39.2 | 43.2 | 57.3 | 2.3 | 55.1 | 59.8 |
| 75 | 44.1 | 2.9 | 42.3 | 46.6 | 59.0 | 2.2 | 57.0 | 61.4 |
| 90 | 46.5 | 3.5 | 42.7 | 49.1 | 60.5 | 2.1 | 58.6 | 62.9 |
| 105 | 49.8 | 2.9 | 48.0 | 52.8 | 61.9 | 2.1 | 60.2 | 64.4 |
| 120 | 52.2 | 2.8 | 49.9 | 54.8 | 63.3 | 2.0 | 61.7 | 65.9 |
| 240 | 72.2 | 2.1 | 69.4 | 74.7 | 76.0 | 1.7 | 74.1 | 78.4 |
| 480 | 95.7 | 2.3 | 91.7 | 98.7 | 91.9 | 1.7 | 89.3 | 94.6 |

TABLE 61

Percent Release in 40% Ethanol

| Time (Min) | OC Mean | OC RSD | OC Minimum | OC Maximum | APAP Mean | APAP RSD | APAP Minimum | APAP Maximum |
|---|---|---|---|---|---|---|---|---|
| 15 | 11.9 | 13.9 | 10.0 | 15.1 | 16.7 | 23.2 | 12.3 | 22.9 |
| 30 | 21.1 | 15.4 | 17.3 | 26.2 | 30.4 | 22.3 | 21.7 | 40.7 |
| 45 | 26.8 | 11.6 | 22.4 | 30.3 | 38.5 | 15.3 | 29.6 | 44.8 |
| 60 | 30.8 | 7.0 | 26.8 | 34.0 | 43.1 | 9.2 | 35.9 | 47.1 |
| 75 | 34.2 | 5.0 | 31.5 | 36.8 | 46.1 | 5.3 | 41.1 | 49.2 |
| 90 | 36.9 | 3.2 | 35.1 | 38.8 | 48.3 | 3.3 | 44.6 | 50.2 |
| 105 | 39.6 | 3.3 | 37.3 | 41.2 | 49.8 | 2.4 | 47.3 | 51.3 |
| 120 | 41.9 | 3.3 | 39.4 | 44.2 | 51.1 | 2.3 | 48.3 | 52.7 |
| 240 | 57.0 | 1.8 | 55.7 | 58.9 | 60.8 | 2.0 | 58.9 | 63.6 |
| 480 | 80.6 | 1.6 | 78.4 | 83.7 | 77.2 | 1.3 | 75.7 | 78.7 |

All references cited herein are hereby incorporated by reference. The foregoing is offered primarily for purposes of illustration. It will be readily apparent to those skilled in the art that further drugs can be included, and that the shapes, components, additives, proportions, methods of formulation, and other parameters described herein can be modified further or substituted in various ways without departing from the spirit and scope of the invention.

What is claimed:

1. A pharmaceutical composition comprising:
   at least one immediate release portion comprising oxycodone or a pharmaceutically acceptable salt of oxycodone, acetaminophen, or a combination thereof;
   at least one extended release portion comprising oxycodone or a pharmaceutically acceptable salt of oxycodone, acetaminophen, and an extended release component;
   wherein the total amount of acetaminophen in the composition is about 325 mg to about 650 mg, and the total amount of oxycodone or salt in the composition is about 7.5 mg to about 15 mg;
   wherein upon oral administration of the composition to a subject, the composition provides an $AUC_{0-1h}$ for acetaminophen of about 1.25 ng·h/mL/mg to about 3.25 ng·h/mL/mg; a mean AUC for acetaminophen of about 35.0 ng·hr/mL/mg to about 60.0 ng·hr/mL/mg; an $AUC_{0-1h}$ for oxycodone or salt of about 0.1 ng·h/mL/mg to about 0.45 ng·h/mL/mg; and a mean AUC for oxycodone or salt of about 9.0 ng·hr/mL/mg to about 18.5 ng·hr/mL/mg; and
   wherein the subject attains therapeutic blood levels of both the oxycodone and the acetaminophen within about one hour after administration of the composition and maintains analgesia for at least about 10 hours after administration of the composition.

2. The pharmaceutical composition of claim 1, wherein the $AUC_{0-1h}$ for acetaminophen is about 1.6 ng·h/mL/mg to about 2.0 ng·h/mL/mg.

3. The pharmaceutical composition of claim 1, wherein the $AUC_{0-1h}$ for acetaminophen is about 2.0 ng·h/mL/mg to about 2.75 ng·h/mL/mg.

4. The pharmaceutical composition of claim 1, wherein the $AUC_{0-1h}$ for oxycodone or salt is about 0.15 ng·h/mL/mg to about 0.25 ng·h/mL/mg.

5. The pharmaceutical composition of claim 1, wherein the $AUC_{0-1h}$ for oxycodone or salt is about 0.25 ng·h/mL/mg to about 0.35 ng·h/mL/mg.

6. The pharmaceutical composition of claim 1, wherein the mean AUC for acetaminophen is about 40.0 ng·h/mL/mg to about 50.0 ng·h/mL/mg.

7. The pharmaceutical composition of claim 1, wherein the mean AUC for acetaminophen is about 35.0 ng·h/mL/mg to about 45.0 ng·h/mL/mg.

8. The pharmaceutical composition of claim 1, wherein the mean AUC for oxycodone or salt is about 11.0 ng·h/mL/mg to about 17.0 ng·h/mL/mg.

9. The pharmaceutical composition of claim 1, wherein the mean AUC for oxycodone or salt is about 12.0 ng·h/mL/mg to about 16.0 ng·h/mL/mg.

10. The pharmaceutical composition of claim 1, wherein the subject attains therapeutic blood levels of both the oxycodone and the acetaminophen within about 30 minutes after administration of the composition.

11. The pharmaceutical composition of claim 1, wherein the composition comprises about 325 mg of acetaminophen and about 7.5 mg of oxycodone or salt.

12. The pharmaceutical composition of claim 11, wherein the composition is in the form of a tablet and a single dose comprises two tablets.

13. The pharmaceutical composition of claim 1, wherein the extended release component comprises at least one extended release polymer.

14. A pharmaceutical composition comprising:
at least one immediate release portion comprising oxycodone or a pharmaceutically acceptable salt of oxycodone, acetaminophen, or a combination thereof;
at least one extended release portion comprising oxycodone or a pharmaceutically acceptable salt of oxycodone, acetaminophen, or a combination thereof;
wherein the total amount of acetaminophen in the composition is about 325 mg to about 650 mg, and the total amount of oxycodone or salt in the composition is about 7.5 mg to about 15 mg;
wherein upon oral administration of the composition to a subject, the composition provides an $AUC_{0-2h}$ for acetaminophen of about 4.25 ng·h/mL/mg to about 8.75 ng·h/mL/mg; mean AUC for acetaminophen of about 35.0 ng·hr/mL/mg to about 60.0 ng·hr/mL/mg; an $AUC_{0-2h}$ for oxycodone or salt of about 0.65 ng·h/mL/mg to about 1.35 ng·h/mL/mg; and a mean AUC for oxycodone or salt of about 9.0 ng·hr/mL/mg to about 18.5 ng·hr/mL/mg; and
wherein the subject attains therapeutic blood levels of both the oxycodone and the acetaminophen within about one hour after administration of the composition and maintains analgesia for about 12 hours after administration of the composition.

15. The pharmaceutical composition of claim 14, wherein the $AUC_{0-2h}$ for acetaminophen is about 5.5 ng·h/mL/mg to about 6.0 ng·h/mL/mg.

16. The pharmaceutical composition of claim 14, wherein the $AUC_{0-2h}$ for acetaminophen is about 6.0 ng·h/mL/mg to about 7.25 ng·h/mL/mg.

17. The pharmaceutical composition of claim 14, wherein the $AUC_{0-2h}$ for oxycodone or salt is about 0.8 ng·h/mL/mg to about 1.0 ng·h/mL/mg.

18. The pharmaceutical composition of claim 14, wherein the $AUC_{0-2h}$ for oxycodone or salt is about 1.0 ng·h/mL/mg to about 1.2 ng·h/mL/mg.

19. The pharmaceutical composition of claim 14, wherein the composition comprises about 325 mg of acetaminophen and about 7.5 mg of oxycodone or salt.

20. The pharmaceutical composition of claim 19, wherein the composition is in the form of a tablet and a single dose comprises two tablets.

* * * * *